US011427576B2

(12) United States Patent
Colabuono et al.

(10) Patent No.: US 11,427,576 B2
(45) Date of Patent: *Aug. 30, 2022

(54) INDOLE COMPOUNDS AND THEIR USE

(71) Applicant: ARIAGEN, INC., Menlo Park, CA (US)

(72) Inventors: Peter Colabuono, Half Moon Bay, CA (US); Graham Johnson, Sanbornton, NH (US); David Douglas Manning, Orchard Park, NY (US); Mark Allan Wolf, Williamsville, NY (US)

(73) Assignee: ARIAGEN, INC., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/179,286

(22) Filed: Feb. 18, 2021

(65) Prior Publication Data

US 2021/0179604 A1 Jun. 17, 2021

Related U.S. Application Data

(63) Continuation of application No. 16/765,315, filed as application No. PCT/US2018/061758 on Nov. 19, 2018.

(60) Provisional application No. 62/717,387, filed on Aug. 10, 2018, provisional application No. 62/588,751, filed on Nov. 20, 2017.

(51) Int. Cl.
| | |
|---|---|
| *C07D 417/14* | (2006.01) |
| *A61P 35/00* | (2006.01) |
| *C07D 209/12* | (2006.01) |
| *C07D 209/26* | (2006.01) |
| *C07D 401/06* | (2006.01) |
| *C07D 403/06* | (2006.01) |
| *C07D 413/14* | (2006.01) |
| *C07D 417/06* | (2006.01) |

(52) U.S. Cl.
CPC ............ *C07D 417/14* (2013.01); *A61P 35/00* (2018.01); *C07D 209/12* (2013.01); *C07D 209/26* (2013.01); *C07D 401/06* (2013.01); *C07D 403/06* (2013.01); *C07D 413/14* (2013.01); *C07D 417/06* (2013.01)

(58) Field of Classification Search
CPC ................ C07D 417/14; A61P 35/00
See application file for complete search history.

(56) References Cited

U.S. PATENT DOCUMENTS

| | | | |
|---|---|---|---|
| 3,946,029 A | 3/1976 | Descamps et al. | |
| 4,046,774 A | 9/1977 | Napier | |
| 6,916,834 B2* | 7/2005 | DeLuca | A61P 17/14 |
| | | | 514/365 |
| 7,002,019 B2 | 2/2006 | DeLuca et al. | |
| 7,419,992 B2 | 9/2008 | DeLuca et al. | |
| 8,604,067 B2* | 12/2013 | Song | E04D 1/30 |
| | | | 514/365 |
| 9,205,148 B2 | 12/2015 | Langermann et al. | |
| 2002/0177594 A1 | 11/2002 | Curtin et al. | |
| 2002/0183524 A1 | 12/2002 | DeLuca et al. | |
| 2007/0043092 A1 | 2/2007 | DeLuca et al. | |
| 2008/0221070 A1 | 9/2008 | William et al. | |
| 2010/0197708 A1 | 8/2010 | Talley et al. | |
| 2012/0214853 A1 | 8/2012 | Song | |
| 2013/0338201 A1 | 12/2013 | Song | |
| 2020/0354353 A1 | 11/2020 | Colabuono et al. | |

FOREIGN PATENT DOCUMENTS

| | | |
|---|---|---|
| EP | 1842541 A1 | 3/2006 |
| GB | 1318300 | 5/1973 |
| WO | WO 1998/039330 | 9/1998 |
| WO | WO 2002/028832 | 4/2002 |
| WO | WO 2003/068742 | 8/2003 |
| WO | WO 2003/105847 | 12/2003 |
| WO | WO 2004/060888 | 7/2004 |
| WO | WO 2006/029862 | 3/2006 |
| WO | WO 2008/019357 | 2/2008 |
| WO | WO 2009/067349 | 5/2009 |
| WO | WO 2009/070645 | 6/2009 |
| WO | WO 2009/117597 | 9/2009 |
| WO | WO 2010/089327 | 8/2010 |
| WO | WO2011/053466 | 5/2011 |
| WO | WO 2012/015914 | 2/2012 |
| WO | WO 2012/145493 | 10/2012 |
| WO | WO 2013/033003 | 3/2013 |
| WO | WO 2013/041468 | 3/2013 |
| WO | WO 2013/116182 | 8/2013 |
| WO | WO2013/163279 | 10/2013 |
| WO | WO 2015/035606 | 3/2015 |
| WO | WO 2015/112800 | 7/2015 |
| WO | WO 2015/112900 | 7/2015 |
| WO | WO2015/131035 | 9/2015 |
| WO | WO2016/023106 | 2/2016 |
| WO | WO2016/040553 | 3/2016 |

(Continued)

OTHER PUBLICATIONS

DeLuca et al (2002) : STN International CAPLUS database, (Columbus, Ohio), Accession No. 2002: 637522.*

Akahoshi et al., "Synthesis, structure-activity relationships, and pharmacokinetic profiles of nonpeptidic α-Keto Heterocycles as novel inhibitors of human chymase," J. Med. Chem. 44:1286-1296 (2001).

(Continued)

*Primary Examiner* — Golam M Shameem

(74) *Attorney, Agent, or Firm* — Steptoe & Johnson LLP

(57) ABSTRACT

The present disclosure relates to indole compounds and pharmaceutical compositions thereof, and their use in stimulating the immune system of patients in need thereof and in treating cancer.

15 Claims, 28 Drawing Sheets

(56) References Cited

FOREIGN PATENT DOCUMENTS

| WO | WO 2016/092419 | 6/2016 |
|---|---|---|
| WO | WO 2018/085348 | 5/2018 |
| WO | WO 2018/120009 | 7/2018 |
| WO | WO 2018/121434 | 7/2018 |
| WO | WO 2018/153893 | 8/2018 |
| WO | WO 2019/057744 | 3/2019 |
| WO | WO 2019/099977 | 5/2019 |

OTHER PUBLICATIONS

Alarma-Estrany et al., "Design of novel melatonin analogs for the reduction of intraocular pressure in normotensive rabbits," J Pharmacol Exp Ther 337(3):703-9 (2011).

Bankoti et al., "Functional and phenotypic effects of AhR activation in inflammatory dendritic cells," Toxicol Appl Pharmacol 246:18-28 (2010).

Baud'Huin et al., "Factor VIII—von Willebrand factor complex inhibits osteoclastogenesis and controls cell survival," J Biol Chem. 284(46):31704-13(2009).

Bermúdez et al., "Beta-naphthoflavone represses dystrophin Dp71 expression in hepatic cells," Biochim. Biophys. Acta. 1759(3-4):152-158 (2006).

Bock et al., "Ah receptor- and TCDD-mediated liver tumor promotion: clonal selection and expansion of cells evading growth arrest and apoptosis," Biochem. Pharmacol. 69(10):1403-1408 (2005).

Boldron et al., "N-[6-(4-Butanoyl-5-methyl-1H-pyrazol-1-yl) pyridazin-3-yl]-5-chloro-1-[2-(4-methylpiperazin-1-yl)-2-oxoethyl]-1H-indole-3-carboxamide (SAR216471), a Novel Intravenous and Oral, Reversible, and Directly Acting P2Y12 Antagonist," Journal of Medical Chemistry 57(17):7293-7316 (2014).

Brauze et al., "The effect of aryl hydrocarbon receptor ligands on the expression of AhR, AhRR, ARNT, Hif1alpha, CYP1A1 and NQO1 genes in rat liver," Toxicol. Lett. 167(3):212-220 (2006).

Brozic et al., "Selective inhibitors of aldo-keto reductases AKR1C1 and AKR1C3 discovered by virtual screening of a fragment library," J. Med. Chem 55(17):7417-24 (2012).

Cavalluzzo et al., "De novo design of small molecule inhibitors targeting the LEDGF/p75-HIV integrase interaction," RSC Advances 2:974-984 (2012).

Cheng et al., "Tryptophan derivatives regulate the transcription of Oct4 in stem-like cancer cells." Nat Commun 6:7209 (2015).

Cook et al., "Angiogenesis Inhibitors: Current Strategies and Future Prospects," http://cajournal.org (2010).

Crestey et al., "Design and synthesis of a new indazole library: direct conversion of N-methoxy-N-methylamides (Weinreb amides) to 3-keto and 3-formylindazoles," Tetrahedron 63(2):419-428 (2007).

Dickson et al., "Rapid synthesis of indole cis-enamides via hydroamidation of indolic alkynes," Tetrahed Letts 54(38):5239-42 (2013).

Dietrich et al., "The aryl hydrocarbon receptor (AhR) in the regulation of cell-cell contact and tumor growth," Carcinogenesis 31(8):1319-1328 (2010).

Dolciami et al., "Binding Mode and Structure-Activity Relationships of ITE as Aryl Hydrocarbon Receptor (AhR) Agonist," ChemMedChem 13(3):270-279 (2018).

Dorbritsa et al., "Development of a High-Throughput Cell-Based Assay for Identifcation of IL-17 Inhibitors," Journal of Biomolecular Screening 18(1):75-84 (2013).

Duarte et al., "Differential influences of the aryl hydrocarbon receptor on Th17 mediated responses in vitro and in vivo," PLoS One 8:e79819 (2013).

Ebos et al., "Accelerated metastasis after short-term treatment with a potent inhibitor of tumor angiogenesis," Cancer Cell 15(3):232-239 (2009).

Elizondo et al., "Altered cell cycle control at the G(2)/M phases in aryl hydrocarbon receptor-null embryo fibroblast," Mol Pharmacol 57(5):1056-63 (2000).

Ellis, "Role of Angiogenesis Inhibitors in Cancer Treatment," Oncology 15:39-46 (2001).

Emtenäs et al., "An enantioselective ketene-imine cycloaddition method for synthesis of substituted ring-fused 2-pyridinones," J Org Chem 66(20):6756-61 (2001).

English et al., "VEGF inhibition and metastasis: possible implications for antiangiogenic therapy," Cancer Biol. Ther. 8(13):1214-1225 (2009).

Forrester et al., "Induction of a chloracne phenotype in an epidermal equivalent model by 2,3,7,8-tetrachlorodibenzo-p-dioxin (TCDD) is dependent on aryl hydrocarbon receptor activation and is not reproduced by aryl hydrocarbon receptor knock down," J Dermatol Sci 73:10-22 (2014).

Fritz et al., "The selective aryl hydrocarbon receptor modulator 6-methyl-1,3,8-trichlorodibenzofuran inhibits prostate tumor metastasis in TRAMP mice," Biochem. Pharmacol. 77(7):1151-1160 (2009).

Fuganti et al., "A general method for the synthesis of the most powerful naturally occurring Maillard flavors," Tetrahedron 63:4762-4767 (2007).

Funcke et al., "The Effect of Alkyl Substitution in Drugs—IV. Pharmacological Properties of Tropinyl 2-Methyl-benzhydryl Ether Hydrobromide (BS 6825)," Journal of Medicinal and Pharmaceutical Chemistry 4(2): 215-224 (1961).

Gierthy et al., "Correlation of in vitro and in vivo growth suppression of MCF-7 human breast cancer by 2,3,7,8-tetrachlorodibenzo-p-dioxin," Cancer Res 53(13):3149-3153 (1993).

Gluschnaider et al., "beta-TrCP inhibition reduces prostate cancer cell growth via upregulation of the aryl hydrocarbon receptor," PLoS ONE 5(2):e9060 (2010).

Gruber et al., "Correlation between the tumoral expression of β3-integrin and outcome in cervical cancer patients who had undergone radiotherapy," Br. J. Cancer 92(1):41-46 (2005).

Grzywacz et al., "A concise synthesis of an AHR endogenous ligand with the indolecarbonylthiazole skeleton," HETEROCYCLES 60:5:1219 (2003).

Hall et al., "Activation of the Aryl-Hydrocarbon Receptor Inhibits Invasive and Metastatic Features of Human Breast Cancer Cells and Promotes Breast Cancer Cell Differentiation," Mol Endocrinol 24:359-369 (2010).

Hao et al., "Inhibitory effect and its mechanism of ITE, an endogenous aryl hydrocarbon receptor (AhR) ligand, on the proliferation of human placental trophoblast cells," Fudan Univ J Med Sci 41:488-493 (2014).

Hawerkamp et al., "Vemurafenib acts as an aryl hydrocarbon receptor antagonist: Implications for inflammatory cutaneous adverse events," Allergy. 74(12):2437-2448 (2019).

Henry et al., "A potential endogenous ligand for the aryl hydrocarbon receptor has potent agonist activity in vitro and in vivo," Arch. Biochem. Biophys. 450(1):67-77 (2006).

Henry et al., "TCDD and a Putative Endogenous AhR Ligand, ITE, Elicit the Same Immediate Changes in Gene Expression in Mouse Lung Fibroblasts," Toxicological Sciences 114:90-100 (2010).

Heravi et al., "An efficient synthesis of thiazol-2-imine derivatives via a onepot, three-component reaction," Tetrahedron Letters 53:392-394 (2012).

Holcomb et al., "Inhibition of 7,12-dimethylbenzanthracene-induced rat mammary tumor growth by 2,3,7,8-tetrachlorodibenzo-p-dioxin," Cancer Lett 82(1):43-7 (1994).

Hu et al., "Synthetic RORg agonists regulate multiple pathways to enhance antitumor immunity," Oncoimmunology 5(12) (2016).

Ishida et al., "Activation of the aryl hydrocarbon receptor pathway enhances cancer cell invasion by upregulating the MMP expression and is associated with poor prognosis in upper urinary tract urothelial cancer," Carcinogenesis 31(2):287-295 (2010).

Jana et al., "Cross-talk between 2,3,7,8-tetrachlorodibenzo-p-dioxin and testosterone signal transduction pathways in LNCaP prostate cancer cells," Biochem Biophys Res Commun 256(3):462-8 (1999).

Jin et al., "Copper-catalyzed oxidative cross-coupling of H-phosphonates and amides to N-acylphosphoramidates," Organic Letters 15(2) (2013).

John et al., "Antiangiogenic therapy and surgical practice," Br J Surg 95(3):281-293 (2008).

(56) References Cited

OTHER PUBLICATIONS

Johnson, et al., "Total synthesis of (-)-Rhazinilam: asymmetric C-H bond activation via the use of chiral auxiliary," J. Am. Chem. Soc. 124:6900-6903 (2002).
Jux et al., "Langerhans cell maturation and contact hypersensitivity are impaired in aryl hydrocarbon receptor-null mice," J. Immunol. 182(11):6709-6717 (2009).
Kajta et al., "Aryl hydrocarbon receptor-mediated apoptosis of neuronal cells: a possible interaction with estrogen receptor signaling," Neuroscience 158(2):811-822 (2009).
Kang et al., "Genome-wide transcriptional profiling of human glioblastoma cells in response to ITE treatment," Genomics Data 5:281-283 (2015).
Katner, "An Improved Synthesis of Indole-3-Carboxylic Acids," Organic Preparations and Procedures 2(4):297-303 (1970).
Kashani et al., "Expression of the aryl hydrocarbon receptor (AhR) and the aryl hydrocarbon receptor nuclear translocator (ARNT) in fetal, benign hyperplastic, and malignant prostate," Prostate 37(2):98-108 (1998).
Kawajiri, et al., "Aryl hydrocarbon receptor suppresses intestinal carcinogenesis in ApcMin/+ mice with natural ligands," Proc. Natl. Acad. Sci. U.S.A. 106(32):13481-13486 (2009).
Kerbel, "Tumor angiogenesis: past, present and the near future," Carcinogenesis 21:505-515 (2000).
King, "Bioisosteres, conformational restriction, and pro-drugs— case history: an example of a conformational restriction approach," Med Chem Principle and Practice 206-208 (1994).
Knerr et al., "Carcinogenicity of 2,3,7,8-tetrachlorodibenzo-p-dioxin in experimental models," Mol Nutr Food Res 50(10):897-907 (2006).
Knölker et al., "Isolation and synthesis of biologically active carbazole alkaloids," Chem Rev. 102(11):4303-427 (2002).
Koliopanos et al., "Increased aryl hydrocarbon receptor expression offers a potential therapeutic target for pancreatic cancer," Oncogene 21(39):6059-70 (2002).
Kurihara et al., "Synthesis and Cycloaddition Reaction of 2-Cyano-3-indoleacetonitriles," Chemical & Pharmaceutical Bulletin 34(11) (1986).
La Regina et al., New Arylthioindoles and Related Bioisosteres at the Sulfur Bridging Group. 4. Synthesis, Tubulin Polymerization, Cell Growth Inhibition, and Molecular Modeling Studies, J Med Chem. 52(23):7512-7527 (2009).
Lehmann et al., "The Aryl Hydrocarbon Receptor Ligand ITE Inhibits TGFβ1-Induced Human Myofibroblast Differentiation," Am J Pathol 178(4):1556-1567 (2011).
Leong et al., "In vitro, in vivo, and in silico analyses of the antitumor activity of 2-(4-amino-3-methylphenyl)-5-fluorobenzothiazoles," Mol Cancer Ther 3(12):1565-75 (2004).
Lin et al., "Overexpression of aryl hydrocarbon receptor in human lung carcinomas," Toxicol Pathol 31(1):22-30 (2003).
Liu et al., "AhR expression is increased in hepatocellular carcinoma," J Mol Histol 44(4):455-61 (2013).
Loges et al., "Silencing or fueling metastasis with VEGF inhibitors: antiangiogenesis revisited," Cancer Cell 15(3):167-170 (2009).
Loughlin et al., "Approaches to the high-throughput synthesis of analogues of dihydroaeruginoic acid," Aust. J. Chem 53:6:457-462 (2000).
Manegold et al., "The Potential of Combined Immunotherapy and Antiangiogenesis for the Synergistic Treatment of Advanced NSCLC," J Thorac OncoL 12(2): 194-207 (2017).
Marlowe et al., "The aryl hydrocarbon receptor displaces p300 from E2F-dependent promoters and represses S phase-specific gene expression," J Biol Chem 279(28):29013-22 (2004).
McDougal, "Methyl-substituted diindolylmethanes as inhibitors of estrogen-induced growth of T47D cells and mammary tumors in rats," Breast Cancer Research and Treatment 66:147-157 (2001).
McDougal et al., "Tamoxifen-induced antitumorigenic/antiestrogenic action synergized by a selective aryl hydrocarbon receptor modulator," Cancer Res 61(10):3902-3907 (2001).

McDougal et al., "Inhibition of 7,12-dimethylbenz [a] anthracene-induced rat mammary tumor growth by aryl hydrocarbon receptor agonists," Cancer Lett 120(1):53-63 (1997).
Medjakovic et al., "Indolylfuran, a potent aryl hydrocarbon receptor agonist from sauerkraut, interacts with the oestrogen pathway," Food Chemistry 127(4):1764-1772 (2011).
Milen et al., "A study on the phosphorylation of indole, imidazole, carbazole, and phenothiazine derivatives," Phosphorus, Sulfur and Silicon and The Related Elements 187(9) (2012).
Milinkevich et al., "Synthesis of 5-(Thiazol-5-yl)-4,5-dihydroisoxazoles from 3-Chloropentane-2,4-dione," J. Comb. Chem. 10:521-525 (2008).
Miyagi et al., "Binding affinity between AhR and exogenous/endogenous ligands: molecular simulations and biological experiment," Molecular Simulation 41(7) (2015).
Miyake et al., "Synthesis of 5-(3-indolyl) oxazole natural products. Structure revision of Almazole D," Tetrahed 66(26):4888-1893 (2010).
Mizzoni et al., "Some thiazolines and thiazolidinones with antituberculous activity," (Jul. 5, 1958).
Mjambili et al., "Synthesis and biological evaluation of 2-aminothiazole derivatives as antimycobacterial and antiplasmodial agents," Biorganic & Medicinal Chemistry Letters 24:560-564 (2014).
Morrow et al., "Aryl hydrocarbon receptor-mediated inhibition of LNCaP prostate cancer cell growth and hormone-induced transactivation," J. Steroid Biochem. Mol. Biol. 88(1):27-36 (2004).
Mouchlis et al., "Molecular docking and 3D-QSAR CoMFA studies on indole inhibitors of GIIA secreted phospholipase A(2)," Chem Inf Model 50(9):1589-1601 (2010).
Murray et al., "Aryl hydrocarbon receptor ligands in cancer: friend and foe," Nat Rev Cancer 14(12):801-14 (2014).
Narender et al., "Aqueous phase synthesis of thiazoles and aminothiazoles in the presence of β-cyclodextrin," Tetrahedron letters 46:5953-5955 (2005).
Neumann et al., "Exploring the oxidative cyclization of substituted N-aryl enamines: Pd-catalyzed formation of indoles from anilines," Chem. Eur. J 17(26):7298-7303 (2011).
Nugent et al., "ITE, A Novel Endogenous Nontoxic Aryl Hydrocarbon Receptor Ligand, Efficiently Suppresses EAU and T-Cell-Mediated Immunity," Invest Ophthalmol Vis Sci 54:7463-7469 (2013).
O'Donnell et al., "The aryl hydrocarbon receptor mediates leflunomide-induced growth inhibition of melanoma cells," PLoS ONE 7(7) (2012).
Oenga et al., "TCDD and PCBs inhibit breast cancer cell proliferation in vitro," Toxicol In Vitro. 18(6):811-9 (2004).
Okino et al., "Toxic and chemopreventive ligands preferentially activate distinct aryl hydrocarbon receptor pathways: implications for cancer prevention," Cancer Prev Res (Phila Pa). 2(3):251-256 (2009).
Ott et al., "Inhibition of immune checkpoints and vascular endothelial growth factor as combination therapy for metastatic melanoma: an overview of rationale, preclinical evidence, and initial clinical data," Frontiers in Oncology, 5:1-7 (2015).
Ozawa et al., "A new synthesis of glutathione via the thiazoline peptide," Bull. Chem. Soc. Jpn., 53:2592-2593 (1980).
Paez-Ribes et al., "Antiangiogenic therapy elicits malignant progression of tumors to increased local invasion and distant metastasis," Cancer Cell 15(3):220-231 (2009).
Park et al., "The aryl hydrocarbon receptor predisposes hepatocytes to Fas mediated apoptosis," Mol Pharmacol. 67(3):612-22 (2005).
Patani et al., "Bioisosterism: A Rational Approach to Design," Chemical Reviews 96(8):3147-3176 (1996).
Peng et al., "Potential therapeutic significance of increased expression of aryl hydrocarbon receptor in human gastric cancer," World J. Gastroenterol. 15(14):1719-1729 (2009).
Piparo et al., "Virtual screening for aryl hydrocarbon receptor binding prediction," J Med Chem 49(19):5702-5709 (2006).
Poellinger, "Mechanistic aspects—the dioxin (aryl hydrocarbon) receptor," Food Addit Contam 17(4):261-6 (2000).
Poland et al., "2,3,7,8-tetrachlorodibenzo-p-dioxin and related halogenated aromatic hydrocarbons: examination of the mechanism of toxicity," Annu. Rev. Pharmacol. Toxicol. 22:517-554 (1982).

(56) References Cited

OTHER PUBLICATIONS

Potewar et al., "Efficient synthesis of 2,4-disubstituted thiazoles using ionic liquid under ambient conditions: a practical approach towards the synthesis of Fanetizole," Tetrahedron 63:45:11066-11069 (2007).
Puga et al., "Ah receptor signals cross-talk with multiple developmental pathways," Biochem Pharmacol. 69(2):199-207 (2005).
Puga et al., "Role of the aryl hydrocarbon receptor in cell cycle regulation," Toxicology 181-182:171-7 (2002).
Quintana et al., "Control of T(reg) and T(H)17 cell differentiation by the aryl hydrocarbon receptor," Nature 453(7191):65-71 (2008).
Quintana et al., "An endogenous aryl hydrocarbon receptor ligand acts on dendritic cells and T cells to suppress experimental autoimmune encephalomyelitis," Proc Natl Acad Sci U S A 107:20768-73 (2010).
Quintana et al., "Aryl Hydrocarbon Receptor Control of Adaptive Immunity," Pharmacol Rev. 65(4):1148-61 (2013).
Radspieler, "Studies on the synthesis of diazonamide A and phorbazol A and C," Sel. Org. React. Database (SORD), no pp. given (2007).
Rajniak, et al., "A new cyanogenic metabolite in Arabidiposis required for inducible pathogen defense," Nature 525(7569):376-379 (2015).
Ramjiawan et al., "Anti-angiogenesis for cancer revisited: Is there a role for combinations with immunotherapy?" Angiogenesis. 20(2):185-204 (2017).
Rasool et al., "Convenient one-pot synthesis and biological evaluation of phosphoramidates and phosphonates containing heterocycles," Phosphorus, Sulfur and Silicon and The Related Elements 193(7) (2018).
Ray et al., "Activation of the aryl hydrocarbon receptor by TCDD inhibits senescence: a tumor promoting event?" Biochem. Pharmacol 77(4):681-688 (2009).
Reji et al., "Synthesis and Cytotoxicity Studies of Thiazole Analogs of the Anticancer Marine Alkaloid Dendrodoine," Indian Journal of Chemistry, Section B: Organic Chemistry Including Medicinal Chemistry 47:7:2: 1145-1150 (2011).
Rose, "A theory of the action of cancer chemotherapeutic drugs," Clin. Exp. Immunol. 2:361-373 (1967).
Safe et al., "Mechanism of action and development of selective aryl hydrocarbon receptor modulators for treatment of hormone dependent cancers," Int J Oncol 20(6):1123-1128 (2002).
Sanderson et al., "2,3,7,8-Tetrachlorodibenzo-p-dioxin and diindolylmethanes differentially induce cytochrome P450 1A1, 1B1, and 19 in H295R human adrenocortical carcinoma cells," Toxicol. Sci. 61(1):40-48 (2001).
Schmidt, "Developing combination strategies using PD-1 checkpoint inhibitors to treat cancer," Semin Immunopathol. 41(1):21-30 (2019).
Schmidt et al., "Occurrence, biogenesis, and synthesis of biologically active carbazole alkaloids," Chem Rev. 112(6):3193-328 (2012).
Schulz et al., "Activation of the aryl hydrocarbon receptor suppresses sensitization in a mouse peanut allergy model," Toxicol Sci 123:491-500 (2011).
Shih et al., "Bevacizumab: an angiogenesis inhibitor for the treatment of solid malignancies," Clin Ther (11): 1779-802 (2006).
Shiizaki et al., "Identification of amino acid residues in the ligand-binding domain of the aryl hydrocarbon receptor causing the species-specific response to omeprazole: possible determinants for binding putative endogenous ligands," Molecular Pharmacology Fast Forward (2013).
Simon et al., "Estimates of cancer potency of 2,3,7,8-tetrachlorixlibenzo(p)dioxin using linear and nonlinear dose-response modeling and toxicokinetics," Toxicological sciences 112(2):490-506 (2009).
Simones et al., "Consequences of AhR Activation in Steady-State Dendritic Cells," Toxicological Sciences 119:293-307 (2011).
Singh et al. "Primary peripheral T cells become susceptible to 2,3,7,8-tetrachlorodibenzo-p-dioxin-mediated apoptosis in vitro upon activation and in the presence of dendritic cells," Mol. Pharmacol. 73(6):1722-1735 (2008).
Smith et al., "Tapinarof is a natural AhR agonist that resolves skin inflammation in mice and humans," J Invest Dermatol. 137(10):2110-2119 (2017).
Solankee, et al., "Thiazoline: synthesis and antitubercular activity of 2-Alkyl/Aryl/-5-(w-carboxy pentyl) thiazolin-4-one," Part II, J. Inst. Chemists (India) vol. 66 (1994).
Song et al., "A ligand for the aryl hydrocarbon receptor isolated from lung," Proc Natl Acad Sci USA. 99(23):14694-9 (2002).
Stevens et al., "The aryl hydrocarbon receptor: a perspective on potential roles in the immune system," Immunology 127(3):299-311 (2009).
Sutter et al., "EGF receptor signaling blocks aryl hydrocarbon receptor mediated transcription and cell differentiation in human epidermal keratinocytes," Proc. Natl. Acad. Sci. U.S.A. 106(11):4266-4271 (2009).
Tchaicha et al., "Abstract 4131: Overcoming aryl hydrocarbon receptor mediated tumor immunosuppression," Immunology, 4131-4131 (2019).
Trapani et al., "DNA damage and cell cycle arrest induced by 2-(4-amino-3-methylphenyl)-5-fluorobenzothiazole (5F 203, NSC 703786) is attenuated in aryl hydrocarbon receptor deficient MCF-7 cells," Br J Cancer. 88(4): 599-605 (2003).
Tsai et al., "Aryl hydrocarbon receptor (AhR) agonists increase airway epithelial matrix metalloproteinase activity," J Mol Med 92:615-628 (2014).
Van Zandt et al., "Discovery of 3-[(4,5,7-Trifluorobenzothiazol-2-yl)methyl]indole-N-acetic acid (lidorestat) and congeners as highly potent and selective inhibitors of aldose reductase for treatment of chronic diabetic complications," J. Med. Chem. 48:3141-3152 (2005).
Veale et al., "Synthesis and MRSA PK inhibitory activity of thiazole containing deoxytopsentin analogues," Tetrahedron 70:43:7845-7853 (2014).
Veldhoen et al., "The aryl hydrocarbon receptor links TH17-cell-mediated autoimmunity to environmental toxins," Nature 453(7191):106-109 (2008).
Wang et al., "The first design and synthesis of [11C]MKC-1 ([11C]Ro 31-7453), a new potential PET cancer imaging agent," Nucl Med Biol 37(7):763-75 (2010).
Wang et al., "The first synthesis of [(11)C]SB-216763, a new potential PET agent for imaging of glycogen synthase kinase-3 (GSK-3)," Bioorg Med Chem Lett 21(1):245-9 (2011).
Wang, et al., "An endogenous aryl hydrocarbon receptor ligand inhibits proliferation and migration of human ovarian cancer cells," Cancer Letters 340:63-71 (2013).
Wang et al., "Activation of the aryl hydrocarbon receptor affects activation and function of human monocyte-derived dendritic cells," Clinical and Experimental Immunology 177:521-530 (2014).
Wang et al., "Decreased Expression of the Aryl Hydrocarbon Receptor in Ocular Behcet's Disease," Mediators Inflamm 2014:195094 (2014).
Wang et al., "Discovery of the Human Immunodeficiency Virus Type 1 (HIV-1) Attachment Inhibitor Temsavir and Its Phosphonooxymethyl Prodrug Fostemsavir," J Med Chem. 61(14):6308-6327 (2018).
Wei et al., "Role of the Aryl Hydrocarbon Receptor in the Pathogenesis of Chronic Rhinosinusitis with Nasal Polyps," Inflammation 37:387-95 (2013).
Wei et al., "An aryl hydrocarbon receptor ligand acts on dendritic cells and T cells to suppress the Th17 response in allergic rhinitis patients," Laboratory Investigation 94:528-535 (2014).
Wei et al., "Increased aryl hydrocarbon receptor expression in patients with allergic rhinitis," QJM 107:107-113 (2014).
Wille et al., "Malassezin-A novel agonist of the arylhydrocarbon receptor from the yeast Malassezia furfur," Bioorg Med Chem. 9(4):955-60 (2001).
Wincent et al., "The suggested physiologic aryl hydrocarbon receptor activator and cytochrome P4501 substrate 6-formylindolo[3,2-b] carbazole is present in humans," J Biol Chem. 284(5):2690-6(2009).
Wu et al., "ITE and TCDD Differentially Regulate the Vascular Remodeling of Rat Placenta via the Activation of AhR," PLoS One 9:e86549 (2014).

(56) References Cited

OTHER PUBLICATIONS

Yan et al., "Synthesis, evaluation, and mechanism study of novel indole-chalcone derivatives exerting effective antitumor activity through microtubule destabilization in vitro and in vivo," J. Med. Chem. 59(11) 5264-5283 (2016).

Yeste et al., "Nanoparticle-mediated codelivery of myelin antigen and a tolerogenic small molecule suppresses experimental autoimmune encephalomyelitis," Proc Natl Acad Sci U S A 109:11270-5 (2012).

Yeste et al., "IL-21 induces IL-22 production in CD4CD4þ T cells," Nat Commun. 5:3753 (2014).

Yeste et al., "Tolerogenic nanoparticles inhibit T cell-mediated autoimmunity through SOCS2," Sci Signal. 9(433):ra61 (2016).

Yoshida et al., "Effects of AhR ligands on the production of immunoglobulins in purified mouse B cells," Biomedical Research 33:67-74 (2012).

Yu et al., "In utero exposure of mice to dibenzo[a,l] pyrene produces lymphoma in the offspring: role of the aryl hydrocarbon receptor," Cancer Res 66(2):755-762 (2006).

Zhao et al., "Akt-mediated phosphorylation of Oct4 is associated with the proliferation of stem-like cancer cells," Oncology Reports 33:1621-1629 (2015).

Zhang et al., "The aryl hydrocarbon receptor as a target for estrogen receptor-negative breast cancer chemotherapy," Endocr Relat Cancer 16(3):835-844 (2009).

Zhang et al., "A Simple Statistical Parameter for Use in Evaluation and Validation of High Throughput Screening Assays," J Biomol Screen 4(2):67-73 (1999).

Zhang et al., "Induction of cytochromes P450 1A1 and 1A2 by tanshinones in human HepG2 hepatoma cell line," Toxicol Appl Pharmacol. 252(1):18-27 (2011).

Zhang et al., "Activation of aryl hydrocarbon receptor suppresses invasion of esophageal squamous cell carcinoma cell lines," Tumori 98(1):152-157 (2012).

Zhang et al, "Rhodium(I)-catalyzed cycloisomerization of nitrogen-tethered indoles and alkylidenecyclopropanes: convenient access to polycyclic indole derivatives," Chemistry 19(41):13668-73 (2013).

Zhang et al., "A novel assay for screening inhibitors targeting HIV integrase LEDGF/p75 interaction based on Ni2+ coated magnetic agarose beads," Sci Rep. 6:33477 (2016).

Zhang et al., "A tryptophan derivative, ITE, enhances liver cell metabolic functions in vitro," Int J Mol Med. 39(1): 101-112 (2017).

Zimmerman et al., "N-substituted prodrugs of mebendazole provide improved aqueous solubility and oral bioavailability in mice and dogs," J Med Chem. 61(9):3918-3929 (2018).

"Fruit juice and medications don't mix," Consumer Reports News (Sep. 2, 2008).

USPTO, PTAB decision on the appeal of U.S. Appl. No. 13/954,834, 17 pages, (filed May 30, 2018).

U.S. Appl. No. 16/473,616, filed Jun. 25, 2019, Luqing Yang.
U.S. Appl. No. 16/908,583, filed Jun. 22, 2020, Jiasheng Song.
U.S. Appl. No. 17/278,579, filed Mar. 22, 2021, Graham Johnson.
U.S. Appl. No. 17/295,132, filed May 19, 2021, Peter Colabuono.

\* cited by examiner

Scheme 1. Substituted Indoles Intermediates

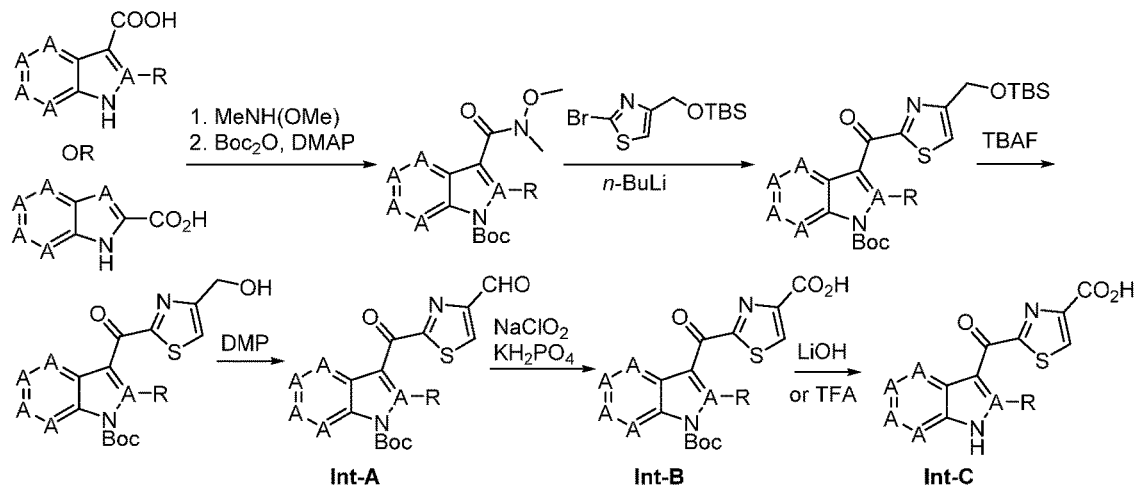

A = Either N, CH or C that is optionally substituted with F, Cl, Br, I, OR, CN
R = H, alkyl
Int-A, In-B, Int-C are either 2 or 3-substituted Indoles. 3-substituted Indoles shown for illustrative purposes

FIG. 1

Scheme 2. Esters and Amides

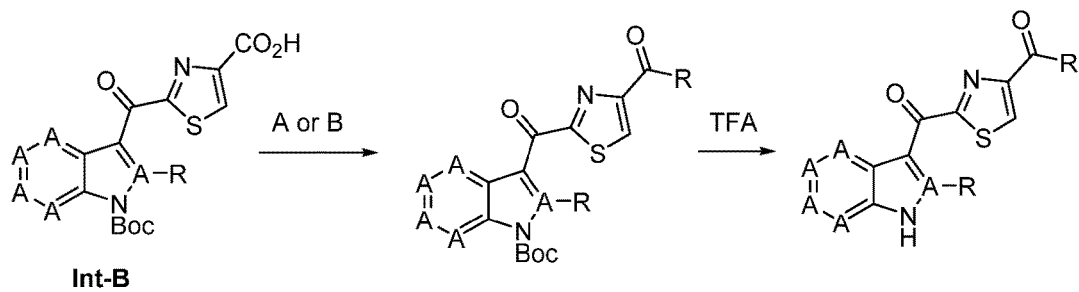

Products are either 2 or 3-substituted Indoles. 3-substituted Indoles shown for illustrative purposes
Conditions: Step 1 (esters) (A) $K_2CO_3$, alkyl iodide; Step 1 (amides); HATU or EDC, HOBt, amine
(B) TFA, solvent

FIG. 2

Scheme 3. Nitriles

Products are either 2 or 3-substituted Indoles. 3-substituted Indoles shown for illustrative purposes

Scheme 4. Ketones

Products are either 2 or 3-substituted Indoles. 3-substituted Indoles shown for illustrative purposes

Scheme 5. Heterocycle (1)

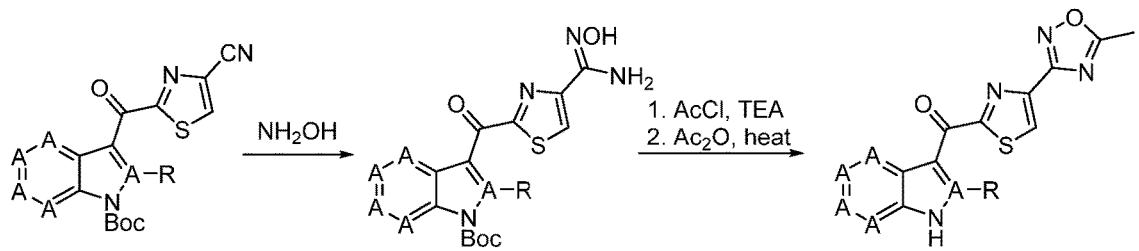

Products are either 2 or 3-substituted Indoles. 3-substituted Indoles shown for illustrative purposes
Nitriles from Scheme 3.

FIG. 5

Scheme 6. Heterocyle (2)

Route A

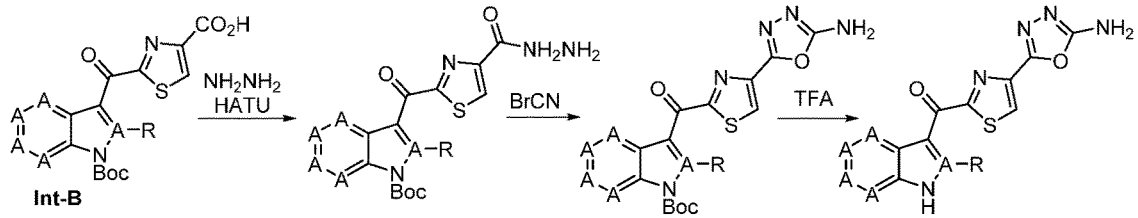

Products are either 2 or 3-substituted Indoles. 3-substituted Indoles shown for illustrative purposes

Route B

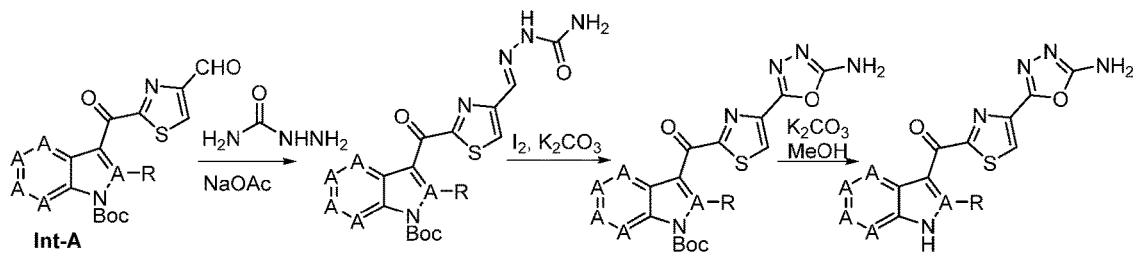

Products are either 2 or 3-substituted Indoles. 3-substituted Indoles shown for illustrative purposes

FIG. 6

Scheme 7. Heterocycle (3)

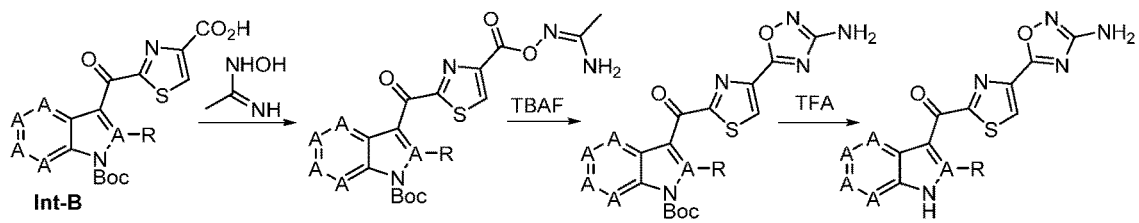

Products are either 2 or 3-substituted Indoles. 3-substituted Indoles shown for illustrative purposes

FIG. 7

Scheme 8. Heterocycle (4)

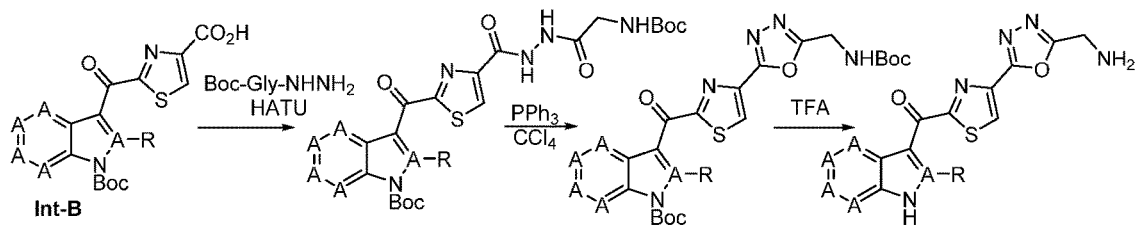

Products are either 2 or 3-substituted Indoles. 3-substituted Indoles shown for illustrative purposes

FIG. 8

Scheme 9. Heterocycle (5)

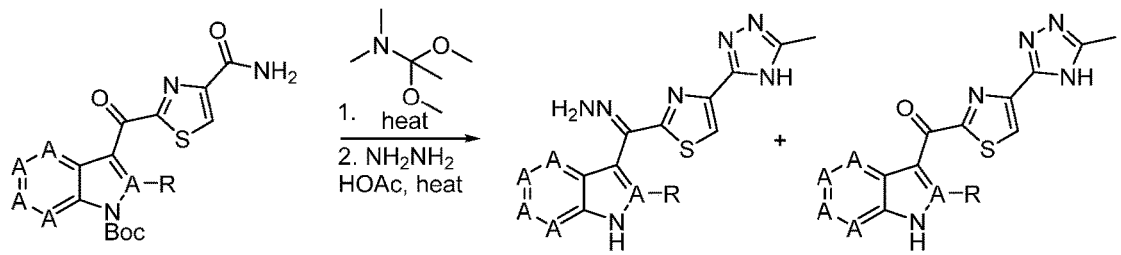

Products are either 2 or 3-substituted Indoles. 3-substituted Indoles shown for illustrative purposes
Amide from scheme 2

FIG. 9

Scheme 10. Heterocycle (6)

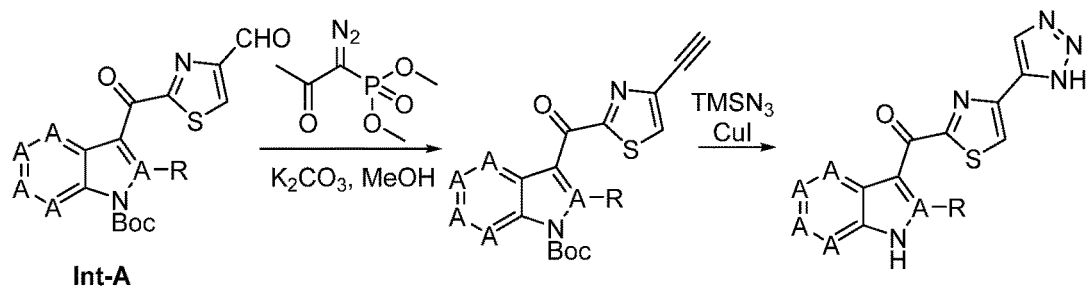

Products are either 2 or 3-substituted Indoles. 3-substituted Indoles shown for illustrative purposes

FIG. 10

Scheme 11. Heterocycle (7)

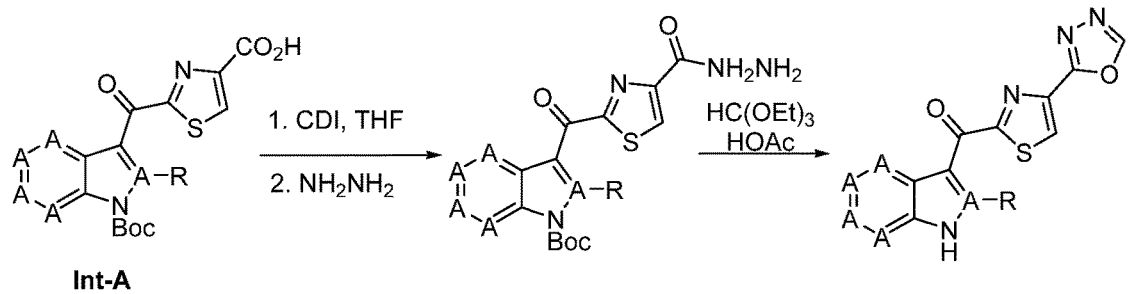

Products are either 2 or 3-substituted Indoles. 3-substituted Indoles shown for illustrative purposes

FIG. 11

Scheme 12. Heterocycle (8)

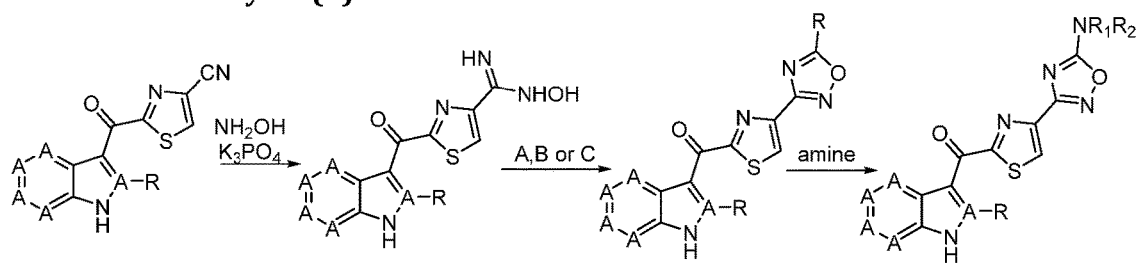

Conditions: (A) trimethylorthoformate, PPTS; R = H; (B) trichloroacetic anhydride, heat, R = CCl$_3$; (C) trifluoroacetic anhydride, R = CF$_3$.

FIG. 12

Scheme 13. CF₃ Ketone

Scheme 14. CF3 Amine

Scheme 15. α-Aminonitrile

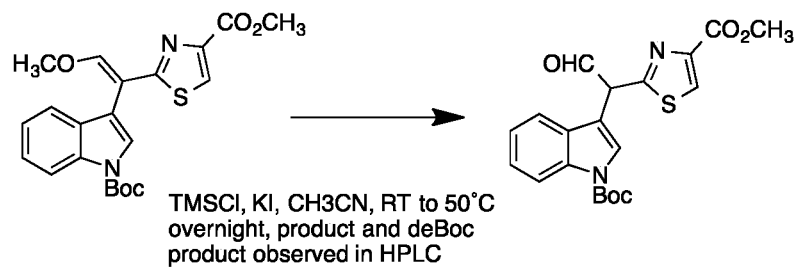
FIG. 56
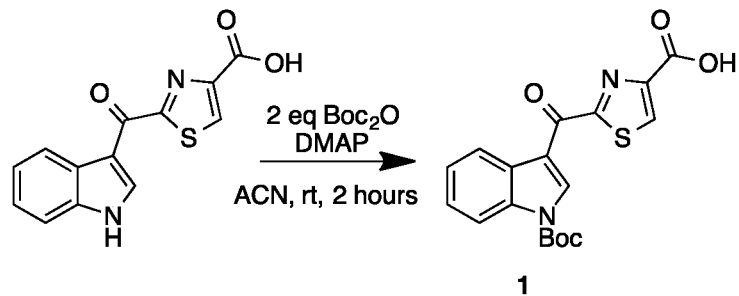
Scheme A
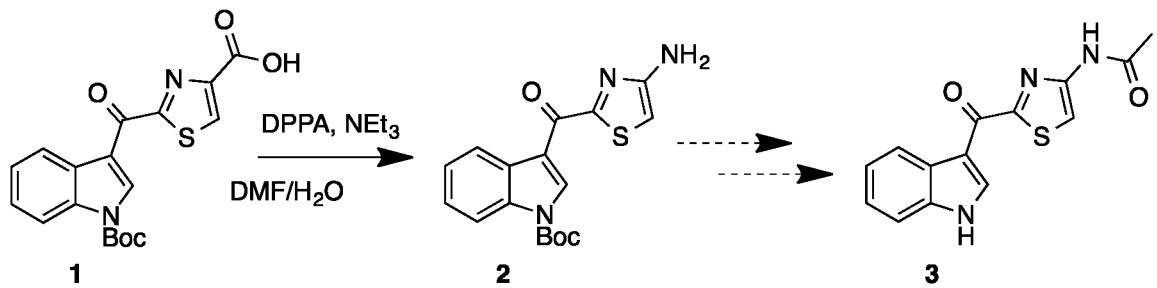
Scheme B
FIG. 57

INDOLE COMPOUNDS AND THEIR USE

CROSS-REFERENCE TO RELATED APPLICATIONS

The present application is a continuation of U.S. application Ser. No. 16/765,315, filed May 19, 2020, which is a national stage application under 35 U.S.C. § 371 of International Patent Application No. PCT/US2018/061758, filed Nov. 19, 2018, which claims priority from U.S. Provisional Application Nos. 62/588,751, filed Nov. 20, 2017, and 62/717,387, filed Aug. 10, 2018. All of the aforementioned priority applications are incorporated herein by reference in their entirety.

FIELD OF THE INVENTION

The present disclosure relates to indole compounds and their use in treating patients in need thereof, such as patients with cancer or in need of immune stimulation.

BACKGROUND OF THE INVENTION

The aryl hydrocarbon (Ah) receptor (AhR) is a ligand-inducible transcription factor and a member of the basic helix-loop-helix/Per-Arnt-Sim (bHLH/PAS) superfamily. Upon binding to its ligand, AhR mediates a series of biological processes, including cell division, apoptosis, cell differentiation, adipose differentiation, hypothalamus actions, angiogenesis, immune system modulation, teratogenicity, tumorigenicity, tumor progression, chloracne, wasting, actions of hormonal systems (e.g., estrogen and androgen), and expression of genes of the P450 family (Poland et al., Annu. Rev. Pharmacol. Toxicol. 22:517-554 (1982); Poellinger et al., Food Addit Contam. 17(4):261-6 (2000); Bock et al., Biochem. Pharmacol. 69(10):1403-1408 (2005); Stevens et al., Immunology 127(3):299-311 (2009); Puga et al., Biochem Pharmacol. 69(2):199-207 (2005); Safe et al., Int J Oncol. 20(6):1123-8 (2002); Dietrich et al., Carcinogenesis 31(8):1319-1328 (2010); U.S. Pat. No. 7,419,992). The liganded receptor participates in biological processes through translocation from cytoplasm into the nucleus, heterodimerization with another factor named Ah receptor nuclear translocator, and binding of the heterodimer to the Ah response element of AhR-regulated genes, resulting in enhancement or inhibition of transcription of those genes.

The AhR is able to bind, with different affinities, to several groups of exogenous chemicals, or artificial ligands, including polycyclic aromatic hydrocarbons, e.g., 3-methylchoranthrene (3-MC), and halogenated aromatic hydrocarbons, e.g., 2,3,7,8-tetrachlorodibenzo-p-dioxin (TCDD). Studies with those AhR artificial ligands have helped in advancing the understanding of the AhR system. An endogenous or physiological ligand for the AhR has been identified as 2-(1'H-indole-3'-carbonyl)-thiazole-4-carboxylic acid methyl ester (ITE), with the following structure:

Structural Formula 1

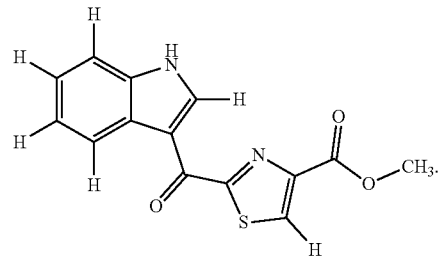

See, e.g., Song et al., PNAS USA 99(23):14694-9 (2002); and U.S. Pat. No. 6,916,834.

SUMMARY OF THE INVENTION

The present disclosure provides novel indole compounds useful in modulating an activity of human aryl hydrocarbon receptor (AhR), pharmaceutical compositions comprising one or more of these compounds, use of these compounds and compositions in treating diseases and conditions in patients who can benefit from modulation of AhR activities.

Provided herein is a compound having the structure of formula 2, or an enantiomer, diastereomer, or pharmaceutically acceptable salt thereof:

Structural Formula 2

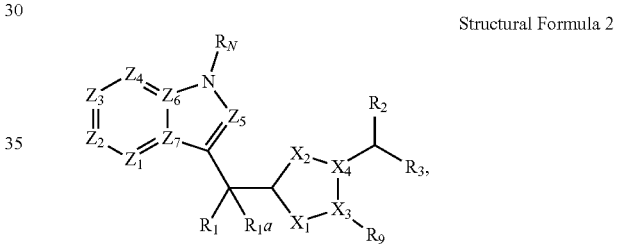

wherein:

$X_1$ is N (nitrogen), O (oxygen), S (sulfur), or C (carbon); $X_2$ is N (nitrogen), O (oxygen) S (sulfur), or C (carbon); $X_3$ is N (nitrogen), O (oxygen), S (sulfur) or C (carbon); and $X_4$ is N (nitrogen) O (oxygen), S (sulfur), or C (carbon), such that at least one of $X_1$, $X_2$, $X_3$ and $X_4$ is N, each of $X_1$, $X_2$, $X_3$ and $X_4$ is optionally selected to form a heteroaromatic, wherein the bond between $X_1$ and the adjacent carbon, between $X_2$ and the adjacent carbon, between $X_1$ and $X_4$, between $X_2$ and $X_3$, and between $X_3$ and $X_4$ can be a single bond or a double bond and the valence of $X_1$, $X_2$, $X_3$ and $X_4$ is completed with H or $C_1$-$C_6$ alkyl (i.e., the ring can be aromatic, partially saturated, or saturated);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_2$ and $R_3$ are together selected from the group consisting of =O, =S, or =$NR_a$ ($R_a$ is H, $C_1$-$C_6$ alkyl, $C_1$-$C_6$ acyl, or —OR, R is H, $C_1$-$C_6$ alkyl, or $C_1$-$C_6$ acyl), or $R_2$ and $R_3$ are each independently selected from the group consisting of —$NR_aR_b$ ($R_a$ and $R_b$ are each independently H, $C_1$-$C_6$ alkyl, or $C_1$-$C_6$ acyl), hydrogen, deuterium, halo, amino, hydroxy, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, R$_{10}$ is directly connected to S), wherein R$_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

R$_4$, R$_5$, R$_6$, R$_7$, R$_8$, and R$_9$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, R$_{11}$ is directly connected to S), wherein R$_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

R$_N$ is H, CN, —C$_1$-C$_6$ alkyl, —OH, —(CO)—OR, or —OR, wherein R is H, C$_1$-C$_6$ alkyl, or C$_1$-C$_6$ acyl; and R$_1$ and R$_{1a}$ are taken together to form =NR$_b$, wherein R$_b$ is H, C$_1$-C$_6$ alkyl, hydroxy, C$_1$-C$_6$ alkoxy (—O-alkyl), C$_1$-C$_6$ acyloxy, amino, or C$_1$-C$_6$ acyl, R$_2$ preferably can be =O, R$_3$ preferably can be —OR, wherein R is H or C$_1$-C$_6$ alkyl, or R$_1$ and R$_{1a}$ are taken together to form =CR$_b$R$_c$, wherein R$_b$ and R$_c$ are each independently H, C$_1$-C$_6$ alkyl, alkoxy (—O-alkyl), thioalkoxy (—S-alkyl), cyano (—CN), or amino, R$_2$ preferably can be =O, R$_3$ preferably can be —OR, wherein R is H or C$_1$-C$_6$ alkyl, or R$_1$ and R$_{1a}$ are taken together to form =O, =NOR$_a$, or =S, R$_2$ and R$_3$ preferably can be each independently —OR or —NR$_a$R$_b$, wherein R, R$_a$, and R$_b$ are each independently H, C$_1$-C$_6$ alkyl, or C$_1$-C$_6$ acyl, or R$_1$ and R$_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{12}$ (n=0 to 2, R$_{12}$ is directly connected to S), wherein R$_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and optionally, adjacent R groups, together, can form a six- to twelve-membered ring.

Also provided herein is a compound having the structure of formula 2a, or an enantiomer, diastereomer, or pharmaceutically acceptable salt thereof:

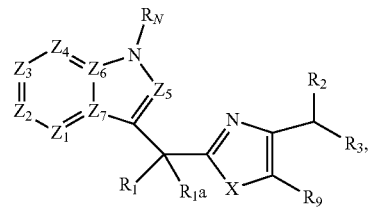

Structural Formula 2a wherein:

X is either O (oxygen) or S (sulfur);

Z$_1$ is N or CR$_4$, Z$_2$ is N or CR$_5$, Z$_3$ is N or CR$_6$, Z$_4$ is N or CR$_7$, Z$_5$ is N or CR$_8$, Z$_6$ is N or C, Z$_7$ is N or C, wherein no more than two of Z$_1$, Z$_2$, Z$_3$, Z$_4$, Z$_5$, Z$_6$, and Z$_7$ are N;

R$_2$ and R$_3$ are together selected from the group consisting of =O, =S, or =NR$_a$ (R$_a$ is H, C$_1$-C$_6$ alkyl, C$_1$-C$_6$ acyl, or —OR, R is H, C$_1$-C$_6$ alkyl, or C$_1$-C$_6$ acyl), or R$_2$ and R$_3$ are each independently selected from the group consisting of —NR$_a$R$_b$ (R$_a$ and R$_b$ are each independently H, C$_1$-C$_6$ alkyl, or C$_1$-C$_6$ acyl), hydrogen, deuterium, halo, amino, hydroxy, cyano, formyl, furyl, nitro, alkyl, haloalkyl, alkenyl, haloalkenyl, alkynyl, haloalkynyl, C$_1$-C$_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, R$_{10}$ is directly connected to S), wherein R$_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

R$_4$, R$_5$, R$_6$, R$_7$, R$_8$, and R$_9$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, R$_{11}$ is directly connected to S), wherein R$_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

R$_N$ is H, CN, C$_1$-C$_6$ alkyl, —OH, —(CO)—OR, or —OR, wherein R is H, C$_1$-C$_6$ alkyl, or C$_1$-C$_6$ acyl; and R$_1$ and R$_{1a}$ are taken together to form =NR$_b$, wherein R$_b$ is H, C$_1$-C$_6$ alkyl, hydroxy, C$_1$-C$_6$ alkoxy (—O-alkyl), C$_1$-C$_6$ acyloxy, amino, or C$_1$-C$_6$ acyl, R$_2$ preferably can be =O, R$_3$ preferably can be —OR, wherein R is H or C$_1$-C$_6$ alkyl, or R$_1$ and R$_{1a}$ are taken together to form =CR$_b$R$_c$, wherein R$_b$ and R$_c$ are each independently H, C$_1$-C$_6$ alkyl, alkoxy (—O-alkyl), thioalkoxy (—S-alkyl), cyano (—CN), or amino, $R_2$ preferably can be =O, $R_3$ preferably can be —OR, wherein R is H or $C_1$-$C_6$ alkyl, or $R_1$ and $R_{1a}$ are taken together to form =O, =NOR$_a$, or =S, $R_2$ and $R_3$ preferably can be each independently —OR or —NR$_a$R$_b$, wherein R, R$_a$, and R$_b$ are each independently H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and optionally, adjacent R groups, together, can form a six- to twelve-membered ring.

Also provided herein is a compound having the structure of formula 3, or an enantiomer, diastereomer, or pharmaceutically acceptable salt thereof:

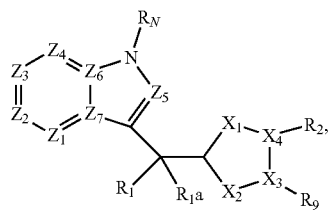

Structural Formula 3 wherein:

$X_1$ is N (nitrogen), O (oxygen), S (sulfur), or C (carbon); $X_2$ is N (nitrogen), O (oxygen) S (sulfur), or C (carbon); $X_3$ is N (nitrogen), O (oxygen), S (sulfur) or C (carbon); and $X_4$ is N (nitrogen) O (oxygen), S (sulfur), or C (carbon), such that at least one of $X_1$, $X_2$, $X_3$ and $X_4$ is N, each of $X_1$, $X_2$, $X_3$ and $X_4$ is optionally selected to form a heteroaromatic, wherein the bond between $X_1$ and the adjacent carbon, between $X_2$ and the adjacent carbon, between $X_1$ and $X_4$, between $X_2$ and $X_3$, and between $X_3$ and $X_4$ can be a single bond or a double bond and the valence of $X_1$, $X_2$, $X_3$ and $X_4$ is completed with H or $C_1$-$C_6$ alkyl (i.e., the ring can be aromatic, partially saturated, or saturated);

$Z_1$ is N or CR$_4$, $Z_2$ is N or CR$_5$, $Z_3$ is N or CR$_6$, $Z_4$ is N or CR$_7$, $Z_5$ is N or CR$_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form =NR$_b$, wherein R$_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form =CR$_b$R$_c$, wherein R$_b$ and R$_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form =O, =NOR$_a$, or =S, wherein R$_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and $R_2$ and $R_9$ are each independently selected from the group consisting of hydrogen, aryl, heteroaryl, cycloalkyl, heterocycloalkyl, alkyl, —NR$_{2a}$C(O)OR$_{2b}$, —NR$_{2a}$C(O)R$_{2b}$, —($C_0$-$C_6$ alkyl)-CONHSO$_2$R$_{2a}$, —($C_0$-$C_6$ alkyl)-CONHSO$_2$NR$_{2a}$R$_{2b}$, —($C_0$-$C_6$ alkyl)-SO$_2$NHCOR$_{2a}$, —($C_0$-$C_6$ alkyl)-SO$_2$NHR$_{2a}$, —($C_0$-$C_6$ alkyl)-CONR$_{2a}$OR$_{2b}$,

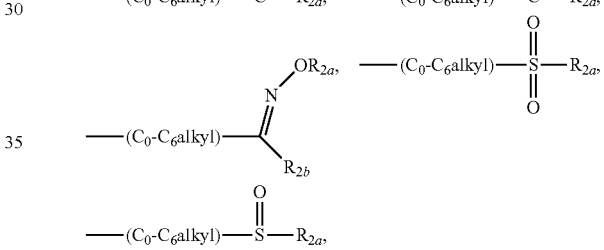

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl; and optionally, adjacent R groups, together, can form a six- to twelve-membered ring.

Further provided herein is a compound having the structure of formula 3a, or an enantiomer, diastereomer, or pharmaceutically acceptable salt thereof:

Structural Formula 3a

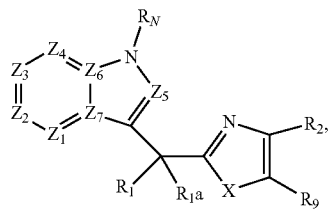

wherein:

X is either O (oxygen) or S (sulfur);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form =$NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form =$CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form =O, =$NOR_a$, or =S, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$$R_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and $R_2$ and $R_9$ are each independently selected from the group consisting of hydrogen, aryl, heteroaryl, cycloalkyl, heterocycloalkyl, alkyl, —$NR_{2a}$C(O)O$R_{2b}$, —$NR_{2a}$C(O)$R_{2b}$, —($C_0$-$C_6$ alkyl)-CONHSO$_2$$R_{2a}$, —($C_0$-$C_6$ alkyl)-CONHSO$_2$$NR_{2a}$$R_{2b}$, —($C_0$-$C_6$ alkyl)-SO$_2$NHCOR$_{2a}$, —($C_0$-$C_6$ alkyl)-SO$_2$NHR$_{2a}$, —($C_0$-$C_6$ alkyl)-CONR$_{2a}$OR$_{2b}$,

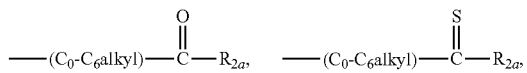

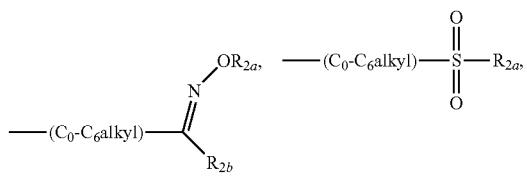

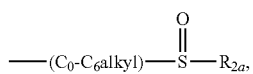

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$$R_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$$R_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl; and optionally, adjacent R groups, together, can form a six- to twelve-membered ring.

Provided further herein is a compound having the structure of formula 3b, or an enantiomer, diastereomer, or pharmaceutically acceptable salt thereof:

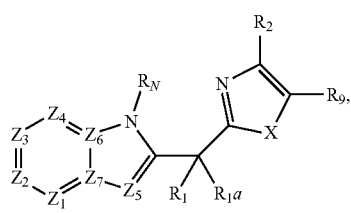

Structural formula 3b wherein:

X is either O (oxygen) or S (sulfur);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form =$NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form =$CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form =O, =$NOR_a$, or =S, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and $R_2$ and $R_9$ are each independently selected from the group consisting of hydrogen, aryl, heteroaryl, cycloalkyl, heterocycloalkyl, alkyl, —NR$_{2a}$C(O)OR$_{2b}$, —NR$_{2a}$C(O)R$_{2b}$, —(C$_0$-C$_6$ alkyl)-CONHSO$_2$R$_{2a}$, —(C$_0$-C$_6$ alkyl)-CONHSO$_2$NR$_{2a}$R$_{2b}$, —(C$_0$-C$_6$ alkyl)-SO$_2$NHCOR$_{2a}$, —(C$_0$-C$_6$ alkyl)-SO$_2$NHR$_{2a}$, —(C$_0$-C$_6$ alkyl)-CONR$_{2a}$OR$_{2b}$,

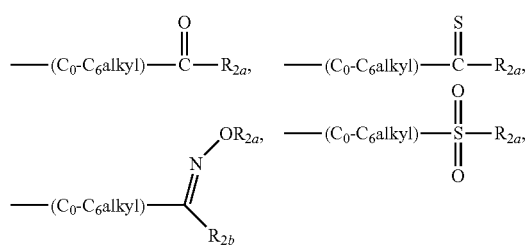

-continued

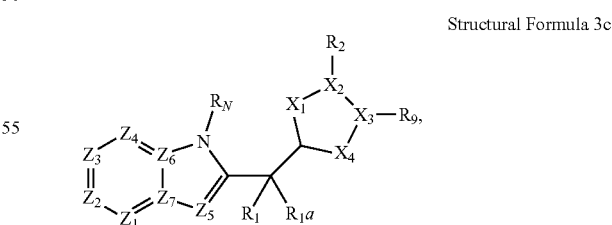

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl; and optionally, adjacent R groups, together, can form a six- to twelve-membered ring.

Provided herein is also a compound having the structure of formula 3c, or an enantiomer, diastereomer, or pharmaceutically acceptable salt thereof:

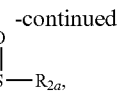

Structural Formula 3c wherein:

$X_1$ is N (nitrogen), O (oxygen), S (sulfur), or C (carbon); $X_2$ is N (nitrogen), O (oxygen) S (sulfur), or C (carbon); $X_3$ is N (nitrogen), O (oxygen), S (sulfur) or C (carbon); and $X_4$ is N (nitrogen) O (oxygen), S (sulfur), or C (carbon), such that at least one of $X_1$, $X_2$, $X_3$ and $X_4$ is N, each of $X_1$, $X_2$, $X_3$ and $X_4$ is optionally selected to form a heteroaromatic, wherein the bond between $X_1$ and the adjacent carbon, between $X_2$ and the adjacent carbon, between $X_1$ and $X_4$, between $X_2$ and $X_3$, and between $X_3$ and $X_4$ can be a single bond or a double bond and the valence of $X_1$, $X_2$, $X_3$ and $X_4$ is completed with H or $C_1$-$C_6$ alkyl (i.e., the ring can be aromatic, partially saturated, or saturated);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form $=NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form $=CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form $=O$, $=NOR_a$, or $=S$, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and $R_2$ and $R_9$ are each independently selected from the group consisting of hydrogen, aryl, heteroaryl, cycloalkyl, heterocycloalkyl, alkyl, —NR$_{2a}$C(O)OR$_{2b}$, —NR$_{2a}$C(O)R$_{2b}$, —(C$_0$-C$_6$ alkyl)-CONHSO$_2$R$_{2a}$, —(C$_0$-C$_6$ alkyl)-CONHSO$_2$NR$_{2a}$R$_{2b}$, —(C$_0$-C$_6$ alkyl)-SO$_2$NHCOR$_{2a}$, —(C$_0$-C$_6$ alkyl)-SO$_2$NHR$_{2a}$, —(C$_0$-C$_6$ alkyl)-CONR$_{2a}$OR$_{2b}$,

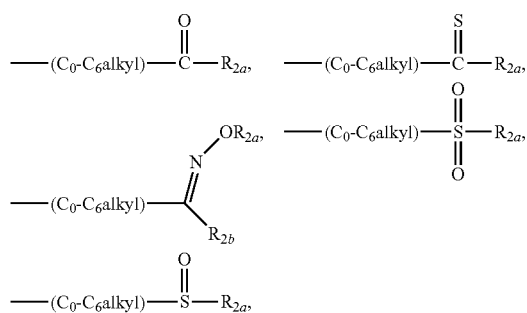

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl; and optionally, adjacent R groups, together, can form a six- to twelve-membered ring.

Also provided herein is a compound having the structure of formula 4, or an enantiomer, diastereomer, or pharmaceutically acceptable salt thereof:

Structural Formula 4

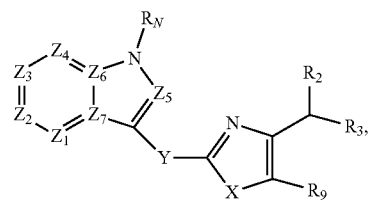

wherein:

X is O (oxygen) or S (sulfur);

Y is a bond, O (oxygen), S (sulfur), or

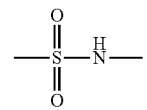

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_4$, $R_5$, $R_6$, $R_7$, $R_8$, and $R_9$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, R$_{10}$ is directly connected to S), wherein R$_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

R$_N$ is H, CN, C$_1$-C$_6$ alkyl, —OH, —(CO)—OR, or —OR, wherein R is H, C$_1$-C$_6$ alkyl, or C$_1$-C$_6$ acyl;

R$_2$ and R$_3$ are together selected from the group consisting of =O, =S, or =NR$_a$ (R$_a$ is H, C$_1$-C$_6$ alkyl, C$_1$-C$_6$ acyl, or —OR, R is H, C$_1$-C$_6$ alkyl, or C$_1$-C$_6$ acyl), or R$_2$ and R$_3$ are each independently selected from the group consisting of —NR$_a$R$_b$ (R$_a$ and R$_b$ are each independently H, C$_1$-C$_6$ alkyl, or C$_1$-C$_6$ acyl), hydrogen, deuterium, halo, amino, hydroxy, cyano, formyl, furyl, nitro, alkyl, haloalkyl, alkenyl, haloalkenyl, alkynyl, haloalkynyl, C$_1$-C$_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, R$_{11}$ is directly connected to S), wherein R$_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and optionally, adjacent R groups, together, can form a six- to twelve-membered ring.

Further provided herein is a compound having the structure of formula 5, or an enantiomer, diastereomer, or pharmaceutically acceptable salt thereof:

Structural Formula 5

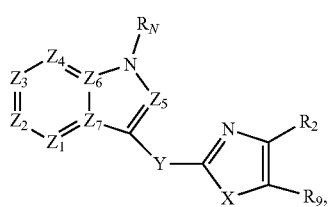

wherein:
X is O (oxygen) or S (sulfur);
Y is a bond, O (oxygen), S (sulfur), or

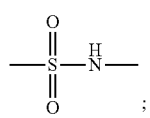

Z$_1$ is N or CR$_4$, Z$_2$ is N or CR$_5$, Z$_3$ is N or CR$_6$, Z$_4$ is N or CR$_7$, Z$_5$ is N or CR$_8$, Z$_6$ is N or C, Z$_7$ is N or C, wherein no more than two of Z$_1$, Z$_2$, Z$_3$, Z$_4$, Z$_5$, Z$_6$, and Z$_7$ are N;

R$_2$ and R$_9$ are each independently selected from the group consisting of hydrogen, aryl, heteroaryl, cycloalkyl, heterocycloalkyl, alkyl, —NR$_{2a}$C(O)OR$_{2b}$, —NR$_{2a}$C(O)R$_{2b}$, —(C$_0$-C$_6$ alkyl)-CONHSO$_2$R$_{2a}$, —(C$_0$-C$_6$ alkyl)-CONHSO$_2$NR$_{2a}$R$_{2b}$, —(C$_0$-C$_6$ alkyl)-SO$_2$NHCOR$_{2a}$, —(C$_0$-C$_6$ alkyl)-SO$_2$NHR$_{2a}$, —(C$_0$-C$_6$ alkyl)-CONR$_{2a}$OR$_{2b}$,

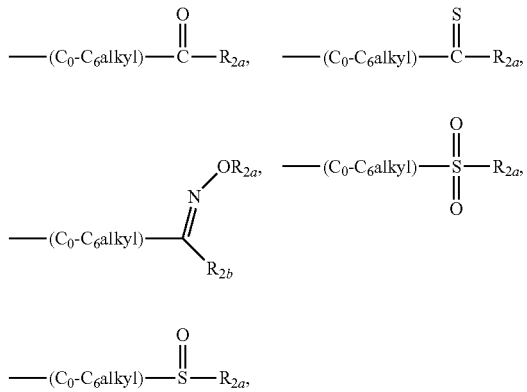

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, R$_{10}$ is directly connected to S), wherein R$_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein R$_{2a}$ and R$_{2b}$ are each independently H, C$_1$-C$_6$ alkyl, alkoxy (—O-alkyl), hydroxy, thioalkoxy (—S-alkyl), cyano (—CN), or amino;

R$_4$, R$_5$, R$_6$, R$_7$, and R$_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, R$_{11}$ is directly connected to S), wherein R$_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

R$_N$ is H, CN, C$_1$-C$_6$ alkyl, —OH, —(CO)—OR, or —OR, wherein R is H, C$_1$-C$_6$ alkyl, or C$_1$-C$_6$ acyl; and optionally, adjacent R groups, together, can form a six- to twelve-membered ring.

Also provided herein is a compound having the structure of formula 6, or an enantiomer, diastereomer, or pharmaceutically acceptable salt thereof:

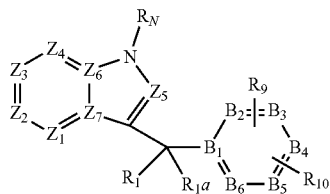

Structural Formula 6 wherein:

$R_1$ and $R_{1a}$ are taken together to form $=NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form $=CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form $=O$, $=NOR_a$, or $=S$, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{14}$ (n=0 to 2, $R_{14}$ is directly connected to S), wherein $R_{14}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl;

$B_1$, $B_2$, $B_3$, $B_4$, $B_5$, and $B_6$ are each independently C or N;

$R_9$ and $R_{10}$, the number of which, together, complete the valence of each of $B_1$, $B_2$, $B_3$, $B_4$, $B_5$, and $B_6$, are each independently selected from the group consisting of hydrogen, aryl, heteroaryl, cycloalkyl, heterocycloalkyl, alkyl, —$NR_{2a}C(O)OR_{2b}$, —$NR_{2a}C(O)R_{2b}$, —$(C_0$-$C_6$ alkyl)-$CONHSO_2R_{2a}$, —$(C_0$-$C_6$ alkyl)-$CONHSO_2NR_{2a}R_{2b}$, —$(C_0$-$C_6$ alkyl)-$SO_2NHCOR_{2a}$, —$(C_0$-$C_6$ alkyl)-$SO_2NHR_{2a}$, —$(C_0$-$C_6$ alkyl)-$CONR_{2a}OR_{2b}$,

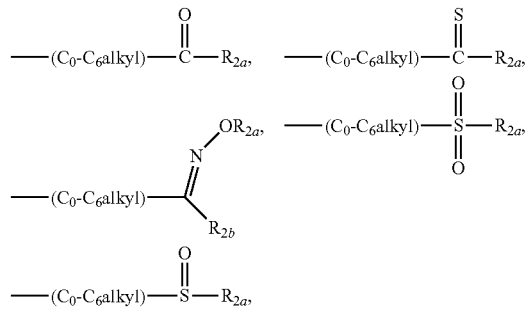

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and

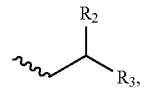

wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino;

wherein $R_2$ and $R_3$ are together selected from the group consisting of $=O$, $=S$, or $=NR_a$ ($R_a$ is H, $C_1$-$C_6$ alkyl, $C_1$-$C_6$ acyl, or —OR, R is H, $C_1$-$C_6$ alkyl, or $C_1$-$C_6$ acyl), or $R_2$ and $R_3$ are each independently selected from the group consisting of —$NR_aR_b$ ($R_a$ and $R_b$ are each independently H, $C_1$-$C_6$ alkyl, or $C_1$-$C_6$ acyl), hydrogen, deuterium, halo, amino, hydroxy, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{13}$ (n=0 to 2, $R_{13}$ is directly connected to S), wherein $R_{13}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and optionally, adjacent R groups, together, can form a six- to twelve-membered ring.

In some embodiments, the invention provides a compound having the structure of formula 7, or an enantiomer, diastereomer, or pharmaceutically acceptable salt thereof:

Structural Formula 7

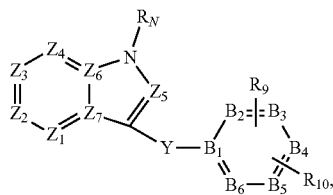

wherein:
Y is a bond, O (oxygen), S (sulfur), or

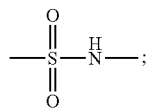

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl;

$B_1$, $B_2$, $B_3$, $B_4$, $B_5$, and $B_6$ are each independently C or N;

$R_9$ and $R_{10}$, the number of which, together, complete the valence of each of $B_1$, $B_2$, $B_3$, $B_4$, $B_5$, and $B_6$, are each independently selected from the group consisting of hydrogen, aryl, heteroaryl, cycloalkyl, heterocycloalkyl, alkyl, —NR$_{2a}$C(O)OR$_{2b}$, —NR$_{2a}$C(O)R$_{2b}$, —(C$_0$-C$_6$ alkyl)-CONHSO$_2$R$_{2a}$, —(C$_0$-C$_6$ alkyl)-CONHSO$_2$NR$_{2a}$R$_{2b}$, —(C$_0$-C$_6$ alkyl)-SO$_2$NHCOR$_{2a}$, —(C$_0$-C$_6$ alkyl)-SO$_2$NHR$_{2a}$, —(C$_0$-C$_6$ alkyl)-CONR$_{2a}$OR$_{2b}$,

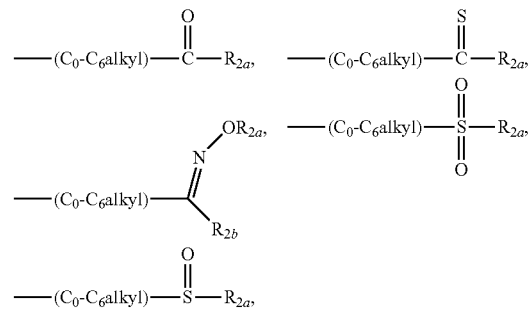

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and

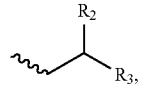

wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino;

wherein $R_2$ and $R_3$ are together selected from the group consisting of =O, =S, or =NR$_a$ (R$_a$ is H, $C_1$-$C_6$ alkyl, $C_1$-$C_6$ acyl, or —OR, R is H, $C_1$-$C_6$ alkyl, or $C_1$-$C_6$ acyl), or $R_2$ and $R_3$ are each independently selected from the group consisting of —NR$_a$R$_b$ (R$_a$ and R$_b$ are each independently H, $C_1$-$C_6$ alkyl, or $C_1$-$C_6$ acyl), hydrogen, deuterium, halo, amino, hydroxy, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{13}$ (n=0 to 2, $R_{13}$ is directly connected to S), wherein $R_{13}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and optionally, adjacent R groups, together, can form a six- to twelve-membered ring.

In each of formulae 2, 2a, 3, 3a, 3b, 3c, 4 and 5, in some embodiments, each of $R_4$, $R_5$, $R_6$, and $R_7$ is hydrogen. In other embodiments, at least one of $R_4$, $R_5$, $R_6$, and $R_7$ can be F, Cl or Br, and the others of $R_4$, $R_5$, $R_6$, and $R_7$ are hydrogen. In still other embodiments, at least two of $R_4$, $R_5$, $R_6$, and $R_7$, independently, can be F, Cl or Br, and the others of $R_4$, $R_5$, $R_6$, and $R_7$ are hydrogen. The F, Cl or Br can be at the indole ring carbon 5, 6, or 7.

In each of formulae 3, 3a, 3b, 3c, and 5, in certain embodiments, $R_8$ can be hydrogen. $R_2$ can be acyl, cyano, hydroxyl-substituted C1-C6 alkyl, amino-substituted C1-C6 alkyl, aryl, or heteroaryl. The aryl or heteroaryl can be substituted or unsubstituted. The substituted aryl or heteroaryl can be substituted with halo, amino, hydroxyl, or C1-C6 alkyl. The amino can be unsubstituted.

In each of formulae 2, 2a, and 4, in certain embodiments, $R_2$ can be hydroxyl or amino and $R_3$ can be alkyl, aryl, nitro, or cyano. $R_9$ can be hydrogen. The amino can be substituted or unsubstituted.

In some embodiments, the invention provides a compound having the structure of formula 8, or an enantiomer, diastereomer, or pharmaceutically acceptable salt thereof:

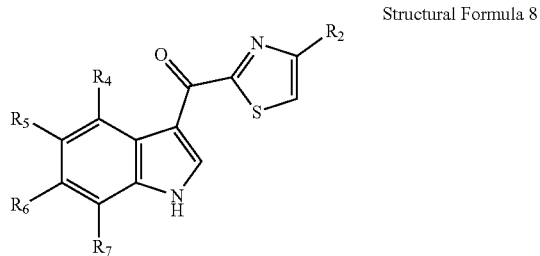

Structural Formula 8 wherein $R_2$ is selected from the group consisting of substituted alkyl, heteroaryl, or

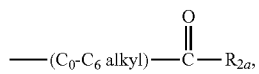

wherein $R_{2a}$ is H, C1-C6 alkyl, alkoxy (—O-alkyl), hydroxy, thioalkoxy (—S-alkyl), cyano (—CN), or amino; and $R_4$, $R_5$, $R_6$, and $R_7$, are each independently selected from the group consisting of hydrogen and halo.

In some embodiments, $R_2$ is substituted alkyl, e.g., a C1-C6 alkyl substituted with one or more hydroxyl, amino, nitro, or cyano. In some embodiments, $R_2$ is heteroaryl, e.g., oxadiazolyl or thiadiazolyl, optionally substituted with one or more hydroxyl, amino, nitro, cyano, C1-C6 alkyl, or C1-C6 alkyl amino. In some embodiments, $R_2$ is —C(O)—$R_{2a}$, and $R_{2a}$ is C1-C6 alkyl.

In one embodiment of the compound of structural formula 8, at least one of $R_4$, $R_5$, $R_6$, and $R_7$ is F, Cl or Br, and the others of $R_4$, $R_5$, $R_6$, and $R_7$ are hydrogen. In another embodiment, at least two of $R_4$, $R_5$, $R_6$, and $R_7$ are F, Cl or Br, and the others of $R_4$, $R_5$, $R_6$, and $R_7$ are hydrogen.

In one embodiment, $R_5$ is F, and $R_4$, $R_6$, and $R_7$ are hydrogen. In another embodiment, $R_6$ is F, and $R_4$, $R_5$, and $R_7$ are hydrogen. In still another embodiment, $R_7$ is F, and $R_4$, $R_5$, and $R_6$ are hydrogen.

In one embodiment, $R_5$ is Cl, and $R_4$, $R_6$, and $R_7$ are hydrogen. In another embodiment, $R_6$ is Cl, and $R_4$, $R_5$, and $R_7$ are hydrogen. In still another embodiment, $R_7$ is Cl, and $R_4$, $R_5$, and $R_6$ are hydrogen.

In one embodiment, $R_5$ and $R_6$ are F, and $R_4$ and $R_7$ are hydrogen. In another embodiment, $R_5$ and $R_7$ are F, and $R_4$ and $R_6$ are hydrogen. In still another embodiment, $R_6$ and $R_7$ are F, and $R_4$ and $R_5$ are hydrogen.

In one embodiment, $R_5$ and $R_6$ are Cl, and $R_4$ and $R_7$ are hydrogen. In another embodiment, $R_5$ and $R_7$ are Cl, and $R_4$ and $R_6$ are hydrogen. In still another embodiment, $R_6$ and $R_7$ are Cl, and $R_4$ and $R_5$ are hydrogen.

In some embodiments, each of $R_4$, $R_5$, $R_6$ and $R_7$ is hydrogen.

In some embodiments, the present disclosure provides a compound selected from a compound in Table 1 (e.g., ARI-017, ARI-018, ARI-019, ARI-020, ARI-031, ARI-060, ARI-083, ARI-087, ARI-090, ARI-118, ARI-120, ARI-140, ARI-143, ARI-145, ARI-146, ARI-148, ARI-149, or ARI-150), or an enantiomer, diastereomer, or pharmaceutically acceptable salt thereof. In some embodiments, the present disclosure provides a compound selected from ARI-087, ARI-140, ARI-143, ARI-149, and ARI-150, or an enantiomer, diastereomer, or pharmaceutically acceptable salt thereof. In some embodiments, the present disclosure provides a compound selected from ARI-031, ARI-060, ARI-083, ARI-090, ARI-118, ARI-120, ARI-145, ARI-146, and ARI-148, or an enantiomer, diastereomer, or pharmaceutically acceptable salt thereof.

The present disclosure also provides a pharmaceutical composition comprising a compound described herein and a pharmaceutically acceptable carrier.

The present disclosure provides a method of stimulating the immune system in a patient in need thereof, comprising administering to the patient a therapeutically effective amount of a compound described herein. In some embodiments, the patient has an increased count of cells selected from the group consisting of white blood cells, macrophages, neutrophils, lymphocytes (e.g., B lymphocytes and/or T lymphocytes), natural killer (NK) cells, dendritic cells, and platelets, or increased levels of cytokines indicative of a stimulated immune system after the administering step. In some embodiments, the compound decreases IL-21 level in the patient. In some embodiments, the patient has cancer.

The present disclosure also provides a method of treating cancer in a patient, comprising administering to the patient a therapeutically effective amount of a compound described herein. In some embodiments, the cancer is a hematological malignancy (e.g., a lymphoma, leukemia, or myeloma), or a solid tumor. In some embodiments, the cancer may be selected from the group consisting of diffuse large B-cell lymphoma, marginal zone lymphoma, chronic lymphocytic leukemia (CLL), small lymphocytic lymphoma, prolymphocytic leukemia, acute lymphocytic leukemia, Waldenström's Macroglobulinemia (WM), follicular lymphoma, mantle cell lymphoma (MCL), Hodgkin lymphoma, non-Hodgkin lymphoma, multiple myeloma, prostate cancer, ovarian cancer, fallopian tube cancer, cervical cancer, breast cancer, lung cancer (e.g., non-small cell lung cancer), skin cancer (e.g., melanoma), colorectal cancer, stomach cancer, pancreatic cancer, liver cancer, kidney cancer, bladder cancer, soft tissue cancer, glioma, and head and neck cancer. In some embodiments, the method further comprises administering to the patient another cancer therapeutic agent, e.g., an immune checkpoint inhibitor (e.g., a PD-1, PD-L1, and/or PD-L2 inhibitor). In some embodiments, the method further comprises administering one or more maintenance doses of the compound while the patient is in remission.

Also provided herein is a compound or pharmaceutical composition described herein for use in stimulating the immune system or treating cancer in a patient in need thereof in a treatment method described herein.

The present disclosure further provides the use of a compound described herein for the manufacture of a medicament for stimulating the immune system or treating cancer in a patient in need thereof in a treatment method described herein.

The present disclosure also provides articles of manufacture, including kits, that comprise a compound described herein.

BRIEF DESCRIPTION OF THE DRAWINGS

FIG. 1 shows a synthesis scheme for substituted indoles intermediates.

FIG. 2 shows a synthesis scheme for esters and amides.

FIG. 5 shows a first synthesis scheme for heterocycle.

FIG. 6 shows a second synthesis scheme for heterocycle.

FIG. 7 shows a third synthesis scheme for heterocycle.

FIG. 8 shows a fourth synthesis scheme for heterocycle.

FIG. 9 shows a fifth synthesis scheme for heterocycle.

FIG. 10 shows a sixth synthesis scheme for heterocycle.

FIG. 11 shows a seventh synthesis scheme for heterocycle.

FIG. 12 shows an eighth synthesis scheme for heterocycle.

FIG. 56 shows a synthesis scheme for an aldehyde intermediate according to Example 149.

FIG. 57 shows a synthesis scheme for ARI-021 according to Example 150.

DETAILED DESCRIPTION OF THE INVENTION

Figure 3:
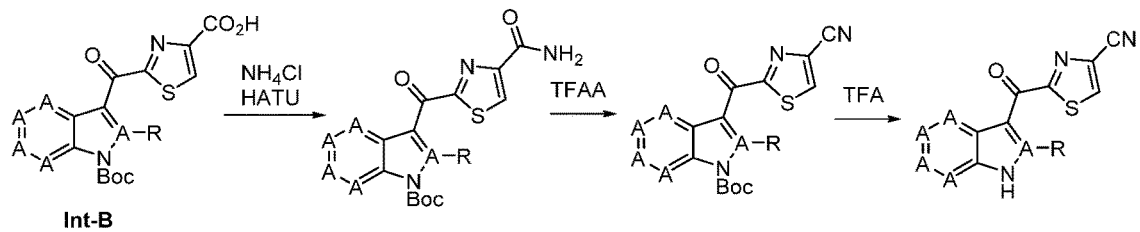
FIG. 3 shows a synthesis scheme for nitriles.
Figure 4:
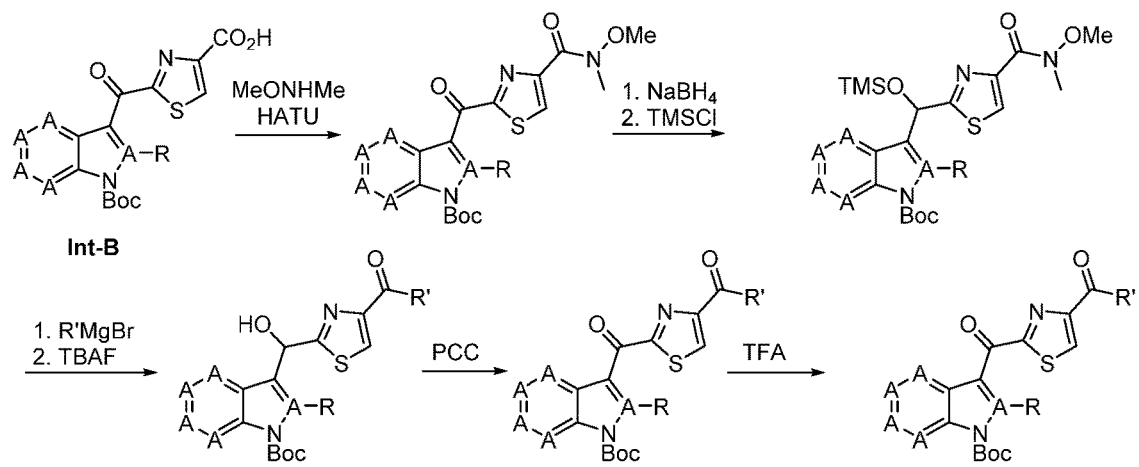
FIG. 4 shows a synthesis scheme for ketones.
Figure 13:
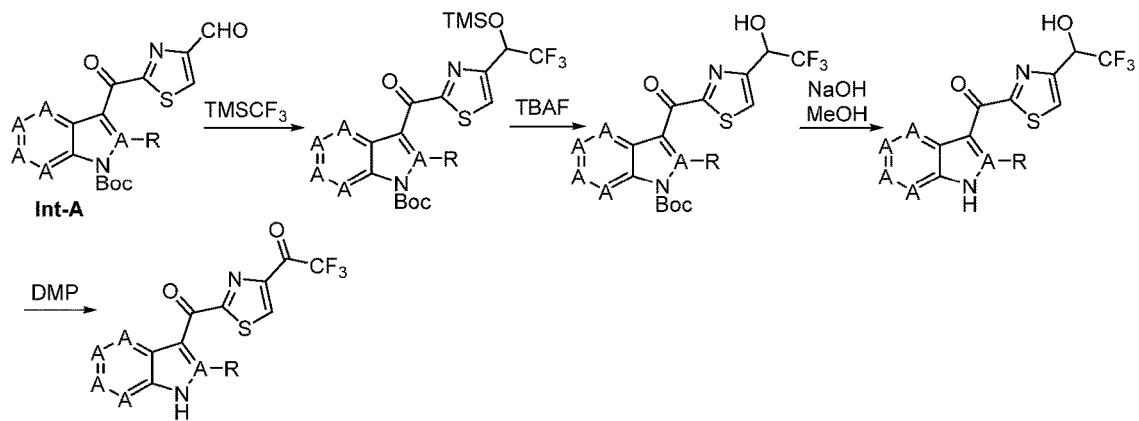
FIG. 13 shows a synthesis scheme for $CF_3$ ketone.
Figure 14:
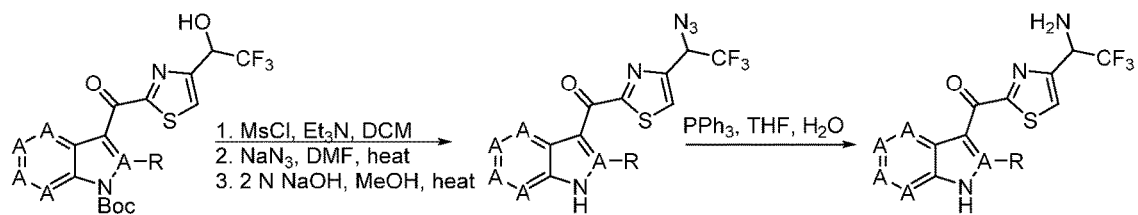
FIG. 14 shows a synthesis scheme for $CF_3$ amine.
Figure 15:
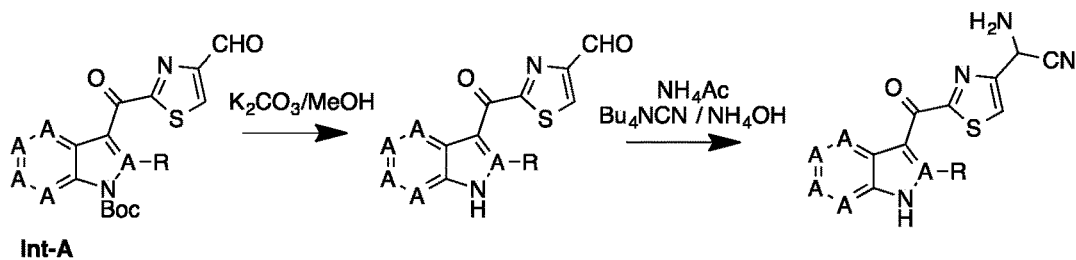
FIG. 15 shows a synthesis scheme for α-aminonitrile.

All technical and scientific terms used herein are the same as those commonly used by those ordinary skilled in the art to which the present invention pertains unless defined specifically otherwise.

The moieties described below can be substituted or unsubstituted. "Substituted" refers to replacement of a hydrogen atom of a molecule or an R-group with one or more additional R-groups such as halogen, alkyl, haloalkyl, alkenyl, alkoxy, alkoxyalkyl, alkylthio, trifluoromethyl, acyloxy, hydroxy, hydroxyalkyl, mercapto, carboxy, cyano, acyl, aryloxy, aryl, arylalkyl, heteroaryl, amino, aminoalkyl, alkylamino, dialkylamino, morpholino, piperidino, pyrrolidin-1-yl, piperazin-1-yl, nitro, phosphine, phosphinate, phosphonate, sulfato, =O, =S, or other R-groups. Unless otherwise indicated, an optionally substituted group may have a substituent at each substitutable position of a group. Combinations of substituents contemplated herein are preferably those that result in the formation of stable (e.g., not substantially altered for a week or longer when kept at a temperature of 40° C. or lower in the absence of moisture or other chemically reactive conditions), or chemically feasible, compounds.

"Hydroxy", "thiol", "cyano", "nitro", and "formyl" refer, respectively, to —OH, —SH, —CN, —NO$_2$, and —CHO.

"Acyloxy" refers to a RC(=O)O— radical, wherein R is alkyl, cycloalkyl, aryl, heteroalkyl, heteroaryl, or heterocycloalkyl, which are as described herein. In some embodiments, it is a $C_1$-$C_4$ acyloxy radical, which refers to the total number of chain or ring atoms of the alkyl, cycloalkyl, aryl, heteroalkyl, heteroaryl, or heterocycloalkyl portion of the acyloxy group plus the carbonyl carbon of acyl, i.e., the other ring or chain atoms plus carbonyl. If the R radical is heteroaryl or heterocycloalkyl, the hetero ring or chain atoms contribute to the total number of chain or ring atoms.

"Alkyl" refers to a group of 1-18, 1-16, 1-12, 1-10, preferably 1-8, more preferably 1-6 unsubstituted or substituted hydrogen-saturated carbons connected in linear, branched, or cyclic fashion, including the combination in linear, branched, and cyclic connectivity. Non-limiting examples include methyl, ethyl, propyl, isopropyl, butyl, and pentyl.

"Cycloalkyl" refers to a monocyclic or polycyclic non-aromatic radical that contains carbon and hydrogen, and may be saturated, or partially unsaturated. Cycloalkyl groups include groups having from 3 to 10 ring atoms (e.g., $C_3$-$C_{10}$ cycloalkyl). Whenever it appears herein, a numerical range such as "3 to 10" refers to each integer in the given range; e.g., "3 to 10 carbon atoms" means that the cycloalkyl group may consist of 3 carbon ring atoms, 4 carbon ring atoms, 5 carbon ring atoms, etc., up to and including 10 carbon ring atoms. In some embodiments, it is a $C_3$-$C_8$ cycloalkyl radical. In some embodiments, it is a $C_3$-$C_5$ cycloalkyl radical. Examples of cycloalkyl group include, but are not limited to, cyclopropyl, cyclobutyl, cyclopentyl, cyclopentenyl, cyclohexyl, cyclohexenyl, cycloseptyl, cyclooctyl, cyclononyl, cyclodecyl, and norbornyl. The term "cycloalkyl" also refers to spiral ring system, in which the cycloalkyl rings share one carbon atom.

"Heterocycloalkyl" refers to a 3- to 18-membered non-aromatic ring (e.g., $C_3$-$C_{18}$ heterocycloalkyl) radical that comprises two to twelve ring carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group may consist of 3 ring atoms, 4 ring atoms, etc., up to and including 18 ring atoms. In some embodiments, it is a $C_5$-$C_{10}$ heterocycloalkyl. In some embodiments, it is a $C_4$-$C_{10}$ heterocycloalkyl. In some embodiments, it is a $C_3$-$C_{10}$ heterocycloalkyl. The heterocycloalkyl radical may be a monocyclic, bicyclic, tricyclic or tetracyclic ring system, which may include fused or bridged ring systems. The heteroatoms in the heterocycloalkyl radical may be optionally oxidized. One or more nitrogen atoms, if present, may optionally be quaternized. The heterocycloalkyl radical may be partially or fully saturated. The heterocycloalkyl may be attached to the rest of the molecule through any atom of the ring(s). Examples of such heterocycloalkyl radicals include, but are not limited to, 6,7-dihydro-5H-cyclopenta[b]pyridine, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In some embodiments, the heterocycloalkyl group is aziridinyl, azetidinyl, pyrrolidinyl, piperidinyl, homopiperidinyl, morpholinyl, thiomorpholinyl, piperazinyl, tetrahydrofuranyl, tetrahydrothienyl, dihydrooxazolyl, tetrahydropyranyl, tetrahydrothiopyranyl, indolinyl, tetrahydroquinolyl, tetrahydroisoquinolin and benzoxazinyl, preferably dihydrooxazolyl and tetrahydrofuranyl.

"Halo" refers to any of halogen atoms fluorine (F), chlorine (Cl), bromine (Br), or iodine (I). A particular example of such halo groups is fluorine.

"Haloalkyl" refers to an alkyl substituted by one or more halo(s).

"Alkenyl" refers to a group of unsubstituted or substituted hydrocarbons containing 2-18, 2-16, 2-12, 2-10, for example, 2-8 (e.g., 2-6) carbons, which are linear, branched, cyclic, or in combination thereof, with at least one carbon-to-carbon double bond.

"Haloalkenyl" refers to an alkenyl substituted by one or more halo(s).

"Alkynyl" refers to a group of unsubstituted or substituted hydrocarbons containing 2-18, 2-16, 2-12, 2-10, for example, 2-8 (e.g., 2-6) carbons, which are linear, branched, cyclic, or in combination thereof, with at least one carbon-to-carbon triple bond.

"Haloalkynyl" refers to an alkynyl substituted by one or more halo(s).

"Amino protecting group" refers to those groups intended to protect an amino group against undesirable reactions during synthetic procedures and which can later be removed to reveal the amine. Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, alpha-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, alpha, alpha-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz.

"Amino" refers to unsubstituted amino and substituted amino groups, for example, primary amines, secondary amines, tertiary amines and quaternary amines. Specifically, "amino" refers to —$NR_aR_b$, wherein $R_a$ and $R_b$, both directly connected to the N, can be independently selected from hydrogen, deuterium, halo, hydroxy, cyano, formyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, a nitrogen protective group, —(CO)-alkyl, —(CO)—O-alkyl, or —$S(O)_nR_c$ (n=0 to 2, $R_c$ is directly connected to S), wherein $R_c$ is independently selected from hydrogen, deuterium, halo, amino, hydroxy, thiol, cyano, formyl, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, or halothiocarbonylthio.

"Aryl" refers to a $C_6$-$C_{14}$ aromatic hydrocarbon. For example, aryl can be phenyl, napthyl, or fluorenyl.

"Heteroaryl" refers to a $C_6$-$C_{14}$ aromatic hydrocarbon having one or more heteroatoms, such as N, O or S. The heteroaryl can be substituted or unsubstituted. Examples of a heteroaryl include, but are not limited to, azepinyl, acridinyl, benzimidazolyl, benzindolyl, 1,3-benzodioxolyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzofurazanyl, benzothiazolyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). In some embodiments, the heteroaryl can be dithiazinyl, furyl, imidazolyl, indolyl, isoquinolinyl, isoxazolyl, oxadiazolyl (e.g., (1,3,4)-oxadiazolyl, or (1,2,4)-oxadiazolyl), oxazolyl, pyrazinyl, pyrazolyl, pyrazyl, pyridazinyl, pyridinyl, pyrimidinyl, pyrimidyl, pyrrolyl, quinolinyl, tetrazolyl, thiazolyl, thienyl, triazinyl, (1,2,3)-triazolyl, (1,2,4)-triazolyl, 1,3,4-oxadiazolyl, 1,2,4-oxadiazolyl, 1,2,4-triazolyl, 1,3,4-thiadiazolyl, 5-amino-1,2,4-oxadiazolyl, 5-amino-1,3,4-oxadiazolyl, 5-amino-1,3,4-oxadiazolyl, 3-methyl-1,2,4-oxadiazolyl, 5-methyl-1,2,4-oxadiazolyl, 5-(trifluoromethyl)-1,2,4-oxadiazolyl, 5-(methylamino)-1,2,4-oxadiazolyl, 5-(aminomethyl)-1,2,4-oxadiazolyl, 5-(aminomethyl)-1,3,4-oxadiazolyl, 5-amino-4-cyanooxazolyl, 5,6-dichloro-1H-indolyl, 5,6-difluoro-1H-indolyl, 5-chloro-1H-indolyl, 5,6-dibromo-1H-indolyl, 5-fluoro-1H-indolyl, 5-methoxy-1H-indolyl, 7-fluoro-1H-indolyl, 6-cyano-1H-indolyl, 5-cyano-1H-indolyl, 4-fluoro-1H-indolyl, 5,6-difluoro-1H-indolyl, 6-fluoro-1H-indolyl, or 5,7-difluoro-1h-indolyl.

The substituent on the heteroaryl group can be alkyl (e.g., C1-C6 alkyl), amino, cyano, halo (e.g., fluoro, bromo, and chloro), alkylamino (e.g., C1-C6 alkylamino), methyleneamino, nitro, or hydroxyl. The heteroaryl group can have two, three or four substituents.

"Carbocycle" refers to a $C_6$-$C_{14}$ cyclic hydrocarbon. For example, aryl can be phenyl, napthyl, or fluorenyl.

"Heterocycle" refers to a $C_6$-$C_{14}$ cyclic hydrocarbon having one or more heteroatoms, such as N, O or S.

"Alkoxy" refers to an alkyl connected to an oxygen atom (—O-alkyl).

"Haloalkoxy" refers to a haloalkyl connected to an oxygen atom (—O-haloalkyl).

"Thioalkoxy" refers to an alkyl connected to a sulfur atom (—S-alkyl).

"Halothioalkoxy" refers to a haloalkyl connected to a sulfur atom (—S-haloalkyl).

"Carbonyl" refers to —(CO)—, wherein (CO) indicates that the oxygen is connected to the carbon with a double bond.

"Alkanoyl" or "acyl" refers to an alkyl connected to a carbonyl group [—(CO)-alkyl].

"Haloalkanoyl" or "haloacyl" refers to a haloalkyl connected to a carbonyl group [—(CO)-haloalkyl].

"Thiocarbonyl" refers to —(CS)—, wherein (CS) indicates that the sulfur is connected to the carbon with a double bond.

"Thioalkanoyl (or thioacyl)" refers to an alkyl connected to a thiocarbonyl group [—(CS)-alkyl].

"Halothioalkanoyl" or "halothioacyl" refers to a haloalkyl connected to a thiocarbonyl group [—(CS)-haloalkyl].

"Carbonyloxy" refers to an alkanoyl (or acyl) connected to an oxygen atom [—O—(CO)-alkyl].

"Halocarbonyloxy" refers to a haloalkanoyl (or haloacyl) connected to an oxygen atom [—O—(CO)-haloalkyl].

"Carbonylthio" refers to an alkanoyl (or acyl) connected to a sulfur atom [—S—(CO)-alkyl].

"Halocarbonylthio" refers to a haloalkanoyl (or haloacyl) connected to a sulfur atom [—S—(CO)-haloalkyl].

"Thiocarbonyloxy" refers to a thioalkanoyl (or thioacyl) connected to an oxygen atom [—O—(CS)-alkyl].

"Halothiocarbonyloxy" refers to a halothioalkanoyl (or halothioacyl) connected to an oxygen atom [—O—(CS)-haloalkyl].

"Thiocarbonylthio" refers to a thioalkanoyl (or thioacyl) connected to a sulfur atom [—S—(CS)-alkyl].

"Halothiocarbonylthio" refers to a halothioalkanoyl (or halothioacyl) connected to a sulfur atom [—S—(CS)-haloalkyl].

Indole Compounds

An aspect of the present disclosure relates to novel indole compounds that can modulate human aryl hydrocarbon receptor (AhR). These compounds bind specifically to AhR. Without wishing to be bound by theory, it is contemplated that AhR bound by one of the present compounds is agonized with respect to the receptor's immune-stimulatory activity.

In some embodiments, the compound has the structure of formula 2, or an enantiomer, diastereomer, or pharmaceutically acceptable salt thereof:

Structural Formula 2

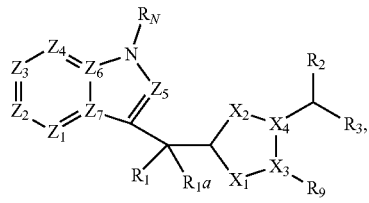

wherein:

$X_1$ is N (nitrogen), O (oxygen), S (sulfur), or C (carbon); $X_2$ is N (nitrogen), O (oxygen) S (sulfur), or C (carbon); $X_3$ is N (nitrogen), O (oxygen), S (sulfur) or C (carbon); and $X_4$ is N (nitrogen) O (oxygen), S (sulfur), or C (carbon), such that at least one of $X_1$, $X_2$, $X_3$ and $X_4$ is N, each of $X_1$, $X_2$, $X_3$ and $X_4$ is optionally selected to form a heteroaromatic, wherein the bond between $X_1$ and the adjacent carbon, between $X_2$ and the adjacent carbon, between $X_1$ and $X_4$, between $X_2$ and $X_3$, and between $X_3$ and $X_4$ can be a single bond or a double bond and the valence of $X_1$, $X_2$, $X_3$ and $X_4$ is completed with H or $C_1$-$C_6$ alkyl (i.e., the ring can be aromatic, partially saturated, or saturated);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_2$ and $R_3$ are together selected from the group consisting of =O, =S, or =$NR_a$ ($R_a$ is H, $C_1$-$C_6$ alkyl, $C_1$-$C_6$ acyl, or —OR, R is H, $C_1$-$C_6$ alkyl, or $C_1$-$C_6$ acyl), or $R_2$ and $R_3$ are each independently selected from the group consisting of —$NR_aR$ ($R_a$ and $R_b$ are each independently H, $C_1$-$C_6$ alkyl, or $C_1$-$C_6$ acyl), hydrogen, deuterium, halo, amino, hydroxy, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_4$, $R_5$, $R_6$, $R_7$, $R_8$, and $R_9$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl; and $R_1$ and $R_{1a}$ are taken together to form =$NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, $R_2$ preferably can be =O, $R_3$ preferably can be —OR, wherein R is H or $C_1$-$C_6$ alkyl, or $R_1$ and $R_{1a}$ are taken together to form =$CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, $R_2$ preferably can be =O, $R_3$ preferably can be —OR, wherein R is H or $C_1$-$C_6$ alkyl, or $R_1$ and $R_{1a}$ are taken together to form =O, =$NOR_a$, or =S, $R_2$ and $R_3$ preferably can be each independently —OR or —$NR_aR_b$, wherein R, $R_a$, and $R_b$ are each independently H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halothiocarbonylthio, thiocarbonyloxy, halothiocarbonyloxy, thiocarbonylthio, and halothiocarbonylthio; and optionally, adjacent R groups, together, can form a six- to twelve-membered ring.

In certain embodiments, $Z_1$ is $CR_4$, $Z_2$ is $CR_5$, $Z_3$ is $CR_6$, $Z_4$ is $CR_7$, $Z_5$ is $CR_8$, $Z_6$ is C, $Z_7$ is C, wherein $R_4$ is halo, cyano, formyl, or nitro and each of $R_5$, $R_6$, $R_7$, and $R_8$ is H. In certain embodiments, at least one of $R_4$, $R_5$, $R_6$, and $R_7$ is halo, e.g., F, Cl or Br.

In some embodiments, the compound has the structure of formula 2a, or an enantiomer, diastereomer, or pharmaceutically acceptable salt thereof:

Structural Formula 2a

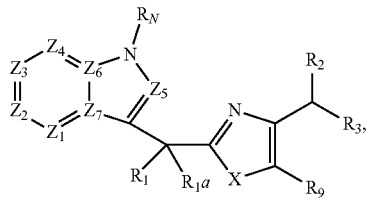

wherein:

X is either O (oxygen) or S (sulfur);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_2$ and $R_3$ are together selected from the group consisting of =O, =S, or =$NR_a$ ($R_a$ is H, $C_1$-$C_6$ alkyl, $C_1$-$C_6$ acyl, or —OR, R is H, $C_1$-$C_6$ alkyl, or $C_1$-$C_6$ acyl), or $R_2$ and $R_3$ are each independently selected from the group consisting of —$NR_aR_b$ ($R_a$ and $R_b$ are each independently H, $C_1$-$C_6$ alkyl, or $C_1$-$C_6$ acyl), hydrogen, deuterium, halo, amino, hydroxy, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_4$, $R_5$, $R_6$, $R_7$, $R_8$, and $R_9$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl; and $R_1$ and $R_{1a}$ are taken together to form =$NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, $R_2$ preferably can be =O, $R_3$ preferably can be —OR, wherein R is H or $C_1$-$C_6$ alkyl, or $R_1$ and $R_{1a}$ are taken together to form =$CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, $R_2$ preferably can be =O, $R_3$ preferably can be —OR, wherein R is H or $C_1$-$C_6$ alkyl, or $R_1$ and $R_{1a}$ are taken together to form =O, =$NOR_a$, or =S, $R_2$ and $R_3$ preferably can be each independently —OR or —$NR_aR_b$, wherein R, $R_a$, and $R_b$ are each independently H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and optionally, adjacent R groups, together, can form a six- to twelve-membered ring.

In certain embodiments, the carbon-carbon double bond of the five-membered nitrogen-containing ring can be saturated. The compounds described herein include stereoisomers or diastereomers of the saturated carbon atoms. The saturation can be hydrogen or $C_1$-$C_6$ alkyl groups added to the carbon-carbon bond. In certain embodiments, $Z_1$ is $CR_4$, $Z_2$ is $CR_5$, $Z_3$ is $CR_6$, $Z_4$ is $CR_7$, $Z_5$ is $CR_8$, $Z_6$ is C, $Z_7$ is C, wherein $R_4$ is halo, cyano, formyl, or nitro and each of $R_5$, $R_6$, $R_7$, and $R_8$ is H. In certain embodiments, at least one of $R_4$, $R_5$, $R_6$, and $R_7$ is halo, e.g., F, Cl or Br.

In some embodiments, the compound has the structure of formula 3, or an enantiomer, diastereomer, or pharmaceutically acceptable salt thereof:

Structural Formula 3

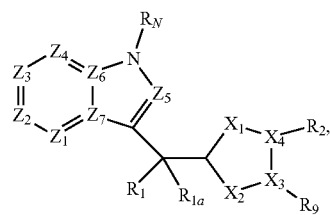

wherein:

$X_1$ is N (nitrogen), O (oxygen), S (sulfur), or C (carbon); $X_2$ is N (nitrogen), O (oxygen) S (sulfur), or C (carbon); $X_3$ is N (nitrogen), O (oxygen), S (sulfur) or C (carbon); and $X_4$ is N (nitrogen) O (oxygen), S (sulfur), or C (carbon), such that at least one of $X_1$, $X_2$, $X_3$ and $X_4$ is N, each of $X_1$, $X_2$, $X_3$ and $X_4$ is optionally selected to form a heteroaromatic, wherein the bond between $X_1$ and the adjacent carbon, between $X_2$ and the adjacent carbon, between $X_1$ and $X_4$, between $X_2$ and $X_3$, and between $X_3$ and $X_4$ can be a single bond or a double bond and the valence of $X_1$, $X_2$, $X_3$ and $X_4$ is completed with H or $C_1$-$C_6$ alkyl (i.e., the ring can be aromatic, partially saturated, or saturated);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form $=NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form $=CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form $=O$, $=NOR_a$, or $=S$, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and $R_2$ and $R_9$ are each independently selected from the group consisting of hydrogen, aryl, heteroaryl, cycloalkyl, heterocycloalkyl, alkyl, —$NR_{2a}C(O)OR_{2b}$, —$NR_{2a}C(O)R_{2b}$, —$(C_0$-$C_6$ alkyl)-$CONHSO_2R_{2a}$, —$(C_0$-$C_6$ alkyl)-$CONHSO_2NR_{2a}R_{2b}$, —$(C_0$-$C_6$ alkyl)-$SO_2NHCOR_{2a}$, —$(C_0$-$C_6$ alkyl)-$SO_2NHR_{2a}$, —$(C_0$-$C_6$ alkyl)-$CONR_{2a}OR_{2b}$,

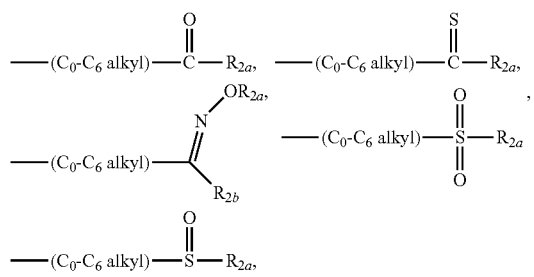

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl; and optionally, adjacent R groups, together, can form a six- to twelve-membered ring.

In certain embodiments, $Z_1$ is $CR_4$, $Z_2$ is $CR_5$, $Z_3$ is $CR_6$, $Z_4$ is $CR_7$, $Z_5$ is $CR_8$, $Z_6$ is C, $Z_7$ is C, wherein $R_4$ is halo, cyano, formyl, or nitro and each of $R_5$, $R_6$, $R_7$, and $R_8$ is H. In certain embodiments, at least one of $R_4$, $R_5$, $R_6$, and $R_7$ is halo, e.g., F, Cl or Br. In certain embodiments, $R_{2a}$ is substituted amino. Substituted amino can include alkyl amino, for example, unsubstituted alkylamino, hydroxyalkylamino or alkoxyalkylamino, or cycloalkyl amino, for example, —$NR_aR_b$ where $R_a$ and $R_b$ together form a 3, 4, 5, 6, 7, or 8 membered alkylene ring. The alkylene ring can be unsubstituted or substituted, for example, with halo, hydroxyl, alkoxy, or alkyl (including substituted alkyl) groups.

In some embodiments, the compound has the structure of formula 3c, or an enantiomer, diastereomer, or pharmaceutically acceptable salt thereof:

Structural Formula 3c

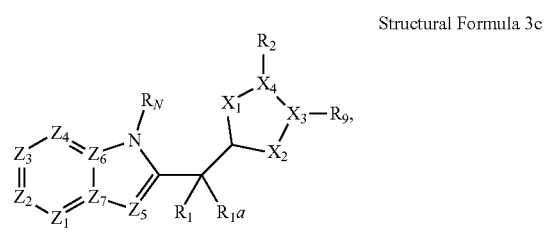

wherein:

$X_1$ is N (nitrogen), O (oxygen), S (sulfur), or C (carbon); $X_2$ is N (nitrogen), O (oxygen) S (sulfur), or C (carbon); $X_3$ is N (nitrogen), O (oxygen), S (sulfur) or C (carbon); and $X_4$ is N (nitrogen) O (oxygen), S (sulfur), or C (carbon), such that at least one of $X_1$, $X_2$, $X_3$ and $X_4$ is N, each of $X_1$, $X_2$, $X_3$ and $X_4$ is optionally selected to form a heteroaromatic, wherein the bond between $X_1$ and the adjacent carbon, between $X_2$ and the adjacent carbon, between $X_1$ and $X_4$, between $X_2$ and $X_3$, and between $X_3$ and $X_4$ can be a single bond or a double bond and the valence of $X_1$, $X_2$, $X_3$ and $X_4$ is completed with H or $C_1$-$C_6$ alkyl (i.e., the ring can be aromatic, partially saturated, or saturated);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form $=NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form $=CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form $=O$, $=NOR_a$, or $=S$, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and $R_2$ and $R_9$ are each independently selected from the group consisting of hydrogen, aryl, heteroaryl, cycloalkyl, heterocycloalkyl, alkyl, —NR$_{2a}$C(O)OR$_{2b}$, —NR$_{2a}$C(O)R$_{2b}$, —(C$_0$-C$_6$ alkyl)-CONHSO$_2$R$_{2a}$, —(C$_0$-C$_6$ alkyl)-CONHSO$_2$NR$_{2a}$R$_{2b}$, —(C$_0$-C$_6$ alkyl)-SO$_2$NHCOR$_{2a}$, —(C$_0$-C$_6$ alkyl)-SO$_2$NHR$_{2a}$, —(C$_0$-C$_6$ alkyl)-CONR$_{2a}$OR$_{2b}$,

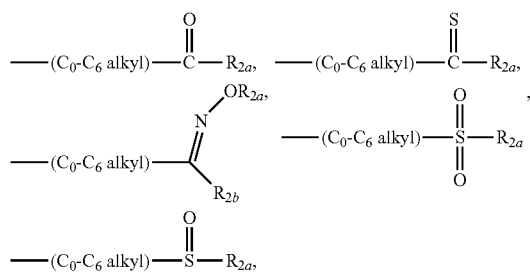

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl; and optionally, adjacent R groups, together, can form a six- to twelve-membered ring.

In certain embodiments, $Z_1$ is $CR_4$, $Z_2$ is $CR_5$, $Z_3$ is $CR_6$, $Z_4$ is $CR_7$, $Z_5$ is $CR_8$, $Z_6$ is C, $Z_7$ is C, wherein $R_4$ is halo, cyano, formyl, or nitro and each of $R_5$, $R_6$, $R_7$, and $R_8$ is H. In certain embodiments, at least one of $R_4$, $R_5$, $R_6$, and $R_7$ is halo, e.g., F, Cl or Br. In certain embodiments, $R_{2a}$ is substituted amino. Substituted amino can include alkyl amino, for example, unsubstituted alkylamino, hydroxyalkylamino or alkoxyalkylamino, or cycloalkyl amino, for example, —NR$_a$R$_b$ where R$_a$ and R$_b$ together form a 3, 4, 5, 6, 7, or 8 membered alkylene ring. The alkylene ring can be unsubstituted or substituted, for example, with halo, hydroxyl, alkoxy, or alkyl (including substituted alkyl) groups.

In some embodiments, the compound has the structure of formula 3a, or an enantiomer, diastereomer, or pharmaceutically acceptable salt thereof:

Structural Formula 3a

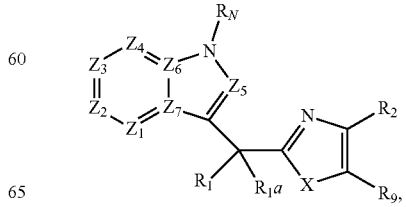

wherein:

X is either O (oxygen) or S (sulfur);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form $=NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form $=CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form $=O$, $=NR_a$, or $=S$, wherein $R_a$ is H, $C_1$-$C_6$ alkyl, or $C_1$-$C_6$ acyl; or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and $R_2$ and $R_9$ are each independently selected from the group consisting of hydrogen, aryl, heteroaryl, cycloalkyl, heterocycloalkyl, alkyl, —$NR_{2a}C(O)OR_{2b}$, —$NR_{2a}C(O)R_{2b}$, —($C_0$-$C_6$ alkyl)-CONHSO$_2R_{2a}$, —($C_0$-$C_6$ alkyl)-CONHSO$_2NR_{2a}R_{2b}$, —($C_0$-$C_6$ alkyl)-SO$_2$NHCOR$_{2a}$, —($C_0$-$C_6$ alkyl)-SO$_2$NHR$_{2a}$, —($C_0$-$C_6$ alkyl)-CONR$_{2a}$OR$_{2b}$,

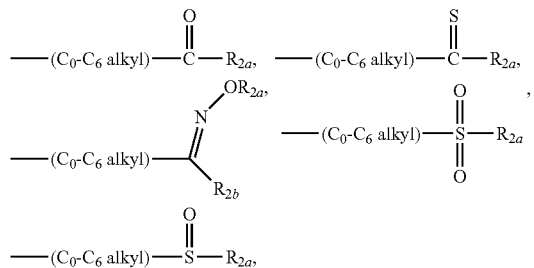

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl; and optionally, adjacent R groups, together, can form a six- to twelve-membered ring.

In certain embodiments, the carbon-carbon double bond of the five-membered nitrogen-containing ring can be saturated. The compounds described herein include stereoisomers or diastereomers of the saturated carbon atoms. The saturation can be hydrogen or $C_1$-$C_6$ alkyl groups added to the carbon-carbon bond. In certain embodiments, $Z_1$ is $CR_4$, $Z_2$ is $CR_5$, $Z_3$ is $CR_6$, $Z_4$ is $CR_7$, $Z_5$ is $CR_8$, $Z_6$ is C, $Z_7$ is C, wherein $R_4$ is halo, cyano, formyl, or nitro and each of $R_5$, $R_6$, $R_7$, and $R_8$ is H. In certain embodiments, $R_{2a}$ is substituted amino. Substituted amino can include alkyl amino, for example, unsubstituted alkylamino, hydroxyalkylamino or alkoxyalkylamino, or cycloalkyl amino, for example, —$NR_aR_b$ where $R_a$ and $R_b$ together form a 3, 4, 5, 6, 7, or 8 membered alkylene ring. The alkylene ring can be unsubstituted or substituted, for example, with halo, hydroxyl, alkoxy, or alkyl (including substituted alkyl) groups. In certain embodiments, at least one of $R_4$, $R_5$, $R_6$, and $R_7$ is halo, e.g., F, Cl or Br.

In some embodiments, the compound has the structure of formula 3b, or an enantiomer, diastereomer, or pharmaceutically acceptable salt thereof:

Structural formula 3b

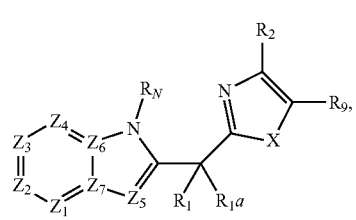

wherein:

X is either O (oxygen) or S (sulfur);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form $=NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form =$CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form =O, =$NOR_a$, or =S, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and $R_2$ and $R_9$ are each independently selected from the group consisting of hydrogen, aryl, heteroaryl, cycloalkyl, heterocycloalkyl, alkyl, —$NR_{2a}C(O)OR_{2b}$, —$NR_{2a}C(O)R_{2b}$, —($C_0$-$C_6$ alkyl)-$CONHSO_2R_{2a}$, —($C_0$-$C_6$ alkyl)-$CONHSO_2NR_{2a}R_{2b}$, —($C_0$-$C_6$ alkyl)-$SO_2NHCOR_{2a}$, —($C_0$-$C_6$ alkyl)-$SO_2NHR_{2a}$, —($C_0$-$C_6$ alkyl)-$CONR_{2a}OR_{2b}$,

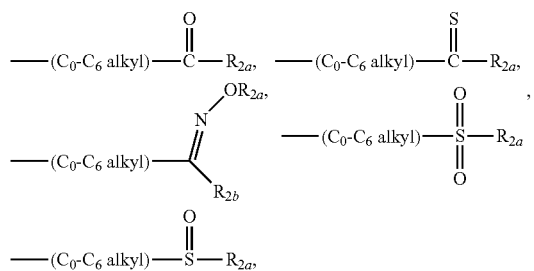

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl; and optionally, adjacent R groups, together, can form a six- to twelve-membered ring.

In certain embodiments, the carbon-carbon double bond of the five-membered nitrogen-containing ring can be saturated. The compounds described herein include stereoisomers or diastereomers of the saturated carbon atoms. The saturation can be hydrogen or $C_1$-$C_6$ alkyl groups added to the carbon-carbon bond. In certain embodiments, $Z_1$ is $CR_4$, $Z_2$ is $CR_5$, $Z_3$ is $CR_6$, $Z_4$ is $CR_7$, $Z_5$ is $CR_8$, $Z_6$ is C, $Z_7$ is C, wherein $R_4$ is halo, cyano, formyl, or nitro and each of $R_5$, $R_6$, $R_7$, and $R_8$ is H. In certain embodiments, $R_{2a}$ is substituted amino. Substituted amino can include alkyl amino, for example, unsubstituted alkylamino, hydroxyalkylamino or alkoxyalkylamino, or cycloalkyl amino, for example, —$NR_aR_b$ where $R_a$ and $R_b$ together form a 3, 4, 5, 6, 7, or 8 membered alkylene ring. The alkylene ring can be unsubstituted or substituted, for example, with halo, hydroxyl, alkoxy, or alkyl (including substituted alkyl) groups. In certain embodiments, at least one of $R_4$, $R_5$, $R_6$, and $R_7$ is halo, e.g., F, Cl or Br.

In some embodiments, the compound has the structure of formula 4, or an enantiomer, diastereomer, or pharmaceutically acceptable salt thereof:

Structural Formula 4

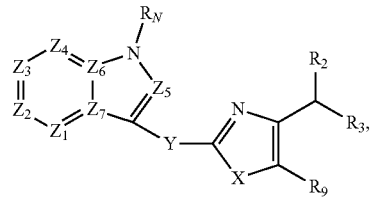

wherein:

X is O (oxygen) or S (sulfur);

Y is a bond, O (oxygen), S (sulfur), or

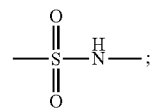

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_4$, $R_5$, $R_6$, $R_7$, $R_8$, and $R_9$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, R$_{10}$ is directly connected to S), wherein R$_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

R$_N$ is H, CN, C$_1$-C$_6$ alkyl, —OH, —(CO)—OR, or —OR, wherein R is H, C$_1$-C$_6$ alkyl, or C$_1$-C$_6$ acyl;

R$_2$ and R$_3$ are together selected from the group consisting of =O, =S, or =NR$_a$ (R$_a$ is H, C$_1$-C$_6$ alkyl, C$_1$-C$_6$ acyl, or —OR, R is H, C$_1$-C$_6$ alkyl, or C$_1$-C$_6$ acyl), or R$_2$ and R$_3$ are each independently selected from the group consisting of —NR$_a$R$_b$ (R$_a$ and R$_b$ are each independently H, C$_1$-C$_6$ alkyl, or C$_1$-C$_6$ acyl), hydrogen, deuterium, halo, amino, hydroxy, cyano, formyl, furyl, nitro, alkyl, haloalkyl, alkenyl, haloalkenyl, alkynyl, haloalkynyl, C$_1$-C$_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, R$_{11}$ is directly connected to S), wherein R$_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and optionally, adjacent R groups, together, can form a six- to twelve-membered ring.

In certain embodiments, the carbon-carbon double bond of the five-membered nitrogen-containing ring can be saturated. The compounds described herein include stereoisomers or diastereomers of the saturated carbon atoms. The saturation can be hydrogen or C$_1$-C$_6$ alkyl groups added to the carbon-carbon bond. In certain embodiments, Z$_1$ is CR$_4$, Z$_2$ is CR$_5$, Z$_3$ is CR$_6$, Z$_4$ is CR$_7$, Z$_5$ is CR$_8$, Z$_6$ is C, Z$_7$ is C, wherein R$_4$ is halo, cyano, formyl, or nitro and each of R$_5$, R$_6$, R$_7$, and R$_8$ is H. In certain embodiments, at least one of R$_4$, R$_5$, R$_6$, and R$_7$ is halo, e.g., F, Cl or Br.

In some embodiments, the compound has the structure of formula 5, or an enantiomer, diastereomer, or pharmaceutically acceptable salt thereof:

Structural Formula 5

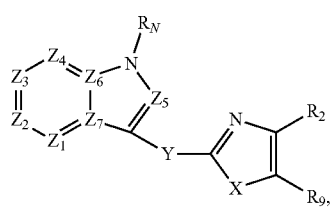

wherein:

X is O (oxygen) or S (sulfur);
Y is a bond, O (oxygen), S (sulfur), or

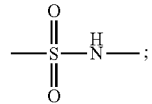

Z$_1$ is N or CR$_4$, Z$_2$ is N or CR$_5$, Z$_3$ is N or CR$_6$, Z$_4$ is N or CR$_7$, Z$_5$ is N or CR$_8$, Z$_6$ is N or C, Z$_7$ is N or C, wherein no more than two of Z$_1$, Z$_2$, Z$_3$, Z$_4$, Z$_5$, Z$_6$, and Z$_7$ are N;

R$_2$ and R$_9$ are each independently selected from the group consisting of hydrogen, aryl, heteroaryl, cycloalkyl, heterocycloalkyl, alkyl, —NR$_{2a}$C(O)OR$_{2b}$, —NR$_{2a}$C(O)R$_{2b}$, —(C$_0$-C$_6$ alkyl)-CONHSO$_2$R$_{2a}$, —(C$_0$-C$_6$ alkyl)-CONHSO$_2$NR$_{2a}$R$_{2b}$, —(C$_0$-C$_6$ alkyl)-SO$_2$NHCOR$_{2a}$, —(C$_0$-C$_6$ alkyl)-SO$_2$NHR$_{2a}$, —(C$_0$-C$_6$ alkyl)-CONR$_{2a}$OR$_{2b}$,

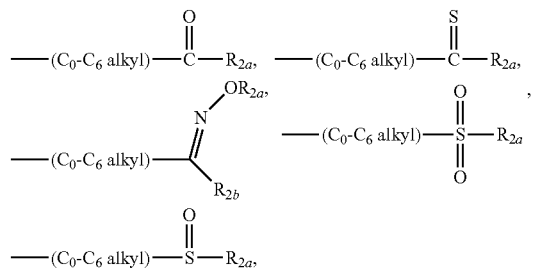

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, R$_{10}$ is directly connected to S), wherein R$_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein R$_{2a}$ and R$_{2b}$ are each independently H, C$_1$-C$_6$ alkyl, alkoxy (—O-alkyl), hydroxy, thioalkoxy (—S-alkyl), cyano (—CN), or amino;

R$_4$, R$_5$, R$_6$, R$_7$, and R$_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, R$_{11}$ is directly connected to S), wherein R$_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl; and optionally, adjacent R groups, together, can form a six- to twelve-membered ring.

In certain embodiments, the carbon-carbon double bond of the five-membered nitrogen-containing ring can be saturated. The compounds described herein include stereoisomers or diastereomers of the saturated carbon atoms. The saturation can be hydrogen or C1-C6 alkyl groups added to the carbon-carbon bond. In certain embodiments, $Z_1$ is $CR_4$, $Z_2$ is $CR_5$, $Z_3$ is $CR_6$, $Z_4$ is $CR_7$, $Z_5$ is $CR_8$, $Z_6$ is C, $Z_7$ is C, wherein $R_4$ is halo, cyano, formyl, or nitro and each of $R_5$, $R_6$, $R_7$, and $R_8$ is H. In certain embodiments, at least one of $R_4$, $R_5$, $R_6$, and $R_7$ is halo, e.g., F, Cl or Br. In certain embodiments, $R_{2a}$ is substituted amino. Substituted amino can include alkyl amino, for example, unsubstituted alkylamino, hydroxyalkylamino or alkoxyalkylamino, or cycloalkyl amino, for example, —$NR_aR_b$ where $R_a$ and $R_b$ together form a 3, 4, 5, 6, 7, or 8 member alkylene ring. The alkylene ring can be unsubstituted or substituted, for example, with halo, hydroxyl, alkoxy, or alkyl (including substituted alkyl) groups.

In still another embodiment, the compound has structural formula 6, or an enantiomer, diastereomer, or pharmaceutically acceptable salt thereof:

Structural Formula 6

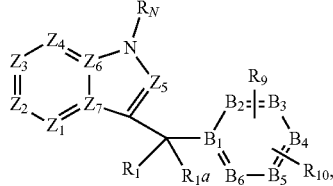

wherein:

$R_1$ and $R_{1a}$ are taken together to form =$NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form =$CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form =O, =$NOR_a$, or =S, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{14}$ (n=0 to 2, $R_{14}$ is directly connected to S), wherein $R_{14}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl;

$B_1$, $B_2$, $B_3$, $B_4$, $B_5$, and $B_6$ are each independently C or N;

$R_9$ and $R_{10}$, the number of which, together, complete the valence of each of $B_1$, $B_2$, $B_3$, $B_4$, $B_5$, and $B_6$, are each independently selected from the group consisting of hydrogen, aryl, heteroaryl, cycloalkyl, heterocycloalkyl, alkyl, —$NR_{2a}C(O)OR_{2b}$, —$NR_{2a}C(O)R_{2b}$, —($C_0$-$C_6$ alkyl)-$CONHSO_2R_{2a}$, —($C_0$-$C_6$ alkyl)-$CONHSO_2NR_{2a}R_{2b}$, —($C_0$-$C_6$ alkyl)-$SO_2NHCOR_{2a}$, —($C_0$-$C_6$ alkyl)-$SO_2NHR_{2a}$, —($C_0$-$C_6$ alkyl)-$CONR_{2a}OR_{2b}$,

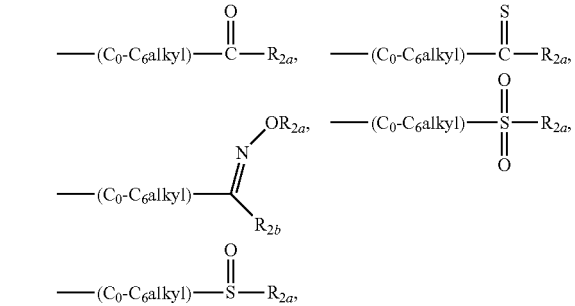

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and

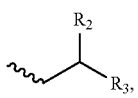

wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino;

wherein $R_2$ and $R_3$ are together selected from the group consisting of =O, =S, or =$NR_a$ ($R_a$ is H, $C_1$-$C_6$ alkyl, $C_1$-$C_6$ acyl, or —OR, R is H, $C_1$-$C_6$ alkyl, or $C_1$-$C_6$ acyl), or $R_2$ and $R_3$ are each independently selected from the group consisting of —$NR_aR_b$ ($R_a$ and $R_b$ are each independently H, $C_1$-$C_6$ alkyl, or $C_1$-$C_6$ acyl), hydrogen, deuterium, halo, amino, hydroxy, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{13}$ (n=0 to 2, $R_{13}$ is directly connected to S), wherein $R_{13}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and optionally, adjacent R groups, together, can form a six- to twelve-membered ring.

In certain embodiments, $Z_1$ is $CR_4$, $Z_2$ is $CR_5$, $Z_3$ is $CR_6$, $Z_4$ is $CR_7$, $Z_5$ is $CR_8$, $Z_6$ is C, $Z_7$ is C, wherein $R_4$ is halo, cyano, formyl, or nitro and each of $R_5$, $R_6$, $R_7$, and $R_8$ is H. In certain embodiments, at least one of $R_4$, $R_5$, $R_6$, and $R_7$ is halo, e.g., F, Cl or Br. In certain embodiments, $R_{2a}$ is substituted amino. Substituted amino can include alkyl amino, for example, unsubstituted alkylamino, hydroxyalkylamino or alkoxyalkylamino, or cycloalkyl amino, for example, —$NR_aR_b$ where $R_a$ and $R_b$ together form a 3, 4, 5, 6, 7, or 8 membered alkylene ring. The alkylene ring can be unsubstituted or substituted, for example, with halo, hydroxyl, alkoxy, or alkyl (including substituted alkyl) groups.

In some embodiments, the compound has structural formula 7, or an enantiomer, diastereomer, or pharmaceutically acceptable salt thereof:

Structural Formula 7

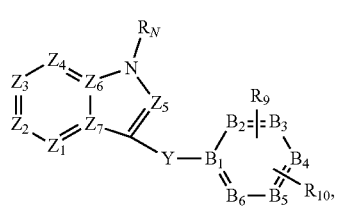

wherein:
Y is a bond, O (oxygen), S (sulfur), or

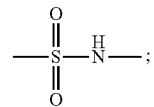

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl;

$B_1$, $B_2$, $B_3$, $B_4$, $B_5$, and $B_6$ are each independently C or N;

$R_9$ and $R_{10}$, the number of which, together, complete the valence of each of $B_1$, $B_2$, $B_3$, $B_4$, $B_5$, and $B_6$, are each independently selected from the group consisting of hydrogen, aryl, heteroaryl, cycloalkyl, heterocycloalkyl, alkyl, —$NR_{2a}C(O)OR_{2b}$, —$NR_{2a}C(O)R_{2b}$, —($C_0$-$C_6$ alkyl)-$CONHSO_2R_{2a}$, —($C_0$-$C_6$ alkyl)-$CONHSO_2NR_{2a}R_{2b}$, —($C_0$-$C_6$ alkyl)-$SO_2NHCOR_{2a}$, —($C_0$-$C_6$ alkyl)-$SO_2NHR_{2a}$, —($C_0$-$C_6$ alkyl)-$CONR_{2a}OR_{2b}$,

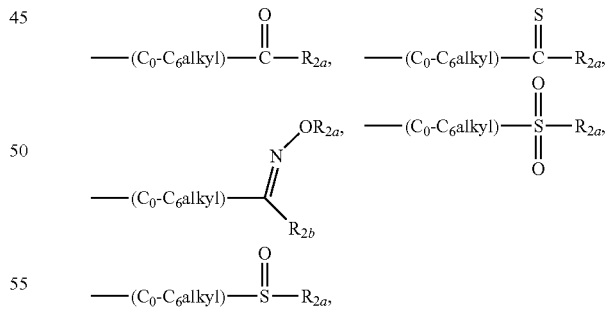

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and

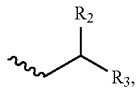

wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino;

wherein $R_2$ and $R_3$ are together selected from the group consisting of =O, =S, or =$NR_a$ ($R_a$ is H, $C_1$-$C_6$ alkyl, $C_1$-$C_6$ acyl, or —OR, R is H, $C_1$-$C_6$ alkyl, or $C_1$-$C_6$ acyl), or $R_2$ and $R_3$ are each independently selected from the group consisting of –$NR_aR_b$ ($R_a$ and $R_b$ are each independently H, $C_1$-$C_6$ alkyl, or $C_1$-$C_6$ acyl), hydrogen, deuterium, halo, amino, hydroxy, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{13}$ (n=0 to 2, $R_{13}$ is directly connected to S), wherein $R_{13}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and optionally, adjacent R groups, together, can form a six- to twelve-membered ring.

In certain embodiments, $Z_1$ is $CR_4$, $Z_2$ is $CR_5$, $Z_3$ is $CR_6$, $Z_4$ is $CR_7$, $Z_5$ is $CR_8$, $Z_6$ is C, $Z_7$ is C, wherein $R_4$ is halo, cyano, formyl, or nitro and each of $R_5$, $R_6$, $R_7$, and $R_8$ is H. In certain embodiments, at least one of $R_4$, $R_5$, $R_6$, and $R_7$ is halo, e.g., F, Cl or Br. In certain embodiments, $R_{2a}$ is substituted amino. Substituted amino can include alkyl amino, for example, unsubstituted alkylamino, hydroxyalkylamino or alkoxyalkylamino, or cycloalkyl amino, for example, —$NR_aR_b$ where $R_a$ and $R_b$ together form a 3, 4, 5, 6, 7, or 8 membered alkylene ring. The alkylene ring can be unsubstituted or substituted, for example, with halo, hydroxyl, alkoxy, or alkyl (including substituted alkyl) groups.

In each of the formulae, in some embodiments, each of $R_4$, $R_5$, $R_6$, and $R_7$ is hydrogen. In other embodiments, at least one of $R_4$, $R_5$, $R_6$, and $R_7$ can be F, Cl or Br and the others of $R_4$, $R_5$, $R_6$, and $R_7$ are hydrogen. In still other embodiments, at least two of $R_4$, $R_5$, $R_6$, and $R_7$, independently, can be F, Cl or Br and the others of $R_4$, $R_5$, $R_6$, and $R_7$ are hydrogen. The F, Cl or Br can be at the indole ring carbon 5, 6, or 7.

In each of formulae 3, 3a, 3b, 3c, and 5, in certain embodiments, $R_8$ can be hydrogen. $R_2$ can be acyl, cyano, hydroxyl-substituted C1-C6 alkyl, amino-substituted C1-C6 alkyl, aryl, or heteroaryl. The aryl or heteroaryl can be substituted or unsubstituted. The substituted aryl or heteroaryl can be substituted with halo, amino, hydroxyl, or C1-C6 alkyl. The amino can be unsubstituted.

In each of formulae 2, 2a, and 4, in certain embodiments, $R_2$ can be hydroxyl or amino and $R_3$ can be alkyl, aryl, nitro, or cyano. $R_8$ can be hydrogen. The amino can be substituted or unsubstituted.

In some embodiments, the compound has structural formula 8, or an enantiomer, diastereomer, or pharmaceutically acceptable salt thereof:

Structural Formula 8

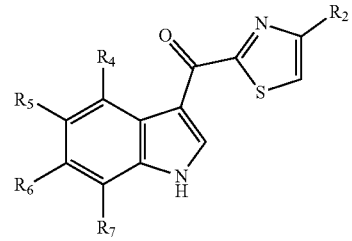

wherein $R_2$ is selected from the group consisting of substituted alkyl, heteroaryl, and

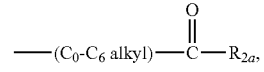

wherein $R_{2a}$ is H, C1-C6 alkyl, alkoxy (—O-alkyl), hydroxy, thioalkoxy (—S-alkyl), cyano (—CN), or amino; and $R_4$, $R_5$, $R_6$, and $R_7$, are each independently selected from the group consisting of hydrogen and halo.

In some embodiments, $R_2$ is substituted alkyl, e.g., a C1-C6 alkyl substituted with one or more hydroxyl, amino, nitro, or cyano. In some embodiments, $R_2$ is heteroaryl, e.g., oxadiazolyl or thiadiazolyl, optionally substituted with one or more hydroxyl, amino, nitro, cyano, C1-C6 alkyl, or C1-C6 alkyl amino. In some embodiments, $R_2$ is —C(O)—$R_{2a}$, and $R_{2a}$ is C1-C6 alkyl.

In one embodiment of the compound of structural formula 8, at least one of $R_4$, $R_5$, $R_6$, and $R_7$ is F, Cl or Br and the others of $R_4$, $R_5$, $R_6$, and $R_7$ are hydrogen. In another embodiment, at least two of $R_4$, $R_5$, $R_6$, and $R_7$ are F, Cl or Br and the others of $R_4$, $R_5$, $R_6$, and $R_7$ are hydrogen.

In one embodiment, $R_5$ is F and $R_4$, $R_6$, and $R_7$ are hydrogen. In another embodiment, $R_6$ is F and $R_4$, $R_5$, and $R_7$ are hydrogen. In still another embodiment, $R_7$ is F and $R_4$, $R_5$, and $R_6$ are hydrogen.

In one embodiment, $R_5$ is Cl and $R_4$, $R_6$, and $R_7$ are hydrogen. In another embodiment, $R_6$ is Cl and $R_4$, $R_5$, and $R_7$ are hydrogen. In still another embodiment, $R_7$ is Cl and $R_4$, $R_5$, and $R_6$ are hydrogen.

In one embodiment, $R_5$ and $R_6$ are F and $R_4$ and $R_7$ are hydrogen. In another embodiment, $R_5$ and $R_7$ are F and $R_4$ and $R_6$ are hydrogen. In still another embodiment, $R_6$ and $R_7$ are F and $R_4$ and $R_5$ are hydrogen.

In one embodiment, $R_5$ and $R_6$ are Cl and $R_4$ and $R_7$ are hydrogen. In another embodiment, $R_5$ and $R_7$ are Cl and $R_4$ and $R_6$ are hydrogen. In still another embodiment, $R_6$ and $R_7$ are Cl and $R_4$ and $R_5$ are hydrogen.

In some embodiments, each of $R_4$, $R_5$, $R_6$ and $R_7$ is hydrogen.

Exemplary compounds of the present disclosure are shown in Table 1.

TABLE 1
Representative Indole Compounds
| ARI-# | Structural Formula | ¹H NMR Data | Mass Characterization |
|---|---|---|---|
| 001 | 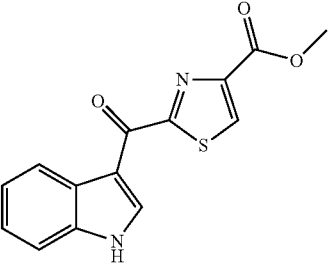 [SMILES: COC(=O)c1csc(C(=O)c2c[nH]c3ccccc23)n1] | | |
| 002 | 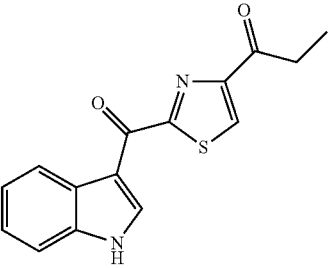 | | |
| 003 | 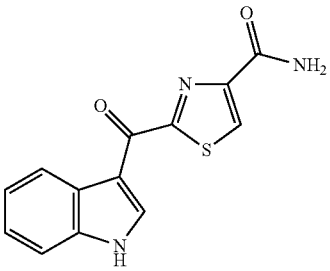 [SMILES: NC(=O)c1csc(C(=O)c2c[nH]c3ccccc23)n1] | | |
| 004 | 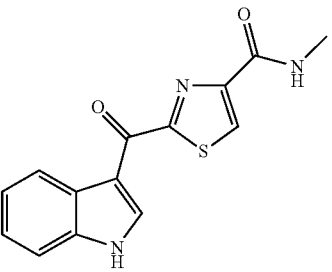 [SMILES: CNC(=O)c1csc(C(=O)c2c[nH]c3ccccc23)n1] | | |
| 005 | 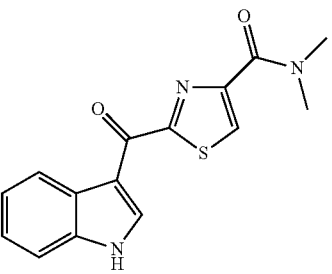 [SMILES: CN(C)C(=O)c1csc(C(=O)c2c[nH]c3ccccc23)n1] | | |

TABLE 1-continued

Representative Indole Compounds

| ARI-# | Structural Formula | $^1$H NMR Data | Mass Characterization |
|---|---|---|---|
| 006 | 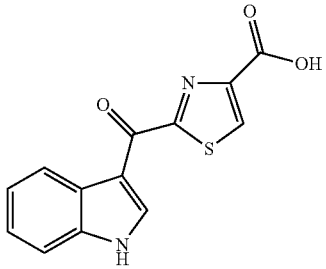 [SMILES: O=C(O)c1csc(C(=O)c2c[nH]c3ccccc23)n1] | | |
| 007 | 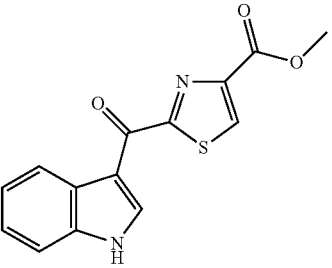 | $^1$H NMR (500 MHz, DMSO-$d_6$) δ 12.81 (s, 1H), 9.12 (s, 1H), 8.89-8.64 (m, 1H), 8.77 (s, 1H), 7.62-7.59 (m, 1H), 7.38-7.35 (m, 2H), 3.90 (s, 3H). | ESI MS m/z 303 [M + H]$^+$ |
| 008 | 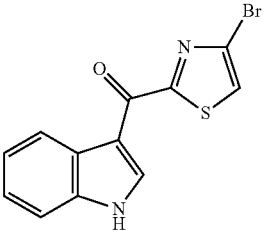 [SMILES: O=C(c1nc(Br)cs1)c1c[nH]c2ccccc12] | 1H NMR (500 MHz, DMSO-$d_6$) δ 12.32 (s, 1H), 8.99 (d, J = 3.5 Hz, 1H), 8.30-8.28 (m, 2H), 7.60-7.57 (m, 1H), 7.32-7.28 (m, 2H). | ESI MS m/z 307 [M + H]$^+$ |
| 009 | 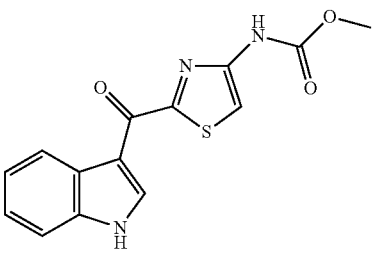 [SMILES: COC(=O)Nc1csc(C(=O)c2c[nH]c3ccccc23)n1] | $^1$H NMR (500 MHz, DMSO-$d_6$) δ 12.81 (s, 1H), 10.77 (s, 1H), 9.15 (s, 1H), 8.31 (dd, J = 6.5, 2.0 Hz, 1H), 7.60 (s, 1H), 7.55 (dd, J = 6.0, 1.5 Hz, 1H), 7.30-7.55 (m, 2H), 3.73 (s, 3H). | ESI MS m/z 302 [M + H]$^+$ |
| 011 | 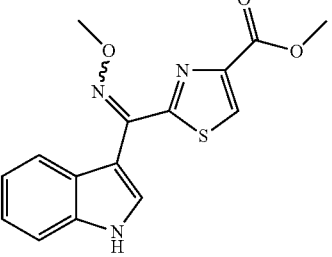 | $^1$H NMR (500 MHz, CDCl$_3$, 1.4:1 mixture of oxime (E), (Z)-isomers) δ 8.77 (s, 1H), 8.51 (d, J = 3.0 Hz, 0.7H), 8.45 (s, 0.7H), 8.39 (s, 0.7H), 8.35-8.34 (m, 0.7H), 8.21 (s, 1H), 7.82 (d, J = 2.5 Hz, 1H), 7.47-7.38 (m, 1.7H), 7.32-7.30 (m, 1H), 7.24-7.20 (m, 1.4H), 7.17-7.14 (m, 1H), 7.11-7.08 (m, 1H), 4.29 (s, 2.1H), 4.13 (s, 3H), 3.97 (s, 2.1H), 3.89 (s, 3H). | ESI MS m/z 316 [M + H]$^+$ |

TABLE 1-continued

Representative Indole Compounds

| ARI-# | Structural Formula | ¹H NMR Data | Mass Characterization |
|---|---|---|---|
| 013 | | ¹H NMR (500 MHz, DMSO-d$_6$) δ 12.43 (s, 1H), 9.12 (d, J = 3.0 Hz, 1H), 8.86 (s, 1H), 8.33-8.31 (m, 1H), 7.61-7.59 (m, 1H), 7.33-7.30 (m, 2H), 2.48 (s, 3H). | ESI MS m/z 303 [M + H]$^+$ |
| 014 | | ¹H NMR (500 MHz DMSO-d$_6$, 3.8:1 mixture of oxime (E), (Z)-isomers) δ 12.81 (s, 1 H), 12.06 (s, 0.26H), 11.68 (s, 0.26H), 11.47 (s, 1H), 8.77 (s, 1H), 8.56 (s, 0.26 H), 8.40 (d, J = 3.0 Hz, 1H), 8.14 (d, J= 8.0 Hz, 1H), 7.87 (d, J = 2.5 Hz, 0.26H), 7.46-7.44 (m, 1.26 H), 7.29 (d, J = 8.0 Hz, 0.26H), 7.18-7.08 (m, 2.26H), 7.00 (t, J = 8.0 Hz, 0.26H), 3.89 (s, 3H), 3.80 (s, 0.82H). | ESI MS m/z 302 [M + H]$^+$ |
| 015 | | ¹H NMR (500 MHz, CDCl$_3$) δ 9.07 (s, 1H), 8.53-8.51 (m, 1H), 8.40 (s, 1H), 7.42-7.36 (m, 3H), 3.04 (s, 3H), 3.94 (s, 3H). | ESI MS m/z 301 [M + H]$^+$ |
| 016 | | ¹H NMR (500 MHz, CDCl$_3$) δ 8.76 (d, J = 3.0 Hz, 1H), 8.70 (s, 1H), 8.44-8.43 (m, 1H), 7.43-7.42 (m, 1H), 7.34-7.32 (m, 2H), 5.0 (s, 1H), 3.85 (s, 3H), 1.79 (s, 3H), 1.4 (s, 3H). | ESI MS m/z 317 [M + H]$^+$ |
| 017 | | ¹H NMR (500 MHz, CDCl$_3$, 2.3:1 mixture of (E) , (Z)-isomers) δ 8.32, 8.29 (s, 1.26 H), 8.16 (s, 1H), 7.94 (s, 0.4 H), 7.85 (s, 0.4 H), 7.60-7.57 (m, 2H), 7.43-7.36 (m, 2.5H), 7.24-7.17 (m, 1.7H), 7.12-7.08 (m, 1.48H), 6.98 (s, 1 H), 4.02 (s, 3H), 1.29 (s, 1.29 H), 3.88 (s, 4.28 H). | ESI MS m/z 315 [M + H]$^+$ |

TABLE 1-continued

Representative Indole Compounds

| ARI-# | Structural Formula | ¹H NMR Data | Mass Characterization |
|-------|--------------------|-------------|------------------------|
| 018 | | ¹H NMR (500 MHz, CDCl₃, 1.8:1 mixture of (E), (Z)-isomers) δ 8.34 (bs, 0.89 H), 8.17-7.16 (m, 1 H), 8.01 (s, 0.94 H), 7.50-7.44 (m, 1.86 H), 7.40-7.28 (m, 4.10 H), 7.25-7.17 (m, 2.37H), 7.13-7.08 (m, 1.61H), 6.40 (q, J = 7.0 Hz, 0.52H), 3.97 (s, 1.67H), 3.96 (s, 3H), 2.19 (d, J = 7.0 Hz, 1.68 H), 1.80 (d, J = 7.0 Hz, 3.0H). | ESI MS m/z 299 [M + H]⁺ |
| 019 | | ¹H NMR (500 MHz, CDCl₃, key protons reported) δ 8.30 (bs, 1H, indole NH), 6.26 (d, J = 0.8 Hz, 1H, olefin), 5.83 (bs, 1H, olefin), 3.96 (s, 3H, methyl ester). | ESI MS m/z 285 [M + H]⁺ |
| 020 | | ¹H NMR (500 MHz, CDCl₃) δ 8.23 (s, 1H), 8.01 (s, 1H), 7.41-7.39 (m, 1H), 7.34-7.32 (m, 1H), 7.22-7.19 (m, 1H), 7.17 (d, J = 2.5 Hz, 1H), 7.10-7.07, (m, 1H), 3.95 (s, 3H), 2.37 (s, 3H), 1.83 (s, 3H). | ESI MS m/z 313 [M + H]⁺ |
| 021 | | ¹H NMR (500 MHz, DMSO-d₆) δ 12.40 (s, 1H), 11.43 (s, 1H), 9.11 (s, 1H), 8.32-8.30 (m, 1H), 7.91 (s, 1H), 7.57-7.55 (m, 1H), 7.31-7.26 (m, 2H), 2.12 (s, 3H). | ESI MS m/z 284 [M − H]⁻ |
| 022 | | ¹H NMR (500 MHz, DMSO-d₆) δ 12.38 (s, 1H), 9.10 (s, 1H), 8.87 (s, 1H), 8.32-8.30 (m, 1H), 7.60-7.58 (m, 1H), 7.32-7.29 (m, 2H), 4.61 (t, J = 5.0 Hz, 1H), 4.40 (app t, J = 6.5 Hz, 2H), 3.58 (app q, J = 6.1, Hz, 2H), 1.90 (quint, J = 6.4 Hz, 2H). | ESI MS m/z 331 [M + H]⁺ |

TABLE 1-continued

Representative Indole Compounds

| ARI-# | Structural Formula | $^1$H NMR Data | Mass Characterization |
|---|---|---|---|
| 023 | | $^1$H NMR (500 MHz, DMSO-$d_6$) δ 12.30 (s, 1H), 9.11 (s, 1H), 8.89 (s, 1H), 8.32-8.30 (m, 1H), 7.60-7.58 (m, 1H), 7.32-7.28 (m, 2H), 4.96 (t, J = 5.0 Hz, 1H), 4.36 (app t, J = 6.0 Hz, 2H), 3.73 (app q, J = 5.5, Hz, 2H). | ESI MS m/z 317 [M + H]$^+$ |
| 024 | | $^1$H NMR (500 MHz, DMSO-$d_6$) δ 11.20 (s, 1H), 8.51 (s, 1H), 7.45 (d, J = 2.5 Hz, 1H), 7.40 (d, J = 8.0 Hz, 1H), 7.37 (d, J = 8.0 Hz, 1H), 7.09-7.06 (m, 1H), 6.95-6.92 (m, 1H), 5.89 (s, 1H), 3.76 (s, 3H), 3.34 (s, 3H). | ESI MS m/z 303 [M + H]$^+$<br>ESI MS m/z 271 [M + H − CH$_3$OH]$^+$ |
| 025 | | $^1$H NMR (500 MHz, CDCl$_3$) δ 9.35 (d, J = 1.5 Hz, 1H), 9.11 (s, 1H), 8.52 (d, J = 2 Hz, 1H), 8.45 (s, 1H), 7.46 (dd, J = 7, 1.5 Hz, 1H), 7.37-7.31 (m, 2H), 4.58-4.57 (m, 2H), 3.91-3.89 (m, 2H), 3.85 (app dd, J = 4.0, 2.0 Hz, 2H), 3.74 (app dd, J = 6.0, 3.0 Hz, 2H). | ESI MS m/z 361 [M + H]$^+$ |
| 026 | | $^1$H NMR (500 MHz, DMSO-$d_6$) δ 12.39 (s, 1H), 9.18 (s, 1H), 9.03 (d, J = 3 Hz, 1H), 8.29-8.28 (m, 1H), 7.60-7.58 (m, 1H), 7.33-7.27 (m, 2H). | ESI MS m/z 254 [M + H]$^+$ |
| 028 | | $^1$H NMR (500 MHz, CDCl$_3$) δ 9.17 (1, J = 3.0 Hz, 1H), 8.74 (s, 1H), 8.53 (dd, J = 8.5, 1.5 Hz, 1H), 7.73 (s, 1H), 7.46-7.44 (m, 1H), 7.37-7.30 (m, 2H), 6.11 (s, 1H), 4.20-4.10 (m, 4H). | ESI MS m/z 301 [M + H]$^+$ |

TABLE 1-continued

Representative Indole Compounds

| ARI-# | Structural Formula | ¹H NMR Data | Mass Characterization |
|---|---|---|---|
| 029 | | ¹H NMR (500 MHz, DMSO-$d_6$) δ 12.26 (s, 1H), 9.04 (s, 1H), 8.32-8.30 (m, 1H), 8.03 (s, 1H), 7.58-7.57 (m, 1H), 7.31-7.25 (m, 2H), 5.68 (d, J = 1.0 Hz, 1H), 3.34 (s, 3H), 3.31 (s, 3H). | ESI MS m/z 303 [M + H]$^+$ |
| 030 | | ¹H NMR (500 Hz, DMSO-$d_6$) δ 12.35 (s, 1H), 9.14 (s, 1H), 8.78 (s, 1H), 8.34-8.31 (m, 1H), 7.61-7.59 (m, 1H), 7.33-7.28 (m, 2H), 2.72 (s, 3H). | ESI MS m/z 309 [M − H]$^-$ |
| 031 | | ¹H NMR (500 MHz, DMSO-$d_6$) δ 12.36 (s, 1H), 9.14 (s, 1H), 9.10 (s, 1H), 8.33-8.31 (m, 1H), 7.62-7.60 (m, 1H), 7.33-7.29 (m, 2H), 2.48 (s, 3H). | ESI MS m/z 309 [M − H]$^-$ |
| 032 | | ¹H NMR (500 MHz, DMSO-$d_6$) δ 12.20 (s, 1H), 9.11 (s, 1H), 8.43-8.39 (m, 1H), 8.30-8.22 (m, 3H), 7.56-7.52 (m, 1H), 7.29-7.26 (m, 2H), 3.98 (s, 3H). | ESI MS m/z 279 [M − H]$^-$ |
| 033 | | ¹H NMR (500 MHz, DMSO-$d_6$) δ 12.35 (s, 1H), 9.43 (d, J = 3.0 Hz, 1H), 8.79 (t, J = 5.5 Hz, 1H), 8.59 (s, 1H), 8.35-8.31 (m, 1H), 7.59-7.55 (m, 1H), 7.32-7.26 (m, 2H), 3.41-3.36 (m, 2H), 1.19 (t, J = 7.0 Hz, 3H). | ESI MS m/z 300 [M + H]$^+$ |

TABLE 1-continued

Representative Indole Compounds

| ARI-# | Structural Formula | $^1$H NMR Data | Mass Characterization |
|---|---|---|---|
| 034 | 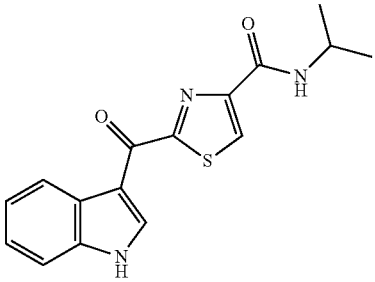 [SMILES: CC(C)NC(=O)c1csc(C(=O)c2c[nH]c3ccccc23)n1] | $^1$H NMR (500 MHz, DMSO-$d_6$) δ 12.42 (s, 1H), 9.38 (s, 1H), 8.59 (s, 1H), 8.42 (d, J = 3.0 Hz, 1H), 8.34-8.30 (m, 1H), 7.57-7.54 (m, 1H), 7.31-7.26 (m, 2H), 4.21-4.14 (m, 1H), 1.26 (s, 3H), 1.25 (s, 3H). | ESI MS m/z 314 [M + H]$^+$ |
| 035 | 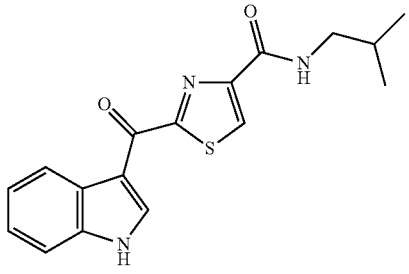 [SMILES: CC(C)CNC(=O)c1csc(C(=O)c2c[nH]c3ccccc23)n1] | $^1$H NMR (500 MHz, DMSO-$d_6$) δ 12.36 (s, 1H), 9.41 (s, 1H), 8.73 (t, J = 6.0 Hz, 1H), 8.59 (s, 1H), 8.33-8.31 (m, 1H), 7.57-7.56 (m, 1H), 7.32-7.28 (m, 2H), 3.18 (t, J = 6.5 Hz, 2H), 1.96-1.90 (m, 1H), 0.93 (s, 3H), 0.92 (s, 3H). | ESI MS m/z 328 [M + H]$^+$ |
| 036 | 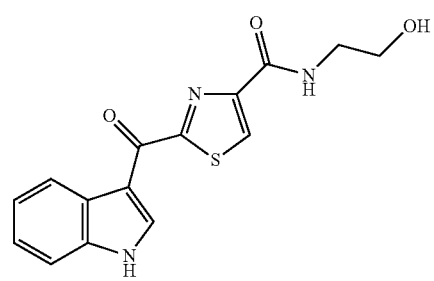 [SMILES: O=C(NCCO)c1csc(C(=O)c2c[nH]c3ccccc23)n1] | $^1$H NMR (500 MHz, DMSO-$d_6$) δ 12.36 (s, 1H), 9.40 (s, 1H), 8.69 (t, J = 5.5 Hz, 1H), 8.61 (s, 1H), 8.33-8.31 (m, 1H), 7.58-7.56 (m, 1H), 7.32-7.26 (m, 2H), 4.81 (t, J = 5.5 Hz, 1H), 3.58 (dd, J = 12.0, 6.5 Hz, 2H), 3.43 (dd, J = 12.0, 6.0 Hz, 2H). | ESI MS m/z 316 [M + H]$^+$ |
| 037 | 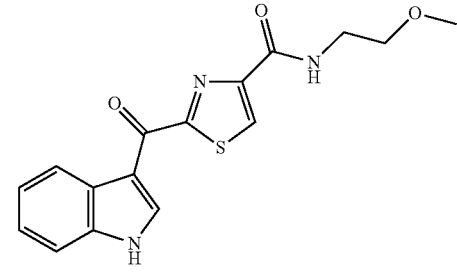 [SMILES: COCCNC(=O)c1csc(C(=O)c2c[nH]c3ccccc23)n1] | $^1$H NMR (500 MHz, DMSO-$d_6$) δ 12.36 (s, 1H), 9.40 (s, 1H), 8.76 (bs, 1H), 8.61 (s, 1H), 8.33-8.31 (m, 1H), 7.58-7.55 (m, 1H), 7.32-7.26 (m, 2H), 3.52-3.51 (m, 4H), 3.30 (s, 3H). | ESI MS m/z 330 [M + H]$^+$ |
| 038 | 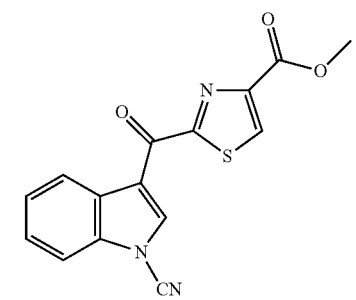 [SMILES: COC(=O)c1csc(C(=O)c2cn(C#N)c3ccccc23)n1] | $^1$H NMR (500 MHz, DMSO-$d_6$) δ 9.32 (s, 1H), 9.01 (s, 1H), 8.38 (d, J = 7.0 Hz, 1H), 7.81 (d, J = 8.0 Hz, 1H), 7.63-7.55 (m, 2H), 3.94 (s, 3H). | ESI MS m/z 312 [M + H]$^+$ |

TABLE 1-continued

Representative Indole Compounds

| ARI-# | Structural Formula | ¹H NMR Data | Mass Characterization |
|---|---|---|---|
| 039 | | ¹H NMR (500 MHz, DMSO-d$_6$) δ 12.44 (s, 1H), 9.28 (d, J = 3.0 Hz, 1H), 8.57 (s, 1H), 8.32-8.29 (m, 1H), 7.81 (bs, 1H), 7.57-7.53 (m, 1H), 7.31-7.26 (m, 2H), 1.46 (s, 9H). | ESI MS m/z 328 [M + H]$^+$ |
| 040 | | ¹H NMR (500 MHz, DMSO-d$_6$) δ 12.32 (s, 1H), 8.97 (s, 1H), 8.32-8.30 (m, 1H), 8.07 (s, 1H), 7.58-7.56 (m, 1H), 7.31-7.27 (m, 2H), 2.88 (s, 4H). | ESI MS m/z 324 [M − H]$^-$ |
| 041 | | ¹H NMR (400 MHz, DMSO-d$_6$) δ 12.38 (s, 1H), 9.10 (s, 1H), 8.87 (s, 1H), 8.30-8.35 (m, 1H), 7.55-7.62 (m, 1H), 7.28-7.33 (m, 2H), 4.39 (q, J = 7.2 Hz, 2H), 1.37 (t, J = 7.2 Hz, 3H). | ESI MS m/z 301 [M + H]$^+$ |
| 042 | | ¹H NMR (400 MHz, DMSO-d$_6$) δ 12.38 (s, 1H), 9.10 (s, 1H), 8.83 (s, 1H), 8.30-8.33 (m, 1H), 7.57-7.61 (m, 1H), 7.26-7.34 (m, 2H), 5.15-5.24 (m, 1H), 1.23 (s, 6H). | ESI MS m/z 315 [M + H]$^+$ |
| 043 | | ¹H NMR (400 MHz, DMSO-d$_6$) δ 12.41 (s, 1H), 9.11 (s, 1H), 8.89 (s, 1H), 8.30-8.33 (m, 1H), 7.57-7.62 (m, 1H), 7.28-7.35 (m, 2H), 4.30 (t, J = 6.4 Hz, 2H), 1.72-1.80 (m, 2H), 1.0 (t, J = 7.2 Hz, 3H). | ESI MS m/z 315 [M + H]$^+$ |

TABLE 1-continued

Representative Indole Compounds

| ARI-# | Structural Formula | ¹H NMR Data | Mass Characterization |
|---|---|---|---|
| 044 | | ¹H NMR (500 MHz, DMSO-d$_6$) δ 12.30 (s, 1H), 9.00 (d, J = 3.5 Hz, 1H), 8.65 (s, 1H), 8.31-8.29 (m, 1H), 7.58-7.55 (m, 1H), 7.32-7.26 (m, 2H), 4.73 (d, J = 7.5 Hz, 2H), 4.12 (d, J = 7.5 Hz, 2H), 2.38-2.31 (m, 2H). | ESI MS m/z 312 [M + H]$^+$ |
| 045 | | ¹H NMR (500 MHz, DMSO-d$_6$) δ 12.36 (s, 1H), 8.99 (d, J = 3.5 Hz, 1H), 8.66 (s, 1H), 8.31-8.29 (m, 1H), 7.58-7.56 (m, 1H), 7.32-7.30 (m, 2H), 5.82 (d, J = 7.0 Hz, 1H), 4.92-4.89 (m, 1H), 4.60-4.5 (m, 1H), 4.43-4.40 (m, 1H), 4.34-4.31 (m, 1H), 3.85 (dd, J = 10.5, 3.5 Hz, 1H). | ESI MS m/z 328 [M + H]$^+$ |
| 046 | | ¹H NMR (500 MHz, DMSO-d$_6$) δ 12.34 (s, 1H), 9.00 (d, J = 3.0 Hz, 1H), 8.68 (s, 1H), 8.31-8.28 (m, 1H), 7.59-7.56 (m, 1H), 7.32-7.28 (m, 2H), 4.90-4.87 (m, 1H), 4.51 (dd, J = 10.0, 2.5 Hz, 1H), 4.34-4.28 (m, 2H), 3.94-3.90 (m, 1H), 3.28 (s, 3H). | ESI MS m/z 342 [M + H]$^+$ |
| 047 | | ¹H NMR (500 MHz, DMSO-d$_6$) δ 12.14 (s, 1H), 8.63 (q, J = 4.5 Hz, 1H), 8.57 (d, J = 3.0 Hz, 1H), 8.38-8.35 (m, 1H), 8.22-8.17 (m, 2H), 8.11 (dd, J = 7.0, 2.5 Hz, 1H), 7.55-7.52 (m, 1H), 7.29-7.25 (m, 2H), 2.87 (d, J = 4.5 Hz, 3H). | ESI MS m/z 280 [M + H]$^+$ |
| 048 | | ¹H NMR (400 MHz, DMSO-d$_6$) δ 12.35 (bs, 1H), 9.12 (s, 1H), 8.88 (s, 1H), 8.30-8.35 (m, 1H), 7.57-7.62 (m, 1H), 7.27-7.35 (m, 2H), 3.80-3.88 (m, 1H), 1.22 (d, J = 6.8 Hz, 6H). | ESI MS m/z 299 [M + H]$^+$ |

TABLE 1-continued

Representative Indole Compounds

| ARI-# | Structural Formula | ¹H NMR Data | Mass Characterization |
|---|---|---|---|
| 049 | | ¹H NMR (400 MHz, DMSO-$d_6$) δ 12.52 (bs, 1H), 9.50 (s, 1H), 8.74 (bs, 1H), 8.62 (s, 1H), 8.30 (d, J = 2.0 Hz, 1H), 7.60 (d, J = 8.8 Hz, 1H), 7.30-7.35 (m, 2H), 2.87 (d, J = 4.8 Hz, 3H). | ESI MS m/z 318 [M − H]⁻ |
| 050 | | ¹H NMR (500 MHz, DMSO-$d_6$) δ 14.42 (s, 1H), 13.88 (s, 1H), 9.47-9.18 (m, 1H), 8.51 (bs, 1H), 8.36 (dd, J = 7.0, 1.0 Hz, 1H), 7.67 (d, J = 7.5 Hz, 1H), 7.38-7.34 (m, 2H), 4.02 (s, 3H), 2.41 (s, 2H). | ESI MS m/z 324 [M + H]⁺ |
| 052 | | ¹H NMR (500 MHz, CDCl$_3$) δ 9.20 (d, J = 3.5 Hz, 1H), 8.71 (bs, 1H), 8.53 (dd, J = 7.0, 2.0 Hz, 1H), 7.79 (s, 1H), 7.48-7.46 (m, 1H), 7.38-7.32 (m, 2H), 3.27 (s, 1H). | ESI MS m/z 253 [M + H]⁺ |
| 053 | | ¹H NMR (500 MHz, DMSO-$d_6$) δ 14.37 (s, 1H), 8.95 (s, 1H), 8.30 (d, J = 8.5 Hz, 1H), 7.78 (d, J = 8.5, Hz, 1H), 7.55 (dt, J = 6.0, 1.0 Hz, 1H), 7.43 (dt, J = 8.0, 0.5 Hz, 1H), 3.91 (s, 3H). | ESI MS m/z 288 [M + H]⁺ |
| 054 | | ¹H NMR (400 MHz, DMSO-$d_6$) δ 12.32 (bs, 1H), 9.07 (s, 1H), 8.31-8.34 (m, 2H), 7.56-7.59 (m, 1H), 7.27-7.31 (m, 1H), 3.97 (s, 3H), 2.90 (q, J = 7.6 Hz, 2H), 1.14-1.25 (m, 3H). | ESI MS m/z 314 [M + H]⁺ |

TABLE 1-continued

Representative Indole Compounds

| ARI-# | Structural Formula | ¹H NMR Data | Mass Characterization |
|---|---|---|---|
| 055 | | ¹H NMR (400 MHz, DMSO-d$_6$) δ 12.52 (s, 1H), 9.12 (s, 1H), 8.92 (s, 1H), 8.28 (d, J = 2.0 Hz, 1H), 7.63 (d, J = 8.4 Hz, 1H), 7.32-7.36 (m, 1H), 3.94 (s, 3H). | ESI MS m/z 319 [M − H]⁻ |
| 056 | | ¹H NMR (500 MHz, DMSO-d$_6$) δ 12.39 (s, 1H), 9.45 (s, 1H), 9.14 (d, J = 3.5 Hz, 1H), 8.96 (s, 1H), 8.33-8.32 (m, 1H), 7.62-7.59 (m, 1H), 7.34-7.28 (m, 2H). | ESI MS m/z 297 [M + H]⁺ |
| 057 | | ¹H NMR (400 MHz, DMSO-d$_6$) δ 12.58 (bs, 1H), 9.49 (d, J = 3.2 Hz, 1H), 8.70-8.74 (m, 1H), 8.62-8.85 (m, 2H), 7.95 (s, 1H), 2.87-2.89 (s, 3H). | ESI MS m/z 440 [M − H]⁻ |
| 058 | | ¹H NMR (400 MHz, DMSO-d$_6$) δ 13.46 (bs, 1H), 12.76 (s, 1H), 9.17 (s, 1H), 8.83 (s, 1H), 8.28 (d, J = 2.0 Hz, 1H), 7.64 (d, J = 8.4 Hz, 1H), 7.31-7.35 (m, 1H). | ESI MS m/z 305 [M − H]⁻ |
| 059 | | ¹H NMR (400 MHz, DMSO-d$_6$) δ 12.40 (bs, 1H), 9.12 (s, 1H), 8.76 (s, 1H), 8.30-8.33 (m, 1H), 7.58-7.61 (m, 1H), 7.28-7.33 (m, 2H), 1.60 (s, 9H). | ESI MS m/z 329 [M + H]⁺ |

TABLE 1-continued

Representative Indole Compounds

| ARI-# | Structural Formula | $^1$H NMR Data | Mass Characterization |
|---|---|---|---|
| 060 | | $^1$H NMR (500 MHz, DMSO-d$_6$) δ 12.38 (s, 1H), 9.12 (d, J = 3.0 Hz, 1H), 8.87 (s, 1H), 8.34-8.31 (m, 1H), 7.62-7.59 (m, 1H), 7.33-7.28 (m, 2H), 2.64 (s, 3H). | ESI MS m/z 311 [M + H]$^+$ |
| 061 | | $^1$H NMR (500 MHz, DMSO-d$_6$) δ 12.39 (s, 1H), 10.08 (s, 1H), 9.15 (s, 1H), 9.03 (s, 1H), 8.32-8.30 (m, 1H), 7.60-7.58 (m, 1H), 7.33-7.28 (m, 2H). | ESI MS m/z 257 [M + H]$^+$ |
| 062 | | $^1$H NMR (500 MHz, DMSO-d$_6$) δ 15.51, 15.19 (bs, 1H), 12.27 (s, 1H), 9.29 (s, 1H), 8.70, 8.40 (bs, 2H), 8.36-8.32 (m, 1H), 7.60-7.57 (m, 1H), 7.32-7.26 (m, 2H). | ESI MS m/z 296 [M + H]$^+$ |
| 063 | | $^1$H NMR (500 MHz, DMSO-d$_6$) δ 12.34 (s, 1H), 9.31 (d, J = 2.5 Hz, 1H), 8.34-8.30 (m, 1H), 8.20 (bs, 3H), 8.00 (d, J = 0.5 Hz, 1H), 7.57-7.53 (m, 1H), 7.30-7.26 (m, 2H), 4.58 (s, 1H). | ESI MS m/z 302 [M + H]$^+$ |
| 064 | | $^1$H NMR (500 MHz, DMSO-d$_6$) δ 14.46, 13.82 (bs, 1H), 12.40, 12.30 (bs, 1H), 8.57, 8.41 (bs, 1H), 8.33 (br d, J = 8.5 Hz, 1H), 7.59 (br d, J = 6.5 Hz, 1H), 7.32-7.28 (m, 2H), 2.45, 2.36 (s, 3H). | ESI MS m/z 310 [M + H]$^+$ |

TABLE 1-continued

Representative Indole Compounds

| ARI-# | Structural Formula | ¹H NMR Data | Mass Characterization |
|---|---|---|---|
| 065 | | ¹H NMR (400 MHz, DMSO-d$_6$) δ 12.52 (bs, 1H), 9.50 (s, 1H), 8.74 (bs, 1H), 8.62 (s, 1H), 7.98-7.99 (m, 1H), 7.58-7.62 (m, 1H), 7.14-7.20 (m, 1H), 2.89 (d, J = 4.8 Hz, 3H). | ESI MS m/z 304 [M + H]$^+$ |
| 066 | | ¹H NMR (400 MHz, DMSO-d$_6$) δ 12.47 (s, 1H), 9.13 (s, 1H), 8.92 (s, 1H), 7.96-8.00 (m, 1H), 7.61-7.65 (m, 1H), 7.17-7.21 (m, 1H), 3.95 (s, 3H). | ESI MS m/z 303 [M − H]$^-$ |
| 067 | | ¹H NMR (400 MHz, DMSO-d$_6$) δ 12.51 (bs, 1H), 9.19 (s, 1H), 8.86 (s, 1H), 8.29 (d, J = 2.0 Hz, 1H), 7.62 (d, J = 8.4 Hz, 1H), 7.31-7.36 (m, 1H), 3.25 (q, J = 7.2 Hz, 2H), 1.15 (t, J = 7.2 Hz, 3H). | ESI MS m/z 317 [M − H]$^-$ |
| 068 | | ¹H NMR (400 MHz, DMSO-d$_6$) δ 12.25 (bs, 1H), 9.15 (d, J = 2.0 Hz, 1H), 8.30-8.34 (m, 1H), 7.82 (s, 1H), 7.55-7.60 (m, 1H), 7.26-7.30 (m, 2H), 5.47 (d, J = 5.2 Hz, 1H), 4.71-4.77 (m, 1H), 1.90-2.00 (m, 1H), 1.75-1.88 (m, 1H), 0.94 (t, J = 5.4 Hz, 3H). | ESI MS m/z 287 [M + H]$^+$ |
| 069 | | ¹H NMR (400 MHz, DMSO-d$_6$) δ 12.32 (bs, 1H), 9.02 (s, 1H), 8.74 (s, 1H), 8.31-8.33 (m, 1H), 7.56-7.59 (m, 1H), 7.28-7.31 (m, 2H), 3.95 (s, 3H), 3.50-3.55 (m, 1H), 1.25 (d, J = 6.8 Hz, 6H). | ESI MS m/z 326 [M − H]$^-$ |

TABLE 1-continued

Representative Indole Compounds

| ARI-# | Structural Formula | $^1$H NMR Data | Mass Characterization |
|---|---|---|---|
| 070 | (This is the syn or anti isomer of 069) | $^1$H NMR (400 MHz, DMSO-d$_6$) δ 12.36 (bs, 1H), 9.09 (s, 1H), 8.30-8.34 (m, 1H), 8.21 (s, 1H), 7.55-7.60 (m, 1H), 7.26-7.30 (m, 2H), 3.95 (s, 3H), 3.65-3.69 (m, 1H), 1.24-1.32 (m, 6H). | ESI MS m/z 328 [M + H]$^+$ |
| 071 | | $^1$H NMR (500 MHz, DMSO-d$_6$) δ 12.37 (s, 1H), 9.82 (s, 1H), 9.15 (d, J = 3.0 Hz, 1H), 8.85 (s, 1H), 8.35-8.31 (m, 1H), 7.62-7.59 (m, 1H), 7.33-7.28 (m, 2H). | ESI MS m/z 297 [M + H]$^+$ |
| 072 | | $^1$H NMR (500 MHz, DMSO-d$_6$) δ 12.07 (s, 1H), 9.28 (d, J = 2.0 Hz, 1H), 8.94 (d, J = 3.0 Hz, 1H), 8.51 (d, J = 2.5 Hz, 1H), 8.38-8.36 (m, 1H), 7.54-7.52 (m, 1H), 7.27-7.22 (m, 2H). | ESI MS m/z 229 [M + H]$^+$ |
| 073 | | $^1$H NMR (500 MHz, DMSO-d$_6$) δ 12.06 (s, 1H), 8.26-8.24 (m, 1H), 7.93 (s, 1H), 7.79-7.77 (m, 2H), 7.62-7.59 (m, 1H), 7.55-7.51 (m, 3H), 7.28-7.22 (m, 2H). | ESI MS m/z 222 [M + H]$^+$ |
| 074 | | $^1$H NMR (500 MHz, DMSO-d$_6$) δ 12.02 (s, 1H), 8.24 (dd, J = 6.5, 1.5 Hz, 1H), 7.92 (d, J = 3.0 Hz, 1H), 7.58-7.56 (m, 2H), 7.52-7.50 (m, 1H), 7.42-7.41 (m, 2H), 7.27-7.21 (m, 2H), 2.41 (s, 3H). | ESI MS m/z 236 [M + H]$^+$ |

TABLE 1-continued

Representative Indole Compounds

| ARI-# | Structural Formula | $^1$H NMR Data | Mass Characterization |
|---|---|---|---|
| 075 | 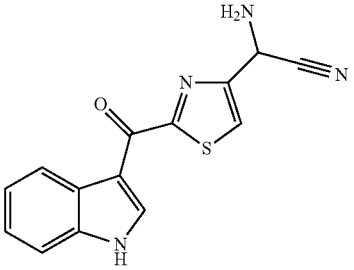 [SMILES: N#CC(N)c1csc(C(=O)c2c[nH]c3ccccc23)n1] | $^1$H NMR (500 MHz, DMSO-$d_6$) δ 12.34 (s, 1H), 9.16 (s, 1H), 8.37-8.30 (m, 1H), 7.92 (d, J = 1.0 Hz, 1H), 7.58-7.55 (m, 1H), 7.31-7.27 (m, 2H), 5.35 (t, J = 8.0 Hz, 1H), 3.04 (d, J = 8.0 Hz, 2H). | ESI MS m/z 283 [M + H]$^+$ |
| 076 | 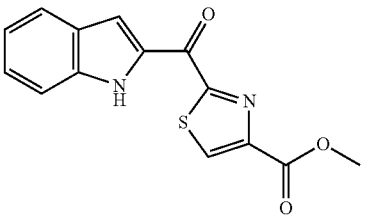 [SMILES: COC(=O)c1csc(C(=O)c2cc3ccccc3[nH]2)n1] | $^1$H NMR (400 MHz, DMSO-$d_6$) δ 12.18 (s, 1H), 9.00 (s, 1H), 8.22 (d, J = 1.2 Hz, 1H), 7.84 (d, J = 8.0 Hz, 1H), 7.50-7.53 (m, 1H), 7.37-7.40 (m, 1H), 7.13-7.16 (m, 1H), 3.95 (s, 3H). | ESI MS m/z 287 [M + H]$^+$ |
| 077 | 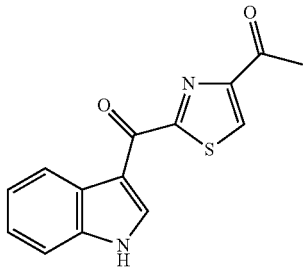 [SMILES: CC(=O)c1csc(C(=O)c2c[nH]c3ccccc23)n1] | $^1$H NMR (400 MHz, DMSO-$d_6$) δ 12.35 (bs, 1H), 9.18 (s, 1H), 8.86 (s, 1H), 8.31-8.34 (m, 1H), 7.58-7.61 (m, 1H), 7.27-7.34 (m, 2H), 2.74 (s, 3H). | ESI MS m/z 270.4 [M + H]$^+$ |
| 078 | 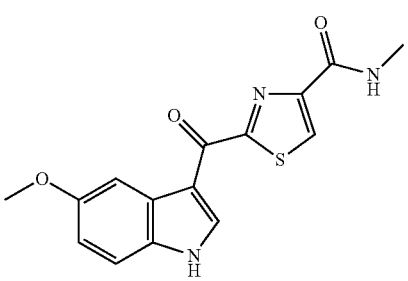 | $^1$H NMR (400 MHz, DMSO-$d_6$) δ 12.25 (bs, 1H), 9.39 (s, 1H), 8.71-8.73 (m, 1H), 8.58 (s, 1H), 7.85 (d, J = 2.4 Hz, 1H), 7.47 (d, J = 8.8 Hz, 1H), 6.91-6.95 (m, 1H), 3.83 (s, 3H), 2.89 (d, J = 4.8 Hz, 3H). | ESI MS m/z 316 [M + H]$^+$ |
| 079 | 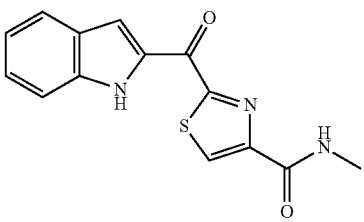 [SMILES: CNC(=O)c1csc(C(=O)c2cc3ccccc3[nH]2)n1] | $^1$H NMR (400 MHz, DMSO-$d_6$) δ 12.08 (bs, 1H), 8.72-8.80 (m, 1H), 8.72 (s, 1H), 8.47 (s, 1H), 7.81 (d, J = 8.0 Hz, 1H), 7.54 (d, J = 8.4 Hz, 1H), 7.35-7.40 (m, 1H), 7.13-7.18 (m, 1H), 2.92 (d, J = 4.8 Hz, 3H). | ESI MS m/z 286 [M + H]$^+$ |

TABLE 1-continued

Representative Indole Compounds

| ARI-# | Structural Formula | ¹H NMR Data | Mass Characterization |
|---|---|---|---|
| 080 | | ¹H NMR (400 MHz, DMSO-$d_6$) δ 12.26 (bs, 1H), 9.03 (s, 1H), 8.88 (s, 1H), 7.83 (d, J = 2.4 Hz, 1H), 7.49 (d, J = 5.6 Hz, 1H), 6.91-6.95 (m, 1H), 3.92 (s, 3H), 3.83 (s, 3H). | ESI MS m/z 317 [M + H]$^+$ |
| 081 | | ¹H NMR (500 MHz, DMSO-$d_6$) δ 12.08 (s, 1H), 8.81 (d, J = 3.0 Hz, 1H), 8.76-8.75 (m, 1H), 8.39-8.37 (m, 1H), 8.04-8.02 (m, 2H), 7.64-7.11 (m, 1H), 7.54-7.51 (m, 1H), 7.27-7.23 (m, 2H). | ESI MS m/z 223 [M + H]$^+$ |
| 082 | | ¹H NMR (500 MHz, DMSO-$d_6$) δ 12.13 (s, 1H), 8.29 (t, J = 1.5 Hz, 1H), 8.24 (dd, J = 8.5, 1.5 Hz, 1H), 8.17 (dt, J = 8.0, 1.5 Hz, 1H), 8.06 (dt, J = 8.0, 1.5 Hz, 1H), 7.98 (d, J = 3.0 Hz, 1H), 7.70 (t, J = 8.0 Hz, 1H), 7.54-7.53 (m, 1H), 7.30-7.24 (m, 2H), 3.89 (s, 3H). | ESI MS m/z 280 [M + H]$^+$ |
| 083 | | ¹H NMR (500 MHz, DMSO-$d_6$) δ 12.39 (s, 1H), 9.08 (s, 1H), 8.54 (s, 1H), 8.33-8.31 (m, 1H), 7.61-7.59 (m, 1H), 7.41 (bs, 2H), 7.33-7.28 (m, 2H). | ESI MS m/z 312 [M + H]$^+$ |
| 085 | | ¹H NMR (400 MHz, DMSO-$d_6$) δ 12.30 (bs, 1H), 9.40-9.44 (m, 2H), 8.59 (s, 1H), 8.32-8.35 (m, 1H), 7.56-7.60 (m, 1H), 7.29-7.32 (m, 2H). | ESI MS m/z 249 [M + H]$^+$ |

TABLE 1-continued

Representative Indole Compounds

| ARI-# | Structural Formula | ¹H NMR Data | Mass Characterization |
|---|---|---|---|
| 086 | | ¹H NMR (400 MHz, DMSO-d$_6$) δ 12.34 (bs, 1H), 9.58 (d, J = 1.6 Hz, 1H), 8.80 (s, 1H), 8.41 (s, 1H), 8.33-8.35 (m, 1H), 7.55-7.58 (m, 1H), 7.28-7.32 (m, 2H), 3.97 (s, 3H). | ESI MS m/z 280 [M − H]$^−$ |
| 087 | | ¹H NMR (400 MHz, DMSO-d$_6$) δ 12.42 (bs, 1H), 9.20 (s, 1H), 8.86 (s, 1H), 7.97-8.00 (m, 1H), 7.60-7.63 (m, 1H), 7.16-7.19 (m, 1H), 3.24 (q, J = 7.2 Hz, 2H), 1.15 (t, J = 7.2 Hz, 3H). | ESI MS m/z 303 [M + H]$^+$ |
| 088 | | ¹H NMR (500 MHz, DMSO-d$_6$) δ 12.32 (s, 1H), 9.09 (s, 1H), 8.30-8.32 (m, 1H), 8.18 (s, 1H), 7.57-7.55 (m, 1H), 7.31-7.25 (m, 2H), 7.15 (d, J = 6.0 Hz, 1H), 5.50 (7, J = 7.0 Hz, 1H). | ESI MS m/z 327 [M + H]$^+$ |
| 089 | | ¹H NMR (500 MHz, CD$_3$OD, partial CD$_3$O-adduct) δ 9.25, 9.17 (s, 1H), 8.39-8.36 (m, 1H), 8.12, 8.07 (s, 1H), 7.51-7.48 (m, 1H), 7.30-7.25 (m, 2H). | As hydrate, ESI MS m/z 343 [M + H + H$_2$O]$^+$ |
| 090 | | ¹H NMR (500 MHz, DMSO-d$_6$) δ 12.38 (bs, 1H), 9.02 (d, J = 3.5 Hz, 1H), 8.53 (s, 1H), 8.34-8.30 (m, 1H), 7.61-7.57 (m, 1H), 7.52 (bs, 2H), 7.33-7.27 (m, 2H). | ESI MS m/z 328 [M + H]$^+$ |

TABLE 1-continued

Representative Indole Compounds

| ARI-# | Structural Formula | $^1$H NMR Data | Mass Characterization |
|---|---|---|---|
| 091 | | $^1$H NMR (500 MHz, DMSO-$d_6$) δ 12.18 (s, 1H), 8.25 (dd, J = 5.0, 1.5 Hz, 1H), 8.18-8.17 (m, 1H), 8.09-8.03 (m, 3H), 7.75 (dt, J = 8.0, 0.5 Hz, 1H), 7.54-7.52 (m, 1H), 7.30-7.24 (m, 2H). | ESI MS m/z 247 [M + H]$^+$ |
| 092 | | $^1$H NMR (400 MHz, DMSO-$d_6$) δ 12.21 (bs, 1H), 9.10 (s, 1H), 8.30-8.34 (m, 1H), 7.82 (s, 1H), 7.55-7.60 (m, 1H), 7.24-7.31 (m, 2H), 5.45 (d, J = 6.8 Hz, 1H), 4.70-7.77 (m, 1H), 1.88-1.95 (m, 1H), 1.75-1.85 (m, 1H), 0.93 (t, J = 6.0 Hz, 3H). | ESI MS m/z 287 [M + H]$^+$ |
| 093 | | $^1$H NMR (400 MHz, DMSO-$d_6$) δ 12.36 (bs, 1H), 9.37 (s, 1H), 9.31 (s, 1H), 8.36 (s, 1H), 8.33-8.37 (m, 1H), 7.55-7.59 (m, 1H), 7.29-7.33 (m, 2H). | ESI MS m/z 248.4 [M + H]$^+$ |
| 094 | | $^1$H NMR (400 MHz, DMSO-$d_6$) δ 12.22 (bs, 1H), 9.10 (s, 1H), 8.30-8.34 (m, 1H), 7.82 (s, 1H), 7.55-7.60 (m, 1H), 7.24-7.31 (m, 2H), 5.45 (d, J = 6.0 Hz, 1H), 4.70-4.77 (m, 1H), 1.88-2.05 (m, 1H), 1.74-1.85 (m, 1H), 0.95 (t, J = 6.0 Hz, 3H). | ESI MS m/z 287 [M + H]$^+$ |
| 095 | | $^1$H NMR (400 MHz, DMSO-$d_6$) δ 12.33 (bs, 1H), 9.34 (d, J = 1.2 Hz, 1H), 9.28 (d, J = 1.2 Hz, 1H), 8.68 (s, 1H), 8.35-8.38 (m, 1H), 7.55-7.58 (m, 1H), 7.29-7.32 (m, 2H). | ESI MS m/z 280 [M − H]$^-$ |

TABLE 1-continued

Representative Indole Compounds

| ARI-# | Structural Formula | ¹H NMR Data | Mass Characterization |
|---|---|---|---|
| 096 | 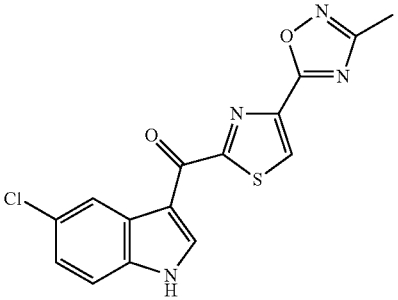 [SMILES: Cc1noc(-c2csc(C(=O)c3c[nH]c4ccc(Cl)cc34)n2)n1] | ¹H NMR (500 MHz, DMSO-d$_6$) δ 12.49 (s, 1H), 9.16 (d, J = 1.5 Hz, 1H), 9.11 (d, J = 2.0 Hz, 1H), 8.29 (m, 1H), 7.65 (d, J = 8.5 Hz, 1H), 7.35-7.33 (m, 1H), 2.48 (s, 3H). | ESI MS m/z 343 [M − H]$^-$ |
| 097 | 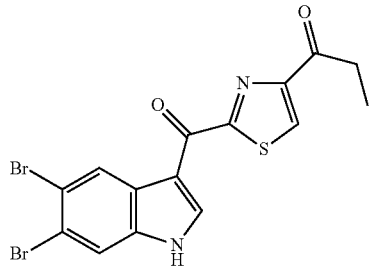 [SMILES: CCC(=O)c1csc(C(=O)c2c[nH]c3cc(Br)c(Br)cc23)n1] | ¹H NMR (400 MHz, DMSO-d$_6$) δ 12.49 (bs, 1H), 9.18 (s, 1H), 8.87 (s, 1H), 8.61 (s, 1H), 8.01 (s, 1H), 3.23-3.26 (m, 2H), 1.13-1.16 (m, 3H). | ESI MS m/z 440 [M + H]$^+$ |
| 099 | 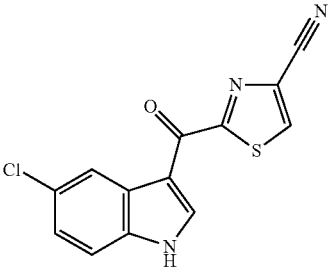 [SMILES: N#Cc1csc(C(=O)c2c[nH]c3ccc(Cl)cc23)n1] | ¹H NMR (500 MHz, DMSO-d$_6$) δ 12.54 (s, 1H), 9.20 (s, 1H), 9.08 (d, J = 3.0 Hz, 1H), 8.26 (d, J = 2.0 Hz, 1H), 7.62 (d, J = 9.0 Hz, 1H), 7.34 (dd, J = 9.0, 5.0 Hz, 1H). | ESI MS m/z 286 [M − H]$^-$ |
| 100 | 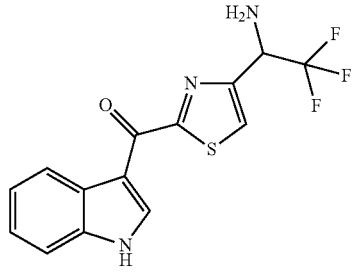 [SMILES: NC(c1csc(C(=O)c2c[nH]c3ccccc23)n1)C(F)(F)F] | ¹H NMR (500 MHz, DMSO-d$_6$) δ 12.27 (s, H), 9.13 (d, J = 3.0 Hz, 1H), 8.32-8.30 (m, 1H), 8.15 (s, 1H), 7.57-7.55 (m, 1H), 7.31-7.55 (m, 2H), 4.86-4.81 (m, 1H), 2.71 (d, J = 8.0 Hz, 2H). | ESI MS m/z 326 [M + H]$^+$ |
| 101 | 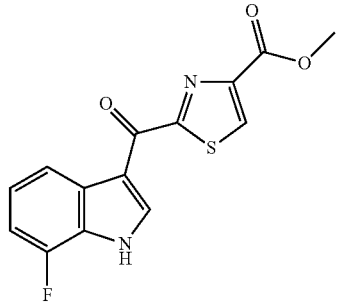 | ¹H NMR (400 MHz, DMSO-d$_6$) δ 12.97 (bs, 1H), 9.11 (s, 1H), 8.92 (s, 1H), 8.12 (d, J = 7.6 Hz, 1H), 7.26-7.30 (m, 1H), 7.15-7.25 (m, 1H), 3.96 (s, 3H). | ESI MS m/z 305 [M + H]$^+$ |

TABLE 1-continued

Representative Indole Compounds

| ARI-# | Structural Formula | $^1$H NMR Data | Mass Characterization |
|---|---|---|---|
| 102 | | $^1$H NMR (400 MHz, DMSO-$d_6$) δ 13.47 (bs, 1H), 12.96 (s, 1H), 9.17 (s, 1H), 8.83 (s, 1H), 8.13 (d, J = 8.0 Hz, 1H), 7.27-7.30 (m, 1H), 7.17-7.20 (m, 1H). | ESI MS m/z 289 [M − H]− |
| 103 | | $^1$H NMR (400 MHz, DMSO-$d_6$) δ 12.29 (bs, 1H), 8.74 (s, 1H), 8.72-8.74 (m, 1H), 8.42 (d, J = 1.2 Hz, 1H), 7.84 (d, J = 2.0 Hz, 1H), 7.56 (d, J = 8.0 Hz, 1H), 7.36-7.40 (m, 1H), 2.92 (d, J = 4.8 Hz, 3H). | ESI MS m/z 320 [M + H]+ |
| 104 | | $^1$H NMR (400 MHz, DMSO-$d_6$) δ 13.05 (bs, 1H), 9.21 (s, 1H), 9.02 (s, 1H), 8.10 (d, J = 8.0 Hz, 1H), 7.26-7.33 (m, 1H), 7.16-7.20 (m, 1H). | ESI MS m/z 270 [M − H]− |
| 105 | | $^1$H NMR (400 MHz, DMSO-$d_6$) δ 13.57 (bs, 1H), 12.27 (s, 1H), 8.92 (s, 1H), 8.23 (s, 1H), 7.65 (m, 1H), 7.51 (m, 1H), 7.25 (m, 1H). | ESI MS m/z 289 [M − H]− |
| 106 | | $^1$H NMR (400 MHz, DMSO-$d_6$) δ 13.56 (bs, 1H), 12.35 (s, 1H), 8.92 (s, 1H), 8.20 (s, 1H), 7.97 (d, J = 4.5 Hz, 1H), 7.53 (d, J = 8.8 Hz, 1H), 7.35-7.39 (m, 1H). | ESI MS m/z 305 [M − H]− |
| 107 | | $^1$H NMR (400 MHz, DMSO-$d_6$) δ 12.31 (s, 1H), 9.30 (s, 1H), 8.14 (s, 1H), 7.63-7.70 (m, 1H), 7.51-7.55 (m, 1H), 7.23-7.30 (m, 1H) | ESI MS m/z 270 [M − H]− |

TABLE 1-continued

Representative Indole Compounds

| ARI-# | Structural Formula | ¹H NMR Data | Mass Characterization |
|---|---|---|---|
| 108 | | ¹H NMR (400 MHz, DMSO-$d_6$) δ 12.21 (bs, 1H), 8.70-8.80 (m, 2H), 8.43 (s, 1H), 7.50-8.60 (m, 2H), 7.26 (m, 1H), 2.92 (d, J = 4.8 Hz, 3H). | ESI MS m/z 302 [M − H]⁻ |
| 109 | | ¹H NMR (500 MHz, DMSO-$d_6$) δ 12.50 (d, J = 2.0 Hz, 1H), 9.16 (d, J = 3.5 Hz, 1H), 8.81 (s, 1H), 8.30 (d, J = 2.0 Hz, 1H), 7.64 (d, J = 8.5 Hz, 1H), 7.34 (dd, J = 8.5, 2.0 Hz, 1H), 2.72 (s, 3H). | ESI MS m/z 343 [M − H]⁻ |
| 110 | | ¹H NMR (500 MHz, DMSO-$d_6$) δ 12.34 (s, 1H), 9.12 (s, 1H), 8.55 (s, 1H), 8.33-8.32 (m, 1H), 8.06 (s, 2H), 7.60-7.59 (m, 1H), 7.32-7.27 (m, 2H). | ESI MS m/z 312 [M + H]⁺ |
| 111 | | ¹H NMR (400 MHz, DMSO-$d_6$) δ 12.80 (bs, 1H), 9.26 (s, 1H), 8.94 (s, 1H), 8.41-8.44 (m, 1H), 8.15 (s, 1H), 7.65-7.69 (m, 1H), 3.93 (s, 3H). | ESI MS m/z 310 [M − H]⁻ |
| 112 | | ¹H NMR (400 MHz, DMSO-$d_6$) δ 12.51 (bs, 1H), 9.21 (s, 1H), 9.08 (s, 1H), 7.93-7.98 (m, 1H), 7.60-7.65 (m, 1H), 7.15-7.22 (m, 1H). | ESI MS m/z 270 [M − H]⁻ |

TABLE 1-continued

Representative Indole Compounds

| ARI-# | Structural Formula | $^1$H NMR Data | Mass Characterization |
|---|---|---|---|
| 113 | | $^1$H NMR (400 MHz, DMSO-$d_6$) δ 12.38 (bs, 1H), 9.30 (s, 1H), 8.12 (s, 1H), 7.96 (s, 1H), 7.52 (d, J = 8.8 Hz, 1H), 7.37 (d, J = 8.4 Hz, 1H). | ESI MS m/z 286 [M − H]$^−$ |
| 114 | | $^1$H NMR (400 Hz, DMSO-$d_6$) δ 12.98 (bs, 1H), 9.16 (s, 1H), 8.82 (s, 1H), 8.14 (d, J = 8.0 Hz, 1H), 7.28-7.31 (m, 1H), 7.16-7.22 (m, 1H), 2.73 (s, 3H). | ESI MS m/z 327 [M − H]$^−$ |
| 116 | | $^1$H NMR (500 MHz, DMSO-$d_6$) δ 12.52 (s, 1H), 9.15 (s, 1H), 9.04 (s, 1H), 8.30 (m, 1H), 7.65 (dd, J = 8.5, 0.5 Hz, 1H), 7.34 (dd, J = 9.0, 2.5 Hz, 1H). | ESI MS m/z 397 [M − H]$^−$ |
| 117 | | $^1$H NMR (500 MHz, DMSO-$d_6$) δ 12.35 (s, 1H), 9.12 (d, J = 3.0 Hz, 1H), 8.59 (s, 1H), 8.46-8.44 (m, 1H), 8.33-8.31 (m, 1H), 7.60-7.58 (m, 1H), 7.32-7.27 (m, 2H), 2.96 (d, J = 4.5 Hz, 3H). | ESI MS m/z 326 [M + H]$^+$ |
| 118 | | $^1$H NMR (400 MHz, DMSO-$d_6$) δ 13.03 (bs, 1H), 9.10 (s, 1H), 8.58 (s, 1H), 8.14 (d, J = 8.0 Hz, 1H), 7.47 (s, 2H), 7.29 (d, J = 5.2 Hz, 1H), 7.16-7.22 (m, 1H). | ESI MS m/z 328 [M − H]$^−$ |

TABLE 1-continued

Representative Indole Compounds

| ARI-# | Structural Formula | ¹H NMR Data | Mass Characterization |
|---|---|---|---|
| 119 | | ¹H NMR (400 MHz, DMSO-$d_6$) δ 12.48 (bs, 1H), 9.17 (s, 1H), 8.80 (s, 1H), 7.97-8.01 (m, 1H), 7.62-7.66 (m, 1H), 7.17-7.19 (m, 1H), 2.72 (s, 3H). | ESI MS m/z 327 [M − H]⁻ |
| 120 | | ¹H NMR (500 MHz, DMSO-$d_6$) δ 12.56 (d, J = 2.5 Hz, 1H), 9.12 (d, J = 3.0 Hz, 1H), 8.57 (s, 1H), 8.45 (s, 1H), 7.89 (s, 1H), 7.39 (s, 2H). | ESI MS m/z 378 [M − H]⁻ |
| 121 | | ¹H NMR (500 MHz, DMSO-$d_6$) δ 12.47 (s, 1H), 9.14 (s, 1H), 8.56 (s, 1H), 8.30 (d, J = 2.0 Hz, 1H), 8.05 (s, 2H), 7.63 (d, J = 8.5 Hz, 1H), 7.32 (dd, J = 8.5, 2.0 Hz, 1H). | ESI MS m/z 344 [M − H]⁻ |
| 123 | | ¹H NMR (400 MHz, DMSO-$d_6$) δ 13.01 (bs, 1H), 9.13 (d, J = 8.0 Hz, 1H), 8.13 (d, J = 8.0 Hz, 1H), 7.27-7.33 (m, 1H), 7.17-7.23 (m, 1H), 2.51 (s, 3H). | ESI MS m/z 327 [M − H]⁻ |

TABLE 1-continued

Representative Indole Compounds

| ARI-# | Structural Formula | $^1$H NMR Data | Mass Characterization |
|---|---|---|---|
| 124 | | $^1$H NMR (400 MHz, DMSO-d$_6$) δ 13.27 (bs, 1H), 9.15 (s, 1H), 8.95 (s, 1H), 8.63 (d, J = 7.6 Hz, 1H), 7.84 (d, J = 7.2 Hz, 1H), 7.45-7.48 (m, 1H), 3.93 (s, 3H). | ESI MS m/z 310 [M − H]$^−$ |
| 125 | | $^1$H NMR (400 MHz, DMSO-d$_6$) δ 12.38 (bs, 1H), 9.27 (d, J = 4.8 Hz, 1H), 8.66 (d, J = 2.4 Hz, 1H), 8.30-8.33 (m, 1H), 8.24-8.27 (m, 1H), 7.57-7.60 (m, 1H), 7.30-7.33 (m, 2H). | ESI MS m/z 247 [M − H]$^−$ |
| 126 | | $^1$H NMR (400 MHz, DMSO-d$_6$) 12.31 (bs, 1H), 8.91 (s, 1H), 8.24 (s, 1H), 7.68 (d, J = 8.8 Hz, 1H), 7.52-7.56 (m, 1H), 7.25-7.28 (m, 1H), 2.74 (s, 3H). | ESI MS m/z 327 [M − H]$^−$ |
| 127 | | $^1$H NMR (400 MHz, DMSO-d$_6$) δ 12.35 (bs, 1H), 9.50 (s, 1H), 9.35 (s, 1H), 8.72 (d, J = 3.2 Hz, 1H), 8.37-8.40 (m, 1H), 7.56-7.59 (m, 1H), 7.28-7.34 (m, 2H), 2.53 (s, 3H). | ESI MS m/z 304 [M − H]$^−$ |
| 128 | | $^1$H NMR (400 MHz, DMSO-d$_6$) δ 13.35 (bs, 1H), 12.43 (s, 1H), 8.83 (s, 1H), 8.12 (s, 1H), 7.44 (d, J = 8.4 Hz, 1H), 7.20-7.23 (m, 1H), 2.63 (s, 3H). | ESI MS m/z 319 [M − H]$^−$ |
| 129 | | $^1$H NMR (400 MHz, DMSO-d$_6$) δ 12.31 (bs, 1H), 8.67 (s, 1H), 8.20 (s, 1H), 7.63 (d, J = 9.6 Hz, 1H), 7.50-7.55 (m, 1H), 7.48 (s, 2H), 7.26-7.30 (m, 1H). | ESI MS m/z 328 [M − H]$^−$ |

TABLE 1-continued

Representative Indole Compounds

| ARI-# | Structural Formula | $^1$H NMR Data | Mass Characterization |
|---|---|---|---|
| 130 | | $^1$H NMR (400 MHz, DMSO-d$_6$) δ 13.36 (bs, 1H), 12.37 (s, 1H), 8.83 (s, 1H), 7.87 (dd, J = 10.8, 1.6 Hz, 1H), 7.40-7.46 (m, 1H), 7.00-7.08 (m, 1H), 2.63 (s, 3H). | ESI MS m/z 303 [M − H]$^-$ |
| 131 | | $^1$H NMR (400 MHz, DMSO-d$_6$) δ 12.38 (bs, 1H), 8.67 (s, 1H), 8.18 (s, 1H), 7.93 (s, 1H), 7.48-7.56 (m, 3H), 7.36-7.40 (m, 1H). | ESI MS m/z 344 [M − H]$^-$ |
| 132 | | $^1$H NMR (400 MHz, DMSO-d$_6$) δ 12.47 (bs, 1H), 9.17 (s, 1H), 9.12 (s, 1H), 7.96-8.00 (m, 1H), 7.62-7.67 (m, 1H), 7.15-7.22 (m, 1H), 2.48 (s, 3H). | ESI MS m/z 327 [M − H]$^-$ |
| 133 | | $^1$H NMR (400 MHz, DMSO-d$_6$) δ 12.60 (bs, 1H), 9.17 (s, 1H), 8.81 (s, 1H), 8.30 (s, 1H), 7.64 (d, J = 8.8 Hz, 1H), 7.32-7.35 (m, 2H), 4.08 (s, 2H), 2.32 (s, 2H). | ESI MS m/z 358 [M − H]$^-$ |
| 134 | | $^1$H NMR (400 MHz, DMSO-d$_6$) δ 12.42 (bs, 1H), 8.58 (s, 1H), 8.01 (s, 1H), 7.45 (d, J = 8.4 Hz, 1H), 7.38 (s, 2H), 7.21 (d, J = 8.4 Hz, 1H), 2.62 (s, 3H). | ESI MS m/z 358 [M − H]$^-$ |

TABLE 1-continued

Representative Indole Compounds

| ARI-# | Structural Formula | ¹H NMR Data | Mass Characterization |
|---|---|---|---|
| 135 | | ¹H NMR (400 MHz, DMSO-d₆) δ 12.36 (bs, 1H), 8.57 (s, 1H), 7.72-7.76 (m, 1H), 7.39-7.45 (m, 3H), 7.04-7.06 (m, 1H), 2.62 (s, 3H). | ESI MS m/z 342 [M − H]⁻ |
| 137 | | ¹H NMR (400 MHz, DMSO-d₆) δ 12.42 (bs, 1H), 9.14 (s, 1H), 8.90 (s, 1H), 8.32-8.35 (m, 1H), 7.60-7.63 (m, 1H), 7.29-7.34 (m, 2H), 4.04 (s, 2H), 1.99 (s, 2H). | ESI MS m/z 326 [M + H]⁺ |
| 138 | | ¹H NMR (400 MHz, DMSO-d₆) δ 12.39 (bs, 1H), 9.15 (s, 1H), 8.80 (s, 1H), 8.32-8.35 (m, 1H), 7.61 (d, J = 5.6 Hz, 1H), 7.30-7.32 (m, 2H), 4.08 (s, 2H), 2.23 (s, 2H). | ESI MS m/z 326 [M + H]⁺ |
| 139 | | ¹H NMR (400 MHz, DMSO-d₆) δ 12.38 (bs, 1H), 9.09 (d, J = 2.8 Hz, 1H), 8.48 (s, 1H), 8.30-9.34 (m, 1H), 8.17 (s, 1H), 7.60 (d, J = 6.4 Hz, 1H), 7.29-7.33 (m, 2H). | ESI MS m/z 334 [M − H]⁻ |

TABLE 1-continued

Representative Indole Compounds

| ARI-# | Structural Formula | ¹H NMR Data | Mass Characterization |
|---|---|---|---|
| 140 | | ¹H NMR (400 MHz, DMSO-d$_6$) δ 12.96 (bs, 1H), 9.17 (s, 1H), 8.88 (s, 1H), 8.13 (d, J = 8.0 Hz, 1H), 7.27-7.30 (m, 1H), 7.17-7.21 (m, 1H), 3.24 (q, J = 7.2 Hz, 2H), 1.15 (t, J = 7.26 Hz, 3H). | ESI MS m/z 301 [M − H]⁻ |
| 141 | | ¹H NMR (400 MHz, DMSO-d$_6$) δ 12.78 (bs, 1H), 9.22 (s, 1H), 8.95 (s, 1H), 8.66 (s, 1H), 7.78-7.82 (d, J = 8.4 Hz, 1H), 7.68-7.72 (d, J = 8.4 Hz, 1H), 3.93 (s, 3H). | LC-MS: m/z 310.1 [M − H]⁻ |
| 142 | | ¹H NMR (400 MHz, DMSO-d$_6$) δ 12.57 (bs, 1H), 9.13 (s, 1H), 8.86 (s, 1H), 7.42 (d, J = 8.0Hz, 1H), 7.29-7.34 (m, 1H), 7.00-7.06 (m, 1H), 3.22 (q, J = 7.2 Hz, 2H), 1.14 (t, J = 7.2 Hz, 3H). | ESI MS m/z 301 [M − H]⁻ |
| 143 | | ¹H NMR (400 MHz, DMSO-d$_6$) δ 12.35 (bs, 1H), 9.17 (d, J = 2.8 Hz, 1H), 8.86 (s, 1H), 8.27-8.33 (m, 1H), 7.39-7.43 (m, 1H), 7.16-7.18 (m, 1H), 3.24 (q, J = 7.2 Hz, 2H), 1.15 (t, J = 7.2 Hz, 3H). | ESI MS m/z 301 [M − H]⁻ |
| 144 | | | |

TABLE 1-continued

Representative Indole Compounds

| ARI-# | Structural Formula | ¹H NMR Data | Mass Characterization |
|---|---|---|---|
| 145 | | ¹H NMR (400 MHz, DMSO-d$_6$) δ 9.15 (s, 1H), 8.91 (s, 1H), 8.12-8.15 (d, J = 7.6 Hz, 1H), 7.26-7.30 (m, 1H), 7.16-7.21 (m, 1H), 4.03 (s, 2H). | LC/MS (m/z) 342.3 [M − H]⁻ |
| 146 | | ¹H NMR (400 MHz, DMSO-d$_6$) δ 9.16 (s, 1H), 8.83 (s, 1H), 8.13-8.16 (d, J = 8.0 Hz, 1H), 7.26-7.31 (m, 1H), 7.16-7.22 (m, 1H), 4.08 (s, 2H). | LC/MS (m/z) 342.4 [M − H]⁻ |
| 147 | | ¹H NMR (400 MHz, DMSO-d$_6$) δ 12.48 (bs, 1H), 9.12 (s, 1H), 8.49 (s, 1H), 8.17 (s, 2H), 7.96-8.00 (m, 1H), 7.61-7.66 (m, 1H), 7.15-7.21 (m, 1H). | ESI MS m/z 352 [M − H]⁻ |
| 148 | | ¹H NMR (400 MHz, DMSO-d$_6$) δ 12.50 (bs, 1H), 9.12 (s, 1H), 8.56 (s, 1H), 7.97-8.01 (m, 1H), 7.60-7.65 (m, 1H), 7.49 (s, 2H), 7.16-7.19 (m, 1H). | ESI MS m/z 328 [M − H]⁻ |

TABLE 1-continued

Representative Indole Compounds

| ARI-# | Structural Formula | ¹H NMR Data | Mass Characterization |
|---|---|---|---|
| 149 | (5,6-difluoro-1H-indol-3-yl)(4-propionyl-thiazol-2-yl)methanone | ¹H NMR (400 MHz, DMSO-$d_6$) δ 12.43 (bs, 1H), 9.19 (s, 1H), 8.87 (s, 1H), 8.13-8.19 (m, 1H), 7.64-7.70 (m, 1H), 3.24 (q, J = 7.2 Hz, 2H), 1.15 (t, J = 7.2 Hz, 3H). | ESI MS m/z 319 [M − H]⁻ |
| 150 | (5,7-difluoro-1H-indol-3-yl)(4-propionyl-thiazol-2-yl)methanone | ¹H NMR (400 MHz, DMSO-$d_6$) δ 13.11 (bs, 1H), 9.19 (s, 1H), 8.88 (s, 1H), 7.83-7.87 (m, 1H), 7.24-7.31 (m, 1H), 3.23-3.28 (q, J = 7.2 Hz, 2H), 1.13-1.18 (t, J = 7.2 Hz, 3H). | LC-MS: m/z 318.9 [M − H]⁻ |
| 154 | (4-(5-amino-1,3,4-oxadiazol-2-yl)thiazol-2-yl)(5,6-difluoro-1H-indol-3-yl)methanone | ¹H NMR (400 MHz, DMSO-$d_6$) δ 12.55 (bs, 1H), 9.11 (s, 1H), 8.58 (s, 1H), 8.13-8.16 (m, 1H), 7.67-7.70 (m, 1H), 7.44 (s, 2H). | LC-MS: m/z 346.0 [M − H]⁻ |

Additional exemplary indole compounds are shown in Table 2 below.

TABLE 2

Additional Exemplary Indole Compounds

| ARI-# | Structural Formula |
|---|---|
| 1001 | alkyl or H ester of 2-(1-(1H-indol-3-yl)vinyl)thiazole-4-carboxylate; R = alkyl or H |
| 1002 | 2-(1-(1H-indol-3-yl)vinyl)thiazole-4-carboxylic acid |

TABLE 2-continued
Additional Exemplary Indole Compounds
| ARI-# | Structural Formula |
|---|---|
| 1003 | 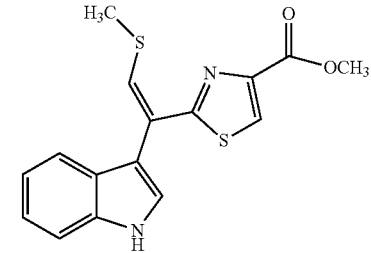 |
| 1004 | |
| 1005 | |
| 1006 | |
| 1007 | |表
TABLE 2-continued
Additional Exemplary Indole Compounds
| ARI-# | Structural Formula |
|---|---|
| 1008 | 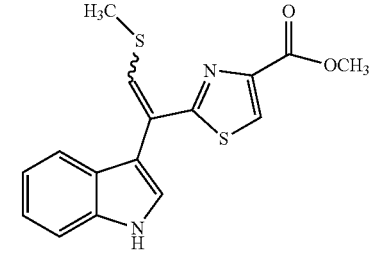 [SMILES: COC(=O)c1csc(C(=CSC)c2c[nH]c3ccccc23)n1] |
| 1009 | |
| 1010 | |
| 1011 | |
| 1012 | |

TABLE 2-continued

Additional Exemplary Indole Compounds

| ARI-# | Structural Formula |
|---|---|
| 1013 | (R = alkyl or H) |
| 1014 | |
| 1015 | |
| 1016 | |
| 1017 | (R = alkyl or H) |
| 1018 | |
| 1019 | |
| 1020 | |
| 1021 | |
| 1022 | |
| 1023 | |

TABLE 2-continued
Additional Exemplary Indole Compounds
| ARI-# | Structural Formula |
|---|---|
| 1024 | 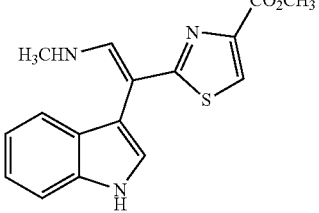 |
| 1025 | 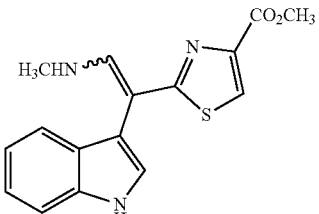 |
| 1026 | 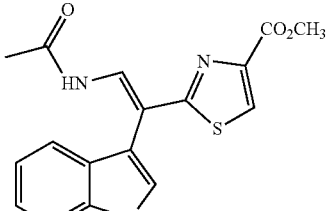 |
| 1027 | 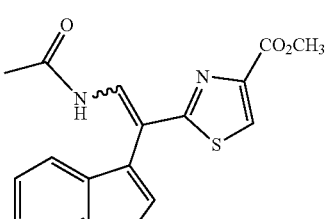 |
| 1028 | 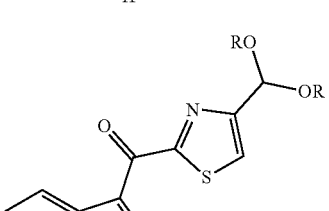 R = alkyl |
| 1029 | 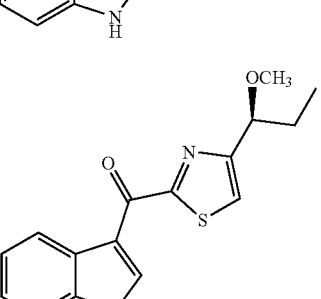 |
| 1030 | 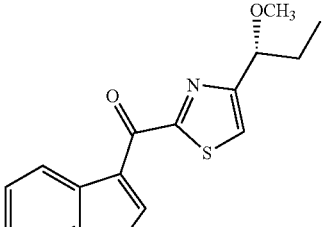 |
| 1031 | 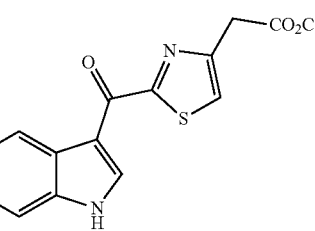 |
| 1032 | 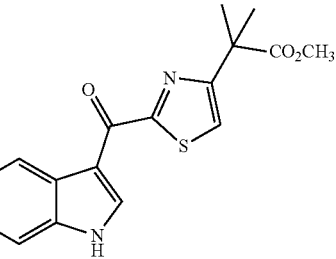 |
| 1033 | 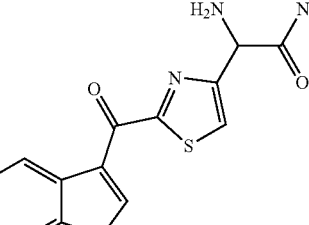 |
| 1034 | 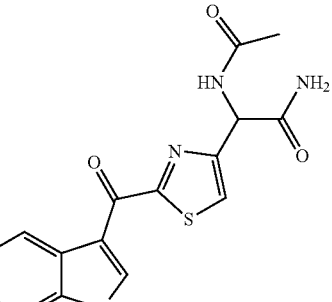 |

TABLE 2-continued
Additional Exemplary Indole Compounds
| ARI-# | Structural Formula |
|---|---|
| 1035 | 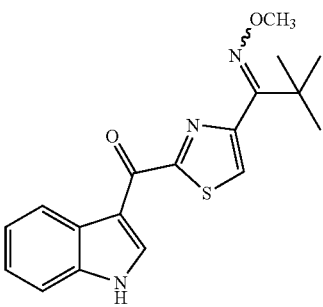 [SMILES: CON=C(c1csc(C(=O)c2c[nH]c3ccccc23)n1)C(C)(C)C] |
| 1036 | 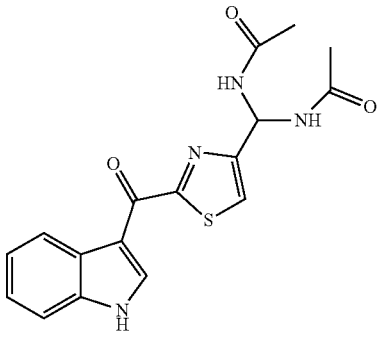 [SMILES: CC(=O)NC(NC(C)=O)c1csc(C(=O)c2c[nH]c3ccccc23)n1] |
| 1037 | 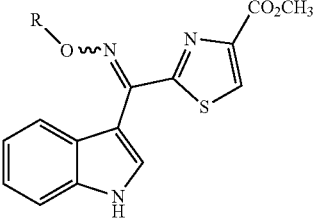 |
| 1038 | 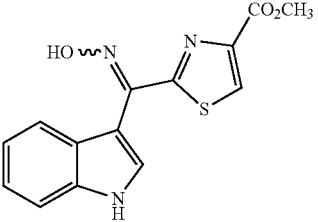 [SMILES: COC(=O)c1csc(C(=NO)c2c[nH]c3ccccc23)n1] |
| 1039 | 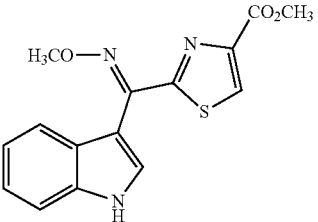 [SMILES: CO/N=C(/c1nc(C(=O)OC)cs1)c1c[nH]c2ccccc12] |
| 1040 | 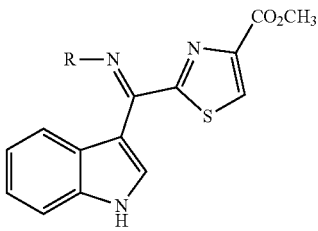 |
| 1041 | 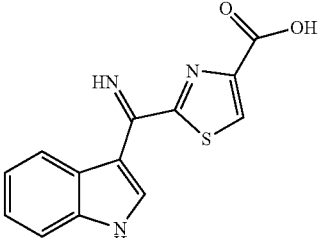 |
| 1042 | 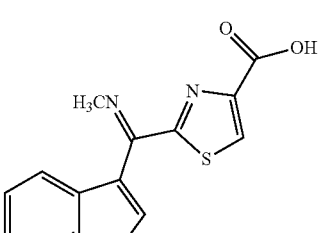 |
| 1043 | 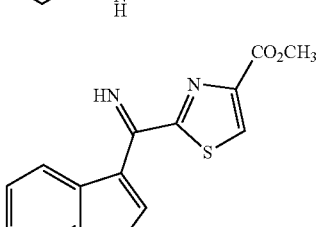 |
| 1044 | 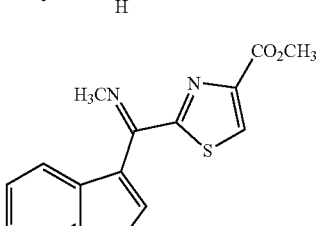 |
| 1045 | 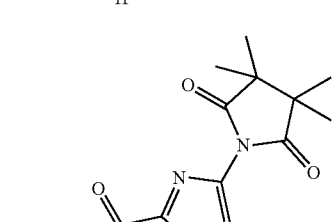 |

TABLE 2-continued

Additional Exemplary Indole Compounds

| ARI-# | Structural Formula |
|---|---|
| 1046 | |
| 1047 | |
| 1048 | |
| 1049 | |
| 1050 | |
| 1051 | |
| 1052 | |
| 1053 | |
| 1054 | |

TABLE 2-continued

Additional Exemplary Indole Compounds

| ARI-# | Structural Formula |
|---|---|
| 1055 | (indole-3-yl)-C(=O)-(5-methyl-thiazol-2-yl)-4-CO₂CH₃ |
| 1056 | (indole-3-yl)-C(=O)-(thiazol-2-yl)-4-CO₂Me (wavy bond at 5-position) |
| 1057 | (indole-3-yl)-C(=O)-(5,5-dimethyl-4,5-dihydrothiazol-2-yl)-4-CO₂CH₃ |
| 1058 | (indole-3-yl)-C(=O)-(5,5-dimethyl-4,5-dihydrothiazol-2-yl)-4-CO₂CH₃ |
| 1059 | (indole-3-yl)-C(=O)-(pyridin-2-yl)-5-CO₂Me |
| 1060 | (indole-3-yl)-C(=O)-(phenyl)-4-CO₂Me |
| 1061 | (indole-3-yl)-C(=NH)-(isoxazol-5-yl)-3-CO₂CH₃ |
| 1062 | (7-azaindole-3-yl)-C(=O)-(thiazol-2-yl)-4-CO₂Me |
| 1063 | (6-azaindole-3-yl)-C(=O)-(thiazol-2-yl)-4-CO₂Me |
| 1064 | (5-azaindole-3-yl)-C(=O)-(thiazol-2-yl)-4-CO₂Me |
| 1065 | (4-azaindole-3-yl)-C(=O)-(thiazol-2-yl)-4-CO₂Me |
| 1066 | (imidazo[1,2-a]pyridin-3-yl)-C(=O)-(thiazol-2-yl)-4-CO₂Me |

TABLE 2-continued

Additional Exemplary Indole Compounds

| ARI-# | Structural Formula |
|---|---|
| 1067 | (indol-3-yl carbonyl thiazole-2-CO2Me) |
| 1068 | (indol-3-yl carbonyl oxazole-4-CO-OCH3) |
| 1069 | (indol-3-yl carbonyl thiazole-4-carboxylate-OCH2CH(OH)CH3) |
| 1070 | (indol-3-yl carbonyl thiazole-4-carboxylate-OCH(CH3)CH2OH) |
| 1071 | (indol-3-yl-CH(OH)- thiazole-4-CO-OMe) |
| 1072 | (indol-3-yl carbonyl thiazole-4-CH(OH)OH) |
| 1073 | (indol-3-yl-CH= thiazole-4-CO-O-) |

Single stereochemical isomers, enantiomers, diastereomers, and pharmaceutically acceptable salts of the above exemplified compounds are also within the scope of the present disclosure. Pharmaceutically acceptable salts may be, for example, derived from suitable inorganic and organic acids and bases.

Acid addition salts can be prepared by reacting the purified compound in its free-based form, if possible, with a suitable organic or inorganic acid and isolating the salt thus formed. Examples of pharmaceutically acceptable acid addition salts include, without limitations, salts of an amino group formed with inorganic acids such as hydrochloric acid, hydrobromic acid, phosphoric acid, sulfuric acid and perchloric acid, or with organic acids such as acetic acid, oxalic acid, maleic acid, tartaric acid, citric acid, succinic acid or malonic acid.

Base addition salts can be prepared by reacting the purified compound in its acid form with a suitable organic or inorganic base and isolating the salt thus formed. Such salts include, without limitations, alkali metal (e.g., sodium, lithium, and potassium), alkaline earth metal (e.g., magnesium and calcium), ammonium and $N^+(C_{1-4}alkyl)_4$ salts.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, and valerate salts.

In some embodiments, the compound may be selected from a group consisting of ARI-017, ARI-018, ARI-019, ARI-020, ARI-031, ARI-060, ARI-083, ARI-087, ARI-090, ARI-118, ARI-120, ARI-140, ARI-143, ARI-145, ARI-146, ARI-148, ARI-149, or ARI-150, or an enantiomer, diastereomer, or pharmaceutically acceptable salt thereof. In some embodiments, the compound may be selected from ARI-087, ARI-140, ARI-143, ARI-149, and ARI-150, or an enantiomer, diastereomer, or pharmaceutically acceptable salt thereof. In some embodiments, the present disclosure provides a compound selected from ARI-031, ARI-060, ARI-083, ARI-090, ARI-118, ARI-120, ARI-145, ARI-146, and ARI-148, or an enantiomer, diastereomer, or pharmaceutically acceptable salt thereof.

The indole compounds' activity in stimulating AhR can be measured by, for example, an EROD assay as described in Example 152 below. The EROD assay may be performed on, e.g., human or mouse hepatocyte cell lines. The indole compounds of the present disclosure may have an $EC_{50}$ of about 100 nM or less (e.g., 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, or 0.1 nM or less) in a human or mouse EROD assay.

The indole compounds' agonistic effect on AhR's immune-stimulatory activity may be measured by the compounds' ability to inhibit IL-21 secretion from $CD4^+$ T cells, as described below in Example 153. In such an assay, the indole compounds of the present disclosure may have an $IC_{50}$ of about 500 nM or less (e.g., 400 nM or less, 300 nM or less, 200 nM or less, 100 nM or less, 50 nM or less, 40 nM or less, 30 nM or less, 20 nM or less, 10 nM or less, 5 nM or less, 1 nM or less, or 0.1 nM or less).

The metabolic and PK profiles of the present indole compounds are exemplified in Examples 154 and 155.

The indole compounds of the present disclosure may be synthesized by methods known in the art or by methods illustrated in Examples 1-151 below.

Pharmaceutical Compositions and Use

An aspect of the present disclosure relates to pharmaceutical compositions comprising one or more indole compounds disclosed herein formulated with one or more pharmaceutically acceptable excipients or carriers (carrier system). The carrier system may include, for example, solvents, diluents, or other liquid vehicle, dispersion or suspension aids, surface active agents, isotonic agents, thickening or emulsifying agents, preservatives, fillers, extenders, disintegrating agents, solid binders, absorbents, lubricants, wetting agents, and the like. The pharmaceutical compositions can be administered to patients, for example, orally, or parenterally (e.g., subcutaneously, intravenously, or intramuscularly), intranasally, or topically. The pharmaceutical compositions may be provided, for example, in a form of cream, capsules, tablets, lozenges, or injectables.

Another aspect of the present disclosure relates to a method of stimulating the immune system in a patient in need thereof, e.g., in a patient suffering from cancer or an infection (e.g., a viral, bacterial, or parasitic infection). The method includes administering to the patient a therapeutically effective amount of one or a combination of the compounds described herein. In some embodiments, the patient has an increased count of white blood cells, T and/or B lymphocytes, macrophases, dendritic cells, neutrophils, natural killer (NK) cells, and/or platelets after the administering step. In some embodiments, the compound decreases IL-21 level in the patient. The patient may have cancer, or may be immune-compromised.

Accordingly, the present disclosure provides a method of treating cancer in a patient in need thereof, comprising administering to the patient a therapeutically effective amount of one or a combination of the compounds described herein. In some embodiments, the patient has a liquid cancer (e.g., a hematological malignancy such as lymphoma, leukemia, and myeloma) or a solid tumor. In some embodiments, the patient has lung cancer (e.g., nonsmall cell lung cancer), ovarian cancer, cancer of the Fallopian tube, cervical cancer, breast cancer, skin cancer (e.g., melanoma), colorectal cancer, stomach cancer, pancreatic cancer, liver cancer, mesothelioma, kidney cancer (e.g., renal cell carcinoma), bladder cancer, prostate cancer, soft tissue cancer, squamous cell carcinoma, head and neck cancer, glioma, or brain tumor. This is by no means to limit the therapeutic scope of the compounds, given their broad cancer inhibition capabilities. In some embodiments, the cancer is metastatic or otherwise advanced.

"Treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment. Treatment of cancer encompasses inhibiting cancer growth (including causing partial or complete cancer regression), inhibiting cancer progression or metastasis, preventing cancer recurrence or residual disease, and/or prolonging the patient's survival. "A therapeutically effective amount" is an amount of the medication that can achieve the desired curative, palliative, or prophylactic effect for the treated condition.

In some embodiments, the effective dose range of a compound is determined by measuring the patient's blood concentration of the compound under a specified dosing regimen to establish a concentration-time profile, consulting with an established correlation between the concentration-time profiles and effects on cancer inhibition or eradication obtained during a trial, and balancing the therapeutic effects achievable with possible toxicity to the patient, with further consideration of the health condition or physical durability of the patient. The dosing frequency of the compound may be determined similarly. The dosing may be continued until the patiunlessent is free from the cancer.

In some embodiments, an effective amount for tumor therapy may be measured by its ability to stabilize disease progression and/or ameliorate symptoms in a patient, and preferably to reverse disease progression, e.g., by reducing tumor size. In some embodiments, a maintenance dosing may be provided after the patient is free of cancer to ensure its complete elimination or eradication, or prevention of residual disease. The duration of the maintenance dosing can be determined based on clinical trial data.

In some embodiments, a compound may be administered in combination with one or more other cancer therapeutic agents that also target AhR or target molecules other than AhR.

Compounds can be formulated either separately from, or together with, the other cancer therapeutic agents. Compounds can be administered either at the same schedule as, or at a different schedule from, the other cancer therapeutic agents. The proportion of a compound relative to other cancer therapeutic agents may be determined by clinical trials. Combining the compounds with the other cancer therapeutic agents may further enhance the efficacy of one another. For example, a compound of the present invention can be administered with an immune checkpoint inhibitor, such as an inhibitor of PD-1, PD-L1 or PD-L2 (e.g., pembrolizumab, nivolumab, or atezolizumab), or administered with CAR-T therapy (e.g., axicabtagene ciloleucel), to achieve additive or synergistic anti-cancer effect.

Dosage regimens may be adjusted to provide the optimum desired response. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the embodied composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values.

It is contemplated that a suitable dose of a compound of the present invention may be in the range of 0.1-100 mg/kg, such as about 0.5-50 mg/kg, e.g., about 1-20 mg/kg. The compound may for example be administered in a dosage of at least 0.25 mg/kg, e.g., at least 0.5 mg/kg, such as at least 1 mg/kg, e.g., at least 1.5 mg/kg, such as at least 2 mg/kg, e.g., at least 3 mg/kg, such as at least 4 mg/kg, e.g., at least 5 mg/kg; and e.g., up to at most 50 mg/kg, such as up to at the most 30 mg/kg, e.g., up to at the most 20 mg/kg, such as up to at the most 15 mg/kg. Administration will normally be repeated at suitable intervals, e.g., twice a day, thrice a day, once a day, once every week, once every two weeks, or once every three weeks, and for as long as deemed appropriate by the responsible doctor, who may optionally increase or decrease the dosage as necessary.

Synthesis

The compounds disclosed herein can be prepared by using one or more of the following general synthetic schemes exemplified below. These general synthetic schemes as well as the examples that follow are for purposes of illustration only and are not to be construed as limiting the scope of the invention in any manner.

Unless otherwise noted, reagents and solvents were used as received from commercial suppliers. Non-commercial indole carboxylic acids were prepared by the methods of A. S. Katner; *Organic Preparations and Procedures* 2(4):297-303 (1970); *J Med Chem* 57(17):7293-7316 (2014); and *Chem. Eur. J* 17(26):7298-7303 (2011). Non-commercial key intermediates methyl 2-(1H-indole-3-carbonyl)thiazole-4-carboxylate and 2-(1H-indole-3-carbonyl)thiazole-4-carboxylic acid were obtained from the literature preparation. The preparation of tert-butyl 3-(methoxy(methyl)carbamoyl)-1H-indazole-1-carboxylate is known. See Crestey, Francois; Stiebing, Silvia; Legay, Remi; Collot, Valerie; Rault, Sylvain; *Tetrahedron* 63(2):419-428 (2007).

All non-aqueous reactions were carried out under an atmosphere of dry nitrogen (unless otherwise noted). Proton nuclear magnetic resonance spectra were obtained on a Bruker Avance III 400 MHz NMR with autosampler, a Bruker Avance II 300 MHz NMR, or a Bruker Ascend 500 spectrometer at 500 MHz. Spectra are given in ppm (δ) and coupling constants, J values, are reported in hertz (Hz). Tetramethylsilane was used as an internal standard for proton nuclear magnetic resonance. Mass spectra and LCMS analyses were obtained using a Waters Acquity UPLC-H Class LC-MS system or a Shimadzu 2020 single quadruple mass spectrometer (DUIS, UP-LCMS). HPLC analyses were performed using a Waters Separations Module 2695/2998 PDA detector.

Intermediate Preparation

Preparation 1: 2-bromo-4-((tert-butyldimethylsilyloxy)methyl)thiazole (1)

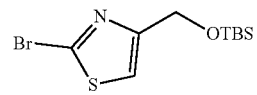

This compound was prepared according to the procedure described in documents WO2013/163279 and Tetrahedron Lett. 1991, 32, 4263. NaBH$_4$ (32.0 g, 0.845 mol) was added portionwise to a solution of ethyl 2-bromothiazole-4-carboxylate (100.0 g, 0.424 mol) in EtOH (800 mL) over 0.5 h at <50° C. with stirring. The suspension was heated under reflux for 5 h. The mixture was cooled to room temperature and the solvent was removed under reduced pressure. The residue was dissolved in CH$_2$Cl$_2$ (500 mL) and the resulting solution was washed with saturated aqueous NaHCO$_3$ (300 mL×3) and brine (300 mL×1), dried over anhydrous Na$_2$SO$_4$ and concentrated to dryness to afford the corresponding alcohol (70 g).

The alcohol was dissolved in dimethylformamide (DMF) (300 mL) and imidazole (36.8 g, 0.54 mol) was added. Then a solution of TBS-Cl (81.5 g, 0.54 mol) in tetrahydrofuran (THF) (200 mL) was added dropwise at room temperature. The reaction mixture was stirred overnight, and then water (100 mL) was added. The resulting mixture was extracted with EtOAc (100 mL×3). The combined organic phases were washed with aqueous 5% KHSO$_4$ (200 mL×3), saturated aqueous NaHCO$_3$ (200 mL×3) and brine (200 mL×1), dried over anhydrous Na$_2$SO$_4$ and concentrated to dryness. The residue was purified by distillation under reduced pressure to afford compound 1 (bp130~140 C/13.3 pa, 96.1 g, 74% yield) as an oil.

Preparation 2: 5-fluoro-1H-indole-3-carboxylic acid (2)

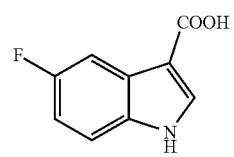

This compound was prepared according to the procedure described in the Journal of Medicinal Chemistry 2014, 57(17), 7293-7316. Trifluoroacetic anhydride (38 mL, 56.0 g, 0.27 mol) was added dropwise to a solution of 5-fluoro- 1H-indole (30.0 g, 0.22 mol) in DMF (300 mL) over 0.5 h at 0° C. The reaction mixture was allowed to warm to room temperature and stirred overnight. The mixture was quenched with water (1 L), after which solids began to form, the mixture was stirred for 0.5 h, then filtered. The solid was collected, washed with water (200 mL×3), then added to aqueous sodium hydroxide (20%, 150 mL, 0.75 mol) and heated under reflux for 8 h. The reaction mixture was cooled and acidified with aqueous 3N HCl to pH of 3 whereupon a precipitate was produced. The solid was collected by filtration, washed with water (200 mL×3), dried to afford compound 2 (27.1 g, 68% yield) as off-white solid.

Preparation 3: 7-fluoro-1H-indole-3-carboxylic acid (3)

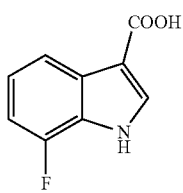

This compound was synthesized according to the protocol described in Preparation 2 from 7-fluoro-1H-indole to give title compound in the form of a yellow solid (75% yield).

Preparation 4: 1H-Indole-5-methoxy-3-carboxylic acid (4)

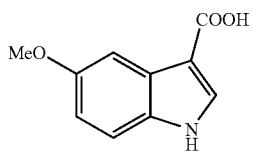

This compound was synthesized according to the protocol described in Preparation 2 from 5-methoxy-1H-indole to give title compound in the form of a yellow solid (65% yield).

Preparation 5: 5-Bromo-1H-Indole-3-carboxylic acid (5)

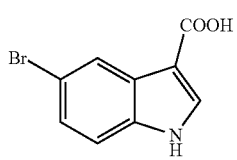

This compound was synthesized according to the protocol described in Preparation 2 from 5-bromo-1H-indole to give title compound in the form of a yellow solid (70% yield).

Preparation 6: 6-Bromo-1H-Indole-3-carboxylic acid (6)

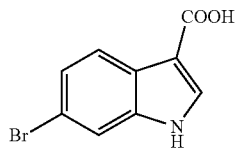

This compound was synthesized according to the protocol described in Preparation 2 from 6-bromo-1H-indole to give title compound in the form of a yellow solid (55% yield).

Preparation 7: 7-Bromo-1H-Indole-3-carboxylic acid (7)

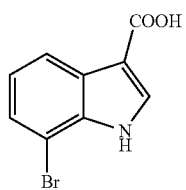

This compound was synthesized according to the protocol described in Preparation 2 from 7-bromo-1H-indole to give title compound in the form of a yellow solid (63% yield).

Preparation 8: 5-chloro-2-methyl-1H-indole-3-carboxylic acid (8)

This compound was prepared according to the procedure described in Chemistry-A European Journal, 2011, 17(26), 7298-7303. $InBr_3$ (5 mg, cat.) and anhydrous $MgSO_4$ (24.0 g, 0.2 mol) were added to a solution of 4-chloroaniline (24.0 g, 0.21 mol) and methyl acetoacetate (28.0 g, 0.24 mol) in dichloromethane (DCM) (200 mL) at room temperature. The reaction mixture was stirred overnight, then filtered. The filtrate was concentrated to dryness. The residue was dissolved in DMF (200 mL), and $Pd(OAc)_2$ (2.2 g, 10 mmol), $Cu(OAc)_2$ (110.0 g, 0.61 mol), $K_2CO_3$ (83.0 g, 0.60 mol) were added. The resulting mixture was heated to 140° C. and stirred for 5 h. The mixture was cooled to room temperature, quenched with water (500 mL) and then extracted with EtOAc (300 mL×3). The combined organic phases were washed with water (500 mL×3), saturated aqueous $NaHCO_3$ (500 mL×3) and brine (500 mL×1), dried ($Na_2SO_4$), filtered and then concentrated to dryness. The residue was purified by flash column chromatography on silica gel (EtOAc:Hexane—1:20 to 1:10) to afford methyl 5-chloro-2-methyl-1H-indole-3-carboxylate (10.1 g, 21% yield).

The above methyl ester (10.0 g, 45 mmol) was added to aqueous sodium hydroxide (10%, 100 mL, 0.25 mol) and heated under reflux for 8 h. The reaction mixture was cooled and acidified with aqueous 3N HCl to a pH of 3 whereupon a precipitate began to form. The solid was collected by filtration, washed with water (20 mL×3), dried to afford compound 8 (6.7 g, 71% yield) as an off-white solid.

Preparation 9:
5-fluoro-2-methyl-1H-indole-3-carboxylic acid (9)

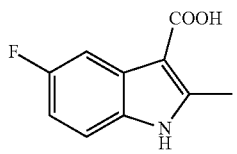

9

This compound was synthesized according to the protocol described in Preparation 8 from 4-fluoroaniline to give title compound in the form of a yellow solid (22% yield).
Preparation of the Key Intermediates Int-A, Int-B and Int-C.

Figure 16:
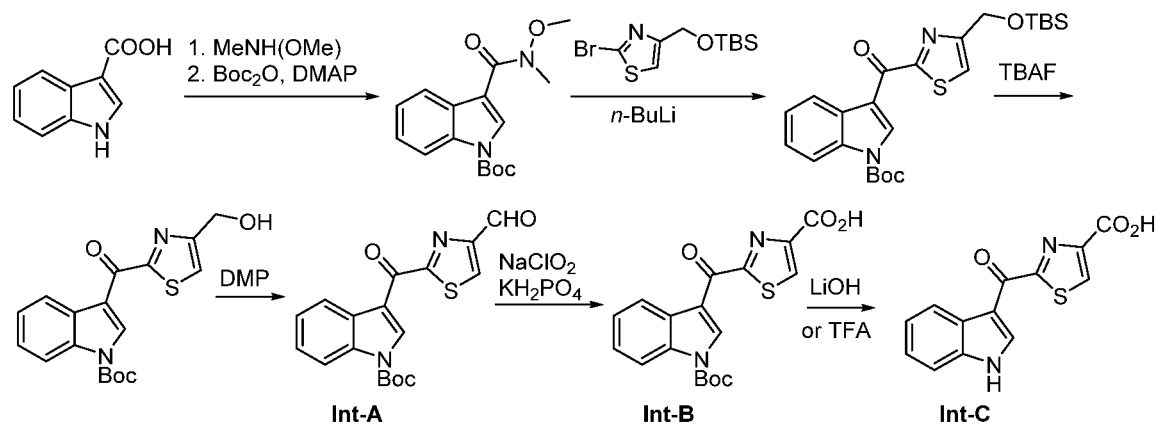
FIG. 16 shows a scheme for preparing the key intermediates Int-A, Int-B and Int-C.

The key intermediates Int-A, Int-B and Int-C were synthesized according to the scheme of FIG. 16 and by the following steps:

Step 1: Oxalyl chloride (473.3 g, 3.73 mol) was added dropwise to a suspension of indol-3-carboxylic acid (400 g, 2.48 mol) in DCM (4 L) at 0° C. over 1 h. The mixture was allowed to warm to room temperature and stirred overnight. The mixture was concentrated to dryness to afford 1H-indole-3-carbonyl chloride (446.0 g).

The above 1H-indole-3-carbonyl chloride (446.0 g) was added portion-wise to a suspension of N,O-dimethylhydroxylamine hydrochloride (266.0 g, 2.73 mol) and TEA (551.1 g, 5.46 mol) in DCM (5 L) at room temperature over 1 h. The mixture was stirred overnight, then quenched with water (2 L). The organic phase was collected and washed with water (2 L×2), saturated aqueous NaHCO$_3$ (2 L×2), and brine (2 L×1), dried (Na$_2$SO$_4$), filtered and concentrated to dryness. The residue and DMAP (15.1 g, 0.124 mol) was dissolved in DMF (1 L) and DCM (4 L), cooled to 0° C. Boc$_2$O (540.64 g, 2.48) and DMAP (15.1 g, 0.124 mol) were added dropwise to over 1 h.

The resulting mixture was allowed to warm to room temperature and stirred overnight. The mixture was quenched with water (2 L). The organic phase was separated and washed with water (2 L×2), saturated aqueous NaHCO$_3$ (2 L×2), and brine (2 L×1), dried (Na$_2$SO$_4$), filtered and concentrated to dryness. The residue was triturated with EtOAc/hexane (1:5, 1 L), filtered and dried to afford tert-butyl 3-(methoxy(methyl)carbamoyl)-1H-indole-1-carboxylate (557.9 g, 75% yield) as off-white solid. $^1$H-NMR (400 MHz, DMSO-d6): δ 8.25 (s, 1H), 8.22 (d, J=8.0 Hz, 1H), 8.13 (d, J=7.6 Hz, 1H), 7.35-7.45 (m, 1H), 7.30-7.35 (m, 1H), 3.74 (s, 3H), 3.32 (s, 3H), 1.67 (s, 9H).

Step 2: A solution of 2-bromo-4-((tert-butyldimethylsilyloxy)methyl)thiazole (135.0 g, 0.44 mol) in THF (1.5 L) was cooled to −78° C., and n-BuLi (1.6 M solution in hexane, 385 mL, 0.62 mol) was added dropwise at −78° C. over 1 h. The mixture was stirred for 0.5 h at this temperature, then a solution of tert-butyl 3-(methoxy(methyl)carbamoyl)-1H-indole-1-carboxylate (120.0 g, 0.4 mol) in THF (500 mL) was added dropwise over 1 h. The mixture was stirred at −78° for 1 h then allowed to warm to 0° C. and quenched with aqueous 10% NH$_4$Cl (1 L). The organic phase was collected and washed with water (1 L×2), saturated aqueous NaHCO$_3$ (1 L×2), and brine (1 L×1), dried (Na$_2$SO$_4$), filtered and concentrated to dryness. The residue was triturated with EtOAc/hexane (1:5, 500 mL), filtered and dried to afford tert-butyl 3-(4-((tert-butyldimethylsilyloxy)methyl)thiazole-2-carbonyl)-1H-indole-1-carboxylate (132.0 g, 70% yield) as off-white solid. $^1$H-NMR (400 MHz, DMSO-d6): δ 9.42 (bs, 1H), 8.39 (d, J=7.6 Hz, 1H), 8.14 (d, J=8.0 Hz, 1H), 8.01 (s, 1H), 7.40-7.52 (m, 2H), 4.93 (s, 2H), 1.69 (s, 9H), 0.92 (s, 9H), 0.14 (s, 6H).

Step 3: A solution of tert-butyl 3-(4-((tert-butyldimethylsilyloxy)methyl)thiazole-2-carbonyl)-1H-indole-1-carboxylate (91.0 g, 0.19 mol) in THF (500 mL) and pyridine (50 mL) was cooled to 0° C., and HF-pyridine (30%, 50 mL) was added dropwise over 10 min. The mixture was stirred for 0.5 h at this temperature, then allowed to warm to room temperature and stirred overnight. The mixture was quenched with aqueous 10% NH$_4$Cl (1 L) and EtOAc (500 mL). The organic phase was collected and washed with water (500 mL×2), saturated aqueous NaHCO$_3$ (500 mL×2), and brine (500 mL×1), dried (Na$_2$SO$_4$), filtered and concentrated to dryness. The residue was triturated with EtOAc/hexane (1:5, 100 mL), filtered and dried to afford tert-butyl 3-(4-(hydroxymethyl)thiazole-2-carbonyl)-1H-indole-1-carboxylate (49.6 g, 73% yield) as off-white solid. $^1$H-NMR (400 MHz, DMSO-d6): δ 9.43 (s, 1H), 8.35-8.40 (m, 1H), 8.13 (d, J=8.0 Hz, 1H), 7.97 (s, 1H), 7.42-7.50 (m, 2H), 5.5557 (t, J=5.6 Hz, 1H), 4.75 (d, J=5.6 Hz, 2H), 1.99 (s, 9H). ESI MS: m/z 359 [M+H]$^+$.

Step 4: To a mixture of tert-butyl 3-(4-(hydroxymethyl)thiazole-2-carbonyl)-1H-indole-1-carboxylate (1.9 g, 5.30 mmol) in DCM (53.0 ml) in a water bath was added 1,1,1-tris(acetyloxy)-1,1-dihydro-1,2-benziodoxol-3-(1H)-one (2.473 g, 5.83 mmol). After 1 h, saturated NaHCO$_3$ (aq) and 10% Na$_2$S$_2$O$_3$ (aq) were added then the mixture stirred for 30 min. The layers were separated and the organic phase was washed with bicarbonate, dried (Na$_2$SO$_4$), filtered and concentrated. Chromatography (silica gel, heptane to CH$_2$Cl$_2$) gave tert-butyl 3-(4-formylthiazole-2-carbonyl)-1H-indole-1-carboxylate (1.63 g) as a white solid. ESI MS m/z 357 [M+H]$^+$.

Step 5: A solution of NaClO$_2$ (19.0 g, 210 mmol) and KH$_2$PO$_4$ (46.7 g, 0.336 mmol) in H$_2$O (200 mL) was added dropwise to a solution of tert-butyl 3-(4-formylthiazole-2-carbonyl)-1H-indole-1-carboxylate (15.0 g, 42 mmol) in tBuOH/H$_2$O/DCM (300 mL/60 mL/60 mL) at room temperature over 0.5 h. The mixture was stirred for 5 h. The mixture was extracted with EtOAc (300 mL×4), the combined organic phases were washed with aqueous 5% KHSO$_4$ (500 mL×3) and brine (500 mL×1), dried (Na$_2$SO$_4$), filtered and concentrated to dryness. The residue was triturated with EtOAc/hexane (1:2, 50 mL), filtered and dried to afford 2-(1-(tert-butoxycarbonyl)-1H-indole-3-carbonyl)thiazole-4-carboxylic acid (13.5 g, 86% yield) as off-white solid. $^1$H-NMR (400 MHz, DMSO-d6): δ 13.48 (bs, 1H), 9.62 (s, 1H), 8.89 (s, 1H), 8.38 (m 1H), 8.18 (d, J=8.0 Hz, 1H), 7.48 (m, 2H), 1.69 (s, 9H). ESI MS m/z 371 [M−H]$^-$.

Alternate Preparation of the Key Intermediate Int-B.

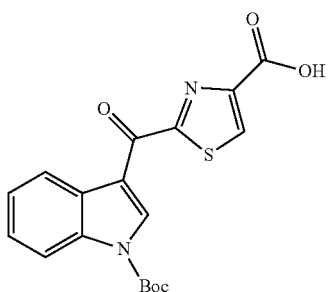

Int-B

To a suspension of methyl 2-(1H-indole-3-carbonyl)thiazole-4-carboxylate (5.00 g, 17.46 mmol) and di-tert-butyl dicarbonate (5.27 ml, 22.70 mmol) in acetonitrile (175 ml) was added DMAP (0.640 g, 5.24 mmol). Upon completion, the reaction mixture was concentrated. Chromatography (silica gel, 1% to 10% MeOH in DCM) gave methyl 2-(1-(tert-butoxycarbonyl)-1H-indole-3-carbonyl)thiazole-4-carboxylate (6.30 g) as an off white solid. ESI MS m/z 373 [M+H]+.

Preparation of the Key Intermediate Int-E.

Figure 17:
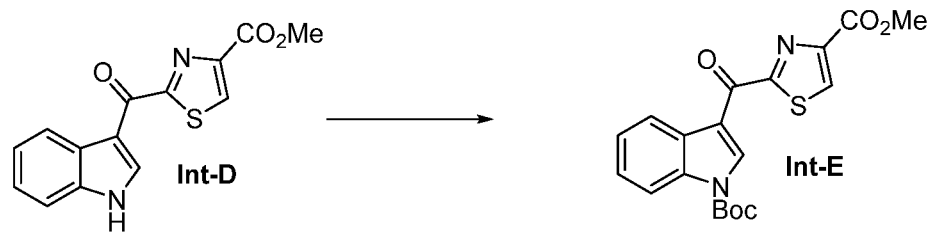
FIG. 17 shows a scheme for preparing the key intermediate Int-E.

The key intermediate Int-E was synthesized according to the scheme of FIG. 17 and by the following method.

To a suspension of methyl 2-(1H-indole-3-carbonyl)thiazole-4-carboxylate (200 mg, 0.699 mmol) and di-tert-butyl dicarbonate (198 mg, 0.908 mmol) in acetonitrile (6986 µl) was added 4-(dimethylamino)pyridine (25.6 mg, 0.210 mmol). Upon completion, the reaction solvent was concentrated. Chromatography (silica gel, heptane to % MeOH/CH$_2$Cl$_2$) gave methyl 2-(1-(tert-butoxycarbonyl)-1H-indole-3-carbonyl)thiazole-4-carboxylate (269 mg) as a white solid. ESI MS m/z 387 [M+H]+.

Figure 64:
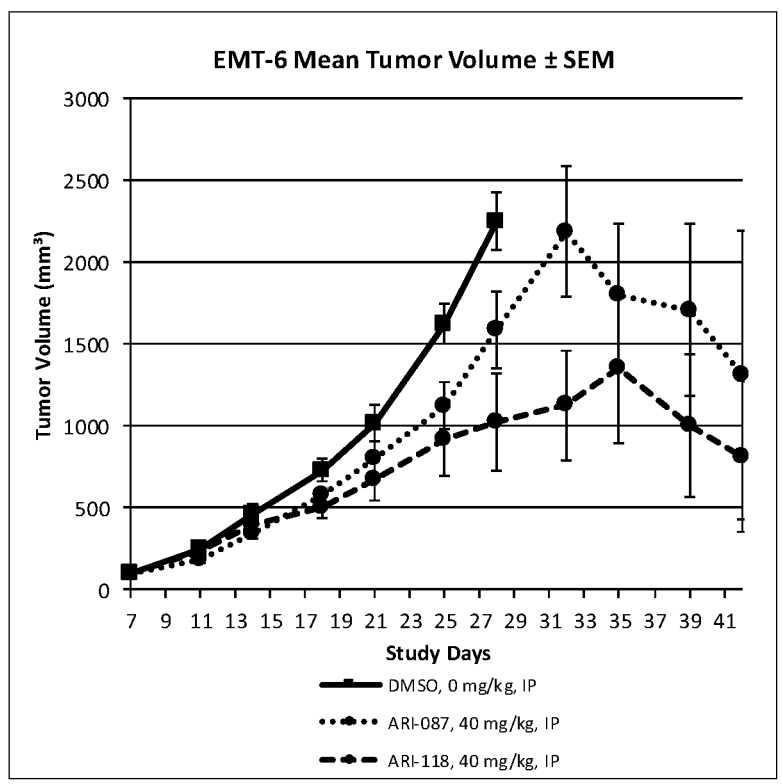
FIG. 64 is a graph comparing the tumor inhibitory activities of ARI-087 and ARI-118 in the EMT-6 syngeneic mouse tumor model.

The following Examples and FIGS. 1-64 are meant to illustrate the synthesis and use of the present indole compounds and should not be construed as limiting the present disclosure in any manner.

EXAMPLES

Example 1: Preparation of methyl 2-(1H-indole-3-carbonothioyl)thiazole-4-carboxylate (ARI-007)

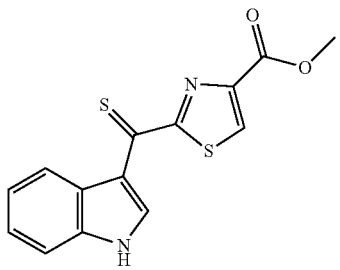 [SMILES: COC(=O)c1csc(C(=S)c2c[nH]c3ccccc23)n1]

Methyl 2-(1H-indole-3-carbonyl)thiazole-4-carboxylate (0.200 g, 0.699 mmol) and Lawesson's Reagent (0.113 g, 0.279 mmol) in THF (6.99 ml) were combined and the mixture heated to 65° C. Upon completion, the reaction was concentrated onto silica gel. Chromatography (silica gel, 0 to 100% heptane to ethyl acetate) followed by reverse phase chromatography (C18, 10% ACN/H$_2$O to ACN) gave methyl 2-(1H-indole-3-carbonothioyl)thiazole-4-carboxylate (75 mg) as a brown solid.

Example 2: Preparation of (4-bromothiazol-2-yl)(1H-indol-3-yl)methanone (ARI-008)

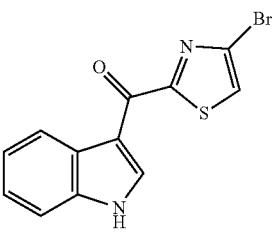 [SMILES: O=C(c1nc(Br)cs1)c1c[nH]c2ccccc12]

Step 1. Conducted by analogy to *Org. Lett.* 2016, 18, 3918-3921. To a solution of 1H-indole (360 mg, 3.07 mmol) in 3 mL of anhydrous THF was added potassium tert-butoxide (1 M in THF) (3.38 mL, 3.38 mmol). After stirring for 30 min, triethylborane (1 M in hexanes) (3.38 mL, 3.38 mmol) was added. After 30 min, the solution was cannulated slowly into an ice-cold mixture of 4-bromothiazole-2-carbonyl chloride (763 mg, 3.37 mmol) in THF (3 mL). Upon completion, the reaction was quenched with saturated NH$_4$Cl (aq). This mixture was extracted 3× with EtOAc. The combined organics were dried over Na$_2$SO$_4$, filtered and concentrated. Chromatography (silica gel, heptane to 10% MeOH/CH$_2$Cl$_2$) gave (4-bromothiazol-2-yl)(1H-indol-3-yl)methanone (760 mg) as an impure orange solid. ESI MS m/z 307 [M+H]+.

Step 2. To a suspension of (4-bromothiazol-2-yl)(1H-indol-3-yl)methanone (0.218 g, 0.710 mmol) and di-tert-butyl dicarbonate (0.214 ml, 0.923 mmol) in acetonitrile (7.10 ml) was added DMAP (0.026 g, 0.213 mmol). Upon completion, the reaction mixture was concentrated under reduced pressure onto silica gel. Chromatography (silica gel, 0 to 50% DCM/heptane) gave tert-butyl 3-(4-bromothiazole-2-carbonyl)-1H-indole-1-carboxylate (0.177 g) as a white solid. ESI MS m/z 407 [M+H]+.

Step 3. To a solution of tert-butyl 3-(4-bromothiazole-2-carbonyl)-1H-indole-1-carboxylate (0.100 g, 0.246 mmol) in dichloromethane (2.5 ml) was added trifluoroacetic acid (TFA) (0.500 ml). Upon completion, the reaction mixture was concentrated. Chromatography (silica gel, heptane to 40% ethyl acetate/heptane) gave (4-bromothiazol-2-yl)(1H-indol-3-yl)methanone (0.060 g) as a yellow solid.

Example 3: Preparation of methyl (2-(1H-indole-3-carbonyl)thiazol-4-yl)carbamate (ARI-009)

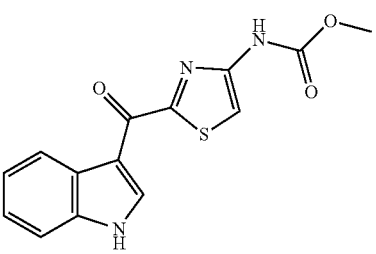 [SMILES: COC(=O)Nc1csc(C(=O)c2c[nH]c3ccccc23)n1]

Triethylamine (0.410 ml, 2.94 mmol) and diphenylphosphoryl azide (0.950 ml, 4.41 mmol) were added to an ice-cold mixture of 2-(1H-indole-3-carbonyl)thiazole-4-carboxylic acid (0.400 g, 1.469 mmol) in dioxane (2.94 ml) at 0° C. After 15 min, the ice bath was removed then methanol (16 ml, 395 mmol) was added dropwise over 10 minutes once gas evolution had ceased. The reaction mixture was stirred overnight. Water was added and the mixture was extracted with ethyl acetate 2×75 mL, then washed with brine, dried over sodium sulfate, filtered and concentrated onto silica gel. Chromatography (silica gel, heptane to 50% ethyl acetate/heptane) gave methyl (2-(1H-indole-3-carbonyl)thiazol-4-yl)carbamate (0.021 g) as a yellow solid.

Example 4: Preparation of methyl 2-((1H-indol-3-yl)(methoxyimino)methyl)thiazole-4-carboxylate (ARI-011)

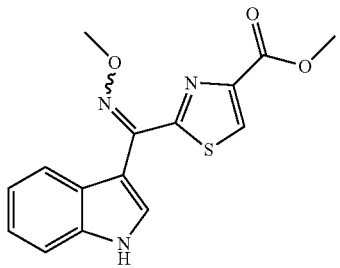 [SMILES: CON=C(c1nc(C(=O)OC)cs1)c1c[nH]c2ccccc12]

A mixture of 2-(1H-indole-3-carbonyl)thiazole-4-carboxylic acid (314 mg, 1.153 mmol) and O-methylhydroxylamine hydrochloride (450 mg, 5.39 mmol) in MeOH was heated in a microwave to 140° C. for 30 min. Upon completion, the mixture was concentrated to dryness. Chromatography (silica gel, heptane to DCM then to 10% MeOH/DCM) gave methyl 2-((1H-indol-3-yl)(methoxyimino)methyl)thiazole-4-carboxylate (163.8, mg) as a mixture of E/Z isomers and as an orange solid after lyophilization from acetonitrile/$H_2O$.

Example 5: Preparation of S-methyl 2-(1H-indole-3-carbonyl)thiazole-4-carbothioate (ARI-013)

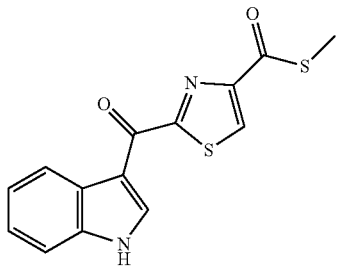 [SMILES: CSC(=O)c1csc(C(=O)c2c[nH]c3ccccc23)n1]

To a suspension of 2-(1H-indole-3-carbonyl)thiazole-4-carboxylic acid (0.500 g, 1.836 mmol) and di-tert-butyl dicarbonate (0.554 ml, 2.387 mmol) in acetonitrile (18.36 ml) was added DMAP (0.067 g, 0.551 mmol) and triethylamine (0.256 ml, 1.836 mmol). After consumption of starting material, sodium methyl mercaptide (0.167 g, 2.387 mmol) was added and the reaction mixture stirred overnight. The reaction mixture was then concentrated under reduced pressure and redissolved in EtOAc, then washed with saturated $NH_4Cl$. The organic layer was dried over magnesium sulfate, then absorbed onto silica gel. Chromatography (silica gel, 12 g, solid load, 0-80% $CH_2Cl_2$/heptane) gave tert-butyl 3-(4-((methylthio)carbonyl)thiazole-2-carbonyl)-1H-indole-1-carboxylate (0.21 g, 0.522 mmol, 28.4% yield). ESI MS: m/z 403 [M+H]+.

To a solution of tert-butyl 3-(4-((methylthio)carbonyl) thiazole-2-carbonyl)-1H-indole-1-carboxylate (0.207 g, 0.514 mmol) in DCM (4 ml) was added TFA (1.8 ml). Upon completion, the reaction mixture was concentrated under reduced pressure and precipitated overnight from methanol to give S-methyl 2-(1H-indole-3-carbonyl)thiazole-4-carbothioate (0.116 g).

Example 6: Preparation of methyl 2-((hydroxyimino)(1H-indol-3-yl)methyl)thiazole-4-carboxylate (ARI-014)

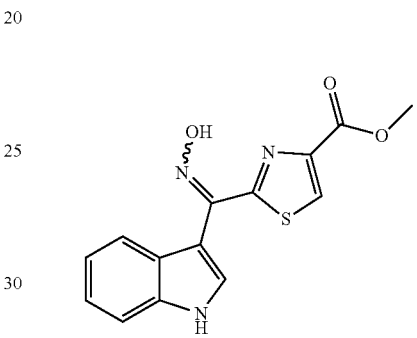

Methyl 2-(1H-indole-3-carbonyl)thiazole-4-carboxylate (0.300 g, 1.048 mmol) and hydroxylamine hydrochloride (0.218 g, 3.14 mmol) were combined with pyridine (11 ml). The reaction mixture was sealed and heated in the microwave at 130° C. Upon completion, the reaction mixture was concentrated onto silica gel. Chromatography (DCM to 1% MeOH/DCM) gave methyl 2-((hydroxyimino)(1H-indol-3-yl)methyl)thiazole-4-carboxylate (214.1, mg) as a yellow glass and as a mixture of E/Z isomers.

Example 7: Preparation of methyl 2-(1-methyl-1H-indole-3-carbonyl)thiazole-4-carboxylate (ARI-015)

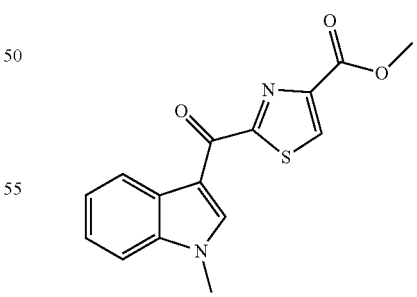

To a suspension of methyl 2-(1H-indole-3-carbonyl)thiazole-4-carboxylate (111 mg, 0.388 mmol) in ice-cold THF (3877 μl) was added potassium hexamethyldisilazide (0.5 M in toluene) (814 μl, 0.407 mmol). DMF (500 uL) was added to improve solubility, the mixture stirred 10 min, then iodomethane (25.3 μl, 0.407 mmol) was added. The reaction mixture was quenched by the addition of anhydrous MeOH, then concentrated to dryness. Chromatography (silica gel, CH$_2$Cl$_2$ to 1% MeOH/CH$_2$Cl$_2$) gave methyl 2-(1-methyl-1H-indole-3-carbonyl)thiazole-4-carboxylate (66.7 mg) as a pale orange solid.

Example 8: Preparation of methyl (S)-2-(1H-indole-3-carbonyl)-5,5-dimethyl-4,5-dihydrothiazole-4-carboxylatecarboxylate (ARI-016)

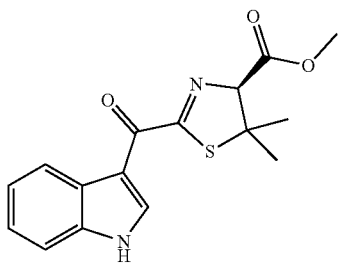 [SMILES: COC(=O)[C@@H]1N=C(C(=O)c2c[nH]c3ccccc23)SC1(C)C]

Step 1. 1H-indole-3-carbonyl cyanide (213 mg, 1.252 mmol) and (S)-2-amino-3-mercapto-3-methylbutanoic acid (187 mg, 1.252 mmol) were combined with DMF (12 mL) then the mixture treated with 1,8-diazabicyclo[5.4.0]undec-7-ene (18.72 µl, 0.125 mmol). The reaction mixture was heated to 40° C. Chromatography (silica gel, heptane to EtOAc+0.1% AcOH) gave (S)-2-(1H-indole-3-carbonyl)-5,5-dimethyl-4,5-dihydrothiazole-4-carboxylic acid (97 mg) as a white solid, ESI MS m/z 303 [M+H]$^+$. Treatment of the solid with sodium methoxide (16.97 mg, 0.314 mmol) in MeOH (10 ml) gave sodium (S)-2-(1H-indole-3-carbonyl)-5,5-dimethyl-4,5-dihydrothiazole-4-carboxylate after the solvent was removed to dryness. The material was used as is.

Step 2. To a solution of sodium (S)-2-(1H-indole-3-carbonyl)-5,5-dimethyl-4,5-dihydrothiazole-4-carboxylate (102 mg, 0.314 mmol) in DMF (6280 µl) was added iodomethane (19.55 µl, 0.314 mmol). After the reaction was complete, the reaction was concentrated to dryness, then partitioned between EtOAc and water. The organic layer was dried with brine, filtered and concentrated. Chromatography (silica gel, CH$_2$Cl$_2$ to 6% MeOH/CH$_2$Cl$_2$) gave methyl (S)-2-(1H-indole-3-carbonyl)-5,5-dimethyl-4,5-dihydrothiazole-4-carboxylatecarboxylate (48.7 mg) as a light yellow solid.

Example 9: Preparation of methyl 2-(1-(1H-indol-3-yl)-2-methoxyvinyl)thiazole-4-carboxylate (ARI-017)

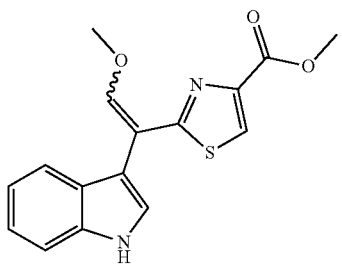 [SMILES: COC=C(c1nc(C(=O)OC)cs1)c1c[nH]c2ccccc12]

Step 1. To an ice-cold solution of (methoxymethyl)triphenylphosphonium chloride (322 mg, 0.939 mmol) in THF (8 mL) was added potassium hexamethyldisilazide (0.5 M in toluene) (1.708 mL, 0.854 mmol). After 30 min, solid methyl 2-(1-(tert-butoxycarbonyl)-1H-indole-3-carbonyl)thiazole-4-carboxylate (300 mg, 0.776 mmol) was added then allowed to slowly warm to room temperature. Upon completion, saturated NH$_4$Cl was added then after 15 min the reaction mixture was partitioned between EtOAc and saturated NH$_4$Cl. The organic layer was dried with brine and Na$_2$SO$_4$, and filtered. Chromatography (silica gel, heptane to 25% EtOAc/heptane) gave methyl 2-(1-(1-(tert-butoxycarbonyl)-1H-indol-3-yl)-2-methoxyvinyl)thiazole-4-carboxylate (276.9 mg) as a pale yellow solid. ESI MS m/z 415 [M+H]$^+$.

Step 2. A mixture of methyl 2-(1-(1-(tert-butoxycarbonyl)-1H-indol-3-yl)-2-methoxyvinyl)thiazole-4-carboxylate (80 mg, 0.193 mmol) and K$_2$CO$_3$ (53.4 mg, 0.386 mmol) was stirred in MeOH (10 mL) with heating to 50° C. The reaction mixture was concentrated. Chromatography (silica gel, CH$_2$Cl$_2$ to 5% MeOH/CH$_2$Cl$_2$) gave methyl 2-(1-(1H-indol-3-yl)-2-methoxyvinyl)thiazole-4-carboxylate (5.7, mg) as an off-white solid and as a mixture of E/Z isomers.

Example 10: Preparation of methyl 2-(1-(1H-indol-3-yl)prop-1-en-1-yl)thiazole-4-carboxylate (ARI-018)

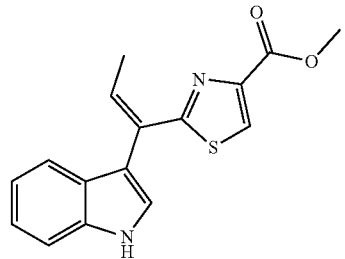 [SMILES: C/C=C(\c1nc(C(=O)OC)cs1)c1c[nH]c2ccccc12]

Prepared according to the method described in Example 9 except that (ethyl)triphenylphosphonium bromide was used instead of (methoxymethyl)triphenylphosphonium chloride.

Example 11: Preparation of methyl 2-(1-(1H-indol-3-yl)vinyl)thiazole-4-carboxylate (ARI-019)

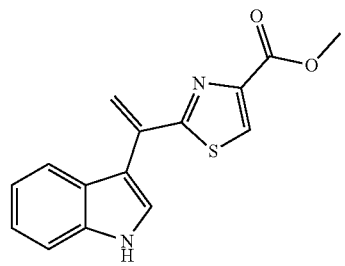 [SMILES: C=C(c1nc(C(=O)OC)cs1)c1c[nH]c2ccccc12]

Prepared according to the method described in Example 9 except that methyltriphenylphosphonium bromide was used instead of (methoxymethyl)triphenylphosphonium chloride.

Example 12: Preparation of methyl 2-(1-(1H-indol-3-yl)-2-methylprop-1-en-1-yl)thiazole-4-carboxylate (ARI-020)

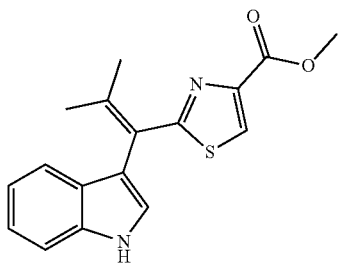 [SMILES: COC(=O)c1csc(C(=C(C)C)c2c[nH]c3ccccc23)n1]

Prepared according to the method described in Example 9 except that isopropyltriphenylphosphonium iodide was used instead of (methoxymethyl)triphenylphosphonium chloride.

Example 13: Preparation of N-(2-(1H-indole-3-carbonyl)thiazol-4-yl)acetamide (ARI-021)

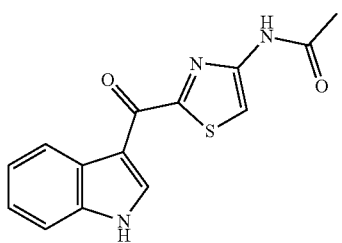 [SMILES: CC(=O)Nc1csc(C(=O)c2c[nH]c3ccccc23)n1]

Step 1. Diphenylphosphoryl azide (0.231 ml, 1.071 mmol) was added to a solution of 2-(1-(tert-butoxycarbonyl)-1H-indole-3-carbonyl)thiazole-4-carboxylic acid (0.266 g, 0.714 mmol) and triethylamine (0.199 ml, 1.429 mmol) in DMF (40 ml) at ambient temperature, then stirred for 30 min. After this time, water (2 ml) was added and the resulting mixture was heated to 80° C. for one hour. The reaction mixture was cooled to ambient temperature, and water was added (50 mL), and the resulting mixture was then extracted with ethyl acetate (3×50 mL). The organic layers were pooled, washed with brine, and dried over sodium sulfate, then filtered and concentrated onto silica gel under reduced pressure. Chromatography (silica gel, heptane to 30% ethyl acetate/heptane) gave tert-butyl 3-(4-aminothiazole-2-carbonyl)-1H-indole-1-carboxylate (0.116 g). ESI MS m/z 344 [M+H]$^+$.

Step 2. Acetyl chloride (0.025 ml, 0.352 mmol) was added to an ice-cold solution of tert-butyl 3-(4-aminothiazole-2-carbonyl)-1H-indole-1-carboxylate (0.110 g, 0.320 mmol) and triethylamine (0.067 ml, 0.480 mmol) in dichloromethane (21 ml). Upon completion, potassium carbonate (0.144 g, 0.320 mmol) and methanol (10.50 ml) were added to remove the Boc group. Upon completion, water was added to the reaction and the mixture extracted with ethyl acetate. The organic was washed with brine wash, dried over magnesium sulfate, filtered and the crude was concentrated onto silica gel. Chromatography (silica gel, heptane to 80% ethyl acetate/heptane) gave N-(2-(1H-indole-3-carbonyl)thiazol-4-yl)acetamide (44.2 mg).

Example 14: Preparation of 3-hydroxypropyl 2-(1H-indole-3-carbonyl)thiazole-4-carboxylate (ARI-022)

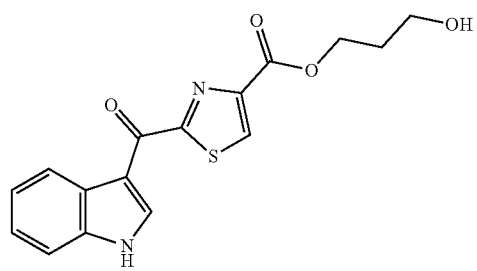 [SMILES: O=C(OCCCO)c1csc(C(=O)c2c[nH]c3ccccc23)n1]

To an ice-cold solution of 2-(1H-indole-3-carbonyl)thiazole-4-carboxylic acid (0.300 g, 1.102 mmol) and 4-(dimethylamino)pyridine (0.013 g, 0.110 mmol) in tetrahydrofuran (11.02 ml) was sequentially added triethylamine (0.192 ml, 1.377 mmol), 1,3-propanediol (0.735 ml, 11.02 mmol), and 3-(((ethylimino)methylene)amino)-N,N-dimethylpropan-1-amine hydrochloride (0.232 g, 1.212 mmol). The reaction mixture was warmed to ambient temperature and stirred. Upon completion, 1M HCl (aq) was added and the subsequent mixture extracted with EtOAc. The combined organics were washed with water, sodium bicarbonate and brine. The crude was filtered and concentrated onto silica gel. Chromatography (silica gel, DCM to 5% MeOH/DCM) gave 3-hydroxypropyl 2-(1H-indole-3-carbonyl)thiazole-4-carboxylate (0.126 g) as a yellow solid.

Example 15: Preparation of 2-hydroxyethyl 2-(1H-indole-3-carbonyl)thiazole-4-carboxylate (ARI-023)

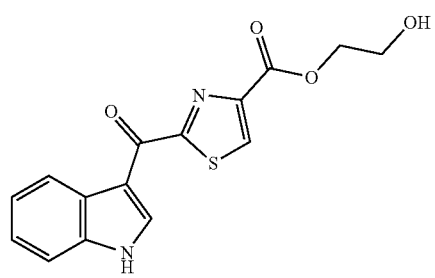 [SMILES: O=C(OCCO)c1csc(C(=O)c2c[nH]c3ccccc23)n1]

Prepared according to the method described in Example 14 except that ethylene glycol was used instead of 1,3-propanediol.

Example 16: Preparation of methyl 2-((1H-indol-3-yl)(methoxy)methyl)thiazole-4-carboxylate (ARI-024)

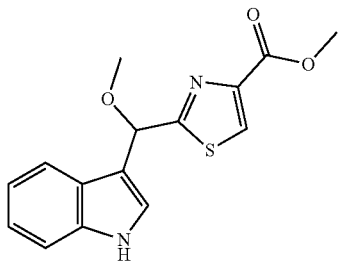 [SMILES: COC(=O)c1csc(C(OC)c2c[nH]c3ccccc23)n1]

Sodium borohydride (0.092 g, 2.445 mmol) was added portionwise to a mixture of methyl 2-(1H-indole-3-carbonyl)thiazole-4-carboxylate (0.200 g, 0.699 mmol) in tetrahydrofuran (6.99 mL) and methanol (6.99 mL). Upon completion, the reaction mixture was quenched with 1M HCl then extracted with DCM. The organic was washed with brine, and dried over sodium sulfate then filtered. Chromatography (silica gel, DCM to 5% MeOH/DCM) gave methyl 2-((1H-indol-3-yl)(methoxy)methyl)thiazole-4-carboxylate (0.035 g) as a pink solid.

Example 17: Preparation of 2-(2-hydroxyethoxy)ethyl 2-(1H-indole-3-carbonyl)thiazole-4-carboxylate (ARI-025)

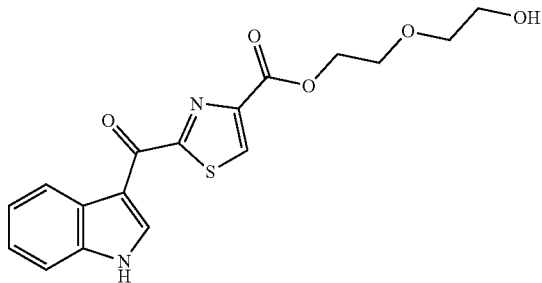 [SMILES: O=C(OCCOCCO)c1csc(C(=O)c2c[nH]c3ccccc23)n1]

Prepared according to the method described in Example 14 except that diethylene glycol was used instead of 1,3-propanediol.

Example 18: Preparation of 2-(1H-indole-3-carbonyl)thiazole-4-carbonitrile (ARI-026)

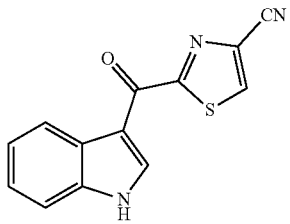 [SMILES: N#Cc1csc(C(=O)c2c[nH]c3ccccc23)n1]

Triethylamine (2.57 ml, 18.43 mmol) was added to an ice-cold suspension of 2-(1H-indole-3-carbonyl)thiazole-4-carboxamide (see WO2018121434A1) (1.00 g, 3.69 mmol) in tetrahydrofuran (36.9 ml). Subsequently trifluoroacetic anhydride (1.302 ml, 9.22 mmol) was added dropwise. The ice bath was removed. Upon completion, the reaction mixture was poured over ice and diluted with ethyl acetate. The organic layer was washed with 2M $Na_2CO_3$ and brine, dried over sodium sulfate, filtered and concentrated onto silica gel. Chromatography (silica gel, heptane to 50% EtOAc/heptane) gave 2-(1H-indole-3-carbonyl)thiazole-4-carbonitrile (0.720 g) as a yellow solid.

Example 19: Preparation of (4-(1,3-dioxolan-2-yl)thiazol-2-yl)(1H-indol-3-yl)methanone (ARI-028)

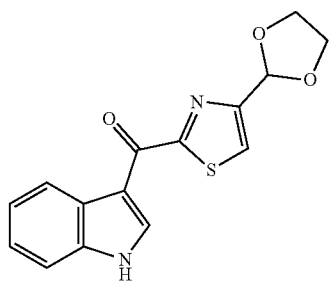 [SMILES: O=C(c1nc(C2OCCO2)cs1)c1c[nH]c2ccccc12]

To a solution of tert-butyl 3-(4-formylthiazole-2-carbonyl)-1H-indole-1-carboxylate (0.200 g, 0.561 mmol) and ethylene glycol (0.094 ml, 1.684 mmol) in dioxane (5.61 ml) was added p-toluenesulfonic acid monohydrate (1.067 mg, 5.61 μmol) and the mixture heated to 50° C. Upon completion, potassium carbonate (0.116 g, 0.842 mmol) and MeOH was added to remove the Boc group. Upon completion, water was added and the pH of the solution was adjusted to 8 with 1M HCl. The mixture was extracted with ethyl acetate and the organic layer was washed with brine, then concentrated onto silica gel. Chromatography (silica gel, heptane to 50% EtOAc/heptane) gave (4-(1,3-dioxolan-2-yl)thiazol-2-yl)(1H-indol-3-yl)methanone (73.4 mg) as a yellow solid.

Example 20: Preparation of (4-(dimethoxymethyl)thiazol-2-yl)(1H-indol-3-yl)methanone (ARI-029)

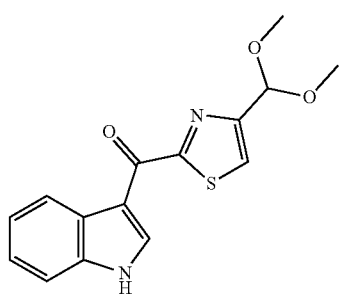 [SMILES: COC(OC)c1csc(C(=O)c2c[nH]c3ccccc23)n1]

Prepared according to the method described in Example 19 except that methanol was used instead of ethylene glycol.

Example 21: Preparation of (1H-indol-3-yl)(4-(5-methyl-1,2,4-oxadiazol-3-yl)thiazol-2-yl)methanone (ARI-030)

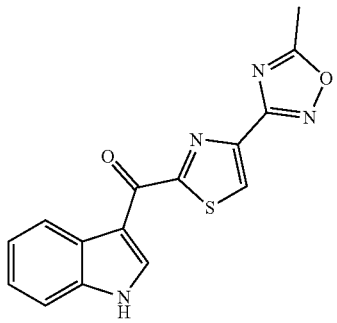 [SMILES: Cc1nc(-c2csc(C(=O)c3c[nH]c4ccccc34)n2)no1]

A mixture of 2-(1H-indole-3-carbonyl)thiazole-4-carbonitrile (50 mg, 0.197 mmol), $K_3PO_4$ (126 mg, 0.592 mmol) and hydroxylamine hydrochloride (34.3 mg, 0.494 mmol) in DMF (2.5 ml) was heated to 100° C. with a microwave for 30 min. Acetyl chloride (0.028 ml, 0.395 mmol) was added and the reaction heated to 110° C. for 2 hr. The DMF was removed under high vacuum. Added water, sonicated then collected the solid by filtration. The solid was rinsed with $H_2O$, then dried at 50° C. under high vacuum to give (1H-indol-3-yl)(4-(5-methyl-1,2,4-oxadiazol-3-yl)thiazol-2-yl)methanone (34 mg) as a yellow solid.

Example 22: Preparation of (1H-indol-3-yl)(4-(3-methyl-1,2,4-oxadiazol-5-yl)thiazol-2-yl)methanone (ARI-031)

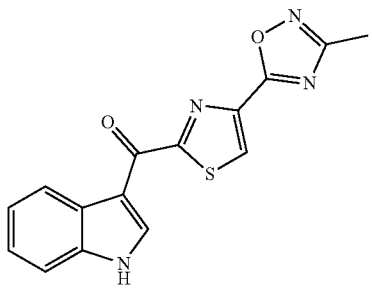 [SMILES: Cc1noc(-c2csc(C(=O)c3c[nH]c4ccccc34)n2)n1]

Step 1. To 2-(1-(tert-butoxycarbonyl)-1H-indole-3-carbonyl)thiazole-4-carboxylic acid (200 mg, 0.537 mmol), N-hydroxyacetamidine (39.8 mg, 0.537 mmol) and triethylamine (299 µl, 2.148 mmol) in ethyl acetate (2685 µl) was added 1-propanephosphonic acid cyclic anhydride (50 wt % in EtOAc) (799 µl, 1.343 mmol) dropwise. The mixture was heated to 80° C. Upon completion, saturated $NaHCO_3$ (aq) was added and the solid collected by filtration. Washed the solid with $H_2O$, and then with a minimum of EtOAc. The solid was dried under high vacuum at 50° C. to give tert-butyl 3-(4-(3-methyl-1,2,4-oxadiazol-5-yl)thiazol-2-carbonyl)-1H-indole-1-carboxylate as an off-white solid. ESI MS m/z 411 $[M+H]^+$.

Step 2. To tert-butyl 3-(4-(3-methyl-1,2,4-oxadiazol-5-yl)thiazole-2-carbonyl)-1H-indole-1-carboxylate (99 mg, 0.241 mmol) was added $K_2CO_3$ (33.3 mg, 0.241 mmol) and MeOH (5 ml). Upon reaction completion, silica gel was added and the mixture concentrated. Chromatography (silica gel, heptane to 40% EtOAc/heptane) gave (1H-indol-3-yl)(4-(3-methyl-1,2,4-oxadiazol-5-yl)thiazol-2-yl)methanone (64 mg) as a yellow solid after drying overnight at 50° C. in the vacuum oven.

Example 23: Preparation of methyl 6-(1H-indole-3-carbonyl)picolinate (ARI-032)

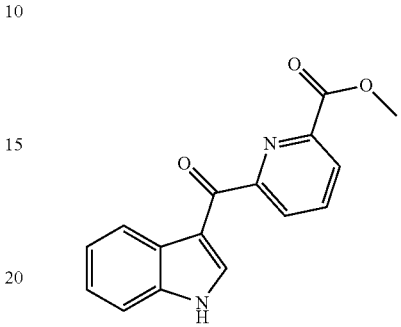

Prepared according to the method described in Example 2 except that methyl 6-(chlorocarbonyl)picolinate hydrochloride was used instead of 4-bromothiazole-2-carbonyl chloride in step 1 and the Boc deprotection was effected as follows. Methyl 6-(1H-indole-3-carbonyl)picolinate (1197 mg, 4.27 mmol) was treated with sodium sulfate (606 mg, 4.27 mmol) and stirred in anhydrous MeOH (50 ml) for 30 min then $K_2CO_3$ (177 mg, 1.281 mmol) was added. Upon completion, the mixture was filtered through Celite, silica gel was added and concentrated to dryness. Chromatography (silica gel, heptane to EtOAc) and then reverse phase (C18, $H_2O$ to $CH_3CN$) gave methyl 6-(1H-indole-3-carbonyl)picolinate as an off-white solid.

Example 24: Preparation of N-ethyl-2-(1H-indole-3-carbonyl)thiazole-4-carboxamide (ARI-033)

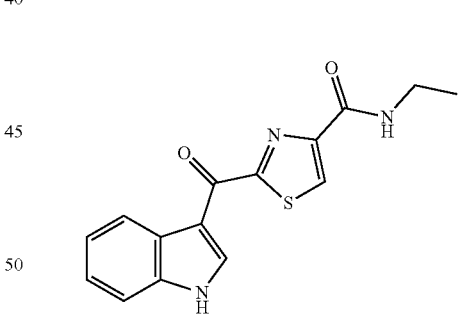

Propylphosphonic anhydride (0.352 ml, 0.591 mmol, 50 wt % in EtOAc) was added to a solution of 2-(1-(tert-butoxycarbonyl)-1H-indole-3-carbonyl)thiazole-4-carboxylic acid (0.200 g, 0.537 mmol), ethanamine (0.322 ml, 0.644 mmol), and DIPEA (0.141 ml, 0.806 mmol) in N,N-dimethylformamide (5.37 ml). Upon completion, the Boc group was removed by adding potassium carbonate (0.300 g, 2.171 mmol) and 10 mL of MeOH and heating the mixture to 50° C. Upon completion, the mixture was concentrated under reduced pressure then to it added 20 mL of water, followed by neutralization with 1M HCl to pH 7. This mixture was extracted with 3×40 mL ethyl acetate. The combined organic layers were washed with 50 mL of 5% LiCl and brine, then concentrated under reduced pressure onto silica gel. Chromatography (silica gel, DCM to 5% MeOH/DCM) gave N-ethyl-2-(1H-indole-3-carbonyl)thiazole-4-carboxamide (89.5 mg) as a yellow solid.

Example 25: Preparation of 2-(1H-indole-3-carbonyl)-N-isopropylthiazole-4-carboxamide (ARI-034)

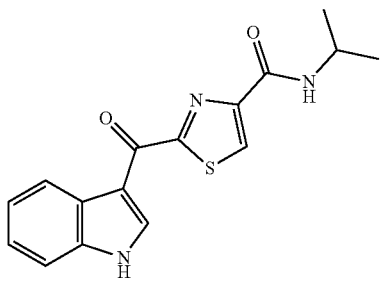 [SMILES: CC(C)NC(=O)c1csc(C(=O)c2c[nH]c3ccccc23)n1]

Prepared according to the method described in Example 24 except that isopropylamine was used instead of ethylamine.

Example 26: Preparation of 2-(1H-indole-3-carbonyl)-N-isobutylthiazole-4-carboxamide (ARI-035)

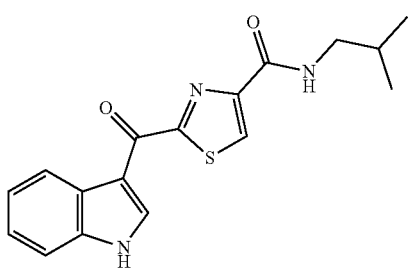 [SMILES: CC(C)CNC(=O)c1csc(C(=O)c2c[nH]c3ccccc23)n1]

Prepared according to the method described in Example 24 except that isobutylamine was used instead of ethylamine.

Example 27: Preparation of N-(2-hydroxyethyl)-2-(1H-indole-3-carbonyl)thiazole-4-carboxamide (ARI-036)

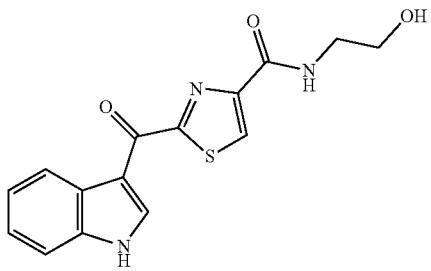 [SMILES: O=C(NCCO)c1csc(C(=O)c2c[nH]c3ccccc23)n1]

To a solution of 2-(1H-indole-3-carbonyl)thiazole-4-carboxylic acid (0.200 g, 0.735 mmol) and hexafluorophosphate azabenzotriazole tetramethyl uronium (HATU) (0.335 g, 0.881 mmol) in N,N-dimethylformamide (7.35 ml) was added N,N-diisopropylethylamine (DIPEA) (0.385 ml, 2.204 mmol) and then ethanolamine (0.222 ml, 3.67 mmol). Upon completion, water was added and the reaction mixture was concentrated under reduced pressure to remove DMF. The reaction mixture was partitioned between EtOAc and H$_2$O. The organic phase was successively washed with 1M HCl, H$_2$O, saturated NaHCO$_3$, and brine, then dried over Na$_2$SO$_4$. After filtration, the crude solution was concentrated onto silica gel. Chromatography (DCM to 25% 80:18:2 CH$_2$Cl$_2$/MeOH/conc. NH$_4$OH) gave N-(2-hydroxyethyl)-2-(1H-indole-3-carbonyl)thiazole-4-carboxamide (0.164 g) as a yellow solid.

Example 28: Preparation of 2-(1H-indole-3-carbonyl)-N-(2-methoxyethyl)thiazole-4-carboxamide (ARI-037)

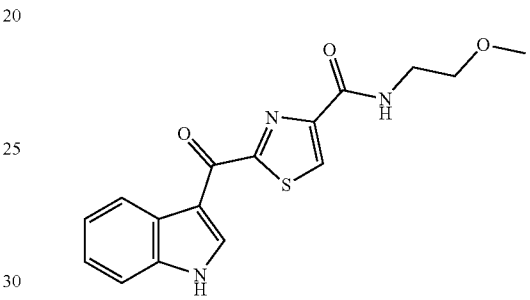

Prepared according to the method described in Example 27 except that 2-methoxyethan-1-amine was used instead of ethanolamine.

Example 29: Preparation of methyl 2-(1-cyano-1H-indole-3-carbonyl)thiazole-4-carboxylate (ARI-038)

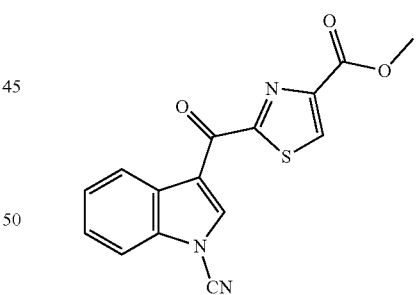

Cyanogen bromide (0.740 g, 6.99 mmol) was added to an ice cold solution of methyl 2-(1H-indole-3-carbonyl)thiazole-4-carboxylate (0.500 g, 1.746 mmol) and cesium carbonate (0.683 g, 2.096 mmol) in acetonitrile (17.46 ml). The reaction suspension was filtered and rinsed with acetonitrile. The filtrate was concentrated under reduced pressure and then treated with boiling DCM and filtered. The filtrate was directly loaded onto a silica gel column. Chromatography (heptane to 50% EtOAc/heptane) gave methyl 2-(1-cyano-1H-indole-3-carbonyl)thiazole-4-carboxylate (0.046 g) as a white solid.

Example 30: Preparation of N-(tert-butyl)-2-(1H-indole-3-carbonyl)thiazole-4-carboxamide (ARI-039)

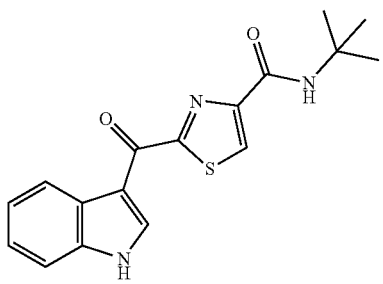 [SMILES: CC(C)(C)NC(=O)c1csc(C(=O)c2c[nH]c3ccccc23)n1]

Prepared according to the method described in Example 24 except that tert-butylamine was used instead of ethylamine.

Example 31: Preparation of 1-(2-(1H-indole-3-carbonyl)thiazol-4-yl)pyrrolidine-2,5-dione (ARI-040)

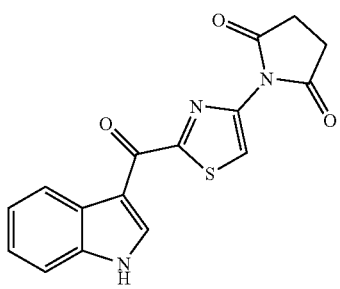 [SMILES: O=C(c1nc(N2C(=O)CCC2=O)cs1)c1c[nH]c2ccccc12]

To a mixture of (4-bromothiazol-2-yl)(1H-indol-3-yl)methanone (217 mg, 0.533 mmol) and succinimide (79 mg, 0.799 mmol) in 2,4,6-trimethylpyridine (1 ml, 0.533 mmol) was added cuprous oxide (45.7 mg, 0.320 mmol). The mixture was then heated in a microwave to 175° C. for 7 hrs. The mixture was diluted with $CH_2Cl_2$ and then 5% $H_2SO_4$ (aq) was added. The solid was removed by filtration. The filtrate was treated with 5% $H_2SO_4$ (aq) then extracted with 2× with $CH_2Cl_2$. The combined organic extracts were dried over $Na_2SO_4$, filtered and concentrated. Chromatography (silica gel, DCM to 1% MeOH/DCM, dry loaded on Celite) gave 1-(2-(1H-indole-3-carbonyl)thiazol-4-yl)pyrrolidine-2,5-dione (7 mg) as a yellow solid.

Example 32: Preparation of (2-(1H-indole-3-carbonyl)thiazol-4-yl)(azetidin-1-yl)methanone (ARI-044)

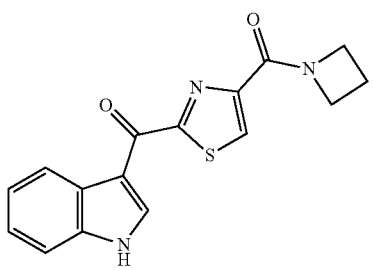 [SMILES: O=C(c1nc(C(=O)N2CCC2)cs1)c1c[nH]c2ccccc12]

Prepared according to the method described in Example 27 except that azetidine hydrochloride was used instead of ethanolamine.

Example 33: Preparation of (2-(1H-indole-3-carbonyl)thiazol-4-yl)(3-methoxyazetidin-1-yl)methanone (ARI-046)

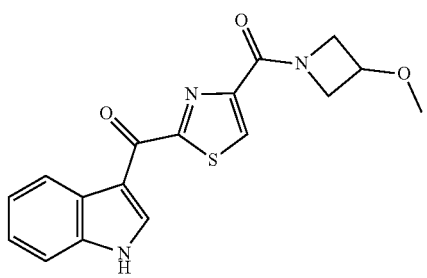 [SMILES: COC1CN(C(=O)c2csc(C(=O)c3c[nH]c4ccccc34)n2)C1]

Prepared according to the method described in Example 27 except that 3-methoxyazetidine hydrochloride was used instead of ethanolamine.

Example 34: Preparation of 6-(1H-indole-3-carbonyl)-N-methylpicolinamide (ARI-047)

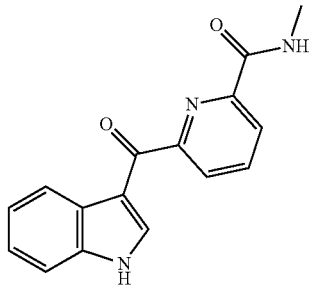 [SMILES: CNC(=O)c1cccc(C(=O)c2c[nH]c3ccccc23)n1]

Step 1. Sodium hydroxide (0.813 ml, 0.813 mmol) was added to a stirring solution of methyl 6-(1H-indole-3-carbonyl)picolinate (0.228 g, 0.813 mmol) in tetrahydrofuran (4.5 ml) and water (3.7 ml). Upon completion, the reaction mixture was diluted with water and extracted with 30 mL of EtOAc to remove unreacted ester. The aqueous layer was adjusted to pH 5 with 1M HCl, then extracted with EtOAc. The organic was washed with brine and dried over $Na_2SO_4$, and filtered. The crude was concentrated onto silica gel. Chromatography (C18, $H_2O$ to 60% ACN/water) gave 6-(1H-indole-3-carbonyl)picolinic acid (0.185 g, 0.695 mmol, 85% yield) as a yellow solid. ESI MS m/z 267 [M+H]$^+$.

Step 2. Prepared according to the method described in Example 27 except that methylamine in THF was used instead of ethanolamine.

Example 35: Preparation of 2-(hydrazineylidene (1H-indol-3-yl)methyl)-4-(5-methyl-4H-1,2,4-triazol-3-yl)thiazole (ARI-050)

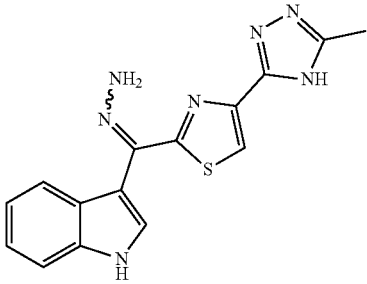 [SMILES: Cc1nnc(-c2csc(C(=NN)c3c[nH]c4ccccc34)n2)[nH]1]

Step 1. To a mixture of 2-(1-(tert-butoxycarbonyl)-1H-indole-3-carbonyl)thiazole-4-carboxylic acid (60 mg, 0.161 mmol), ammonium chloride (60.3 mg, 1.128 mmol), HOBt (37.0 mg, 0.242 mmol), and ethylene dichloride (EDC) (93 mg, 0.483 mmol) was added N,N-dimethylformamide (1.6 mL) and then DIPEA (0.169 mL, 0.967 mmol). Upon completion, the reaction mixture was diluted with water and saturated NaHCO$_3$. The precipitate was collected, washed with water, and dried in vacuo to provide tert-butyl 3-(4-carbamoylthiazole-2-carbonyl)-1H-indole-1-carboxylate (56.6 mg, 0.152 mmol) as a yellow solid. ESI MS m/z 372 [M+H]$^+$.

Step 2. A mixture of tert-butyl 3-(4-carbamoylthiazole-2-carbonyl)-1H-indole-1-carboxylate (56.6 mg, 0.152 mmol) and 1,1-dimethoxy-N,N-dimethylethan-1-amine (1.0 mL, 6.84 mmol) was stirred at 80° C. Upon completion, the reaction mixture was cooled to room temperature and concentrated to a dark brown viscous oil. The oil was dissolved in acetic acid (1.0 ml) then hydrazine hydrate (24 µL, 0.762 mmol) was added. The reaction mixture was stirred at 80° C. for 1 h. The reaction mixture was concentrated to dryness. Chromatography (C18, H$_2$O to 60% MeCN) gave 2-(hydrazineylidene(1H-indol-3-yl)methyl)-4-(5-methyl-4H-1,2,4-triazol-3-yl)thiazole (18 mg) as a yellow solid.

Example 36: Preparation of (4-ethynylthiazol-2-yl)(1H-indol-3-yl)methanone (ARI-052)

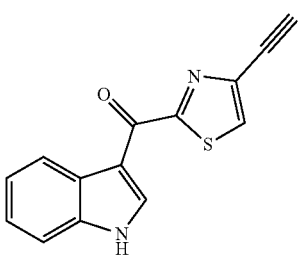 [SMILES: C#Cc1csc(C(=O)c2c[nH]c3ccccc23)n1]

To a stirred solution of tert-butyl 3-(4-formylthiazole-2-carbonyl)-1H-indole-1-carboxylate (71 mg, 0.200 mmol) in anhydrous methanol (2.0 mL) was added K$_2$CO$_3$ (55.3 mg, 0.400 mmol) followed by dimethyl (1-diazo-2-oxopropyl) phosphonate (53.8 mg, 0.280 mmol). Upon completion, the reaction mixture was concentrated to dryness. The residue was treated with brine and EtOAc. Organic layer was separated and the aqueous layer was extracted twice with EtOAc. The combined organic layers were dried (Na$_2$SO$_4$), filtered, and concentrated. Chromatography (silica gel, heptane to 50% EtOAc/heptane) gave (4-ethynylthiazol-2-yl)(1H-indol-3-yl)methanone (28 mg) as a yellow solid.

Example 37: Preparation of methyl 2-(1H-indazole-3-carbonyl)thiazole-4-carboxylate (ARI-053)

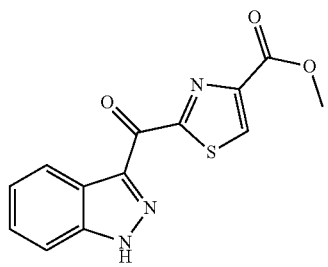 [SMILES: COC(=O)c1csc(C(=O)c2n[nH]c3ccccc23)n1]

To a −78° C. suspension of methyl 2-bromothiazole-4-carboxylate (0.775 g, 3.49 mmol) in THF (8.19 ml) was added iPrMgiCl—LiCl (1.3 M in THF) (2.52 ml, 3.28 mmol). After 15 min, a solution of tert-butyl 3-(methoxy(methyl)carbamoyl)-1H-indazole-1-carboxylate (1.0 g, 3.28 mmol) in THF (8.19 ml) was added dropwise to the wine colored Grignard. After 1.5 hrs, 1 N HCl (aq) was added with the bath temperature held at −10° C. The mixture was extracted with EtOAc then washed with saturated NaHCO$_3$ (aq), and brine, dried (Na$_2$SO$_4$), filtered and concentrated to a solid. Chromatography (silica gel, heptane to 20% EtOAc/heptane) gave impure methyl 2-(1-(tert-butoxycarbonyl)-1H-indazole-3-carbonyl)thiazole-4-carboxylate (317 mg, 0.818 mmol). To remove the Boc group, this was treated with anhydrous MeOH (10 mL) and then K$_2$CO$_3$ (113 mg, 0.818 mmol) was added. Upon reaction completion, 1 N HCl was added to acidify then the mixture was extracted with EtOAc. The extract was washed with saturated sodium bicarbonate then brine, dried over Na$_2$SO$_4$, filtered and concentrated. Chromatography (C18, H$_2$O to CH$_3$CN both with 0.1% TFA modifier) gave a solid that was triturated with hot MeOH then dried under vacuum at 50° C. to give methyl 2-(1H-indazole-3-carbonyl)thiazole-4-carboxylate (64, mg) as a yellow solid.

Example 38: Preparation of (4-(1,3,4-oxadiazol-2-yl)thiazol-2-yl)(1H-indol-3-yl)methanone (ARI-056)

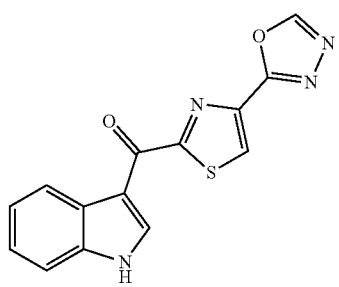 [SMILES: O=C(c1nc(-c2nnco2)cs1)c1c[nH]c2ccccc12]

Step 1. A solution of 2-(1-(tert-butoxycarbonyl)-1H-indole-3-carbonyl)thiazole-4-carboxylic acid (200 mg, 0.537 mmol) and carbonyldiimidazole (113 mg, 0.698 mmol) in tetrahydrofuran (2.0 mL) was stirred at room temperature for 3 h. A precipitate had formed. The crude was carried forward. The mixture was cooled in an ice bath then hydrazine hydrate (78 µL, 1.612 mmol) was added. The reaction was allowed to warm to room temperature overnight then concentrated. The crude was carried forward. ESI MS m/z 387 [M+H]+.

Step 2. A mixture of crude tert-butyl 3-(4-(hydrazinecarbonyl)thiazole-2-carbonyl)-1H-indole-1-carboxylate (208 mg, 0.538 mmol), triethyl orthoformate (2.7 mL, 16.21 mmol), and acetic acid (1.0 mL, 17.47 mmol) was stirred at 100° C. A yellow precipitate formed. Upon completion, the reaction mixture was cooled to room temperature, diluted with CH$_2$Cl$_2$ and the mixture sonicated. The precipitate was collected, washed with CH$_2$Cl$_2$, and dried in vacuo to provide of (4-(1,3,4-oxadiazol-2-yl)thiazol-2-yl)(1H-indol-3-yl)methanone (98 mg) as a yellow solid.

Example 39: Preparation of (1H-indol-3-yl)(4-(5-methyl-1,3,4-oxadiazol-2-yl)thiazol-2-yl)methanone (ARI-060)

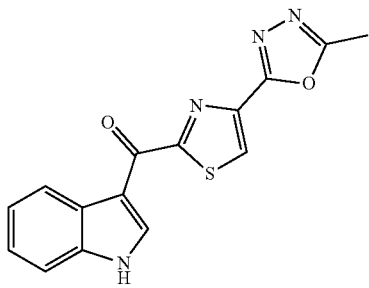 [SMILES: Cc1nnc(-c2csc(C(=O)c3c[nH]c4ccccc34)n2)o1]

Step 1. To a stirred suspension of 2-(1-(tert-butoxycarbonyl)-1H-indole-3-carbonyl)thiazole-4-carboxylic acid (200 mg, 0.537 mmol) in dichloromethane (7.0 mL) at room temperature was added HATU (408 mg, 1.074 mmol) followed by DIPEA (0.141 mL, 0.806 mmol). N,N-Dimethylformamide (0.7 mL) was added to aid solubility. After 10 min, acetohydrazide (47.7 mg, 0.644 mmol) was added. Upon completion, the reaction mixture was absorbed on silica gel. Chromatography (silica gel, CH$_2$Cl$_2$ to 10% MeOH/CH$_2$Cl$_2$) gave tert-butyl 3-(4-(2-acetylhydrazine-1-carbonyl)thiazole-2-carbonyl)-1H-indole-1-carboxylate as an off-white solid (347, mg). ESI MS m/z 427 [M–H]−.

Step 2. To a stirred suspension of tert-butyl 3-(4-(2-acetylhydrazine-1-carbonyl)thiazole-2-carbonyl)-1H-indole-1-carboxylate (230 mg, 0.537 mmol) in dichloromethane (20 mL) at room temperature was added triethylamine (0.374 mL, 2.68 mmol) followed by tosyl-chloride (307 mg, 1.610 mmol). The reaction mixture was heated to 65° C. with stirring for 3 h. A clear solution formed. The reaction mixture was then absorbed on silica gel. Chromatography (silica gel, heptane to 65% EtOAc/heptane) gave tert-butyl 3-(4-(5-methyl-1,3,4-oxadiazol-2-yl)thiazole-2-carbonyl)-1H-indole-1-carboxylate (172, mg) as an off-white solid. ESI MS m/z 411[M+H]+.

Step 3. To a stirred suspension of tert-butyl 3-(4-(5-methyl-1,3,4-oxadiazol-2-yl)thiazole-2-carbonyl)-1H-indole-1-carboxylate (162 mg, 0.395 mmol) in methanol (8 mL) at room temperature was added potassium carbonate (164 mg, 1.184 mmol). Upon completion, the mixture was cooled in an ice-water bath, and neutralized with 2 M HCl. The precipitate was collected by filtration, washed with water and methanol, and dried in vacuo to provide (1H-indol-3-yl)(4-(5-methyl-1,3,4-oxadiazol-2-yl)thiazol-2-yl)methanone (130 mg) as a yellow solid.

Example 40: Preparation of 2-(1H-indole-3-carbonyl)thiazole-4-carbaldehyde (ARI-061)

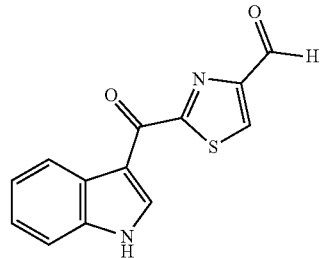 [SMILES: O=Cc1csc(C(=O)c2c[nH]c3ccccc23)n1]

Potassium carbonate (0.175 g, 1.263 mmol) and tert-butyl 3-(4-formylthiazole-2-carbonyl)-1H-indole-1-carboxylate (0.150 g, 0.421 mmol) were suspended in methanol (4.21 ml). Upon completion, the reaction mixture was acidified with 1M HCl and extracted with EtOAc. The organic was then concentrated onto silica gel. Chromatography (silica gel, heptane to 50% EtOAc/heptane) gave 2-(1H-indole-3-carbonyl)thiazole-4-carbaldehyde (0.090 g) as a yellow solid.

Example 41: Preparation of (4-(1H-1,2,3-triazol-5-yl)thiazol-2-yl)(1H-indol-3-yl)methanone (ARI-062)

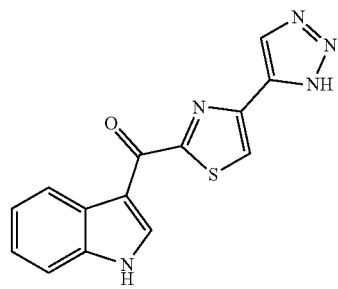 [SMILES: O=C(c1nc(-c2cnn[nH]2)cs1)c1c[nH]c2ccccc12]

To a stirred solution of (4-ethynylthiazol-2-yl)(1H-indol-3-yl)methanone (150 mg, 0.595 mmol), and copper(I) iodide (5.66 mg, 0.030 mmol) in N,N-dimethylformamide (4.5 mL)/methanol (0.500 mL) was added TMSN$_3$ (0.118 mL, 0.892 mmol). The reaction mixture was stirred in a sealed reaction vessel at 100° C. for 6 h. The reaction mixture was concentrated in vacuo. The residue was dissolved in hot MeOH/water, filtered and the filtrate concentrated to dryness. The resulting residue was triturated with CH$_2$Cl$_2$ and dried in vacuo to provide (4-(1H-1,2,3-triazol-5-yl)thiazol-2-yl)(1H-indol-3-yl)methanone (154 mg) as a yellow solid.

Example 42: Preparation of 2-(2-(1H-indole-3-carbonyl)thiazol-4-yl)-2-aminoacetic acid (ARI-063)

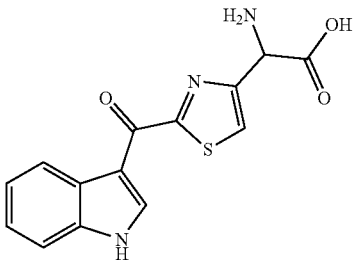 [SMILES: NC(C(=O)O)c1csc(C(=O)c2c[nH]c3ccccc23)n1]

Step 1. To a solution of ammonium acetate (130 mg, 1.684 mmol), sodium cyanide (30.3 mg, 0.617 mmol) and ammonium hydroxide (170 μL, 1.268 mmol) in water (500 μL)/ethanol (500 μL) at room temperature was added tert-butyl 3-(4-formylthiazole-2-carbonyl)-1H-indole-1-carboxylate (200 mg, 0.561 mmol). The cloudy reaction mixture was stirred for 18.5 h. More ethanol (500 μL), ammonium acetate (130 mg, 1.684 mmol), ammonium hydroxide (170 μL, 1.268 mmol), and sodium cyanide (30.3 mg, 0.617 mmol) were added. Stirring was continued for an additional 19.5 h. More ethanol (500 μL), ammonium acetate (130 mg, 1.684 mmol), ammonium hydroxide (170 μL, 1.268 mmol), and tetrabutylammonium cyanide (166 mg, 0.617 mmol) were added. Stirring was continued for 24 h. The reaction mixture was diluted with EtOAc (3 mL), washed with water (1 mL), dried over $Na_2SO_4$, filtered, and concentrated. The residue was dried in vacuo to an orange-brown sticky solid (293 mg). The crude was carried forward. ESI MS m/z 383 $[M+H]^+$.

Step 2. To a stirred solution of crude tert-butyl 3-(4-(amino(cyano)methyl)thiazole-2-carbonyl)-1H-indole-1-carboxylate (215 mg, 0.562 mmol) in acetic acid (4.0 mL) at room temperature was added concentrated hydrochloric acid (2.0 mL, 24.36 mmol). The reaction mixture was stirred at 100° C. for 17 h. The reaction mixture was cooled to room temperature and then concentrated to dryness. Chromatography (C18, $H_2O$ to 50% $MeCN/H_2O$) gave 2-(2-(1H-indole-3-carbonyl)thiazol-4-yl)-2-aminoacetic acid (26.1 mg) as a light red solid.

Example 43: Preparation of (1H-indol-3-yl)(4-(5-methyl-4H-1,2,4-triazol-3-yl)thiazol-2-yl)methanone (ARI-064)

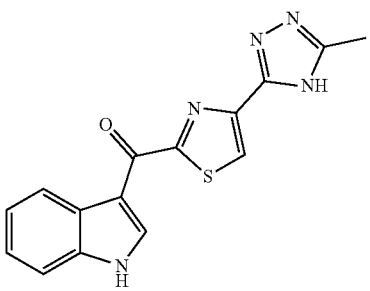 [SMILES: Cc1nnc(-c2csc(C(=O)c3c[nH]c4ccccc34)n2)[nH]1]

Step 1. To a stirred mixture of 2-(1-(tert-butoxycarbonyl)-1H-indole-3-carbonyl)thiazole-4-carboxylic acid (240 mg, 0.644 mmol), ammonium chloride (241 mg, 4.51 mmol), HOBt (148 mg, 0.967 mmol) and EDC (371 mg, 1.933 mmol) were added N,N-dimethylformamide (6.5 mL) and then DIPEA (0.675 mL, 3.87 mmol). Upon completion, the reaction mixture was diluted with water and saturated $NaHCO_3$ (aq). The precipitate was collected by filtration, washed with water, and dried in vacuo to provide tert-butyl 3-(4-carbamoylthiazole-2-carbonyl)-1H-indole-1-carboxylate (224 mg) as a light yellow solid. ESI MS m/z 372 $[M+H]^+$.

Step 2. To an ice-cold, stirred solution of tert-butyl 3-(4-carbamoylthiazole-2-carbonyl)-1H-indole-1-carboxylate (200 mg, 0.538 mmol) in methanol (10.0 mL) was added sodium borohydride (61.1 mg, 1.615 mmol) in two portions. The reaction mixture was stirred at 0° C. for 1 h. Then, the reaction mixture was quenched with 2 M HCl until pH reached 5-6 and then concentrated to dryness. The residue was partitioned between EtOAc and water. The organic was washed with brine, dried ($Na_2SO_4$), filtered, and concentrated to give tert-butyl 3-((4-carbamoylthiazol-2-yl)(hydroxy)methyl)-1H-indole-1-carboxylate (224 mg) as a colorless syrup. The crude was carried forward. ESI MS m/z 374 $[M+H]^+$.

Step 3. To a stirred solution of tert-butyl 3-((4-carbamoylthiazol-2-yl)(hydroxy)methyl)-1H-indole-1-carboxylate (224 mg, 0.538 mmol) and dihydropyran (98 μL, 1.072 mmol) in dichloromethane (5.5 mL) at room temperature was added pyridinium p-toluenesulfonate (6.76 mg, 0.027 mmol). The reaction mixture was stirred for 20.5 h. The reaction mixture was absorbed on silica gel. Chromatography (silica gel, heptane to 70% EtOAc/heptane) gave tert-butyl 3-((4-carbamoylthiazol-2-yl)((tetrahydro-2H-pyran-2-yl)oxy)methyl)-1H-indole-1-carboxylate (244 mg) as a light yellow syrup. ESI MS m/z 458 $[M+H]^+$.

Step 4. A mixture of tert-butyl 3-((4-carbamoylthiazol-2-yl)((tetrahydro-2H-pyran-2-yl)oxy)methyl)-1H-indole-1-carboxylate (5 mg, 10.93 μmol) and 1,1-dimethoxy-N,N-dimethylethan-1-amine (150 μL, 1.026 mmol) was stirred at 80° C. for 15 h. The reaction mixture was concentrated and residue dried in vacuo to provide tert-butyl (E)-3-((4-((1-(dimethylamino)ethylidene)carbamoyl)thiazol-2-yl)((tetrahydro-2H-pyran-2-yl)oxy)methyl)-1H-indole-1-carboxylate as a brown viscous oil, which was used in the next step without purification. ESI MS m/z 527 $[M+H]^+$.

Step 5. A solution of crude tert-butyl (E)-3-((4-((1-(dimethylamino)ethylidene)carbamoyl)thiazol-2-yl)((tetrahydro-2H-pyran-2-yl)oxy)methyl)-1H-indole-1-carboxylate (261 mg, 0.496 mmol) and hydrazine hydrate (77 2.478 mmol) in acetic acid (3.5 mL) was stirred at 80° C. Upon completion, the reaction mixture was cooled to room temperature and absorbed onto silica gel. Chromatography (silica gel, $CH_2Cl_2$ to 50% 80:18:2 $CH_2Cl_2$/MeOH/concentrated $NH_4OH$) gave tert-butyl 3-(hydroxy(4-(5-methyl-4H-1,2,4-triazol-3-yl)thiazol-2-yl)methyl)-1H-indole-1-carboxylate (41 mg) as a yellow solid. ESI MS m/z 496 $[M+H]^+$.

Step 6. To a stirred solution of tert-butyl 3-(hydroxy(4-(5-methyl-4H-1,2,4-triazol-3-yl)thiazol-2-yl)methyl)-1H-indole-1-carboxylate (41 mg, 0.100 mmol) in dichloromethane (2.5 mL) at room temperature was added Dess-Martin periodinane (54.9 mg, 0.130 mmol). Upon completion the reaction was quenched with saturated $NaHCO_3$ (2 mL) and 10% $Na_2S_2O_3$ (2 mL). The organic layer was separated. The aqueous layer was extracted with $CH_2Cl_2$ (2×). The combined organic layers were dried ($Na_2SO_4$), filtered, and concentrated. Chromatography (silica gel, $CH_2Cl_2$ to 10% MeOH/$CH_2Cl_2$) gave tert-butyl 3-(4-(5-methyl-4H-1,2,4-triazol-3-yl)thiazol-2-carbonyl)-1H-indole-1-carboxylate (29.1 mg) as a yellow solid. ESI MS m/z 410 $[M+H]^+$.

Step 7. To a stirred suspension of tert-butyl 3-(4-(5-methyl-4H-1,2,4-triazol-3-yl)thiazole-2-carbonyl)-1H-indole-1-carboxylate (29 mg, 0.071 mmol) in methanol (2.4 mL) at room temperature was added potassium carbonate (29.4 mg, 0.212 mmol). Upon completion, the reaction mixture was neutralized with 2 M HCl while cooled in an ice-water bath. The resulting precipitate was collected, washed with water and dried in vacuo to provide (1H-indol-3-yl)(4-(5-methyl-4H-1,2,4-triazol-3-yl)thiazol-2-yl)methanone (19.1 mg) as a light yellow solid.

Figure 18:
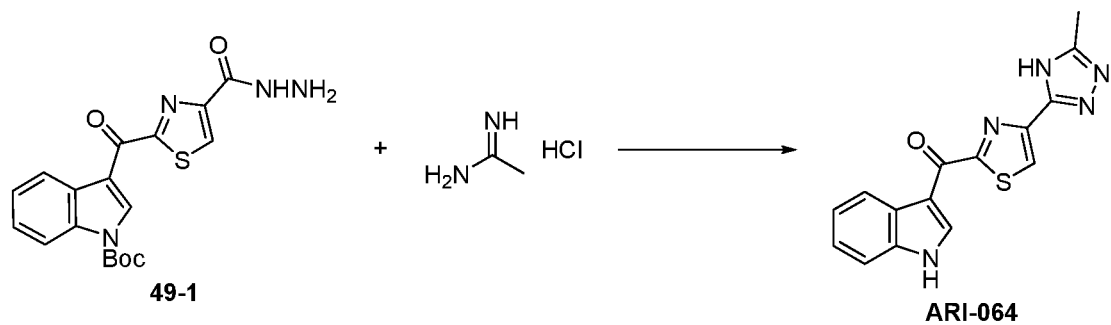
FIG. 18 shows a synthesis scheme for ARI-064 according to Example 43.

Alternatively, ARI-064 was synthesized according to the scheme of FIG. 18 and by the following method:

Step: (1H-indol-3-yl)(4-(5-methyl-4H-1,2,4-triazol-3-yl)thiazol-2-yl)methanone (ARI-064)

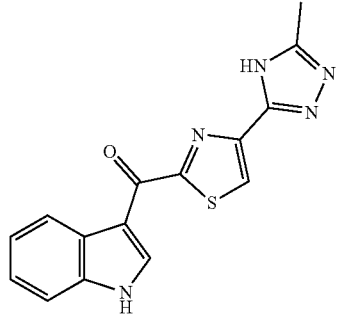

ARI-064

A suspension of compound 49-1 (1.45 g, 3.7 mmol), acetimidamide hydrochloride (700 mg, 7.5 mmol) and NaOH (300 mg, 7.5 mmol) in dioxane (20 mL) was stirred for 30 min at 110° C. under microware. After cooled to room temperature, the mixture was filtered, and the solid was collected, washed with EtOAc (20 mL×3) and MeOH (20 mL×3), dried to afford compound ARI-064 (880 mg, 76% yield) in the form of a yellow solid. $^1$H-NMR (400 MHz, DMSO-d6): δ 12.39 (bs, 1H), 9.38 (s, 1H), 8.51 (s, 1H), 8.33~8.36 (m, 1H), 7.28~7.62 (d, J=6.4 Hz, 1H), 7.29~7.32 (m, 2H), 2.51 (s, 3H). LC-MS: m/z 308.1 [M–H]$^-$.

Example 44: Preparation of (4-(1,2,4-oxadiazol-3-yl)thiazol-2-yl)(1H-indol-3-yl)methanone (ARI-071)

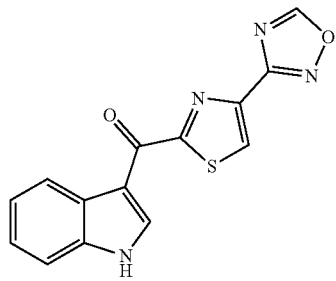 [SMILES: O=C(c1nc(-c2ncon2)cs1)c1c[nH]c2ccccc12]

Step 1. A mixture of 2-(1H-indole-3-carbonyl)thiazole-4-carbonitrile (160 mg, 0.632 mmol), K$_3$PO$_4$ (402 mg, 1.895 mmol) and hydroxylamine hydrochloride (110 mg, 1.579 mmol) in DMF (10 mL) was heated to 100° C. in a microwave reactor for 30 min. Triethyl orthoformate (3.16 mL, 18.97 mmol), pyridinium p-toluenesulfonate (PPTS) (31.8 mg, 0.126 mmol) and TFA (0.317 mL, 4.11 mmol) was added. The reaction mixture was further heated to 100° C. on a microwave reactor for 2 h. The reaction mixture was concentrated in vacuo. The residue was triturated with water by sonication. The precipitate was collected, washed with water, dried. Chromatography (silica gel, CH$_2$Cl$_2$ to 6% MeOH/CH$_2$Cl$_2$) gave (4-(1,2,4-oxadiazol-3-yl)thiazol-2-yl) (1H-indol-3-yl)methanone (69 mg) as a yellow solid.

Example 45: Preparation of (1H-indol-3-yl)(thiazol-4-yl)methanone (ARI-072)

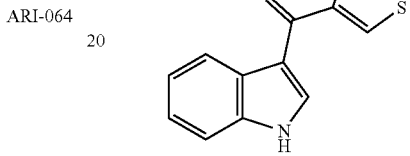

Prepared according to the method described in Example 2 except that ethyl 4-(chlorocarbonyl)thiazole-2-carboxylate was used instead of 4-bromothiazole-2-carbonyl chloride in Step 1 and the Boc deprotection was effected using NaOH in methanol.

Ethyl 4-(chlorocarbonyl)thiazole-2-carboxylate was obtained from commercial ethyl 4-(chlorocarbonyl)thiazole-2-carboxylate as follows. To an ice-cold suspension of 2-(ethoxycarbonyl)thiazole-4-carboxylic acid (1 g, 4.97 mmol) in DCM (9.94 ml) was added 2 drops of DMF then oxalyl chloride (0.505 ml, 5.96 mmol) was added dropwise. The bath was removed and a large bubbler was added. Upon nearing room temperature CO$_2$ evolution was observed and after 3 h, gas evolution ceased. The solution was concentrated under reduced pressure and used as crude.

Example 46: Preparation of (1H-indol-3-yl)(phenyl)methanone (ARI-073)

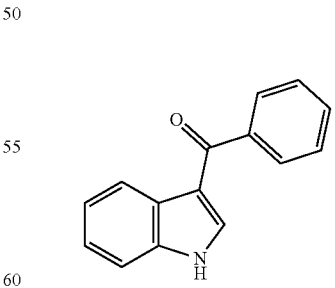

Prepared according to the method described in Example 2 except that benzoyl chloride was used instead of 4-bromothiazole-2-carbonyl chloride.

Example 47: Preparation of (1H-indol-3-yl)(m-tolyl)methanone (ARI-074)

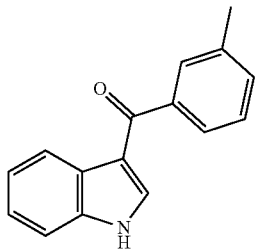 [SMILES: Cc1cccc(C(=O)c2c[nH]c3ccccc23)c1]

Prepared according to the method described in Example 2 except that 3-methylbenzoyl chloride was used instead of 4-bromothiazole-2-carbonyl chloride.

Example 48: Preparation of 2-(2-(1H-indole-3-carbonyl)thiazol-4-yl)-2-aminoacetonitrile (ARI-075)

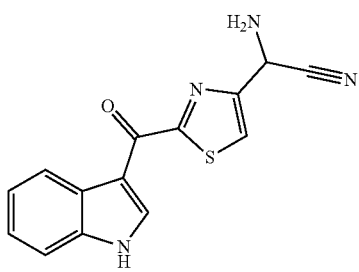 [SMILES: N#CC(N)c1csc(C(=O)c2c[nH]c3ccccc23)n1]

Step 1. A solution of ammonium acetate (195 mg, 2.53 mmol), tetrabutylammonium cyanide (249 mg, 0.926 mmol), and ammonium hydroxide (0.255 mL, 1.902 mmol) in water (1.2 mL) was added to a suspension of tert-butyl 3-(4-formylthiazole-2-carbonyl)-1H-indole-1-carboxylate (300 mg, 0.842 mmol) in ethanol (1.2 mL) at room temperature. The cloudy reaction mixture was stirred for 26 h. The reaction mixture was diluted with EtOAc, washed with water, dried over $Na_2SO_4$, filtered, and concentrated. Chromatography (silica gel, $CH_2Cl_2$ to 4.5% $MeOH/CH_2Cl_2$) and then (C18, $H_2O$ to $CH_3CN$)) gave 2-(2-(1H-indole-3-carbonyl)thiazol-4-yl)-2-aminoacetonitrile (37.6 mg) as a yellow solid.

Figure 19:
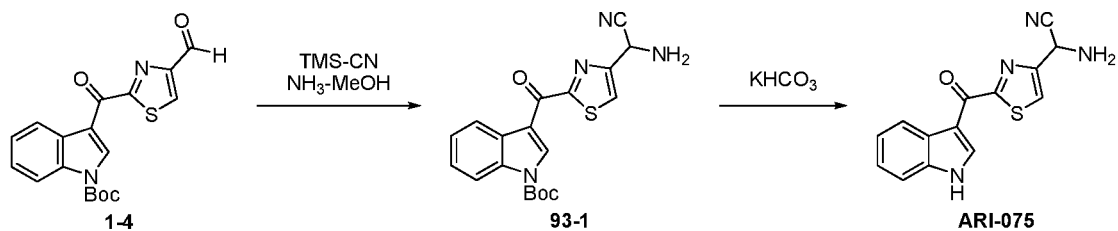
FIG. 19 shows a synthesis scheme for ARI-075 according to Example 48.

Alternatively, ARI-075 was synthesized according to the scheme of FIG. 19 and by the following method:

Step 1: tert-Butyl 3-(4-(amino(cyano)methyl)thiazole-2-carbonyl)-1H-indole-1-carboxylate (93-1)

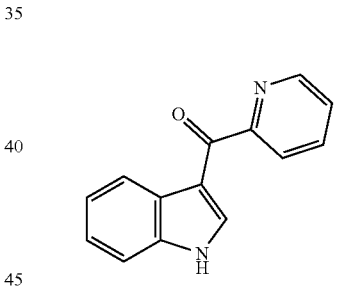

Trimethylsilyl cyanide (0.74 mL, 5.5 mmol) was added to a solution of compound 1-4 (1.40 g, 4 mmol) in THF (5 mL) and $NH_3$-MeOH (7M solution, 20 mL) at room temperature. The mixture was stirred for 2 h, then concentrated to dryness to afford compound 93-1 (2.0 g, ~100% yield), which was used for next step without further purification.

Step 2: 2-(2-(1H-indole-3-carbonyl)thiazol-4-yl)-2-aminoacetonitrile (ARI-075)

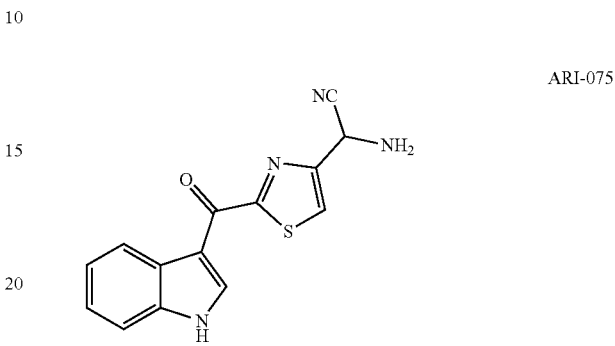

The BOC group of compound 93-1 (2.00 g, 5 mmol) was removed as described in Example 24 (treatment with $K_2CO_3$ in methanol held at 50° C.) to give title compound ARI-075 in the form of a yellow solid (680 mg, 43% yield). $^1$H-NMR (400 MHz, DMSO-d6): δ 12.37 (bs, 1H), 9.17 (s, 1H), 8.31~8.35 (m, 1H), 8.07 (s, 1H), 7.56~7.59 (d, J=6.0 Hz, 1H), 7.28~7.33 (m, 2H), 5.34~5.39 (t, J=8.0 Hz, 1H), 3.05~3.08 (d, J=8.0 Hz, 1H). LC-MS: m/z 281.0 [M–H]$^-$.

Example 49: Preparation of (1H-indol-3-yl)(pyridin-2-yl)methanone (ARI-081)

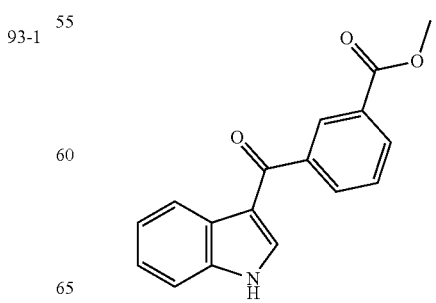

Prepared according to the method described in Example 2 except that picolinoyl chloride hydrochloride was used instead of 4-bromothiazole-2-carbonyl chloride.

Example 50: Preparation of methyl 3-(1H-indole-3-carbonyl)benzoate (ARI-082)

Prepared according to the method described in Example 2 except that methyl 3-(chlorocarbonyl)benzoate was used instead of 4-bromothiazole-2-carbonyl chloride. The carboxylic acid was the primary product which was subsequently esterified by treatment with sulfuric acid in methanol at 100° C.

Example 51: Preparation of (4-(5-amino-1,3,4-oxadiazol-2-yl)thiazol-2-yl)(1H-indol-3-yl)methanone (ARI-083)

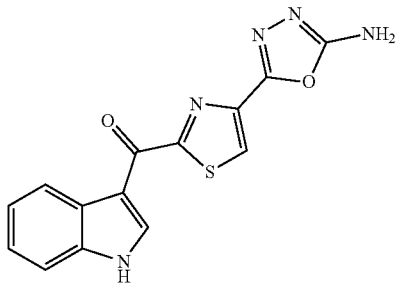 [SMILES: Nc1nnc(-c2csc(C(=O)c3c[nH]c4ccccc34)n2)o1]

Step 1. To a stirred suspension of tert-butyl 3-(4-formylthiazole-2-carbonyl)-1H-indole-1-carboxylate (150 mg, 0.421 mmol) in methanol (0.90 mL)/N,N-dimethylformamide (0.900 mL) at room temperature was added a solution of hydrazinecarboxamide (46.9 mg, 0.421 mmol) and sodium acetate (34.5 mg, 0.421 mmol) in water (0.900 mL). The reaction mixture was stirred for 21.5 h. The reaction mixture was concentrated to dryness and the residue was dried in vacuo to provide tert-butyl 3-(4-((2-carbamoylhydrazono)methyl)thiazole-2-carbonyl)-1H-indole-1-carboxylate as a light yellow solid which was carried forward as crude. ESI MS m/z 414 [M+H]⁺.

Step 2. To a stirred cloudy solution of crude tert-butyl 3-(4-((2-carbamoylhydrazono)methyl)thiazole-2-carbonyl)-1H-indole-1-carboxylate (174 mg, 0.421 mmol) in 1,4-dioxane (30 mL) at room temperature was added potassium carbonate (174 mg, 1.263 mmol) followed by iodine (128 mg, 0.505 mmol). The reaction mixture was stirred at 80° C. for 25 h. The reaction mixture was cooled to room temperature and diluted with water (30 mL). The resulting precipitate was collected, washed with water, and dried in vacuo to provide tert-butyl 3-(4-(5-amino-1,3,4-oxadiazol-2-yl)thiazole-2-carbonyl)-1H-indole-1-carboxylate (155 mg) as a yellow solid. ESI MS m/z 410 [M−H]⁻.

Step 3. To a stirred suspension of tert-butyl 3-(4-(5-amino-1,3,4-oxadiazol-2-yl)thiazole-2-carbonyl)-1H-indole-1-carboxylate (155 mg, 0.377 mmol) in methanol (12.5 mL) at room temperature was added potassium carbonate (156 mg, 1.130 mmol). The reaction mixture was stirred for 15.5 h. The reaction mixture was cooled in an ice-water bath and neutralized with 2M HCl. The resulting precipitate was collected, washed with water, and dried in vacuo to provide (4-(5-amino-1,3,4-oxadiazol-2-yl)thiazol-2-yl)(1H-indol-3-yl)methanone (87.5 mg) as a yellow solid.

Example 52: Preparation of (1H-indol-3-yl)(4-(2,2,2-trifluoro-1-hydroxyethyl)thiazol-2-yl)methanone (ARI-088)

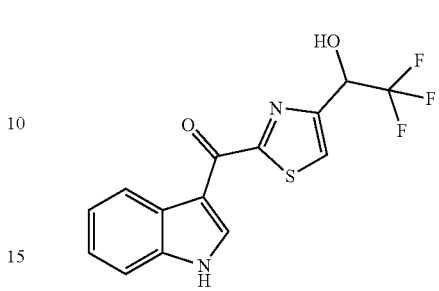

Step 1. To a −35° C. solution of tert-butyl 3-(4-formylthiazole-2-carbonyl)-1H-indole-1-carboxylate (1.63 g, 4.57 mmol) and tetrabutylammonium acetate (0.034 g, 0.114 mmol) in DCM (100 ml) was added trimethyl(trifluoromethyl)silane (0.676 ml, 4.57 mmol) dropwise. The reaction was allowed to slowly warm to room temperature. Upon completion, saturated NaCl was added. The layers were separated and the organic dried (Na₂SO₄), filtered and concentrated. Chromatography (silica gel, heptane to CH₂Cl₂) gave tert-butyl 3-(4-(2,2,2-trifluoro-1-hydroxyethyl)thiazole-2-carbonyl)-1H-indole-1-carboxylate (1.67 g) as a colorless hard film. ESI MS m/z 427 [M+H]⁺.

Step 2. To tert-butyl 3-(4-(2,2,2-trifluoro-1-hydroxyethyl)thiazole-2-carbonyl)-1H-indole-1-carboxylate (2.145 g, 5.03 mmol) was added MeOH (10.06 ml) then 1 M NaOH (aq) (10.06 ml, 10.06 mmol) was added and the mixture heated to 65° C. for 30 min. The solvent was concentrated and the residue partitioned between 1 N HCl and EtOAc. The organic phase was separated, washed with water and then brine, dried (Na₂SO₄), filtered and concentrated onto silica gel. Chromatography (silica gel, heptane to 45% EtOAc/heptane) gave (1H-indol-3-yl)(4-(2,2,2-trifluoro-1-hydroxyethyl)thiazol-2-yl)methanone (1.44, g) as a yellow solid.

Example 53: Preparation of 1-(2-(1H-indole-3-carbonyl)thiazol-4-yl)-2,2,2-trifluoroethan-1-one (ARI-089)

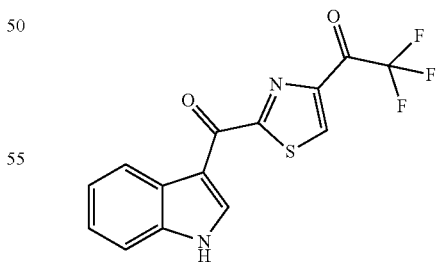

Step 1. To tert-butyl 3-(4-(2,2,2-trifluoro-1-hydroxyethyl)thiazole-2-carbonyl)-1H-indole-1-carboxylate (417 mg, 0.978 mmol) and 1,1,1-tris(acetyloxy)-1,1-dihydro-1,2-benziodoxol-3-(1H)-one (539 mg, 1.271 mmol) was added CH₂Cl₂ (10 mL). After 1 hr, the reaction was quenched by the addition of saturated NaHCO₃ and 10% Na₂S₂O₃. After stirring 20 min, CH₂Cl₂ was added. After separation, the organic phase was washed with a second portion of bicarbonate, dried over Na$_2$SO$_4$, filtered and concentrated. Chromatography (silica gel, heptane to 25% EtOAc/heptane) gave tert-butyl 3-(4-(2,2,2-trifluoro-1,1-dihydroxyethyl)thiazole-2-carbonyl)-1H-indole-1-carboxylate (409.7 mg) as a yellow solid. The mass spectrum for the product shows that the product may exist as the diol ESI MS m/z 443 [M+H+H$_2$O]$^+$.

Step 2. To a solution of tert-butyl 3-(4-(2,2,2-trifluoro-1,1-dihydroxyethyl)thiazole-2-carbonyl)-1H-indole-1-carboxylate (180 mg, 0.407 mmol) in THF (2 ml) was added 2 M NaOH (aq) (1.2 ml, 2.4 mmol) and the mixture was heated to 40° C. Upon completion, the reaction was neutralized with 1 N HCl (aq). Chromatography (C18, H$_2$O to CH$_3$CN, liquid load) gave 1-(2-(1H-indole-3-carbonyl)thiazol-4-yl)-2,2,2-trifluoroethan-1-one (80 mg) as a yellow solid.

Example 54: Preparation of (4-(5-amino-1,3,4-thiadiazol-2-yl)thiazol-2-yl)(1H-indol-3-yl)methanone (ARI-090)

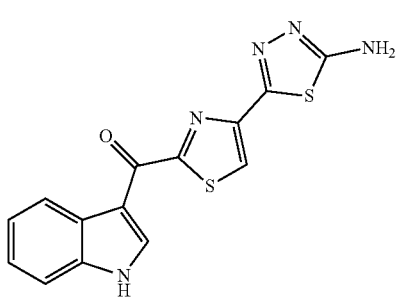

Prepared according to the method described in Example 51 except that hydrazinecarbothioamide was used instead of hydrazinecarboxamide.

Example 55: Preparation of 3-(1H-indole-3-carbonyl)benzonitrile (ARI-091)

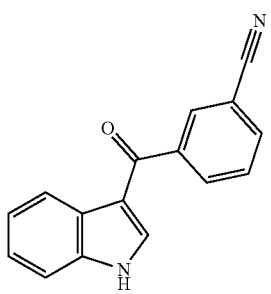 [SMILES: N#Cc1cccc(C(=O)c2c[nH]c3ccccc23)c1]

Step 1. Oxalyl chloride (0.119 ml, 1.357 mmol) was added dropwise to an ice-cold suspension of 3-(1H-indole-3-carbonyl)benzoic acid (0.300 g, 1.131 mmol) in tetrahydrofuran (10 ml). The ice bath was removed and the reaction stirred at ambient temperature. One drop of DMF was added and gas inflow switched from nitrogen inlet to a bubbler. After the bubbling of CO$_2$ ceased, ammonium hydroxide (0.944 ml, 6.79 mmol) was added at 0° C. Upon completion, the reaction mixture was concentrated under reduced pressure, then triturated with water then dried to give 3-(1H-indole-3-carbonyl)benzamide. The crude solid was used as is. ESI MS m/z 264 [M−H]$^-$.

Step 2. A solution of 3-(1H-indole-3-carbonyl)benzamide (0.267 g, 1.010 mmol) and triethylamine (0.704 ml, 5.05 mmol) in tetrahydrofuran (10.10 ml) was stirred in an ice bath for 10 minutes. Trifluoroacetic anhydride (0.357 ml, 2.53 mmol) was added dropwise. Upon completion, the reaction mixture was poured over ice and diluted with ethyl acetate. The organic layer was washed with 2M Na$_2$CO$_3$ and brine, then dried over sodium sulfate, filtered and concentrated onto silica gel. Chromatography (silica gel, heptane to 50% EtOAc/heptane) gave 3-(1H-indole-3-carbonyl)benzonitrile (109.7 mg) as an off-white solid.

Example 56: Preparation of (5-chloro-1H-indol-3-yl)(4-(3-methyl-1,2,4-oxadiazol-5-yl)thiazol-2-yl)methanone (ARI-096)

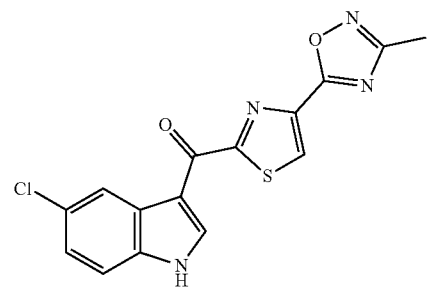 [SMILES: Cc1noc(-c2csc(C(=O)c3c[nH]c4ccc(Cl)cc34)n2)n1]

Prepared according to the method described in Example 22 except that 2-(1-(tert-butoxycarbonyl)-5-chloro-1H-indole-3-carbonyl)thiazole-4-carboxylic acid, derived from 5-chloro-1H-indole-3-carboxylic acid was used instead of 2-(1-(tert-butoxycarbonyl)-1H-indole-3-carbonyl)thiazole-4-carboxylic acid.

Example 57: Preparation of 2-(5-chloro-1H-indole-3-carbonyl)thiazole-4-carbonitrile (ARI-099)

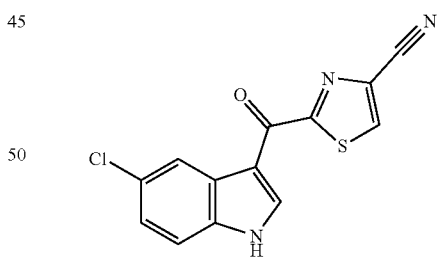

Step 1. Oxalyl chloride (0.129 ml, 1.475 mmol) was added dropwise to an ice-cold suspension of 2-(1-(tert-butoxycarbonyl)-5-chloro-1H-indole-3-carbonyl)thiazole-4-carboxylic acid (0.500 g, 1.229 mmol) in tetrahydrofuran (24 ml). The ice bath was removed and the reaction stirred at ambient temperature. Upon completion, the reaction mixture was concentrated under reduced pressure then resuspended in tetrahydrofuran (24 ml) and chilled in an ice bath. Ammonium hydroxide (1.026 ml, 7.37 mmol) was added at 0° C. Upon completion, the reaction mixture was concentrated under reduced pressure, then triturated with water and concentrated. The solid (0.357 g, 0.880 mmol) was suspended in methanol (8.80 ml) and potassium carbonate (0.365 g, 2.64 mmol) was added. Upon completion, the reaction mixture was concentrated, then suspended in water and adjusted to pH 4 with 1M HCl, the biphasic mixture was filtered and dried to give 2-(5-chloro-1H-indole-3-carbonyl) thiazole-4-carboxamide (0.244 g, 0.798 mmol) as a yellow solid. ESI MS m/z 306 [M+H]$^+$.

Step 2. Triethylamine (0.556 ml, 3.99 mmol) was added to an ice-cold suspension of 2-(5-chloro-1H-indole-3-carbonyl)thiazole-4-carboxamide (0.244 g, 0.798 mmol) in tetrahydrofuran (7.98 ml), then stirred for ten minutes. Trifluoroacetic anhydride (0.282 ml, 1.995 mmol) was added dropwise to the reaction mixture. Upon completion, the reaction mixture was poured over ice, then diluted with ethyl acetate. The biphasic mixture was filtered and washed with water to provide 2-(5-chloro-1H-indole-3-carbonyl)thiazole-4-carbonitrile (0.192 g) as a yellow solid.

Example 58: Preparation of (4-(1-amino-2,2,2-trifluoroethyl)thiazol-2-yl)(1H-indol-3-yl)methanone (ARI-100)

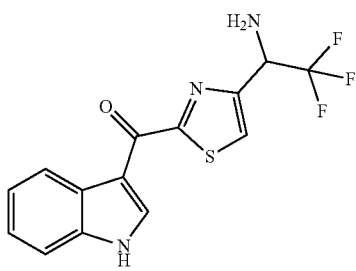 [SMILES: NC(c1csc(C(=O)c2c[nH]c3ccccc23)n1)C(F)(F)F]

Step 1. To an ice-cold solution of tert-butyl 3-(4-(2,2,2-trifluoro-1-hydroxyethyl)thiazole-2-carbonyl)-1H-indole-1-carboxylate (0.305 g, 0.715 mmol) in CH$_2$Cl$_2$ (7153 μl) was added triethylamine (299 μl, 2.146 mmol) then methanesulfonylchloride (83 μl, 1.073 mmol) dropwise. Upon completion, the cold reaction mixture was poured into saturated NaHCO$_3$. The organic phase was separated and then dried (Na$_2$SO$_4$), filtered and concentrated to give tert-butyl 3-(4-(2,2,2-trifluoro-1-((methylsulfonyl)oxy)ethyl)thiazole-2-carbonyl)-1H-indole-1-carboxylate (422 mg) as a yellow gum. Used as is. ESI MS m/z 505 [M+H]$^+$.

Step 2. To a mixture of tert-butyl 3-(4-(2,2,2-trifluoro-1-((methylsulfonyl)oxy)ethyl)thiazole-2-carbonyl)-1H-indole-1-carboxylate (0.361 g, 0.715 mmol) and sodium azide (0.279 g, 4.29 mmol) was added DMF. The reaction was heated to 60° C. and stirred overnight. Partial Boc removal was observed. Concentrated the DMF under vacuum. The residue was partitioned between EtOAc and 5% aqueous LiCl. The organic phase was washed with brine, dried (Na$_2$SO$_4$), filtered and concentrated to a yellow solid (340 mg). The solid was treated with MeOH (20 mL) and 2 mL of 2N NaOH (aq). then heated the mixture to 50° C. Upon completion, the mixture was neutralized with 1 N HCl then most of MeOH was evaporated. The mixture was then partitioned between EtOAc and H$_2$O. The organic was dried over Na$_2$SO$_4$, and filtered to give (4-(1-azido-2,2,2-trifluoroethyl)thiazol-2-yl)(1H-indol-3-yl)methanone (245 mg) as a yellow solid which was used as is. ESI MS m/z 352 [M+H]$^+$.

Step 3. A stirred solution of crude (4-(1-azido-2,2,2-trifluoroethyl)thiazol-2-yl)(1H-indol-3-yl)methanone (242 mg, 0.689 mmol) in a mixture of THF (10 ml) and water (3.33 ml) was heated to 60° C. overnight. The mixture was absorbed onto a SCX-2 5 g column. Eluted with 10% concentrated NH$_4$OH in MeOH and then further concentrated. Chromatography (C18, H$_2$O to CH$_3$CN) gave (4-(1-amino-2,2,2-trifluoroethyl)thiazol-2-yl)(1H-indol-3-yl) methanone (90 mg) as a yellow solid.

Example 59: Preparation of (5-chloro-1H-indol-3-yl)(4-(5-methyl-1,2,4-oxadiazol-3-yl)thiazol-2-yl) methanone (ARI-109)

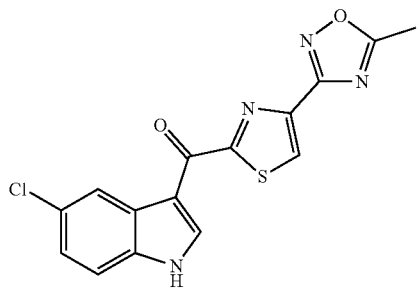 [SMILES: Cc1nc(-c2csc(C(=O)c3c[nH]c4ccc(Cl)cc34)n2)no1]

Step 1. A mixture of tert-butyl 5-chloro-3-(4-cyanothiazole-2-carbonyl)-1H-indole-1-carboxylate (0.860 g, 2.217 mmol) and potassium carbonate (0.919 g, 6.65 mmol) were stirred in methanol (44.3 ml). Upon completion, the reaction mixture was neutralized with 1M HCl, and extracted with ethyl acetate then concentrated onto silica gel. Chromatography (silica gel, heptane to EtOAc then 20% MeOH/DCM) gave methyl 2-(5-chloro-1H-indole-3-carbonyl)thiazole-4-carbimidate (0.705 g). ESI MS m/z 320 [M+H]$^+$.

Step 2. Methyl 2-(5-chloro-1H-indole-3-carbonyl)thiazole-4-carbimidate (0.200 g, 0.625 mmol), potassium phosphate (0.398 g, 1.876 mmol) and hydroxylamine hydrochloride (0.109 g, 1.564 mmol) in N,N-dimethylformamide (7.82 ml) were heated to 100° C. in the microwave for 30 minutes. Acetyl chloride (0.36 ml, 5.06 mmol) was added and the reaction mixture was resubjected to heating to 100° C. in the microwave for 5 h. After this time, the reaction mixture was concentrated under reduced pressure and triturated with water and then with hot methanol to provide (5-chloro-1H-indol-3-yl)(4-(5-methyl-1,2,4-oxadiazol-3-yl) thiazol-2-yl)methanone (144 mg). ESI MS m/z 345 [M+H]$^+$.

Step 3. DMAP (0.017 g, 0.136 mmol) was added to a suspension of (5-chloro-1H-indol-3-yl)(4-(5-methyl-1,2,4-oxadiazol-3-yl)thiazol-2-yl)methanone (0.188 g, 0.545 mmol) and Boc$_2$O (0.165 ml, 0.709 mmol) in acetonitrile (5.45 ml) at ambient temperature. Upon completion, the reaction mixture was concentrated under reduced pressure onto silica gel. Chromatography (silica gel, heptane to 50% EtOAc/heptane) followed by reverse phase chromatography (C18, 5% to 100% acetonitrile/water) gave tert-butyl 5-chloro-3-(4-(5-methyl-1,2,4-oxadiazol-3-yl)thiazole-2-carbonyl)-1H-indole-1-carboxylate (24 mg). ESI MS m/z 445 [M+H]$^+$.

Step 4. To a suspension of tert-butyl 5-chloro-3-(4-(5-methyl-1,2,4-oxadiazol-3-yl)thiazole-2-carbonyl)-1H-indole-1-carboxylate (0.024 g, 0.054 mmol) in methanol (0.539 ml) was added potassium carbonate (0.030 g, 0.216 mmol) and the mixture was stirred at ambient temperature overnight. The reaction mixture was concentrated under reduced pressure, suspended in water and acidified with 1 M HCl. The solid was collected by filtration to afford (5-chloro-1H-indol-3-yl)(4-(5-methyl-1,2,4-oxadiazol-3-yl)thiazol-2-yl)methanone (11.7 mg) as an off-white solid.

Example 60: Preparation of (4-(5-amino-1,2,4-oxadiazol-3-yl)thiazol-2-yl)(1H-indol-3-yl)methanone (ARI-110)

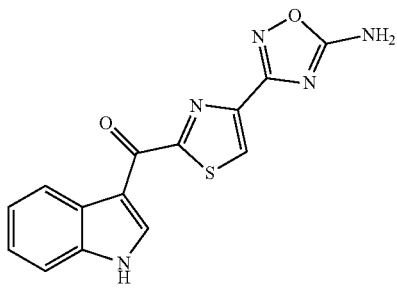 [SMILES: Nc1nc(-c2csc(C(=O)c3c[nH]c4ccccc34)n2)no1]

Step 1. A mixture of 2-(1H-indole-3-carbonyl)thiazole-4-carbonitrile (25 mg, 0.099 mmol), phosphoric acid, potassium salt (62.9 mg, 0.296 mmol) and hydroxylamine hydrochloride (17.15 mg, 0.247 mmol) in DMF (1.1 mL) was heated to 100° C. in a microwave reactor for 30 min. The reaction mixture was concentrated to dryness. The residue was diluted with brine and EtOAc. The precipitate was collected by filtration, washed with water (3×), and then dried in vacuo to provide N'-hydroxy-2-(1H-indole-3-carbonyl)thiazole-4-carboximidamide (23.4 mg) as a yellow solid. ESI MS m/z 287 [M+H]$^+$.

Step 2. A mixture of N'-hydroxy-2-(1H-indole-3-carbonyl)thiazole-4-carboximidamide (23.4 mg, 0.082 mmol) and 2,2,2-trichloroacetic anhydride (150 μL, 0.821 mmol) was stirred at 150° C. (bath temperature) for 2 h. The reaction mixture was cooled to room temperature and diluted with water and EtOAc. After stirring for 30 min, the organic layer was separated, washed with saturated NaHCO$_3$ and brine, dried (Na$_2$SO$_4$), filtered and concentrated. Chromatography (silica gel, heptane to 30% EtOAc) gave (1H-indol-3-yl)(4-(5-(trichloromethyl)-1,2,4-oxadiazol-3-yl)thiazol-2-yl)methanone (19 mg). ESI MS m/z 413 [M−H]$^−$.

Step 3. Ammonia (7 N) in methanol (2.0 mL, 14.0 mmol) was added to (1H-indol-3-yl)(4-(5-(trichloromethyl)-1,2,4-oxadiazol-3-yl)thiazol-2-yl)methanone (19 mg, 0.046 mmol) at room temperature. The reaction mixture was stirred for 15 h then concentrated to dryness and the residue was dried in vacuo to provide (4-(5-amino-1,2,4-oxadiazol-3-yl)thiazol-2-yl)(1H-indol-3-yl)methanone (15.4 mg) as a yellow solid.

Example 61: Preparation of (5-chloro-1H-indol-3-yl)(4-(5-(trifluoromethyl)-1,2,4-oxadiazol-3-yl)thiazol-2-yl)methanone (ARI-116)

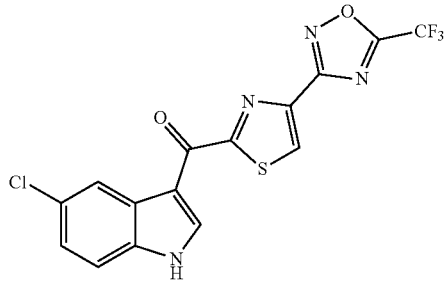 [SMILES: O=C(c1nc(-c2noc(C(F)(F)F)n2)cs1)c1c[nH]c2ccc(Cl)cc12]

A mixture of 2-(5-chloro-1H-indole-3-carbonyl)thiazole-4-carbonitrile (0.250 g, 0.869 mmol), hydroxylamine hydrochloride (0.151 g, 2.172 mmol), and potassium phosphate, tribasic (0.553 g, 2.61 mmol) in N,N-dimethylformamide (10.86 ml) were heated to 100° C. in the microwave for 1 h. Trifluoroacetic anhydride (0.491 ml, 3.48 mmol) was then added to the cooled solution and the reaction was again heated to 100° C. in a microwave reactor for an additional hour. The reaction mixture was concentrated. Chromatography (C18, 0 to 100% ACN/water) gave and (5-chloro-1H-indol-3-yl)(4-(5-(trifluoromethyl)-1,2,4-oxadiazol-3-yl)thiazol-2-yl)methanone (41.9 mg) as a yellow solid.

Example 62: Preparation of (1H-indol-3-yl)(4-(5-(methylamino)-1,2,4-oxadiazol-3-yl)thiazol-2-yl)methanone (ARI-117)

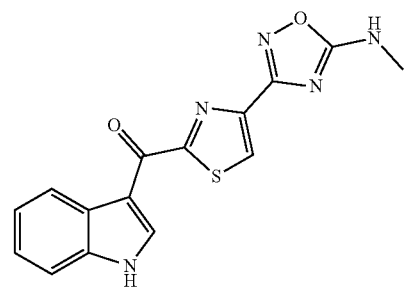 [SMILES: CNc1nc(-c2csc(C(=O)c3c[nH]c4ccccc34)n2)no1]

Methylamine (2.0 M in THF, 15 mL, 30.0 mmol) was added to (1H-indol-3-yl)(4-(5-(trichloromethyl)-1,2,4-oxadiazol-3-yl)thiazol-2-yl)methanone (120 mg, 0.290 mmol) at 0° C. The reaction mixture was stirred for 22 h with gradual warming to room temperature. The reaction mixture was concentrated to dryness and the residue was dried in vacuo to provide (1H-indol-3-yl)(4-(5-(methylamino)-1,2,4-oxadiazol-3-yl)thiazol-2-yl)methanone (79 mg) as a yellow solid.

Example 63: Preparation of (4-(5-amino-1,3,4-oxadiazol-2-yl)thiazol-2-yl)(5,6-dichloro-1H-indol-3-yl)methanone (ARI-120)

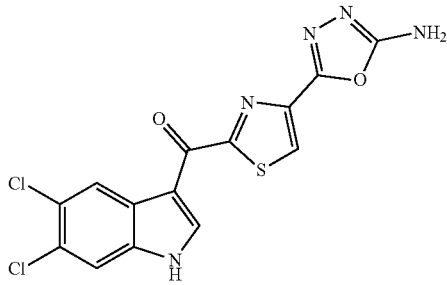 [SMILES: Nc1nnc(-c2csc(C(=O)c3c[nH]c4cc(Cl)c(Cl)cc34)n2)o1]

Prepared according to the method described in Example 131 except that 5,6-dichloro-1H-indole instead of 5,6-difluoro-1H-indole was used in Step 1.

Example 64: Preparation of (4-(5-amino-1,3,4-oxadiazol-2-yl)thiazol-2-yl)(5,6-dichloro-1H-indol-3-yl)methanone (ARI-121)

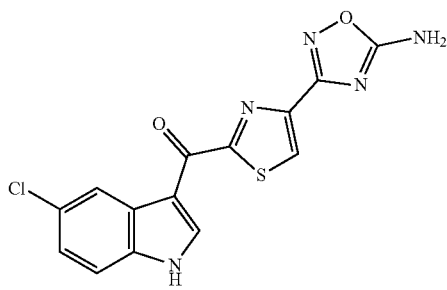 [SMILES: Nc1nc(-c2csc(C(=O)c3c[nH]c4ccc(Cl)cc34)n2)no1]

Figure 20:
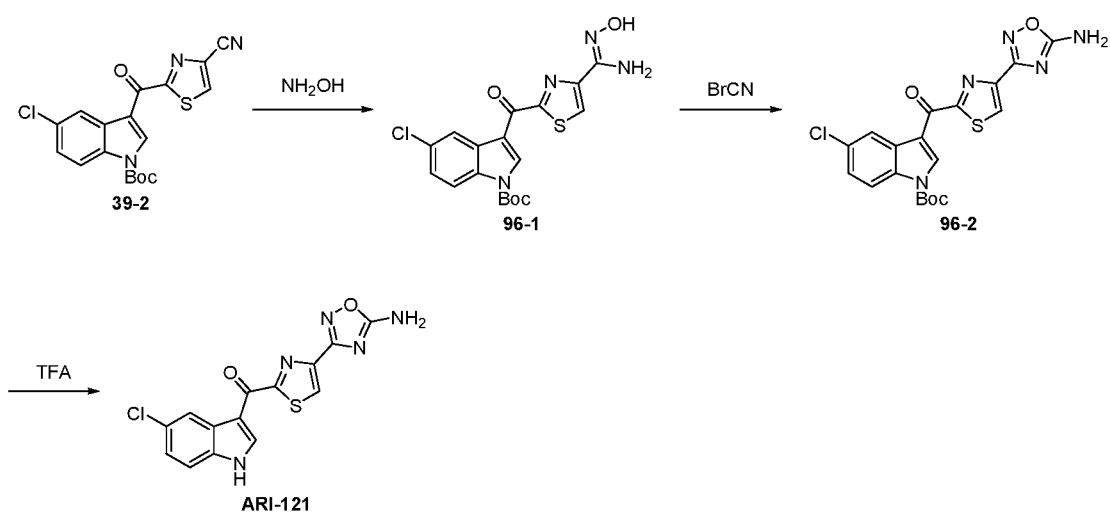
FIG. 20 shows a synthesis scheme for ARI-121 according to Example 64.

ARI-121 was synthesized according to the scheme of FIG. 20 and by the following method:

Step 1: tert-Butyl 5-chloro-3-(4-(N'-hydroxycarbamimidoyl)thiazole-2-carbonyl)-1H-indole-1-carboxylate (96-1)

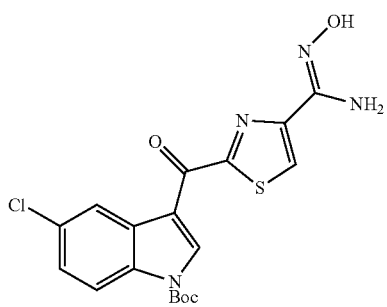

This compound was synthesized according to the protocol described in Example 21 step 1 from compound 39-2 to give title compound 96-1 in the form of a yellow solid (2.10 g, 83% yield).

Step 2: tert-Butyl 3-(4-(5-amino-1,2,4-oxadiazol-3-yl)thiazole-2-carbonyl)-5-chloro-1H-indole-1-carboxylate (96-2)

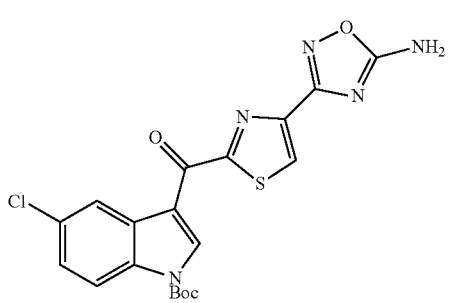

BrCN (1.0 g, 9 mmol) was added to a suspension of compound 96-1 (420 mg, 1 mmol) in EtOH (200 mL) and H$_2$O (50 mL) at room temperature. The mixture was heated to 65° C. and stirred for 20 h. After cooled to room temperature, the mixture was filtered to collect the solid. The solid was washed with EtOH (10 mL×3), dried to afford compound 96-2 (290 mg, 65% yield) as yellow solid.

Step 3: (4-(5-amino-1,2,4-oxadiazol-3-yl)thiazol-2-yl)(5-chloro-1H-indol-3-yl)methanone (ARI-121)

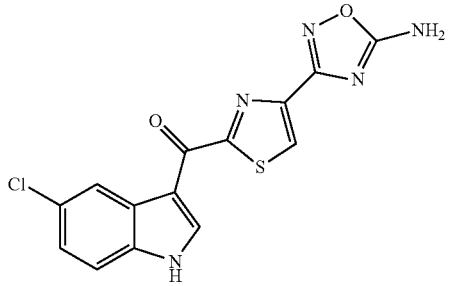

This compound was synthesized according to the protocol described in Example 116 step 2 from compound 96-2 (380 mg, 0.85 mmol) to give title compound ARI-121 in the form of a yellow solid (228 mg, 78% yield). $^1$H-NMR (400 MHz, DMSO-d6): δ 12.53 (bs, 1H), 9.14~9.16 (d, J=2.4 Hz, 1H), 8.59 (s, 1H), 8.30 (s, 1H), 8.10 (s, 2H), 7.63~7.66 (d, J=8.4 Hz, 1H), 7.33~7.36 (m, 1H). LC-MS: m/z 344.3 [M–H]$^-$.

Example 65: Preparation of ethyl 2-(1H-indole-3-carbonyl)thiazole-4-carboxylate (PTC17341-17, ARI-041)

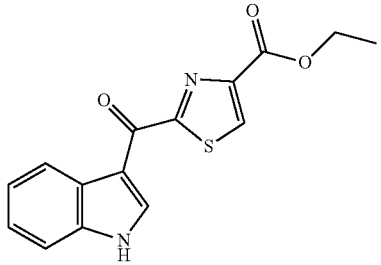 [SMILES: CCOC(=O)c1csc(C(=O)c2c[nH]c3ccccc23)n1]

Figure 21:
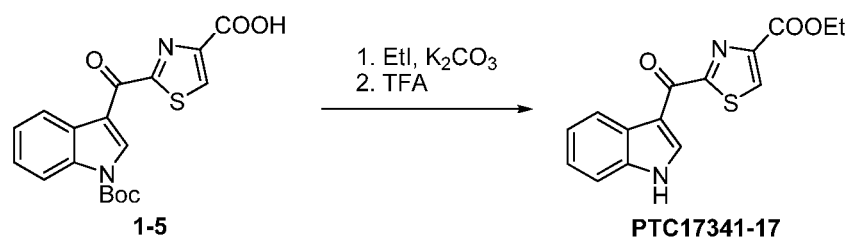
FIG. 21 shows a synthesis scheme for ARI-041 (PTC17341-17) according to Example 65.

ARI-041 was synthesized according to the scheme of FIG. 21 and by the following method:

Step: Ethyl 2-(1H-indole-3-carbonyl)thiazole-4-carboxylate $K_2CO_3$ (1.85 g, 13.4 mmol) was added to a solution of compound 1-5 (2.5 g, 6.7 mmol) in DMF (30 mL) at room temperature. The mixture was stirred for 5 min, then iodoethane (1.57 g, 10.1 mmol) was added. The resulting mixture was stirred for 2 h, then quenched with water (200 mL). The mixture was stirred for 0.5 h, then filtered to collect the solid. The solid was washed with water (30 mL×3) and EtOAc (30 mL×3), dried to afford ethyl ester (2.52 g, 94% yield) as off-white solid.

The above ethyl ester (2.50 g, 6.3 mmol) was dissolved in THF/DCM (10 mL/10 mL) at 0° C., and the mixture was allowed to warm to room temperate and was then stirred for 2 h. The mixture was concentrated to dryness. The residue was suspended in saturated aqueous $NaHCO_3$ (50 mL) and EtOAc (50 mL), stirred for 0.5 h, then filtered to collect the solid. The solid was washed with water (30 mL×3) and EtOAc (30 mL×3), dried to afford ethyl 2-(1H-indole-3-carbonyl)thiazole-4-carboxylate (1.70 g, 91% yield) as yellow solid. $^1$H-NMR (400 MHz, DMSO-d6): δ 12.38 (s, 1H), 9.10 (s, 1H), 8.87 (s, 1H), 8.30-8.35 (m, 1H), 7.55~7.62 (m, 1H), 7.28~7.33 (m, 2H), 4.35~4.44 (q, J=7.2 Hz, 2H), 1.34~1.40 (t, J=7.2 Hz, 3H). LC-MS: m/z 301.2 [M+H]$^+$.

Example 66: Preparation of isopropyl 2-(1H-indole-3-carbonyl)thiazole-4-carboxylate (ARI-042)

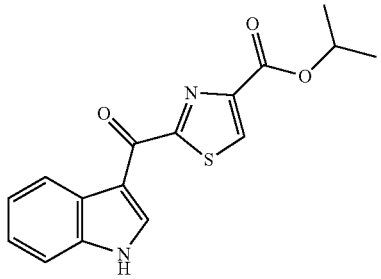 [SMILES: CC(C)OC(=O)c1csc(C(=O)c2c[nH]c3ccccc23)n1]

Prepared according to the method described in Example 14 except that isopropanol was used instead of 1,3-propanediol.

Example 67: Preparation of propyl 2-(1H-indole-3-carbonyl)thiazole-4-carboxylate (ARI-043)

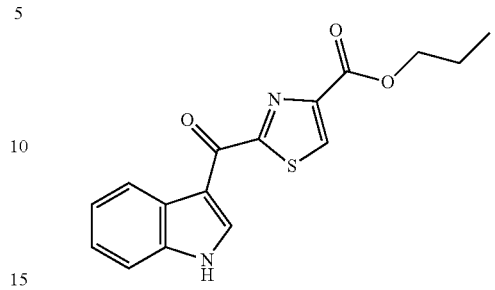

Prepared according to the method described in Example 14 except that propanol was used instead of 1,3-propanediol.

Example 68: Preparation of 2-(5-chloro-1H-indole-3-carbonyl)-N-methylthiazole-4-carboxamide (PTC17341-06) (ARI-049)

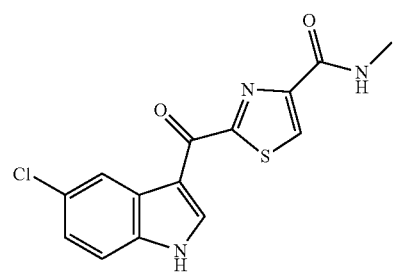 [SMILES: CNC(=O)c1csc(C(=O)c2c[nH]c3ccc(Cl)cc23)n1]

Figure 22:
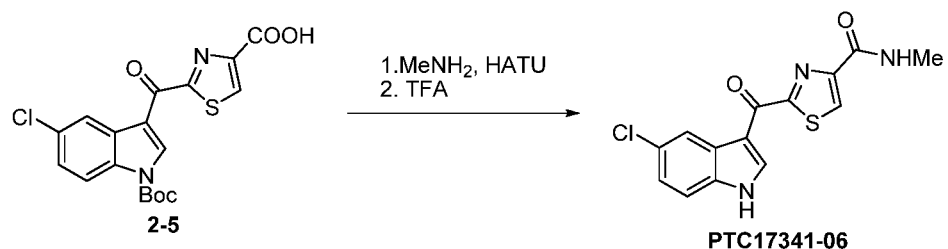
FIG. 22 shows a synthesis scheme for ARI-049 (PTC17341-06) according to Example 68.

ARI-049 was synthesized according to the scheme of FIG. 22 and by the following method:

Step: 2-(5-Chloro-1H-indole-3-carbonyl)-N-methyl-thiazole-4-carboxamide (PTC17341-06, ARI-049)

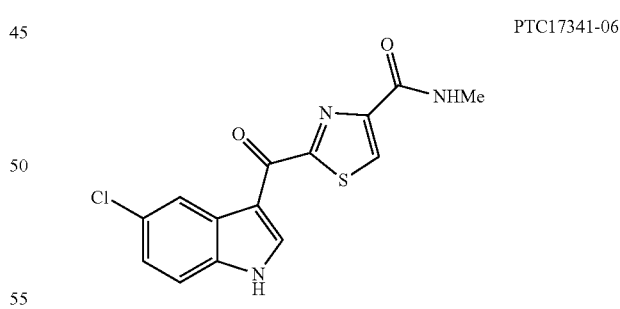

HATU (2.40 g, 6.4 mmol) and DIPEA (1.90 g, 14.7 mmol) were added to a suspension of compound 2-5 (2.00 g, 4.9 mmol) and methylamine hydrochloride (0.50 g, 7.4 mmol) in DMF (20 mL) at room temperature. The mixture was stirred overnight, then quenched with $H_2O$ (100 mL). The mixture was stirred for 0.5 h, then filtered to collect the solid. The solid was washed with water (30 mL×3) and EtOAc (30 mL×3), dried to afford amide (1.20 g, 58% yield) as off-white solid.

The above amide (1.20 g, 2.8 mmol) was dissolved in THF/DCM (10 mL/10 mL) at 0° C., then the mixture was allowed to warm to room temperate and stirred for 2 h. The mixture was concentrated to dryness. The residue was suspended in saturated aqueous NaHCO$_3$ (50 mL) and EtOAc (50 mL), stirred for 0.5 h, then filtered to collect the solid. The solid was washed with water (30 mL×3) and EtOAc (30 mL×3), dried to afford PTC17341-06 (ARI-049) (820 mg, 89% yield) as yellow solid. $^1$H-NMR (400 MHz, DMSO-d6): δ 12.52 (bs, 1H), 9.50 (s, 1H), 8.74 (bs, 1H), 8.62 (s, 1H), 8.30-8.31 (d, J=2.0 Hz, 1H), 7.58-7.62 (d, J=8.8 Hz, 1H), 7.30-7.35 (m, 2H), 2.85-2.90 (d, J=4.8 Hz, 3H). LC-MS: m/z 318.0 [M–H]$^-$.

Example 69: Preparation of methyl 2-(5-chloro-1H-indole-3-carbonyl)thiazole-4-carboxylate (ARI-055)

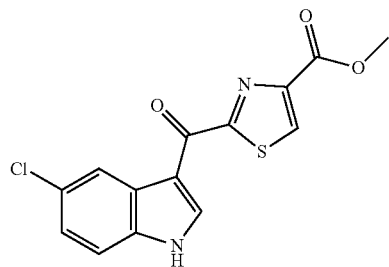 [SMILES: COC(=O)c1csc(C(=O)c2c[nH]c3ccc(Cl)cc23)n1]

Prepared according to the method described in Example 14 except that 2-(5-chloro-1H-indole-3-carbonyl)thiazole-4-carboxylic acid and methanol were used.

Example 70: Preparation of 2-(5,6-dibromo-1H-indole-3-carbonyl)-N-methylthiazole-4-carboxamide (ARI-057)

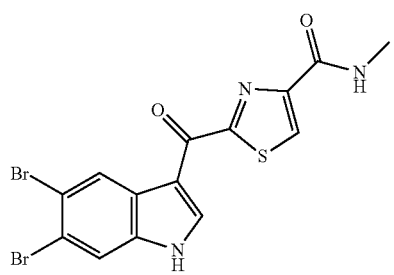 [SMILES: CNC(=O)c1csc(C(=O)c2c[nH]c3cc(Br)c(Br)cc23)n1]

BOC-protected ARI-004 (2.3 g) was dissolved in glacial acetic acid (25 mL). Br$_2$ (3 eq) was added dropwise. The resulting mixture was stirred at 20~30° C. for 72 h. The acetic acid was removed under vacuum to afford the crude product as a 3:1 mixture of 5,6 dibromo and monobromo carboxamido products. The crude product mixture was recrystallized from hot glacial acetic acid to afford 2.3 gm of ARI-057 as an off-white solid.

Example 71: Preparation of 2-(5-chloro-1H-indole-3-carbonyl)thiazole-4-carboxylic acid (PTC17341-05, ARI-058)

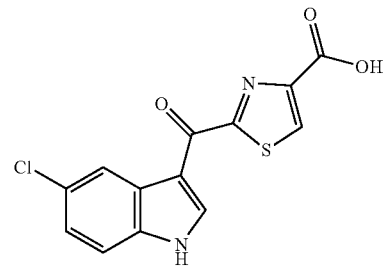 [SMILES: O=C(O)c1csc(C(=O)c2c[nH]c3ccc(Cl)cc23)n1]

Figure 23:
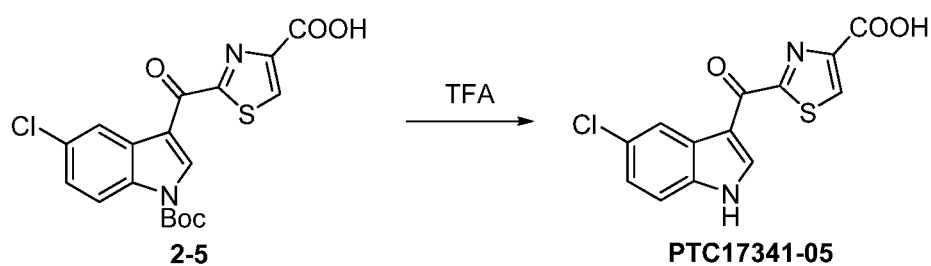
FIG. 23 shows a synthesis scheme for ARI-058 (PTC17341-05) according to Example 71.

ARI-058 was synthesized according to the scheme of FIG. 23 and by the following method:

Step: 2-(5-chloro-1H-indole-3-carbonyl)thiazole-4-carboxylic acid (PTC17341-05, ARI-058)

A solution of compound 2-5 (1.5 g, 3.7 mmol) in DCM (10 mL) and TFA (10 mL) was stirred at room temperature for 3 h. The mixture was concentrated to dryness. The residue was suspended in EtOAc (20 mL), alkalified by saturated aqueous NaHCO$_3$ to pH of 7~8, then acidified by aqueous 1N HCl to pH of 3. The mixture was filtered to collect the solid. The solid was washed with water (10 mL×3) and EtOAc (10 mL×3), dried to afford ARI-058 (HCl salt, 1.1 g, 87% yield) as yellow solid. $^1$H-NMR (400 MHz, DMSO-d6): δ 13.46 (bs, 1H), 12.76 (s, 1H), 9.17 (s, 1H), 8.83 (s, 1H), 8.28~8.29 (d, J=2.0 Hz, 1H), 7.63~7.66 (d, J=8.4 Hz, 1H), 7.31~7.35 (m, 1H) LC-MS: m/z 305.0 [M–H]$^-$.

Example 72: Preparation of tert-butyl 2-(1H-indole-3-carbonyl)thiazole-4-carboxylate (ARI-059)

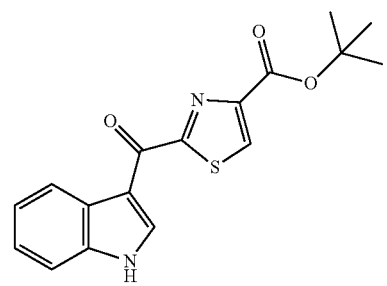 [SMILES: CC(C)(C)OC(=O)c1csc(C(=O)c2c[nH]c3ccccc23)n1]

Prepared according to the method described in Example 14 except that tert-butanol was used instead of 1,3-propanediol.

Example 73: Preparation of 2-(5-fluoro-1H-indole-3-carbonyl)-N-methylthiazole-4-carboxamide (ARI-065)

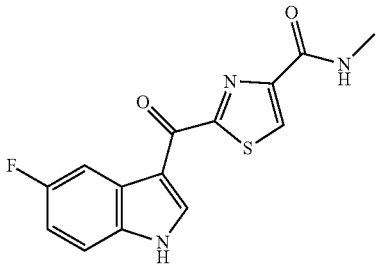 [SMILES: CNC(=O)c1csc(C(=O)c2c[nH]c3ccc(F)cc23)n1]

Prepared according to the method described in Example 24 except that 5-fluoro-1H-indole-3-carboxylic acid and methylamine were used.

Example 74: Preparation of methyl 2-(5-fluoro-1H-indole-3-carbonyl)thiazole-4-carboxylate (ARI-066)

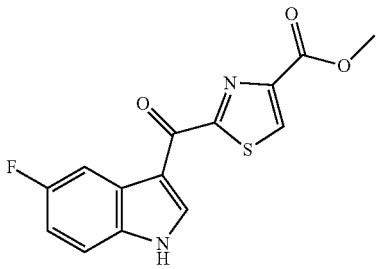 [SMILES: COC(=O)c1csc(C(=O)c2c[nH]c3ccc(F)cc23)n1]

Prepared according to the method described in Example 14 except that methanol was used instead of 1,3-propanediol.

Example 75: Preparation of 1-(2-(1H-indole-3-carbonyl)thiazol-4-yl)ethan-1-one (ARI-077)

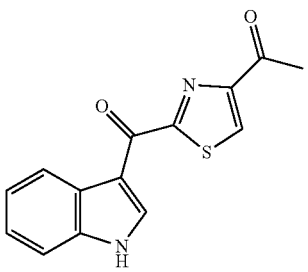 [SMILES: CC(=O)c1csc(C(=O)c2c[nH]c3ccccc23)n1]

Figure 24:
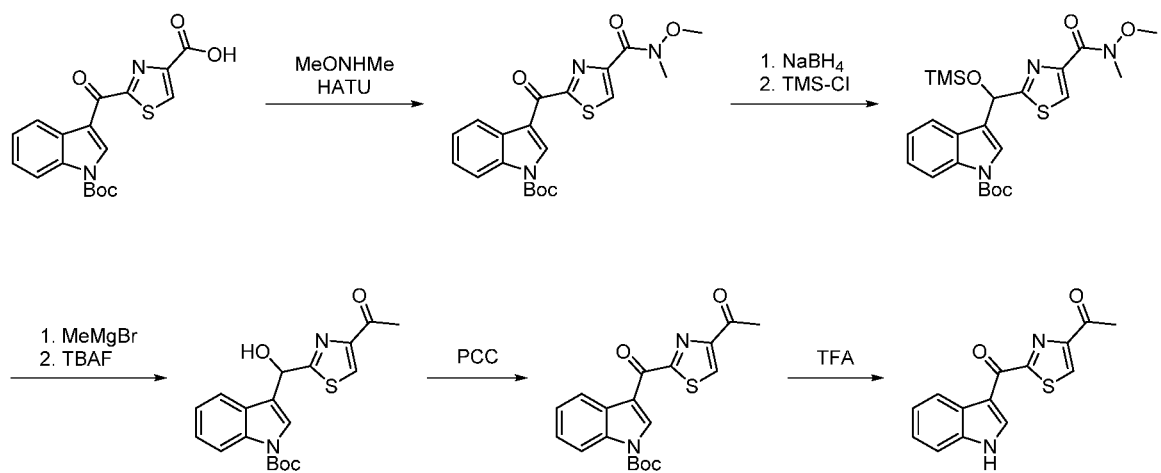
FIG. 24 shows a synthesis scheme for ARI-077 according to Example 75.

ARI-077 was synthesized according to the scheme of FIG. 24 and by the following method:

Step 1. HATU (12.9 g, 34 mmol) and DIPEA (10.1 g, 78 mmol) were added to a suspension of 2-(1-(tert-butoxycarbonyl)-1H-indole-3-carbonyl)thiazole-4-carboxylic acid (10.0 g, 26 mmol) and N,O-dimethylhydroxyamine hydrochloride (3.7 g, 38 mmol) in DMF (50 mL) at room temperature. The mixture was stirred overnight, then quenched with H$_2$O (200 mL). The mixture was stirred for 0.5 h, then filtered to collect the solid. The solid was washed with water (50 mL×3) and EtOAc (50 mL×3), dried to afford tert-butyl 3-(4-(methoxy(methyl)carbamoyl)thiazole-2-carbonyl)-1H-indole-1-carboxylate (9.1 g, 84% yield) as off-white solid.

Step 2. NaBH$_4$ (0.54 g, 14 mmol) was added portionwise to a solution of compound tert-butyl 3-(4-(methoxy(methyl)carbamoyl)thiazole-2-carbonyl)-1H-indole-1-carboxylate (5.88 g, 14 mmol) in DCM (50 mL) and EtOH (50 mL) at 0° C. over 10 min. The resulting mixture was stirred for 0.5 h, then quenched with water (100 mL), extracted with DCM (100 mL×3). The combined organic phases were washed with brine (200 mL×2), dried, concentrated to afford alcohol (~6.0 g) as an oil. The alcohol (6.0 g, 14 mmol) and triethanolamine (TEA) (2.2 g, 28 mmol) were dissolved in THF (60 mL), and cooled to 0° C., then TMSCl (2.2 g, 20 mmol) was added dropwise over 10 min. The resulting mixture was stirred for 2 h, then quenched with water (100 mL), extracted with EtOAc (50 mL×3). The combined organic phases were washed with saturated aqueous NaHCO$_3$ (50 mL×2) and brine (200 mL×2), dried, concentrated to afford compound tert-butyl 3-((4-(methoxy(methyl)carbamoyl)thiazol-2-yl) (trimethyl silyloxy)methyl)-1H-indole-1-carboxylate (6.9 g, ~100% yield) as an oil, which was used for next step without further purification.

Step 3. MeMgBr (2 M in Et$_2$O, 5 mL, 10 mmol) was added portionwise to a solution of compound tert-butyl 3-((4-(methoxy(methyl)carbamoyl)thiazol-2-yl) (trimethyl silyloxy)methyl)-1H-indole-1-carboxylate (2.0 g, 4.1 mmol) in THF (20 mL) at 0° C. over 10 min. The resulting mixture was stirred for 0.5 h, then quenched with saturated aqueous NH$_4$Cl (50 mL), extracted with EtOAc (50 mL×3). The combined organic phases were washed with brine (100 mL×2), dried, concentrated to afford ketone (~1.8 g) as an oil.

The above ketone (1.8 g) was dissolved in THF (20 mL), tetrabutylammonium fluoride (TBAF) (1.1 g, 4 mmol) was added. The mixture was stirred for 2 h at room temperature, then quenched with water (50 mL), extracted with EtOAc (50 mL×3). The combined organic phases were washed with brine (100 mL×2), dried, concentrated to dryness. The residue was purified by silica gel chromatography (EtOAc/Hexane=1:3) to afford tert-butyl 3-((4-acetylthiazol-2-yl)(hydroxy)methyl)-1H-indole-1-carboxylate (950 mg, 62% yield).

Step 4. Pyridinium chlorochromate (PCC) (0.8 g, 3.7 mmol) was added to a solution of compound tert-butyl 3-((4-acetylthiazol-2-yl)(hydroxy)methyl)-1H-indole-1-carboxylate (950 mg, 2.6 mmol) in DCM (50 mL) at room temperature. The resulting mixture was stirred overnight, then quenched with water (50 mL). The mixture was filtered, and the filtrate was extracted with DCM (50 mL×3). The combined organic phases were washed with brine (100 mL×2), dried, concentrated to dryness. The residue was purified by silica gel chromatography (EtOAc/Hexane/THF=1:3:1) to afford tert-butyl 3-(4-acetylthiazole-2-carbonyl)-1H-indole-1-carboxylate (670 mg, 69% yield).

Step 5. A solution of tert-butyl 3-(4-acetylthiazole-2-carbonyl)-1H-indole-1-carboxylate (1.5 g, 3.7 mmol) in DCM (10 mL) and TFA (10 mL) was stirred at room temperature. Upon completion, the mixture was concentrated to dryness. The residue was suspended in EtOAc basified with saturated aqueous NaHCO$_3$ to pH of 7-8, then acidified by aqueous 1N HCl to pH of 3. The mixture was filtered to collect the solid. The solid was washed with water and EtOAc, dried to afford 1-(2-(1H-indole-3-carbonyl)thiazol-4-yl)ethan-1-one in the form of a yellow solid (660 mg, 90% yield). ¹H-NMR (400 MHz, DMSO-d6): δ 12.35 (bs, 1H), 9.18 (s, 1H), 8.86 (s, 1H), 8.32 (m, 1H), 7.59 (m, 1H), 7.31 (m, 2H), 2.74 (s, 3H). LC-MS: m/z 270 [M+H]⁺.

Example 76: Preparation of 1-(2-(5-chloro-1H-indole-3-carbonyl)thiazol-4-yl)propan-1-one (ARI-067)

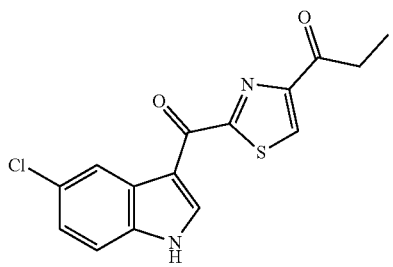 [SMILES: CCC(=O)c1csc(C(=O)c2c[nH]c3ccc(Cl)cc23)n1]

Prepared according to the method described in Example 75 except that 2-(1-(tert-butoxycarbonyl)-5-chloro-1H-indole-3-carbonyl)thiazole-4-carboxylic acid was used.

Example 77: Synthesis of (4-(1-hydroxypropyl)thiazol-2-yl)(1H-indol-3-yl)methanone (PTC17341-16, ARI-068)

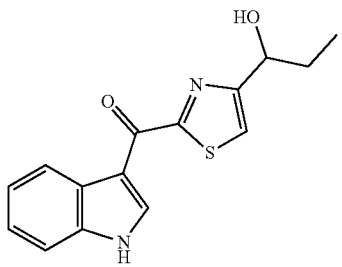 [SMILES: CCC(O)c1csc(C(=O)c2c[nH]c3ccccc23)n1]

(S)-(4-(1-hydroxypropyl)thiazol-2-yl)(1H-indol-3-yl)methanone (PTC17341-16A, ARI-092) and (R)-(4-(1-hydroxypropyl)thiazol-2-yl)(1H-indol-3-yl)methanone (PTC17341-16B, ARI-094)

Figure 25:
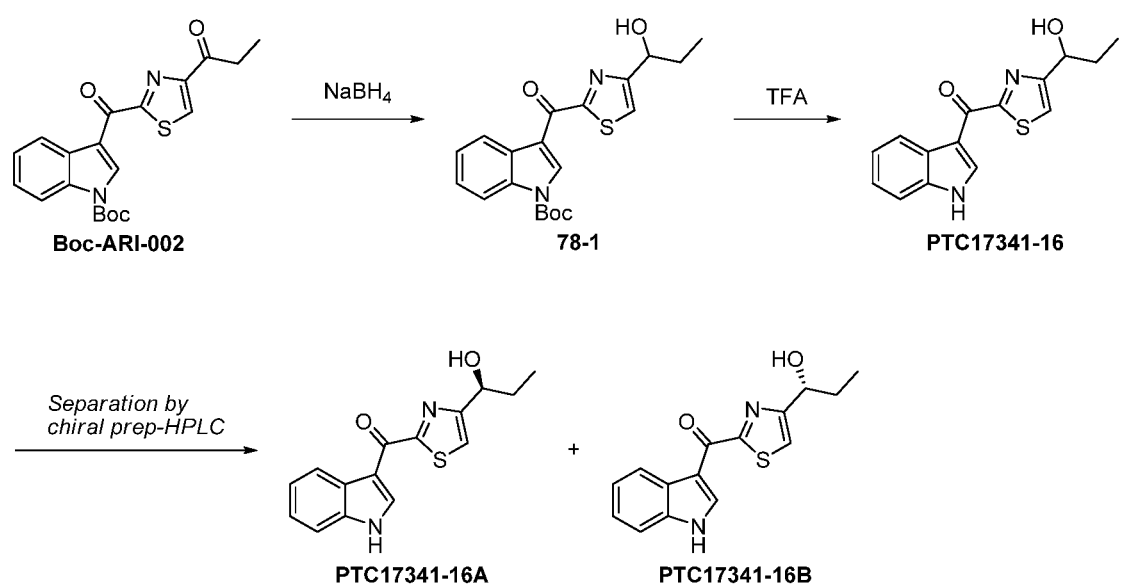
FIG. 25 shows a synthesis scheme for ARI-068 (PTC17341-16), ARI-092 (PTC17341-16A), and ARI-094 (PTC17341-16B) according to Example 77.

ARI-068 was synthesized according to the scheme of FIG. 25 and by the following method:

Step 1: tert-Butyl 3-(4-(1-hydroxypropyl)thiazole-2-carbonyl)-1H-indole-1-carboxylate (78-1)

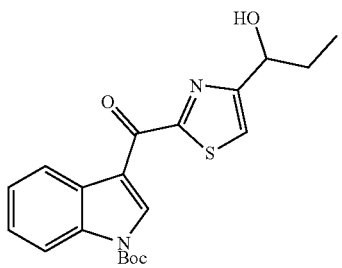

78-1

NaBH₄ (60 mg, 1.6 mmol, 0.6 eq) was added portionwise to a solution of compound Boc-ARI-002 (1.0 g, 2.6 mmol) in DCM (30 mL) and MeOH (20 mL) at 0° C. The mixture was stirred for 2 h, then quenched with H₂O (30 mL), extracted with EtOAc (50 mL×3). The combined organic phases were washed with brine (50 mL×3), dried over anhydrous Na₂SO₄, filtered and concentrated in vacuo. The residue was purified by silica gel column chromatography (hexane/EtOAc=2:1) to give compound 78-1 (700 mg, 70% yield) as an oil.

Step 2: (4-(1-Hydroxypropyl)thiazol-2-yl)(1H-indol-3-yl)methanone (PTC17341-16)

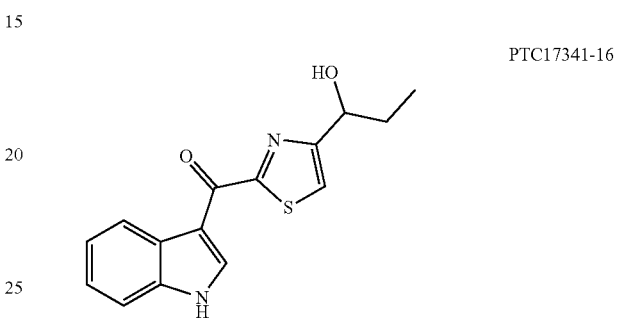

PTC17341-16

This compound was synthesized according to the protocol described in Example 71 from compound 78-1 (2.2 g, 5.7 mmol) to give title compound PTC17341-16 (ARI-068) in the form of a yellow solid (1.4 g, 86% yield). ¹H-NMR (400 MHz, DMSO-d6): δ 12.25 (bs, 1H), 9.15 (d, J=2.0 Hz, 1H), 8.30~8.34 (m, 1H), 7.82 (s, 1H), 7.55~7.60 (m, 1H), 7.26~7.30 (m, 2H), 5.46~5.48 (d, J=5.2 Hz, 1H), 4.71~4.77 (m, 1H), 1.90~2.00 (m, 1H), 1.75~1.88 (m, 1H), 0.90~0.99 (t, J=5.4 Hz, 3H). LC-MS: m/z 287.2 [M+H]⁺.

Step 3: (S)-(4-(1-Hydroxypropyl)thiazol-2-yl)(1H-indol-3-yl)methanone (PTC17341-16A) and (R)-(4-(1-Hydroxypropyl)thiazol-2-yl)(1H-indol-3-yl)methanone (PTC17341-16B)

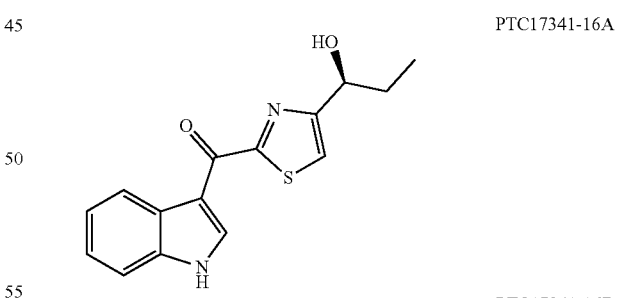

PTC17341-16A

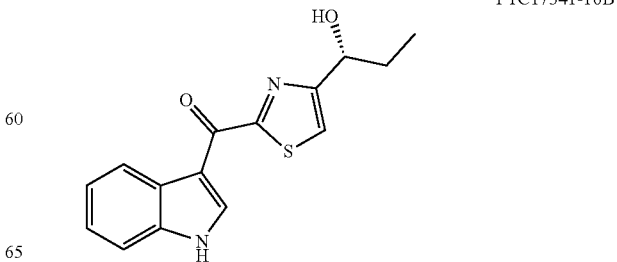

PTC17341-16B

Compound PTC17341-16 (1.0 g, 3.5 mmol) was separated by chiral prep-HPLC to afford compound PTC17341-16A (ARI-092) (140 mg, 14% yield) and PTC17341-16B (ARI-094) (128 mg, 13% yield).

PTC17341-16A (ARI-092): yellow solid, $^1$H-NMR (400 MHz, DMSO-d6): δ 12.21 (bs, 1H), 9.10 (s, 1H), 8.30~8.34 (m, 1H), 7.82 (s, 1H), 7.55~7.60 (m, 1H), 7.24~7.31 (m, 2H), 5.44~5.47 (d, J=6.8 Hz, 1H), 4.70~7.77 (m, 1H), 1.88~1.95 (m, 1H), 1.75~1.85 (m, 1H), 0.90~0.96 (t, J=6.0 Hz, 3H). LC-MS: m/z 287.2 [M+H]$^+$.

PTC17341-16B (ARI-094): yellow solid, $^1$H-NMR (400 MHz, DMSO-d6): δ 12.22 (bs, 1H), 9.10 (s, 1H), 8.30~8.34 (m, 1H), 7.82 (s, 1H), 7.55~7.60 (m, 1H), 7.24~7.31 (m, 2H), 5.44~5.47 (d, J=6.0 Hz, 1H), 4.70~4.77 (m, 1H), 1.88~2.05 (m, 1H), 1.74~1.85 (m, 1H), 0.92~0.98 (t, J=6.0 Hz, 3H). LC-MS: m/z 287.2 [M+H]$^+$.

Example 78: Synthesis of (E)-(1H-indol-3-yl)(4-(1-(methoxyimino)-2-methyl propyl)thiazol-2-yl)methanone (PTC17341-22-A) and (Z)-(1H-indol-3-yl)(4-(1-(methoxyimino)-2-methylpropyl)thiazol-2-yl)methanone (PTC17341-22-B) (ARI-069 and ARI-070)

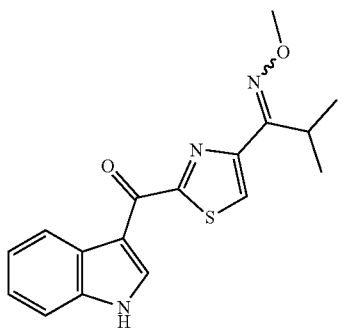 [SMILES: CON=C(c1csc(C(=O)c2c[nH]c3ccccc23)n1)C(C)C]

Figure 26:
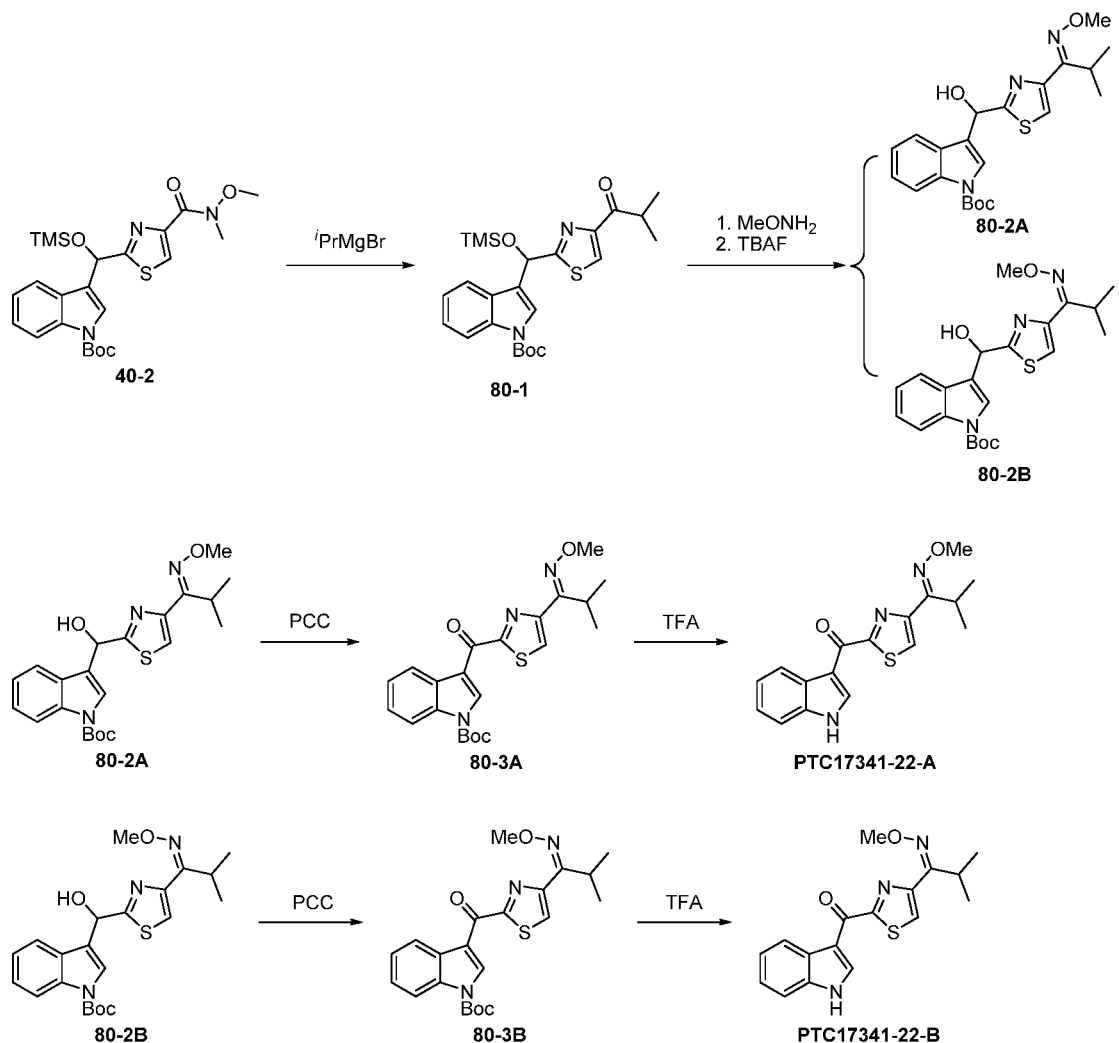
FIG. 26 shows a synthesis scheme for ARI-069 and ARI-070 (PTC17341-22-A and PTC17341-22-B) according to Example 78.

ARI-069 and ARI-070 were synthesized according to the scheme of FIG. 26 and by the following method:

Step 1: tert-Butyl 3-((4-isobutyrylthiazol-2-yl)(trimethylsilyloxy)methyl)-1H-indole-1-carboxylate (80-1)

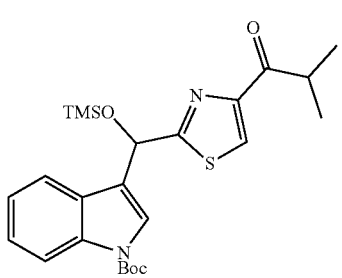

80-1

This compound was synthesized according to the protocol described in Example 127 from compound 40-2 (23.0 g, 47 mmol) to give title compound 80-1 (15.3 g, 69% yield).

Step 2: (E)-tert-Butyl 3-(hydroxy(4-(1-(methoxyimino)-2-methylpropyl)thiazol-2-yl)methyl)-1H-indole-1-carboxylate (80-2A) and (Z)-tert-butyl 3-(hydroxyl(4-(1-(methoxyimino)-2-methylpropyl)thiazol-2-yl)methyl)-1H-indole-1-carboxylate (80-2B)

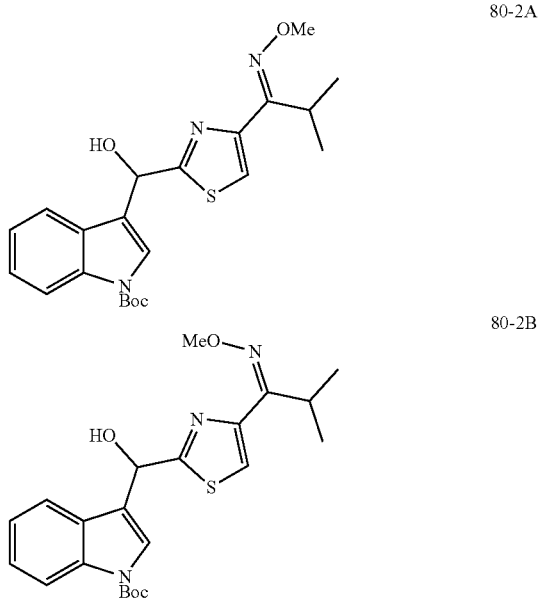

NaOAc (2.64 g, 32 mmol) and methoxylamine hydrochloride (1.34 g, 16 mmol) were added to a solution of compound 80-1 (3.80 g, 8 mmol) in EtOH (20 mL) and H$_2$O (50 mL) at room temperature. The mixture was heated to 70° C. and stirred for 2 h. After cooling to room temperature, the mixture was concentrated in vacuo. The residue was dissolved in THF (20 mL), and TBAF (2.30 g, 8.8 mmol) was added. The mixture was stirred for 2 h at room temperature, then quenched with water (50 mL), extracted with EtOAc (50 mL×3). The combined organic phases were washed with brine (100 mL×2), dried, concentrated to dryness. The residue was purified by silica gel chromatography (EtOAc/Hexan=1:15) and afforded compound 80-2A (600 mg, 17% yield) and 80-2B (598 mg, 17% yield).

Step 3a: (E)-tert-Butyl 3-(4-(1-(methoxyimino)-2-methylpropyl)thiazole-2-carbonyl)-1H-indole-1-carboxylate (80-3A)

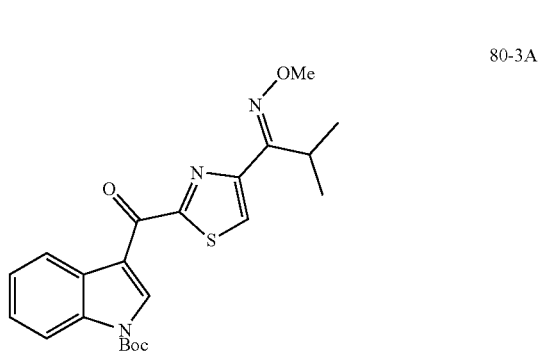 [SMILES: CO/N=C(/c1csc(C(=O)c2cn(C(=O)OC(C)(C)C)c3ccccc23)n1)C(C)C]

This compound was synthesized according to the protocol described in Example 127 from compound 80-2A (600 mg, 1.4 mmol) to give title compound 80-3A (310 mg, 52% yield).

Step 3b: (Z)-tert-Butyl 3-(4-(1-(methoxyimino)-2-methylpropyl)thiazole-2-carbonyl)-1H-indole-1-carboxylate (80-3B)

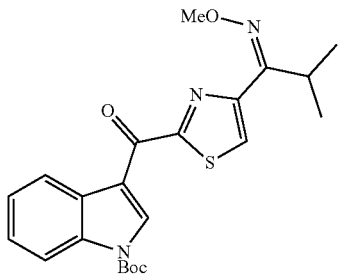

80-3B

This compound was synthesized according to the protocol described in Example 127 from compound 80-2B (598 mg, 1.4 mmol) to give title compound 80-3B (301 mg, 50% yield).

Step 4a: (E)-(1H-indol-3-yl)(4-(1-(methoxyimino)-2-methylpropyl)thiazol-2-yl)methanone (PTC17341-22-A, ARI-069)

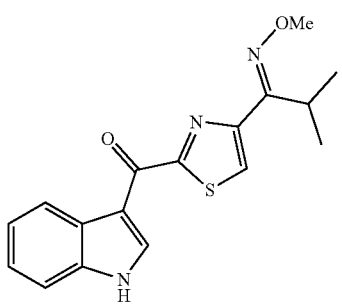

PTC17341-22-A

This compound was synthesized according to the protocol described in Example 71 from compound 80-3A (300 mg, 0.7 mmol) to give the title compound ARI-069 (PTC17341-22-A) in the form of a yellow solid (130 mg, 57% yield). $^1$H-NMR (400 MHz, DMSO-d6): δ 12.36 (bs, 1H), 9.09 (s, 1H), 8.30~8.34 (m, 1H), 8.21 (s, 1H), 7.55~7.60 (m, 1H), 7.26~7.30 (m, 2H), 3.95 (s, 3H), 3.65~3.69 (m, 1H), 1.24~1.32 (m, 6H). LC-MS: m/z 328.3 [M+H]$^+$.

Step 4b: (Z)-(1H-indol-3-yl)(4-(1-(methoxyimino)-2-methylpropyl)thiazol-2-yl)methanone (PTC17341-22-B)

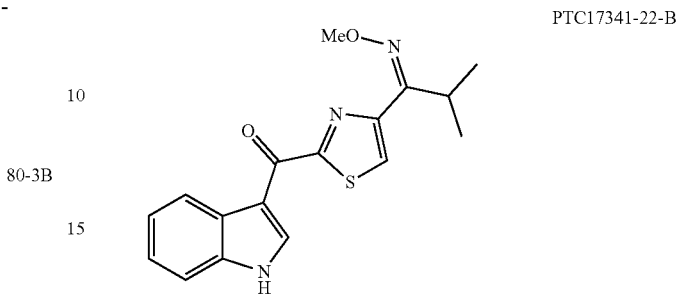

PTC17341-22-B

This compound was synthesized according to the protocol described in Example 71 from compound 80-3B (300 mg, 0.7 mmol) to give the title compound ARI-070 (PTC17341-22-B) in the form of a yellow solid (172 mg, 75% yield). $^1$H-NMR (400 MHz, DMSO-d6): δ 12.32 (bs, 1H), 9.02 (s, 1H), 8.74 (s, 1H), 8.31~8.33 (m, 1H), 7.56~7.59 (m, 1H), 7.28~7.31 (m, 2H), 3.95 (s, 3H), 3.50~3.55 (m, 1H), 1.24~1.26 (d, J=6.8 Hz, 6H). LC-MS: m/z 326.3 [M−H]$^-$.

Example 79: Preparation of methyl 2-(1H-indole-2-carbonyl)thiazole-4-carboxylate (ARI-076)

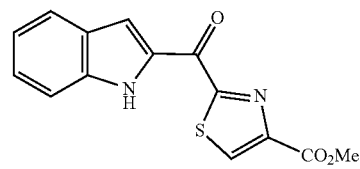 [SMILES: COC(=O)c1csc(C(=O)c2cc3ccccc3[nH]2)n1]

Prepared from indole 2-carboxylic acid by the method described in Example 130 to obtain 2-(1-(tert-butoxycarbonyl)-1H-indole-2-carbonyl) thiazole-4-carboxylic acid. 2-(1-(tert-butoxycarbonyl)-1H-indole-2-carbonyl) thiazole-4-carboxylic acid was then transformed to methyl 2-(1H-indole-2-carbonyl)thiazole-4-carboxylate (ARI-076) according to the method described in Example 65 except that iodomethane instead of iodoethane was used.

Example 80: Preparation of 2-(5-methoxy-1H-indole-3-carbonyl)-N-methylthiazole-4-carboxamide (ARI-078)

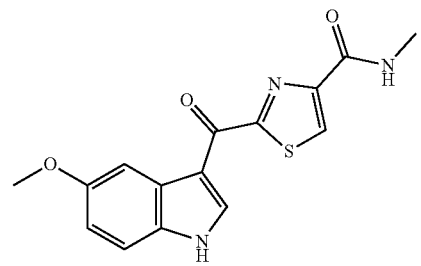

Prepared according to the method for preparing the key intermediate 2-(1H-indole-3-carbonyl)thiazole-4-carboxylic acid using 5-methoxy-1H-indole-3-carboxylic acid to obtain 2-(1-(tert-butoxycarbonyl)-5-methoxy-1H-indole-3-carbonyl)thiazole-4-carboxylic acid which was transformed to the final product using the HATU and TFA methods. See Example 27: Preparation of N-(2-hydroxyethyl)-2-(1H-indole-3-carbonyl)thiazole-4-carboxamide (ARI-036).

Example 81: Preparation of 2-(1H-indole-2-carbonyl)-N-methylthiazole-4-carboxamide (ARI-079)

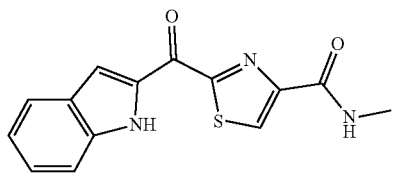 [SMILES: CNC(=O)c1csc(C(=O)c2cc3ccccc3[nH]2)n1]

Prepared according to the method for preparing the key intermediate 2-(1H-indole-3-carbonyl)thiazole-4-carboxylic acid using 1H-indole-2-carboxylic acid to obtain 2-(1-(tert-butoxycarbonyl)-1H-indole-2-carbonyl)thiazole-4-carboxylic acid which was transformed to the methylamide using conditions described in Example 24.

Example 82: Preparation of 6-(1H-indole-3-carbonyl)pyrazine-2-carbonitrile (PTC17341-46, ARI-085)

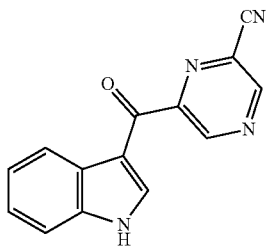 [SMILES: N#Cc1cncc(C(=O)c2c[nH]c3ccccc23)n1]

Figure 27:
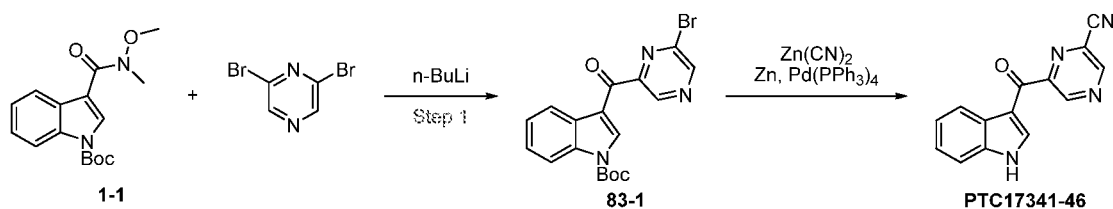
FIG. 27 shows a synthesis scheme for ARI-085 (PTC17341-46) according to Example 82.

ARI-085 was synthesized according to the scheme of FIG. 27 and by the following method:

Step 1: tert-Butyl 3-(6-bromopyrazine-2-carbonyl)-1H-indole-1-carboxylate (83-1)

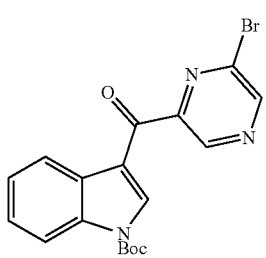

A solution of compound 1-1 (2.00 g, 6.6 mmol) and 2,6-dibromopyrazine (5.50 g, 23 mmol) in THF (100 mL) was cooled to −78° C., and n-BuLi (1.6 M solution in hexane, 8.4 mL, 13.4 mmol) was added dropwise at −78° C. over 10 min. The mixture was stirred for 0.5 h at this temperature, then allowed to warm to 0° C. and quenched with aqueous 10% NH$_4$Cl (100 mL) and EtOAc (100 mL). The organic phase was collected and washed with water (100 mL×2), saturated aqueous NaHCO$_3$ (100 mL×2), and brine (100 mL×1), dried (Na$_2$SO$_4$), filtered and concentrated to dryness. The residue was purified by silica gel chromatography (EtOAc/Hexane=1:5) and afforded compound 83-1 (2.10 g, 79% yield).

Step 2: 6-(1H-indole-3-carbonyl)pyrazine-2-carbonitrile (PTC17341-46, ARI-085)

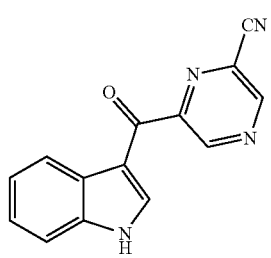

This compound was synthesized according to the protocol described in Example 118 from compound 83-1 (1.00 g, 2.5 mmol) to give title compound PTC17341-46 (ARI-085) in the form of a yellow solid (101 mg, 16% yield). $^1$H-NMR (400 MHz, DMSO-d6): δ 12.30 (bs, 1H), 9.40~9.44 (m, 2H), 8.59 (s, 1H), 8.32~8.35 (m, 1H), 7.56~7.60 (m, 1H), 7.29~7.32 (m, 2H). LC-MS: m/z 248.8 [M+H]$^+$.

Example 83: Synthesis of methyl 6-(1H-indole-3-carbonyl)pyrimidine-4-carboxylate (PTC17341-35) (ARI-086)

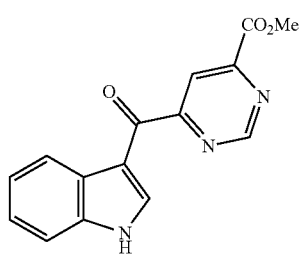 [SMILES: COC(=O)c1cc(C(=O)c2c[nH]c3ccccc23)ncn1]

Figure 28:
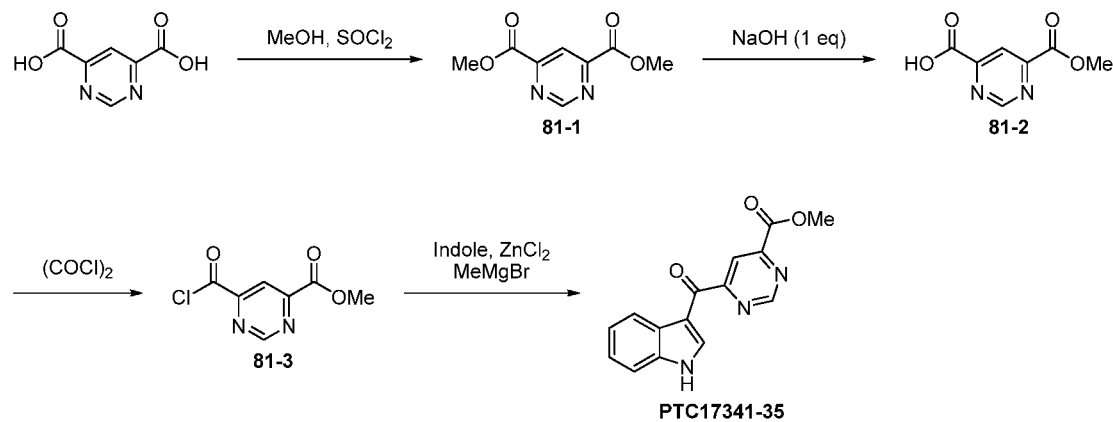
FIG. 28 shows a synthesis scheme for ARI-086 (PTC17341-35) according to Example 83.

ARI-086 was synthesized according to the scheme of FIG. 28 and by the following method:

Step 1: Dimethyl pyrimidine-4,6-dicarboxylate (81-1)

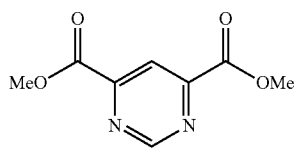

SOCl$_2$ (4.76 g, 4 mmol) was added to a solution of pyrimidine-4,6-dicarboxylic acid (3.40 g, 2 mmol) in MeOH (250 mL) at 0° C. The mixture was heated under reflux and stirred for 5 h. After cooling to room temperature, the mixture was concentrated in vacuo. The residue was diluted with saturated aqueous NaHCO$_3$ (100 mL), and extracted with EtOAc (100 mL×3). The combined organic phases were washed with brine (100 mL×2), dried, concentrated to dryness. The residue was purified by silica gel chromatography (EtOAc/Hexan=1:5) and afforded compound 81-1 (3.10 g, 79% yield).

Step 2:
6-(Methoxycarbonyl)pyrimidine-4-carboxylic acid (81-2)

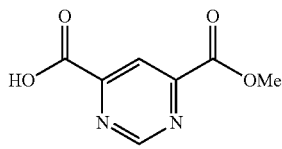
81-2

Sodium hydroxide (632 mg, 15.8 mmol) was added to a solution of compound 81-1 (3.10 g, 15.8 mmol) in MeOH (60 mL) and H$_2$O (6 mL) at 0° C. The resulting mixture was stirred for 2 h at room temperature, then acidified with 1M HCl aqueous to pH of 3. The mixture was concentrated to dryness. The residue was azeotroped two times with THF (50 mL portions) to afford crude compound 81-2 (3.30 g, ~100% yield), which was used for next step without further purification.

Step 3: Methyl 6-(chlorocarbonyl)pyrimidine-4-carboxylate (81-3)

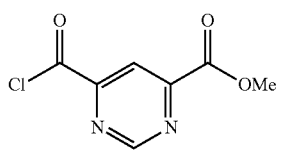
81-3

This compound was synthesized according to the protocol described in Example 84 from compound 81-2 (3.00 g, 16.5 mmol) to give title compound 81-3 (3.25 g, ~100% yield), which was used for next step without further purification.

Step 4: Methyl 6-(1H-indole-3-carbonyl)pyrimidine-4-carboxylate (PTC17341-35, ARI-086)

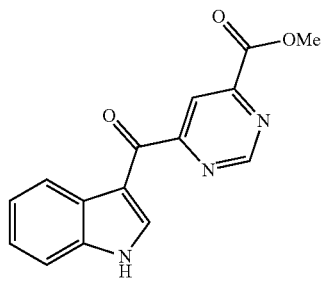
PTC17341-35

This compound was synthesized according to the protocol described in Example 84 from compound 81-3 (3.25 g, 16.5 mmol) to give title compound PTC17341-35 (ARI-086) in the form of a yellow solid (275 mg, 6% yield). $^1$H-NMR (400 MHz, DMSO-d6): δ 12.34 (bs, 1H), 9.58~9.59 (d, J=1.6 Hz, 1H), 8.80 (s, 1H), 8.41 (s, 1H), 8.33~8.35 (m, 1H), 7.55~7.58 (m, 1H), 7.28~7.32 (m, 2H), 3.97 (s, 3H). LC-MS: m/z 280.2 [M+H]$^+$.

Example 84: Preparation of 1-(2-(5-fluoro-1H-indole-3-carbonyl)thiazol-4-yl)propan-1-one (ARI-087)

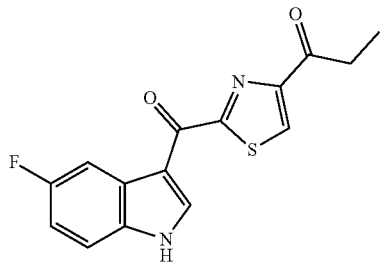 [SMILES: CCC(=O)c1csc(C(=O)c2c[nH]c3ccc(F)cc23)n1]

Figure 29:
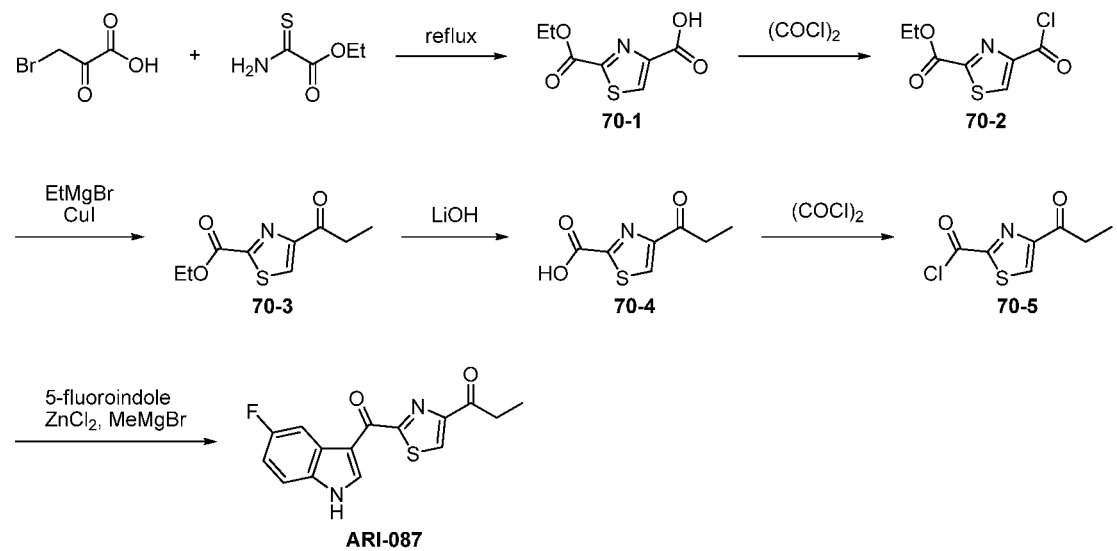
FIG. 29 shows a synthesis scheme for ARI-087 according to Example 84.

ARI-087 was synthesized according to the scheme of FIG. 29 and by the following method:

Step 1: 2-(Ethoxycarbonyl)thiazole-4-carboxylic acid (70-1)

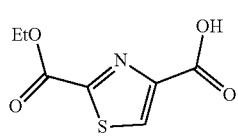
70-1

Ethyl thiooxamate (1.0 Kg, 7.52 mol) was added portionwise to a solution of 2-bromopyruvic acid (1.38 Kg, 8.27 mol) in THF (4 L) over 20 min while the reaction was cooled with water bath. The reaction mixture was stirred for 12 h at room temperature. The reaction mixture was filtered to remove solid. The filtrate was concentrated to dryness to afford crude compound 70-1 (1.8 kg). The crude 70-1 was triturated with EtOAc/hexane/H$_2$O (1:3:2, 6 L), filtered, and the solid was further triturated with EtOAc/hexane (1:8, 3 L), filtered, and the solid was dissolved in DCM (6 L), dried over anhydrous Na$_2$SO$_4$, concentrated to afford compound 70-1 (617 g, 41% yield based on ethyl thiooxamate) as light yellow solid. $^1$H NMR (400 MHz, CDCl$_3$): δ 8.79 (s, 1H), 4.38~4.46 (q, J=7.2 Hz, 2H), 1.3~1.38 (t, J=7.2 Hz, 3H).

Step 2: Ethyl 4-(chlorocarbonyl)thiazole-2-carboxylate (70-2)

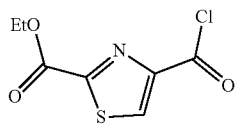

70-2

Oxalyl chloride (63.1 g, 0.497 mol) was added dropwise to a suspension of compound 70-2 (50.0 g, 0.248 mol) in DCM (500 mL) at room temperature over 0.5 h. The reaction mixture was stirred for 4 h, then concentrated. The residue was azeotroped two times with DCM (500 mL portions) to afford crude compound 70-2 (55.1 g, ~100% yield), which was used for next step without further purification.

Step 3: Ethyl 4-propionylthiazole-2-carboxylate (70-3)

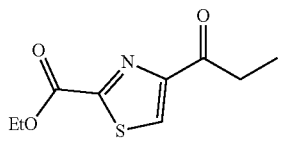

70-3

A mixture of compound 70-2 (55.1 g, 0.248 mol) and copper(I) iodide (9.5 g, 50 mmol) was stirred and cooled to −60° C. under N$_2$. EtMgBr (2M in THF, 150 mL) was added dropwise at −60~−45° C. over 1 h. The mixture was stirred for 2 h at this temperature, and then quenched with saturated NH$_4$Cl aqueous (500 mL). The mixture was warmed to room temperature, then extracted with EtOAc (500 mL×3). The combined organic phases were washed with brine (500 mL×2), dried, concentrated to dryness. The residue was purified by silica gel column chromatography (hexane/EtOAc=20:1) to give compound 70-3 (23.7 g, 45% yield) as yellow solid. $^1$H NMR (400 MHz, DMSO-d6): δ 8.83 (s, 1H), 4.39~4.46 (q, J=7.2 Hz, 2H), 3.07~3.14 (q, J=7.2 Hz, 2H), 1.33~1.38 (t, J=7.2 Hz, 3H), 1.07~1.11 (t, J=7.2 Hz, 3H).

Step 4: 4-Propionylthiazole-2-carboxylic acid (70-4)

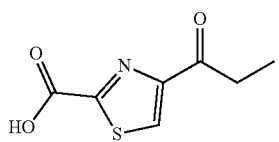

70-4

Lithium hydroxide monohydrate (3.8 g, 90 mmol) was added to a solution of compound 70-3 (6.4 g, 30 mmol) in THF (60 mL) and H$_2$O (6 mL) at 0° C. The resulting mixture was stirred for 2 h at room temperature, then acidified with 1M HCl aqueous to pH of 3. The mixture was concentrated to dryness. The residue was azeotroped two times with THF (50 mL portions) to afford crude compound 70-4 (10.9 g, ~100% yield), which was used for next step without further purification.

Step 5: 4-Propionylthiazole-2-carbonyl chloride (70-5)

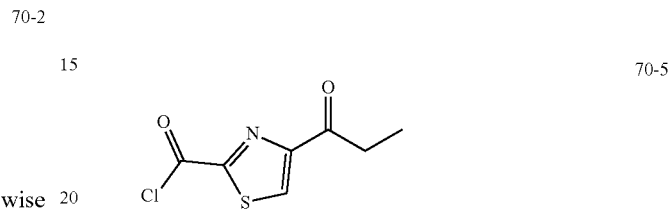

70-5

Oxalyl chloride (961 mg, 7.6 mol) was added dropwise to a suspension of compound 70-4 (700 mg, 3.8 mmol) in DCM (20 mL) at room temperature. The reaction mixture was stirred for 4 h, then concentrated. The residue was azeotroped two times with DCM (20 mL portions) to afford crude compound 70-5 (750 mg, ~100% yield), which was used for next step without further purification.

Step 6: 1-(2-(5-Fluoro-1H-indole-3-carbonyl)thiazol-4-yl)propan-1-one (ARI-087)

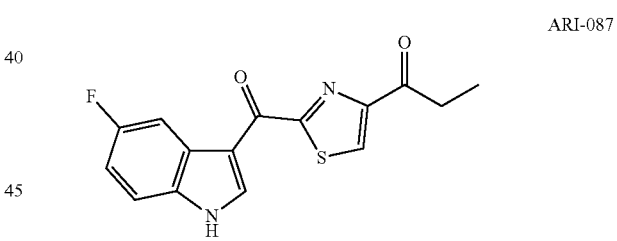

ARI-087

MeMgBr (3M in THF, 1.5 mL, 4.4 mmol) was added dropwise to a mixture of 7-fluoroindole (500 mg, 3.7 mmol) and anhydrous zinc chloride (1.5 g, 11 mmol) in DCM (20 mL) at 0° C. under N$_2$. The mixture was stirred for 1 h at this temperature, and then a solution of compound 70-5 (750 mg, 3.7 mmol) in THF (20 mL) was added at 0° C. The reaction mixture was allowed to warm to room temperature and stirred overnight. The mixture was quenched with saturated aqueous NH$_4$Cl (100 mL), stirred for 20 min, filtered. The solid was collected, washed with water (30 mL×3), EtOAc (30 mL×3) and MeOH (30 mL×3), dried to afford ARI-087 (620 mg, 55% yield from compound 70-3) as yellow solid. $^1$H-NMR (400 MHz, DMSO-d6): δ 12.42 (bs, 1H), 9.20 (s, 1H), 8.86 (s, 1H), 7.97~8.00 (m, 1H), 7.60~7.63 (m, 1H), 7.16~7.19 (m, 1H), 3.22~3.26 (q, J=7.2 Hz, 2H), 1.13~1.18 (t, J=7.2 Hz, 3H). LC-MS: m/z 302.7 [M+H]$^+$.

Example 85: Preparation of 5-(1H-indole-3-carbonyl)pyrazine-2-carbonitrile (ARI-093)

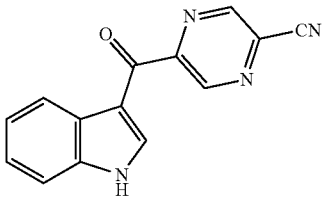 [SMILES: N#Cc1cnc(C(=O)c2c[nH]c3ccccc23)cn1]

Prepared from 2,5-dibromopyrazine according to the method described in Example 82.

Example 86: Preparation of methyl 5-(1H-indole-3-carbonyl)pyrazine-2-carboxylate (ARI-095)

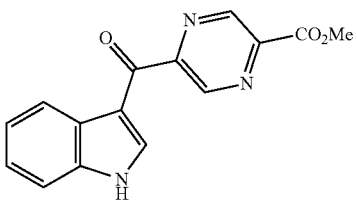 [SMILES: COC(=O)c1cnc(C(=O)c2c[nH]c3ccccc23)cn1]

Prepared according to the method described in Example 83, except that 3,6-carboxymethylpyrazine was used as the staring material.

Example 87: Preparation of 1-(2-(5,6-dibromo-1H-indole-3-carbonyl)thiazol-4-yl)propan-1-one (ARI-097)

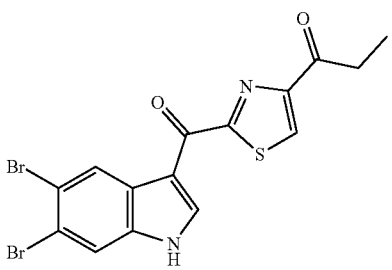 [SMILES: CCC(=O)c1csc(C(=O)c2c[nH]c3cc(Br)c(Br)cc23)n1]

Figure 30:
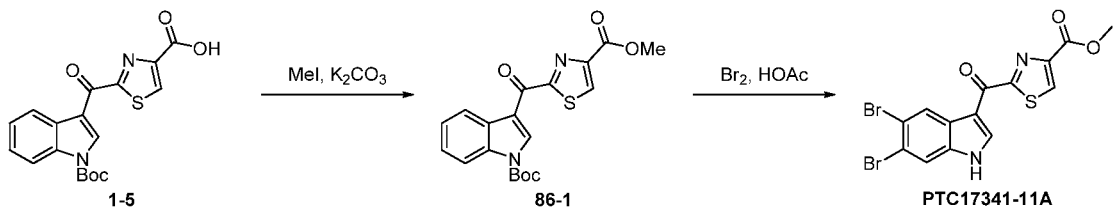
FIG. 30 shows a synthesis scheme for PTC17341-11A according to Example 87.

Starting with methyl 2-(5,6-dibromo-1H-indole-3-carbonyl) thiazole-4-carboxylate (PTC17341-11A) (prepared as shown below and as shown in the scheme of FIG. 30) according to the method described in Example 75 except that ethylmagnesium bromide was used instead of methylmagnesium bromide.

Step 1: Methyl 2-(1-(tert-butoxycarbonyl)-1H-indole-3-carbonyl)thiazole-4-carboxylate (86-1)

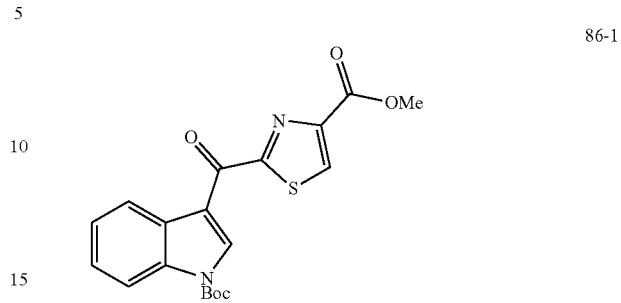

This compound was synthesized according to the protocol described in Example 65 from compound 1-5 (10.00 g, 27 mmol) with MeI to give title compound 86-1 in the form of a yellow solid (9.8 g, 94% yield).

Step 2: Methyl 2-(5,6-dibromo-1H-indole-3-carbonyl)thiazole-4-carboxylate (PTC17341-11A)

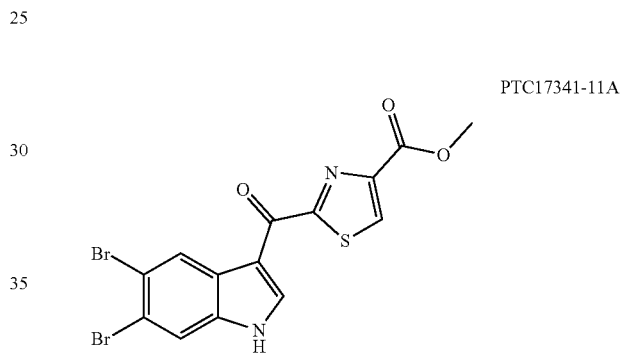

Compound 86-1 (3.0 g, 7.8 mmol) was dissolved in HOAc (25 mL), then bromine (5.0 g, 31 mmol) was added at room temperature. The mixture was stirred at 50° C. for 72 h. After cooled to room temperature, the mixture was filtered, and the solid was collected, washed by HOAc (10 mL×2) to afford crude PTC17341-11A. The crude was recrystallized with DMF/H2O (2:1, 50 mL) to give compound PTC17341-11A (2.3 g, 67% yield). $^{1}$H-NMR (400 MHz, DMSO-d6): δ 12.49 (bs, 1H), 9.07 (s, 1H), 8.90 (s, 1H), 8.57 (s, 1H), 8.00 (s, 1H), 3.93 (s, 3H). LC-MS: m/z 422.6 [M+H]$^{+}$.

Example 88: Preparation of methyl 2-(7-fluoro-1H-indole-3-carbonyl)thiazole-4-carboxylate (ARI-101)

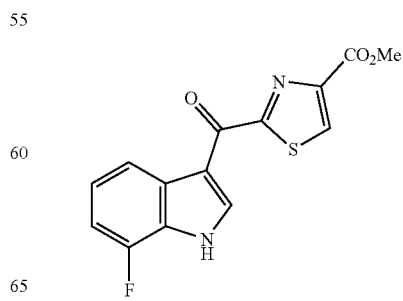

Starting from 7-fluoroindole-3-carboxylic acid, ARI-101 was prepared as described in Example 130 to obtain 2-(1-(tert-butoxycarbonyl)-7-fluoro-1H-indole-3-carbonyl)thiazole-4-carboxylate, which was then transformed to ARI-101 in the presence of $K_2CO_3$, MeI, and TFA by a method described in Example 65.

Example 89: Preparation of methyl 2-(7-fluoro-1H-indole-3-carbonyl)thiazole-4-carboxylate (ARI-102)

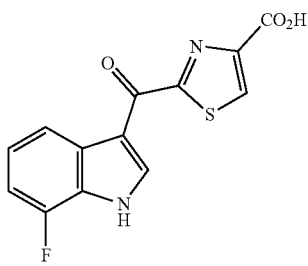 [SMILES: O=C(O)c1csc(C(=O)c2c[nH]c3c(F)cccc23)n1]

Prepared according to the method for preparing the key intermediate 2-(1H-indole-3-carbonyl)thiazole-4-carboxylic acid using 7-fluoro-1H-indole-3-carboxylic acid.

Example 90: Preparation of 2-(5-chloro-1H-indole-2-carbonyl)-N-methylthiazole-4-carboxamide (ARI-103)

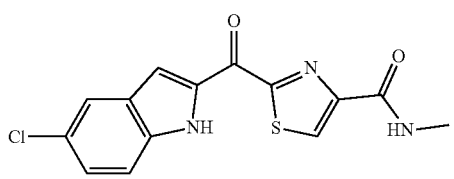 [SMILES: CNC(=O)c1csc(C(=O)c2cc3cc(Cl)ccc3[nH]2)n1]

Prepared according to the method for preparing the key intermediate 2-(1H-indole-3-carbonyl)thiazole-4-carboxylic acid using 5-chloro-1H-indole-2-carboxylic acid to obtain 2-(1-(tert-butoxycarbonyl)-5-chloro-1H-indole-2-carbonyl)thiazole-4-carboxylic acid which was transformed to the final product using conditions described in Example 24 or the HATU and TFA method described in Example 68.

Example 91: Preparation of 2-(7-fluoro-1H-indole-3-carbonyl)thiazole-4-carbonitrile (ARI-104)

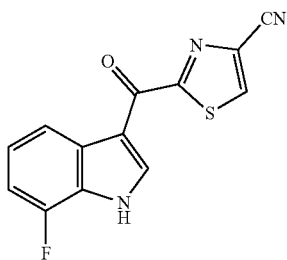 [SMILES: N#Cc1csc(C(=O)c2c[nH]c3c(F)cccc23)n1]

Prepared according to the method for preparing the key intermediate 2-(1H-indole-3-carbonyl)thiazole-4-carboxylic acid using 7-fluoro-1H-indole-3-carboxylic acid to obtain 2-(1-(tert-butoxycarbonyl)-7-fluoro-1H-indole-3-carbonyl)thiazole-4-carboxylic acid which was transformed to the final product using the method described in Example 57.

Example 92: Preparation of 2-(5-fluoro-1H-indole-2-carbonyl)thiazole-4-carboxylic acid (ARI-105)

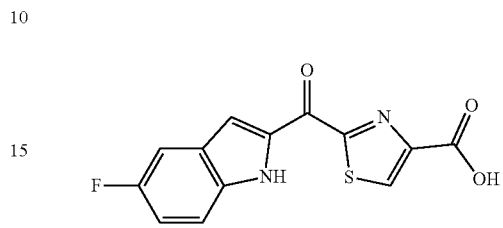

Prepared according to the method for preparing the key intermediate 2-(1H-indole-3-carbonyl)thiazole-4-carboxylic acid described in Example 130 using 5-fluoro-1H-indole-2-carboxylic acid.

Example 93: Preparation of 2-(5-chloro-1H-indole-2-carbonyl)thiazole-4-carboxylic acid (ARI-106)

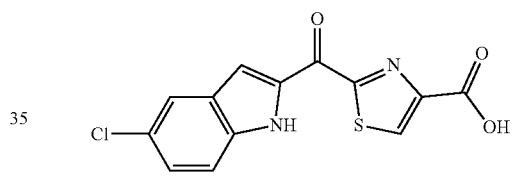

Prepared according to the method for preparing the key intermediate 2-(1H-indole-3-carbonyl)thiazole-4-carboxylic acid (Example 130) using 5-chloro-1H-indole-2-carboxylic acid.

Example 94: Preparation of 2-(5-fluoro-1H-indole-2-carbonyl)thiazole-4-carbonitrile (ARI-107)

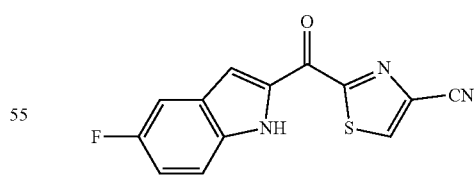

Prepared according to the method for preparing the key intermediate 2-(1H-indole-3-carbonyl)thiazole-4-carboxylic acid using 5-fluoro-1H-indole-2-carboxylic acid to obtain 2-(1-(tert-butoxycarbonyl)-7-fluoro-1H-indole-3-carbonyl)thiazole-4-carboxylic acid which was transformed to the final product using the method described in Example 57.

Example 95: Preparation of 2-(5-fluoro-1H-indole-2-carbonyl)-N-methylthiazole-4-carboxamide (ARI-108)

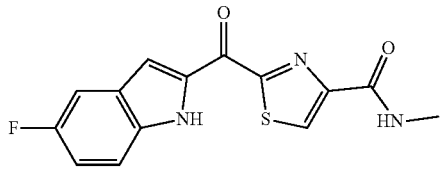 [SMILES: CNC(=O)c1csc(C(=O)c2cc3cc(F)ccc3[nH]2)n1]

Prepared according to the method for preparing the key intermediate 2-(1H-indole-3-carbonyl)thiazole-4-carboxylic acid using 5-fluoro-1H-indole-2-carboxylic acid to obtain 2-(1-(tert-butoxycarbonyl)-7-fluoro-1H-indole-3-carbonyl)thiazole-4-carboxylic acid which was transformed to the final product using methods described in Examples 24 or the HATU and TFA method described in Example 68.

Example 96: Preparation of methyl 2-(6-cyano-1H-indole-3-carbonyl)thiazole-4-carboxylate (ARI-111)

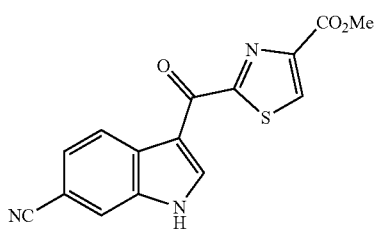 [SMILES: COC(=O)c1csc(C(=O)c2c[nH]c3cc(C#N)ccc23)n1]

Prepared according to the method described in Example 118 except that 6-bromoindole-3-carboxylic acid instead of 5-bromoindole 3-carboxylic acid was used.

Example 97: Preparation of 2-(5-fluoro-1H-indole-3-carbonyl)thiazole-4-carbonitrile (ARI-112)

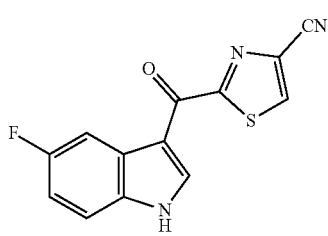 [SMILES: N#Cc1csc(C(=O)c2c[nH]c3ccc(F)cc23)n1]

Prepared according to the method for preparing the key intermediate 2-(1H-indole-3-carbonyl)thiazole-4-carboxylic acid using 5-fluoro-1H-indole-2-carboxylic acid to obtain 2-(1-(tert-butoxycarbonyl)-7-fluoro-1H-indole-3-carbonyl)thiazole-4-carboxylic acid which was transformed to the final 4-cyanothiazole product by the previously described trifluoroacetic anhydride (TFAA)-mediated dehydration of the primary amide (see method described in Example 57).

Example 98: Preparation of 2-(5-chloro-1H-indole-2-carbonyl)thiazole-4-carbonitrile (ARI-113)

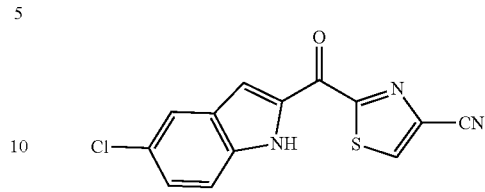

Prepared according to the method for preparing the key intermediate 2-(1H-indole-3-carbonyl)thiazole-4-carboxylic acid using 5-chloro-1H-indole-2-carboxylic acid to obtain 2-(1-(tert-butoxycarbonyl)-5-chloro-1H-indole-2-carbonyl)thiazole-4-carboxylic acid which was transformed to the final 4-cyanothiazole product by the previously described trifluoroacetic anhydride (TFAA)-mediated dehydration of the primary amide (see method described in Example 57).

Example 99: Preparation of (7-fluoro-1H-indol-3-yl)(4-(5-methyl-1,2,4-oxadiazol-3-yl)thiazol-2-yl)methanone (ARI-114)

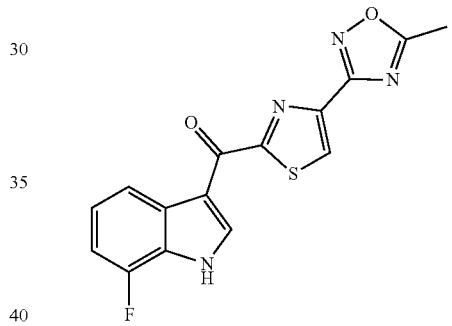

Prepared from 2-(1-(tert-butoxycarbonyl)-7-fluoro-1H-indole-2-carbonyl)thiazole-4-carboxylic acid (itself prepared from 7-fluoroindole-3-carboxylic acid by the methods described in Example 130) by the method described in Example 59.

Example 100: Preparation of (4-(5-amino-1,3,4-oxadiazol-2-yl)thiazol-2-yl)(7-fluoro-1H-indol-3-yl)methanone (ARI-118)

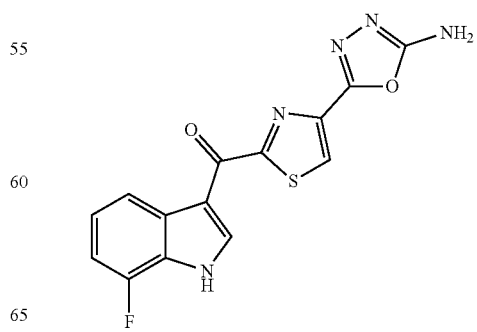

Prepared according to the method described in Example 131 except that 7-fluoroindole was used instead of 5,6-difluoroindole.

Example 101: Preparation of (5-fluoro-1H-indol-3-yl)(4-(5-methyl-1,2,4-oxadiazol-3-yl)thiazol-2-yl)methanone (ARI-119)

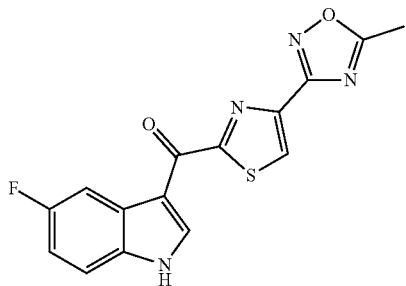 [SMILES: Cc1nc(-c2csc(C(=O)c3c[nH]c4ccc(F)cc34)n2)no1]

Prepared from 2-(1H-indole-5-fluoro-3-carbonyl)thiazole-4-carbonitrile according to the method described in Example 21.

Example 102: Preparation of (7-fluoro-1H-indol-3-yl)(4-(3-methyl-1,2,4-oxadiazol-5-yl)thiazol-2-yl)methanone (PTC17341-95, ARI-123)

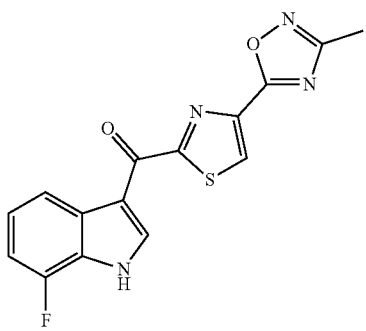 [SMILES: Cc1noc(-c2csc(C(=O)c3c[nH]c4c(F)cccc34)n2)n1]

Figure 31:
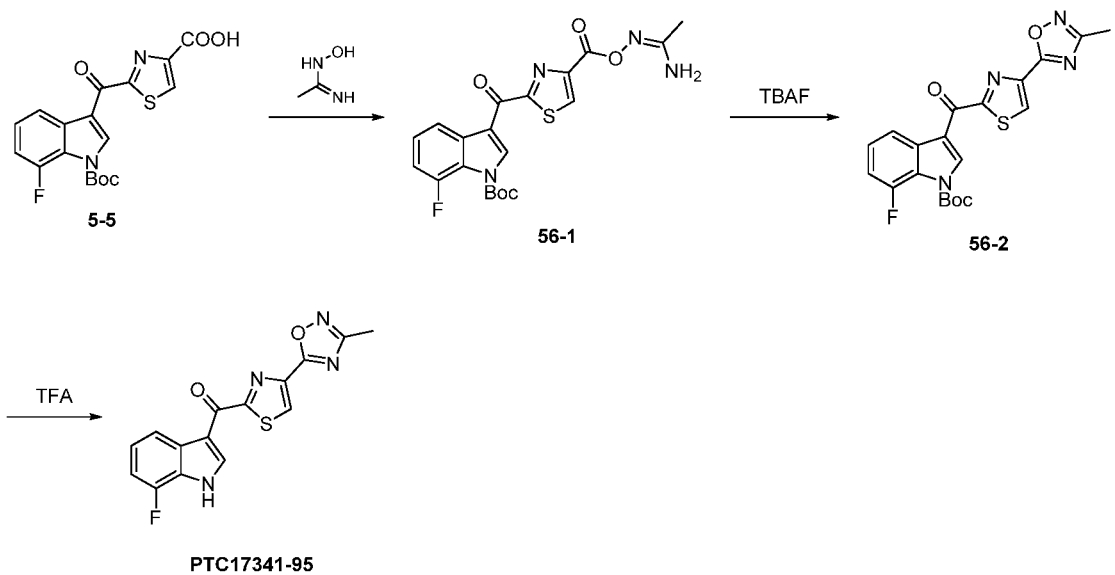
FIG. 31 shows a synthesis scheme for ARI-123 (PTC17341-95) according to Example 102.

ARI-123 was synthesized according to the scheme of FIG. 31 and by the following method:

Step 1: tert-Butyl 3-(4-(((1-aminoethylideneaminooxy)carbonyl)thiazole-2-carbonyl)-7-fluoro-1H-indole-1-carboxylate (56-1)

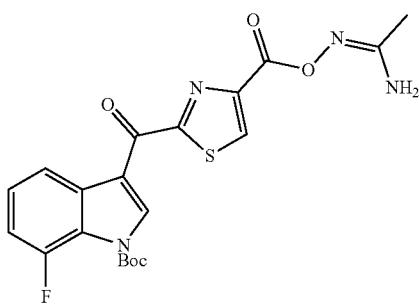

Oxalyl chloride (500 mg, 4 mmol) was added to a suspension of compound 5-5 (780 mg, 2 mmol) in DCM (20 mL) at 0° C. The mixture was allowed to warm to room temperature and stirred 5 h. The mixture was concentrated to dryness. The residue was dissolved in DCM (5 mL) and added dropwise to a suspension of N-hydroxyacetimidamide (220 mg, 3 mmol) and TEA (410 mg, 4 mmol) in DCM (20 mL) at 0° C. over 10 min. The resulting mixture was allowed to warm to room temperature and stirred 1 h. The mixture was concentrated to dryness. And the residue was purified by silica gel chromatography (EtOAc/Hexane/DCM=2:1:1) and afforded compound 56-1 (450 mg, 50% yield).

Step 2: tert-Butyl 7-fluoro-3-(4-(3-methyl-1,2,4-oxadiazol-5-yl)thiazole-2-carbonyl)-1H-indole-1-carboxylate (56-2)

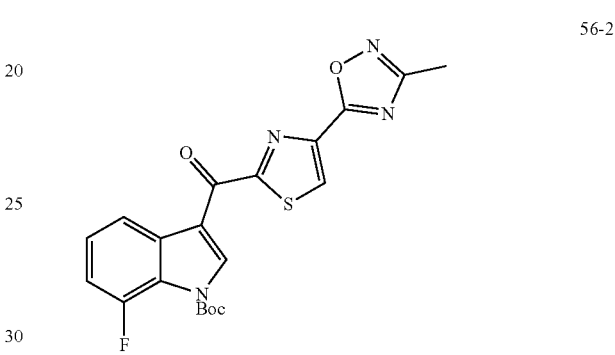

A solution of compound 56-1 (450 mg, 1 mmol) and TBAF (780 mg, 3 mmol) in THF (20 mL) was heated under reflux for 4 h. The mixture was cooled to room temperature, Boc$_2$O (430 mg, 2 mmol) and 4-dimethylaminopyridine (DMAP) (10 mg, cat.) were added to. The mixture was stirred for 2 h at room temperature, then concentrated to dryness. The residue was purified by silica gel chromatography (EtOAc/Hexane/DCM=1:2:1) and afforded compound 56-2 (150 mg, 35% yield).

Step 3: (7-fluoro-1H-indol-3-yl)(4-(3-methyl-1,2,4-oxadiazol-5-yl)thiazol-2-yl)methanone (PTC17341-95, ARI-123)

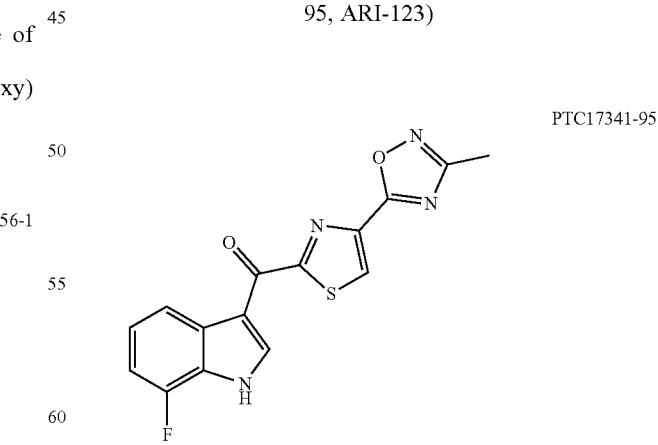

This compound was synthesized according to the protocol described in Example 71 from compound 56-2 (150 mg, 0.35 mmol) to give title compound PTC17341-95 (ARI-123) in the form of a yellow solid (85% yield). $^1$H-NMR (400 MHz, DMSO-d6): δ 13.01 (bs, 1H), 9.12~9.15 (d, J=8.0 Hz, 1H), 8.12~8.15 (d, J=8.0 Hz, 1H), 7.27~7.33 (m, 1H), 7.17~7.23 (m, 1H), 2.51 (s, 3H). LC-MS: m/z 327.2 [M−H]⁻.

Example 103: Preparation of methyl 2-(7-cyano-1H-indole-3-carbonyl)thiazole-4-carboxylate (ARI-124)

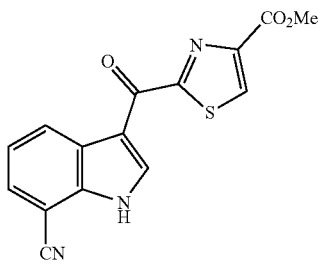 [SMILES: COC(=O)c1csc(C(=O)c2c[nH]c3c(C#N)cccc23)n1]

Prepared according to the method described in Example 118 except that 7-bromoindole-3-carboxylic acids was used.

Example 104: Preparation of 4-(1H-indole-3-carbonyl)pyrimidine-2-carbonitrile (ARI-125)

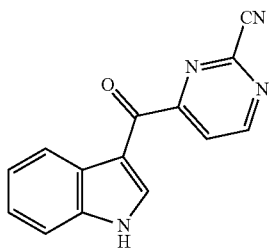 [SMILES: N#Cc1nccc(C(=O)c2c[nH]c3ccccc23)n1]

Prepared from 2,4-dibromopyrimidine as described in Example 82.

Example 105: Preparation of (5-fluoro-1H-indol-2-yl)(4-(3-methyl-1,2,4-oxadiazol-3-yl)thiazol-2-yl)methanone (ARI-126)

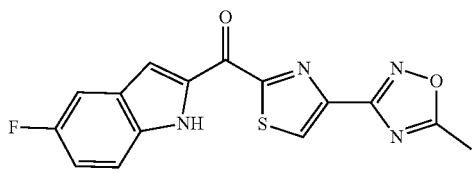 [SMILES: Cc1nc(-c2csc(C(=O)c3cc4cc(F)ccc4[nH]3)n2)no1]

Prepared from 2-(1H-indole-2-carbonyl)thiazole-4-carbonitrile according to the method described in Examples 21.

Example 106: Preparation of (1H-indol-3-yl)(5-(3-methyl-1,2,4-oxadiazol-5-yl)pyrazin-2-yl)methanone (PTC17341-54, ARI-127)

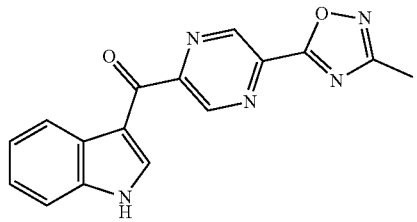 [SMILES: Cc1noc(-c2cnc(C(=O)c3c[nH]c4ccccc34)cn2)n1]

Figure 32:
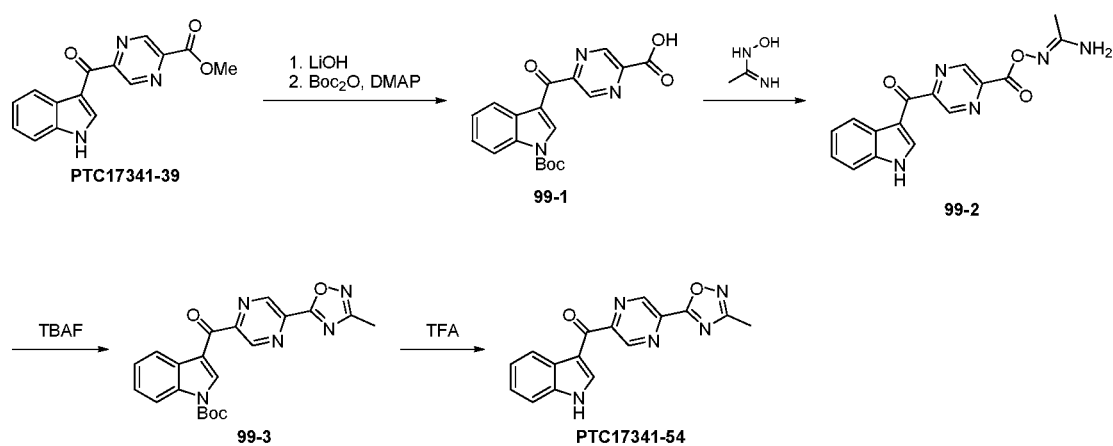
FIG. 32 shows a synthesis scheme for ARI-127 (PTC17341-54) according to Example 106.

ARI-127 was synthesized according to the scheme of FIG. 32 and by the following method:

Step 1: 5-(1-(tert-Butoxycarbonyl)-1H-indole-3-carbonyl)pyrazine-2-carboxylic acid (99-1)

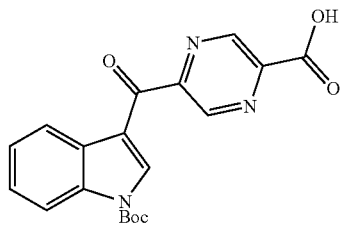

Lithium hydroxide monohydrate (380 mg, 9 mmol) was added to a solution of compound PTC17341-39 (840 mg, 3 mmol) in THF (10 mL) and H$_2$O (10 mL) at 0° C. The resulting mixture was stirred for 2 h at room temperature, then acidified with 1M HCl aqueous to pH of 3. The mixture was concentrated to dryness. The residue was azeotroped two times with THF (50 mL portions), then dissolved in DMF (10 mL). DMAP (730 mg, 6 mmol) and Boc$_2$O (1.3 g, 6 mmol) were added to. The resulting mixture was stirred overnight. The mixture was diluted with water (50 mL), acidified with 1M HCl aqueous to pH of 3, extracted with EtOAc (50 mL×3). The combined organic phases were washed with water (50 mL×2), and brine (50 mL×1), dried (Na$_2$SO$_4$), filtered and concentrated to dryness. The residue was triturated with EtOAc/hexane (1:5, 50 mL), filtered and dried to afford compound 99-1 (810 mg, 73% yield).

Step 2: tert-Butyl 3-(5-(((1-aminoethylideneaminooxy)carbonyl)pyrazine-2-carbonyl)-1H-indole-1-carboxylate (99-2)

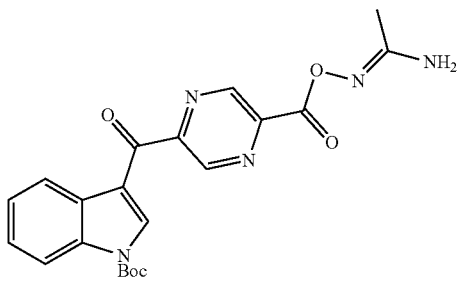

This compound was synthesized according to the protocol described in Example 102 step 1 from compound 99-1 (800 mg, 2.2 mmol) to give title compound 99-2 (1.10 g, ~100% yield).

Steps 3/4: (1H-Indol-3-yl)(5-(3-methyl-1,2,4-oxadiazol-5-yl)pyrazin-2-yl)methanone (PTC17341-54, ARI-127)

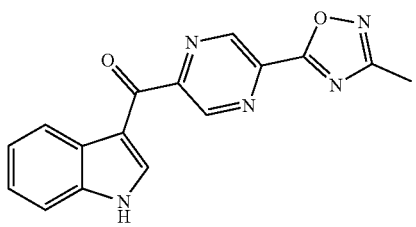

This compound was synthesized according to the protocol described in Example 102 step 2 and 3 from compound 99-2 (1.10 g, 2.2 mmol) to give title compound PTC17341-54 (ARI-127) in the form of a yellow solid (80 mg, 12% yield for two steps). $^1$H-NMR (400 MHz, DMSO-d6): δ 12.35 (bs, 1H), 8.73~8.72 (d, J=3.2 Hz, 1H), 8.37~8.40 (d, m, 1H), 7.56~7.60 (m, 1H), 7.29~7.33 (m, 2H), 2.53 (s, 3H). LC-MS: m/z 303.6 [M–H]$^-$.

Example 107: Preparation of 2-(5-chloro-2-methyl-1H-indole-3-carbonyl)thiazole-4-carboxylic acid (ARI-128)

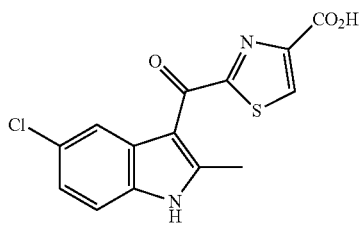 [SMILES: Cc1[nH]c2ccc(Cl)cc2c1C(=O)c1nc(C(=O)O)cs1]

Starting with 2-methyl-indole-3-carboxylic acid, prepared as described in Example 130.

Example 108: Preparation of (4-(5-amino-1,3,4-oxadiazol-2-yl)thiazol-2-yl)(5-fluoro-1H-indol-2-yl)methanone (ARI-129)

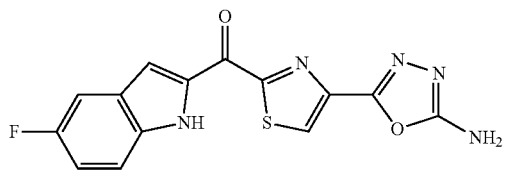 [SMILES: Nc1nnc(-c2csc(C(=O)c3cc4cc(F)ccc4[nH]3)n2)o1]

Prepared from 2-(1H-5-fluoro-indole-2-carbonyl)thiazole-4-carboxylic acid according to the method described in Example 131.

Example 109: Preparation of (4-(5-amino-1,3,4-oxadiazol-2-yl)thiazol-2-yl)(5-fluoro-1H-indol-2-yl)methanone (ARI-131)

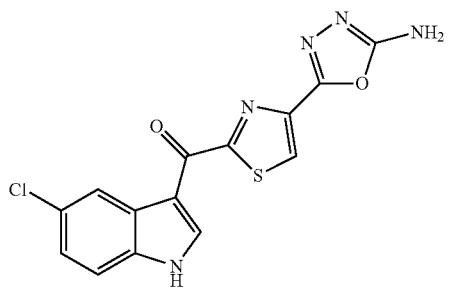 [SMILES: Nc1nnc(-c2csc(C(=O)c3c[nH]c4ccc(Cl)cc34)n2)o1]

Prepared from 2-(1H-5-chloro-indole-3-carbonyl)thiazole-4-carboxylic acid according to the method described in Example 131.

Example 110: Preparation of 2-(5-fluoro-2-methyl-1H-indole-3-carbonyl)thiazole-4-carboxylic acid (ARI-130)

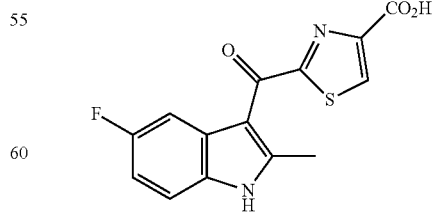

Prepared from 2-methyl-5-fluoroindole-3-carboxylic acid according to the method described in Example 130.

Example 111: Preparation of (5-fluoro-1H-indol-3-yl)(4-(3-methyl-1,2,4-oxadiazol-5-yl)thiazol-2-yl)methanone (ARI-132)

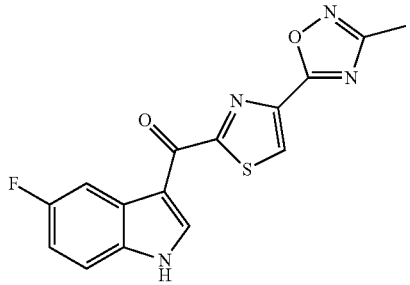 [SMILES: Cc1noc(-c2csc(C(=O)c3c[nH]c4ccc(F)cc34)n2)n1]

Prepared from 2-(1H-5-fluoro-indole-3-carbonyl)thiazole-4-carboxylic acid according to the method described in Example 22.

Example 112: Preparation of (4-(5-(aminomethyl)-1,2,4-oxadiazol-3-yl)thiazol-2-yl)(5-chloro-1H-indol-3-yl)methanone (ARI-133)

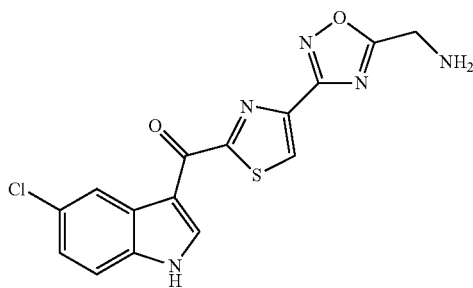 [SMILES: NCc1nc(-c2csc(C(=O)c3c[nH]c4ccc(Cl)cc34)n2)no1]

Starting from 2-(1H-indole-5-chloro-3-carbonyl)thiazole-4-hydroxyimidate (prepared as described in Example 21), this compound was prepared as described in Example 115.

Example 113: Preparation of (4-(5-amino-1,3,4-oxadiazol-2-yl)thiazol-2-yl)(5-chloro-2-methyl-1H-indol-3-yl)methanone (ARI-134)

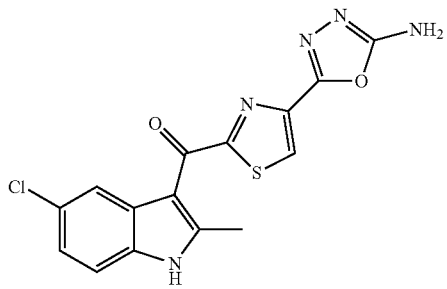 [SMILES: Cc1[nH]c2ccc(Cl)cc2c1C(=O)c1nc(-c2nnc(N)o2)cs1]

Prepared from 2-(1H-indole-2-methyl-5-chloro-3-carbonyl)thiazole-4-carboxylate according to the method described in Example 131.

Example 114. Preparation of (4-(5-(aminomethyl)-1,3,4-oxadiazol-2-yl)thiazol-2-yl)(1H-indol-3-yl)methanone (PTC17341-108, ARI-137)

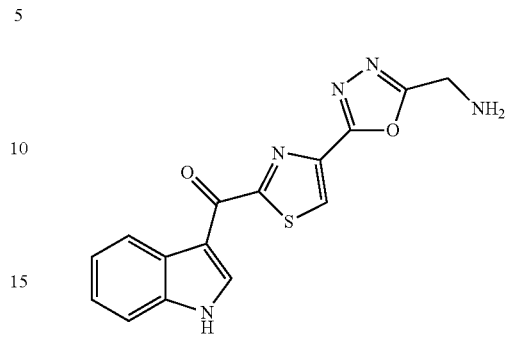

Figure 33:
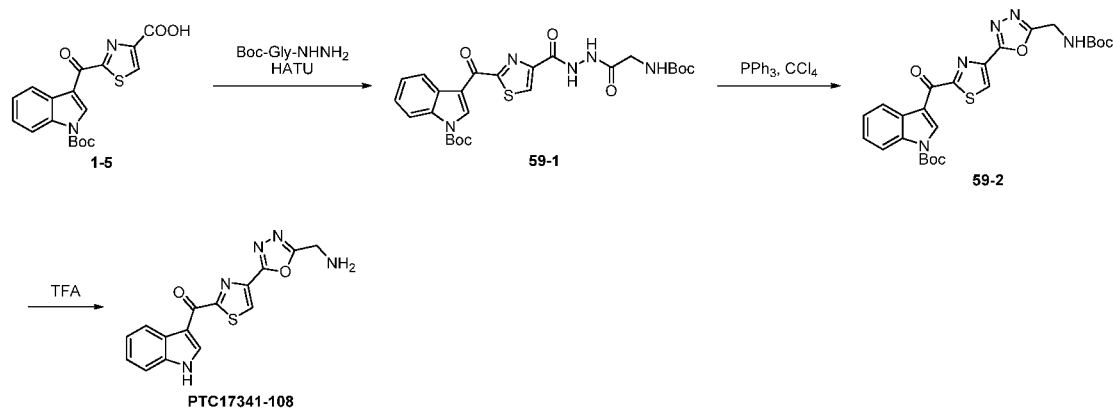
FIG. 33 shows a synthesis scheme for ARI-137 (PTC17341-108) according to Example 114.

ARI-137 was synthesized according to the scheme of FIG. 33 and by the following method:

Step 1: tert-Butyl 3-(4-(2-(2-(tert-butoxycarbonylamino)acetyl)hydrazine carbonyl)thiazole-2-carbonyl)-1H-indole-1-carboxylate (59-1)

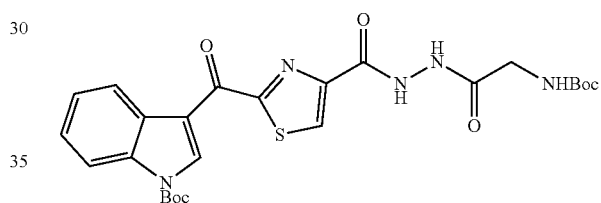

HATU (664 mg, 17. mmol) and DIPEA (520 mg, 4 mmol) were added to a solution of compound 1-5 (500 mg, 1.3 mmol) and Boc-glycine hydrazide (305 mg, 1.6 mmol) in DMF (10 mL) at room temperature. The mixture was stirred overnight, then quenched with H₂O (50 mL). The mixture was stirred for 0.5 h, then filtered to collect the solid. The solid was washed with water (10 mL×3) and EtOAc (10 mL×3), dried to afford 59-1 (700 mg, ~100% yield) as off-white solid.

Step 2: tert-Butyl 3-(4-(5-((tert-butoxycarbonylamino)methyl)-1,3,4-oxadiazol-2-yl)thiazole-2-carbonyl)-1H-indole-1-carboxylate (59-2)

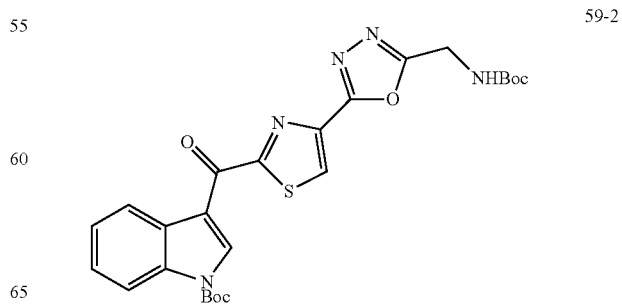

Triphenylphosphine (470 mg, 1.8 mmol) and TEA (209 mg, 2.1 mmol) were added to a solution of compound 59-1 (700 mg, 1.3 mmol) in ACN (20 mL) at room temperature. The mixture was stirred for 20 min, then was added CCl₄ (320 mg, 2.1 mmol). The mixture was heated to 50° C. and stirred for 5 h. The mixture was cooled to room temperature, then concentrated. The residue was purified by silica gel chromatography (EtOAc/Hexane/DCM=1:1:1) and afforded compound 59-2 (290 mg, 42% yield).

Step 3: (4-(5-(Aminomethyl)-1,3,4-oxadiazol-2-yl)thiazol-2-yl)(1H-indol-3-yl)methanone (PTC17341-108, ARI-137)

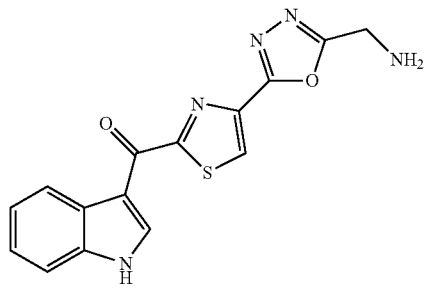 [SMILES: NCc1nnc(-c2csc(C(=O)c3c[nH]c4ccccc34)n2)o1]

PTC17341-108

This compound was synthesized according to the protocol described in Example 71 from compound 59-2 (290 mg, 0.55 mmol) to give title compound PTC17341-108 (ARI-137) in the form of a yellow solid (80% yield). ¹H-NMR (400 MHz, DMSO-d6): δ 12.42 (bs, 1H), 9.14 (s, 1H), 8.90 (s, 1H), 8.32~8.35 (m, 1H), 7.60~7.63 (m, 1H), 7.29~7.34 (m, 2H), 4.04 (s, 2H), 1.99 (s, 2H). LC-MS: m/z 326.4 [M+H]⁺.

Example 115: Preparation of (4-(5-(Aminomethyl)-1,2,4-oxadiazol-3-yl)thiazol-2-yl)(1H-indol-3-yl)methanone (PTC17341-107, ARI-138)

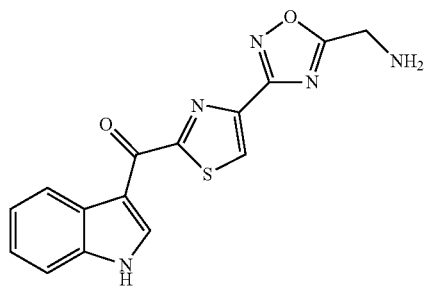 [SMILES: NCc1nc(-c2csc(C(=O)c3c[nH]c4ccccc34)n2)no1]

Figure 34:
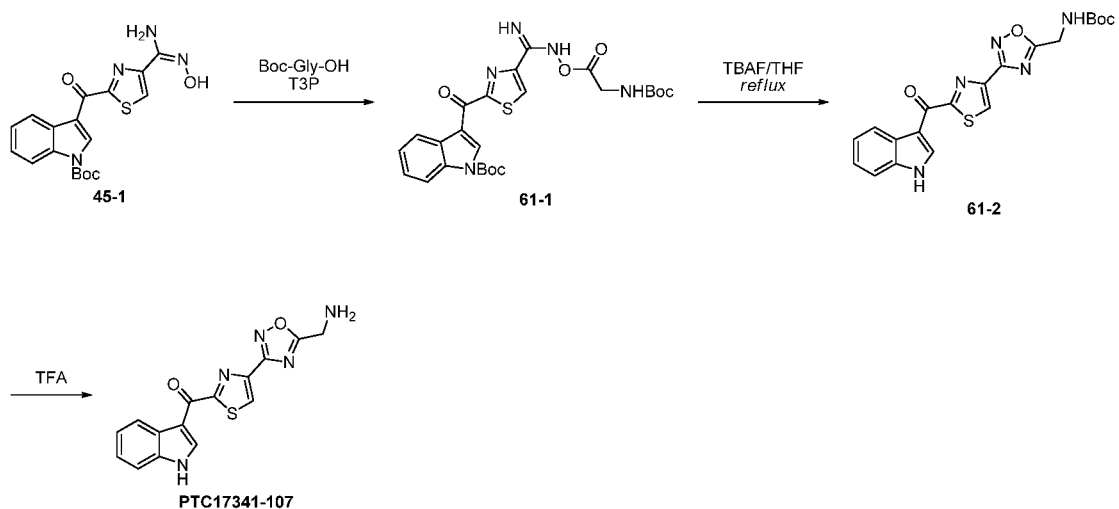
FIG. 34 shows a synthesis scheme for ARI-138 (PTC17341-107) according to Example 115.

ARI-138 was synthesized according to the scheme of FIG. 34 and by the following method:

Step 1: tert-Butyl 3-(4-(N-(2-(tert-butoxycarbonylamino)acetoxy)carbamimidoyl)thiazole-2-carbonyl)-1H-indole-1-carboxylate (61-1)

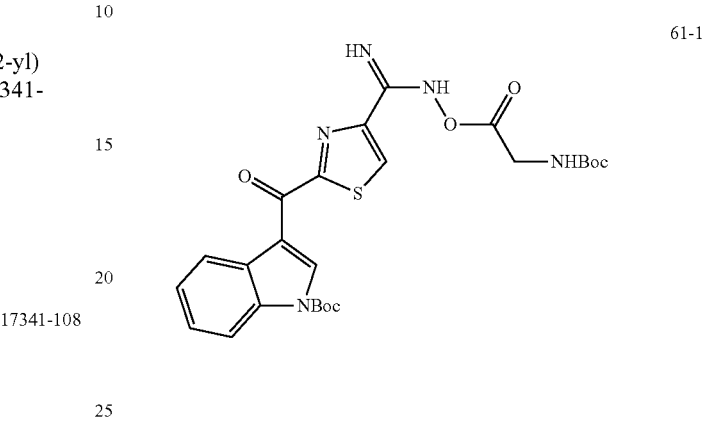

61-1

T3P (50% solution in EtOAc, 1.5 g, 5 mmol) and TEA (606 mg, 6 mmol) were added to a solution of compound 45-1 (770 mg, 2 mmol) and Boc-glycine (350 mg, 2 mmol) in EtOAc (150 mL) at room temperature. The mixture was heated under reflux for 8 h. The mixture was cooled to room temperature, washed with brine (100 mL×3), dried, concentrated to afford compound 61-1 (~1 g), which was used for next step without further purification.

Step 2: tert-Butyl (3-(2-(1H-indole-3-carbonyl)thiazol-4-yl)-1,2,4-oxadiazol-5-yl)methylcarbamate (61-2)

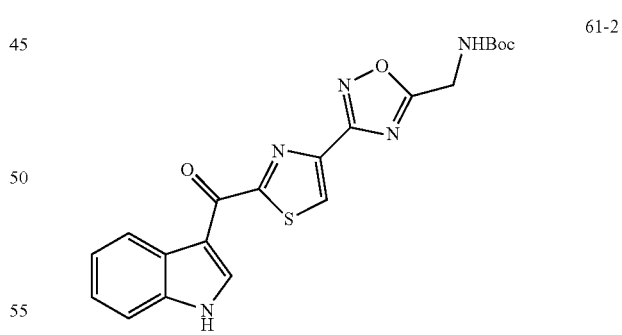

61-2

A solution of crude compound 61-1 (~1 g) and TBAF (1.05 g, 4 mmol) in THF (50 mL) was heated under reflux for 4 h. The mixture was cooled to room temperature, then concentrated to dryness. The residue was purified by silica gel chromatography (EtOAc/Hexane/DCM=1:2:1) and afforded compound 61-2 (220 mg, 26% yield from compound 45-1).

Step 3: (4-(5-(Aminomethyl)-1,2,4-oxadiazol-3-yl)thiazol-2-yl)(1H-indol-3-yl)methanone (PTC17341-107, ARI-138)

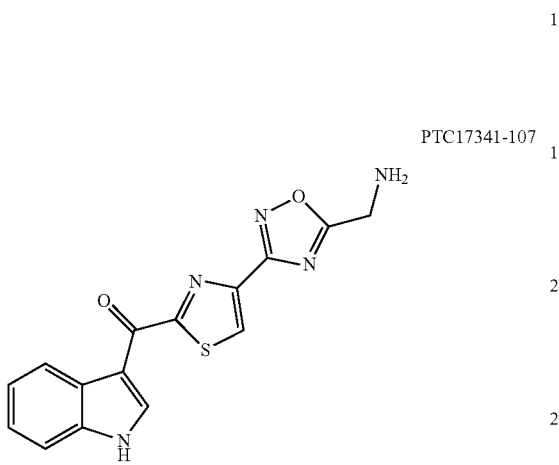

This compound was synthesized according to the protocol described in Example 71 from compound 61-2 (220 mg, 0.52 mmol) to give title compound PTC17341-107 (ARI-138) in the form of a yellow solid (70% yield). $^1$H-NMR (400 MHz, DMSO-d6): δ 12.39 (bs, 1H), 9.15 (s, 1H), 8.80 (s, 1H), 8.32~8.35 (m, 1H), 7.60~7.62 (d, J=5.6 Hz, 1H), 7.30~7.32 (m, 2H), 4.08 (s, 2H), 2.23 (s, 2H). LC-MS: m/z 326.4 [M+H]$^+$.

Example 116: Preparation of 2-(2-(1H-indole-3-carbonyl)thiazol-4-yl)-5-aminooxazole-4-carbonitrile (PTC17341-109, ARI-139)

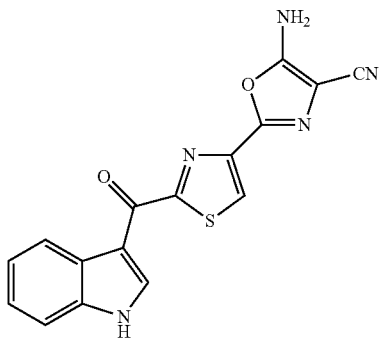 [SMILES: N#Cc1nc(-c2csc(C(=O)c3c[nH]c4ccccc34)n2)oc1N]

Figure 35:
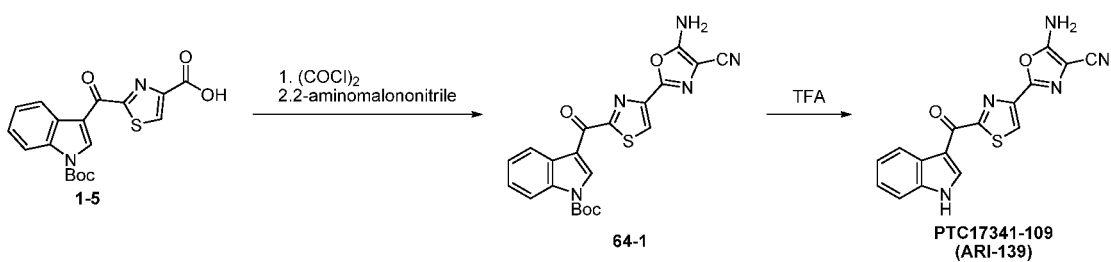
FIG. 35 shows a synthesis scheme for ARI-139 (PTC17341-109) according to Example 116.

ARI-139 was synthesized according to the scheme of FIG. 35 and by the following method:

Step 1: tert-butyl 3-(4-(5-amino-4-cyanooxazol-2-yl)thiazole-2-carbonyl)-1H-indole-1-carboxylate (64-1)

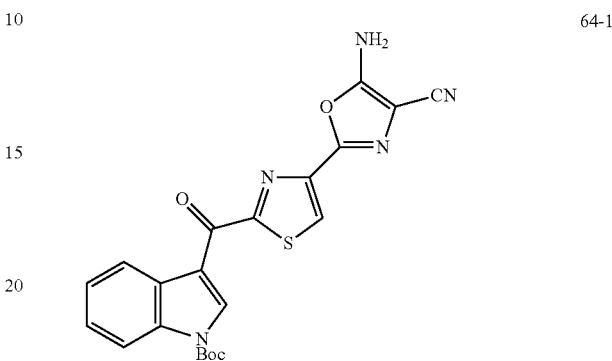

Oxalyl chloride (890 mg, 5.3 mmol) was added to a suspension of compound 1-5 (1.3 g, 3.5 mmol) in DCM (20 mL) at 0° C. The mixture was allowed to warm to room temperature and stirred 5 h. The mixture was concentrated to dryness. The residue was dissolved in N-methyl-2-pyrrolidone (NMP) (5 mL) and 2-aminomalononitrile 4-methylbenzenesulfonate (1.15 g, 4.5 mmol) was added to at room temperature. The resulting mixture was stirred for 1 h. The mixture was diluted with H$_2$O (20 mL), extracted with EtOAc/THF (1:1, 30 mL×3). The combined organic phases were washed with brine (50 mL×2), dried, concentrated to dryness. The residue was purified by silica gel chromatography (EtOAc/Hexane/DCM=1:1:1) and afforded compound 64-1 (440 mg, 29% yield).

Step 2: 2-(2-(1H-indole-3-carbonyl)thiazol-4-yl)-5-aminooxazole-4-carbonitrile (PTC17341-109, ARI-139)

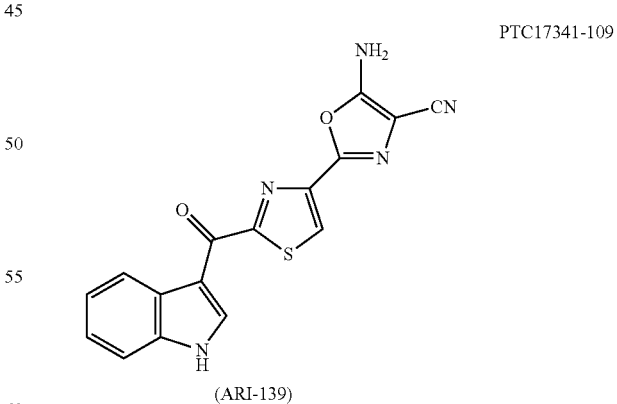

Compound 64-1 (440 mg, 1 mmol) was dissolved in THF (5 mL) and MeOH (5 mL), KHCO$_3$ (1.0 g) and Na$_2$CO$_3$ (1.0 g) were added. The mixture was stirred overnight at room temperature. The mixture was diluted with H$_2$O (20 mL), extracted with EtOAc/THF (1:1, 30 mL×3). The combined organic phases were washed with brine (50 mL×2), dried, concentrated to dryness. The residue was triturated with EtOAc (20 mL) and MeOH (20 mL) to give title compound PTC17341-109 (ARI-139) in the form of a yellow solid (190 mg, 57% yield). ¹H-NMR (400 MHz, DMSO-d6): δ12.38 (bs, 1H), 9.08~9.10 (d, J=2.8 Hz, 1H), 8.48 (s, 1H), 8.30~9.34 (m, 1H), 8.17 (s, 1H), 7.58~7.62 (d, J=6.4 Hz, 1H), 7.29~7.33 (m, 2H). LC-MS: m/z 326.4 [M+H]⁺.

Example 117: Preparation of 1-(2-(7-fluoro-1H-indole-3-carbonyl)thiazol-4-yl)propan-1-one (ARI-140)

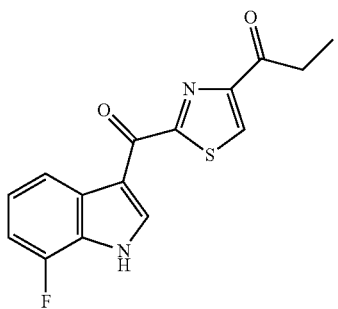 [SMILES: CCC(=O)c1csc(C(=O)c2c[nH]c3c(F)cccc23)n1]

Starting with 7-fluoroindole and using the procedure described in Example 84—Step 6, the title compound was prepared.

Example 118: Preparation of methyl 2-(5-cyano-1H-indole-3-carbonyl)thiazole-4-carboxylate (PTC17341-60) (ARI-141)

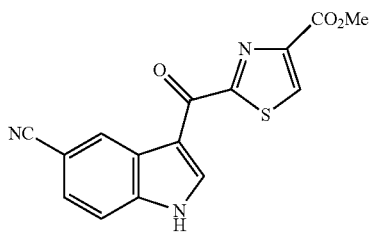 [SMILES: COC(=O)c1csc(C(=O)c2c[nH]c3ccc(C#N)cc23)n1]

Figure 36:
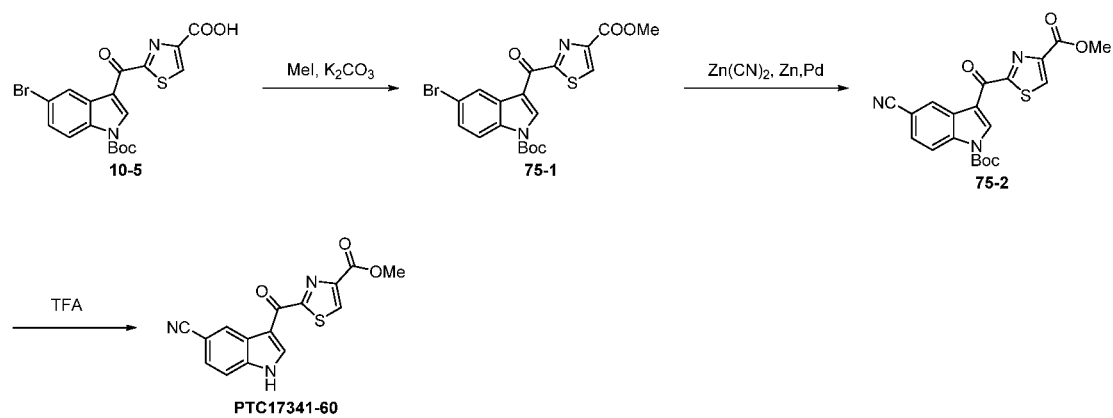
FIG. 36 shows a synthesis scheme for ARI-141 (PTC17341-60) according to Example 118.

ARI-141 was synthesized according to the scheme of FIG. 36 and by the following method:

Step 1: Methyl 2-(5-bromo-1-(tert-butoxycarbonyl)-1H-indole-3-carbonyl)thiazole-4-carboxylate (75-1)

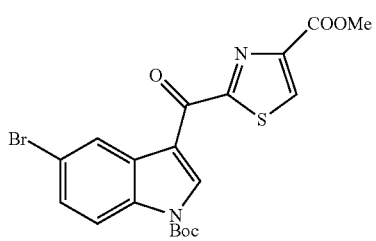

This compound was synthesized according to the protocol described in Example 65 from compound 10-5 (1.0 g, 2.2 mmol) to give title compound 75-1 in the form of an off-white solid (0.93 g, 91% yield).

Step 2: Methyl 2-(1-(tert-butoxycarbonyl)-5-cyano-1H-indole-3-carbonyl)thiazole-4-carboxylate (75-2)

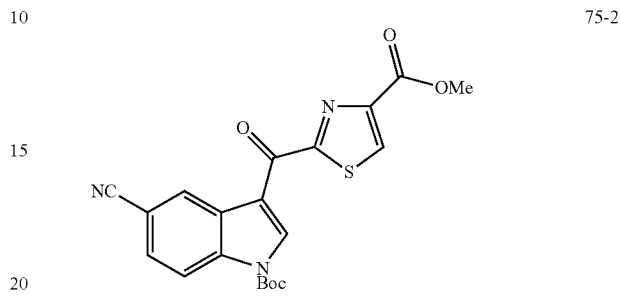

A mixture of compound 75-1 (800 mg, 1.7 mmol), Zn(CN)₂ (600 mg, 5.2 mmol), activated Zn (28 mg, 0.4 mmol) and fresh prepared Pd(PPh₃)₄ (0.5 g) in dry DMF (30 mL) was stirred at 120° C. under a nitrogen atmosphere overnight. The reaction mixture was cooled to room temperature and quenched with H₂O (50 mL), then extracted with EtOAc/THF (1:1, 50 mL×3). The combined organic phases were washed with brine (50 mL×3), dried over anhydrous Na₂SO₄, filtered and concentrated in vacuo to afford crude. The crude was triturated with EtOAc (20 mL), filtered, dried and afford 75-2 (250 mg, 35% yield).

Step 3: Methyl 2-(5-cyano-1H-indole-3-carbonyl)thiazole-4-carboxylate (PTC17341-60, ARI-141)

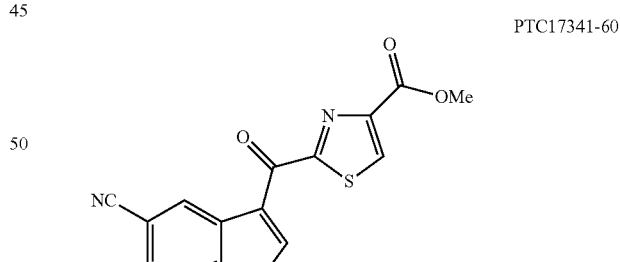

This compound was synthesized according to the protocol described in Example 71 from compound 75-2 (250 mg, 0.6 mmol) to give title compound in the form of a yellow solid (65% yield). ¹H-NMR (400 MHz, DMSO-d6): δ 12.78 (bs, 1H), 9.22 (s, 1H), 8.95 (s, 1H), 8.66 (s, 1H), 7.78~7.82 (d, J=8.4 Hz, 1H), 7.68~7.72 (d, J=8.4 Hz, 1H), 3.93 (s, 3H). LC-MS: m/z 310.1 [M−H]⁻.

Example 119: Preparation of (4-(5-amino-1,3,4-oxadiazol-2-yl)thiazol-2-yl)(5-fluoro-1H-indol-3-yl)methanone (ARI-148)

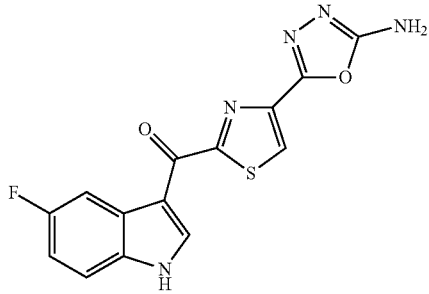 [SMILES: Nc1nnc(-c2csc(C(=O)c3c[nH]c4ccc(F)cc34)n2)o1]

Starting with 5-fluoroindole and using the procedure described in Example 131 the title compound was prepared.

Example 120: Preparation of 1-(2-(4-fluoro-1H-indole-3-carbonyl)thiazol-4-yl)propan-1-one (ARI-142)

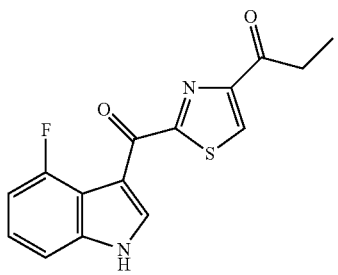 [SMILES: CCC(=O)c1csc(C(=O)c2c[nH]c3cccc(F)c23)n1]

Starting with 4-fluoroindole and using the procedure described in Example 84—Step 6, the title compound was prepared.

Example 121: Preparation of 5-amino-2-(2-(7-fluoro-1H-indole-3-carbonyl)thiazol-4-yl)oxazole-4-carbonitrile (ARI-144)

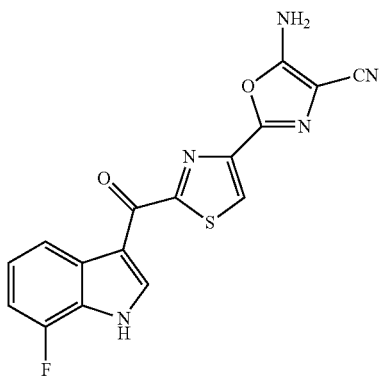 [SMILES: N#Cc1nc(-c2csc(C(=O)c3c[nH]c4c(F)cccc34)n2)oc1N]

Starting with 2-(1H-indole-7-fluoro-3-carbonyl)thiazole-4-carboxylic acid and using the method described in Example 116 the title compound was prepared.

Example 122: Preparation of (4-(5-(aminomethyl)-1,3,4-oxadiazol-2-yl)thiazol-2-yl)(7-fluoro-1H-indol-3-yl)methanone (ARI-145)

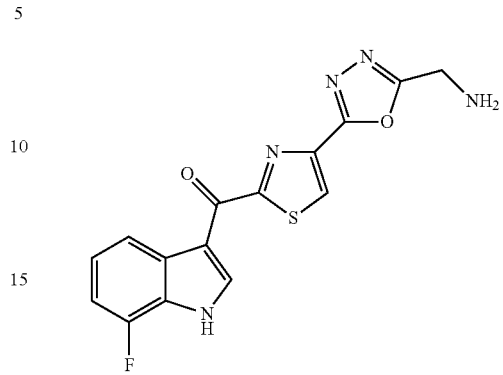

Starting with 2-(1H-indole-7-fluoro-3-carbonyl)thiazole-4-carboxylate and using the procedure outlined in Example 114, the title compound was prepared.

Example 123: Preparation of (4-(5-(aminomethyl)-1,2,4-oxadiazol-3-yl)thiazol-2-yl)(7-fluoro-1H-indol-3-yl)methanone (ARI-146)

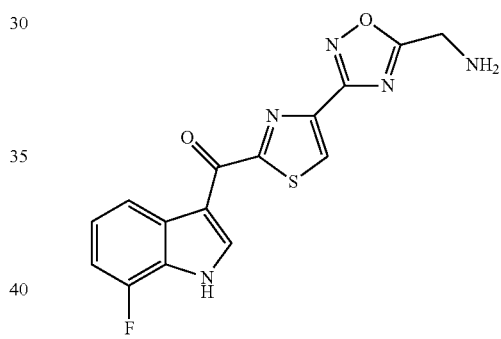

Starting with 2-(1H-indole-7-fluoro-3-carbonyl)thiazole-4-hydroxyimidate and using the procedure described in Example 115 the title compound was prepared.

Example 124: Preparation of 5-amino-2-(2-(5-fluoro-1H-indole-3-carbonyl)thiazol-4-yl)oxazole-4-carbonitrile (ARI-147)

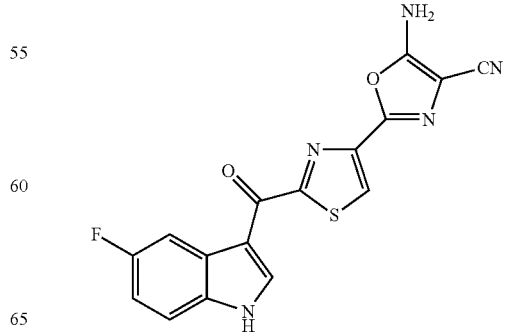

Starting with 2-(1H-indole-5-fluoro-3-carbonyl)thiazole-4-carboxylic acid and the procedure described in Example 116 the title compound was prepared.

Example 125: Preparation of 1-(2-(5,6-difluoro-1H-indole-3-carbonyl)thiazol-4-yl)propan-1-one (ARI-149)

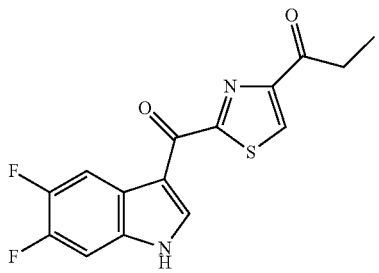

ARI-149

Figure 37:
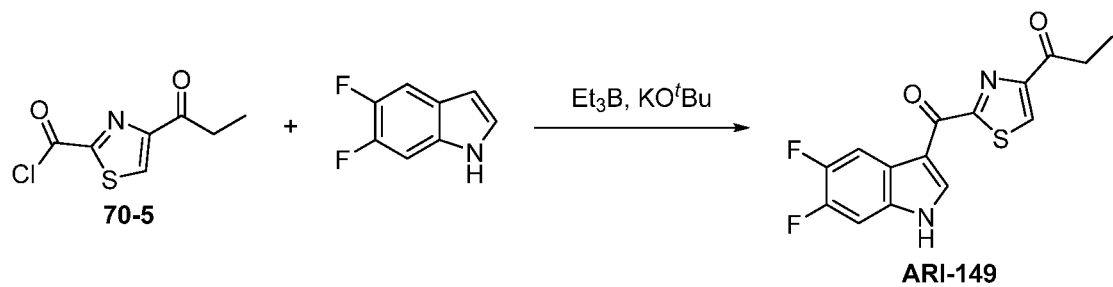
FIG. 37 shows a synthesis scheme for ARI-149 according to Example 125.

ARI-149 was synthesized according to the scheme of FIG. 37 and by the following method. Potassium tert-butoxide (1.76 g, 16 mmol) was added to a solution of 6,7-difluoroindole (2.0 g, 13 mmol) in THF (100 mL) at 0° C. under $N_2$. The mixture was stirred for 1 h at this temperature, and then a solution of compound 70-5 (2.6 g, 13 mmol) in THF (20 mL) was added to it at 0° C. The reaction mixture was allowed to warm to room temperature and stirred overnight. The mixture was quenched with saturated $NH_4Cl$ aqueous (100 mL), stirred for 20 min, and filtered. The solid was collected, washed with water (30 mL×3), EtOAc (30 mL×3) and MeOH (30 mL×3), dried to afford ARI-149 (459 mg, 11% yield) as yellow solid. $^1$H-NMR (400 MHz, DMSO-d6): δ 12.43 (bs, 1H), 9.19 (s, 1H), 8.87 (s, 1H), 8.13~8.19 (m, 1H), 7.64~7.70 (m, 1H), 3.21~3.28 (q, J=7.2 Hz, 2H), 1.13~1.18 (t, J=7.2 Hz, 3H). LC-MS: m/z 319.4 [M−H]−.

Example 126: Preparation of 1-(2-(1H-indole-3-carbonyl)thiazol-4-yl)-2-methylpropan-1-one (ARI-048)

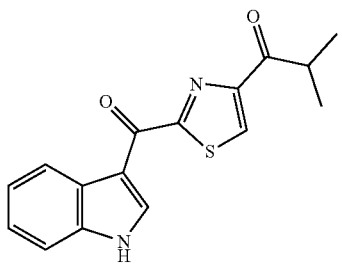 [SMILES: CC(C)C(=O)c1csc(C(=O)c2c[nH]c3ccccc23)n1]

Starting with 2-(1H-indole-3-carbonyl)thiazole-4-carboxylic acid and isopropylmagnesium bromide instead of methylmagnesium bromide using the procedure described in Example 75 the title compound was prepared.

Example 127: Preparation of (1H-indol-3-yl)(4-(1-(methoxyimino) propyl)thiazol-2-yl)methanone (PTC17341-21, ARI-054)

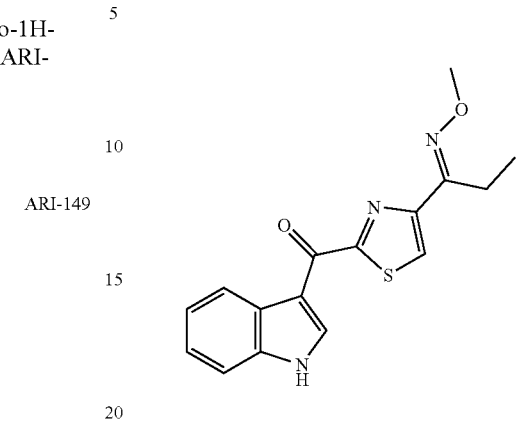

Figure 38:
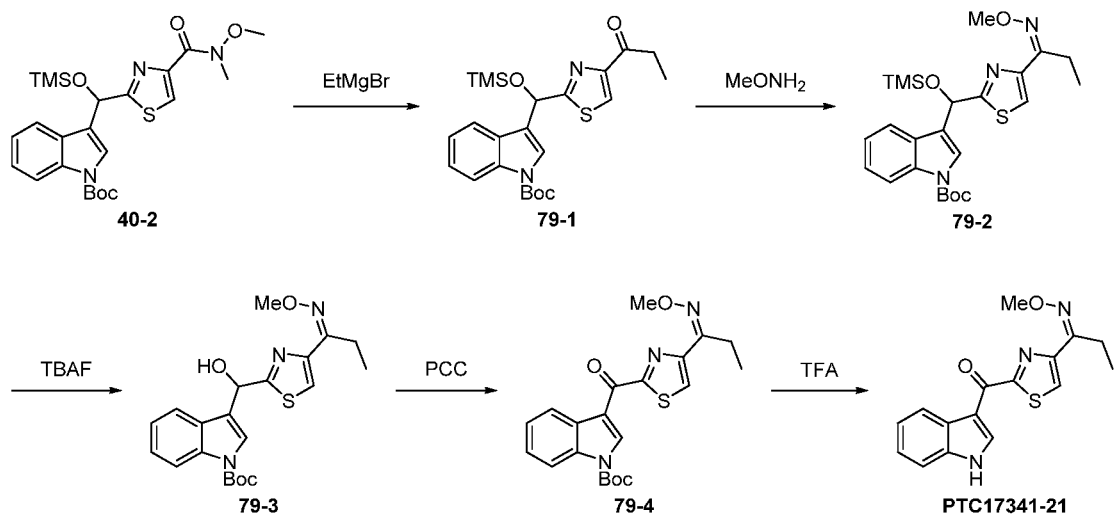
FIG. 38 shows a synthesis scheme for ARI-054 (PTC17341-21) according to Example 127.

ARI-054 was synthesized according to the scheme of FIG. 38 and by the following method:

Step 1: tert-Butyl 3-((4-propionylthiazol-2-yl)(trimethylsilyloxy)methyl)-1H-indole-1-carboxylate (79-1)

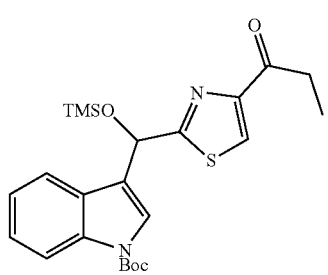

79-1

EtMgBr (2M in $Et_2O$, 40 mL, 80 mmol) was added portionwise to a solution of compound 40-2 (13.0 g, 26.6 mmol) in THF (200 mL) at 0° C. over 30 min. The resulting mixture was stirred for 0.5 h, then quenched with saturated aqueous $NH_4Cl$ (500 mL), extracted with EtOAc (250 mL×3). The combined organic phases were washed with brine (500 mL×2), dried, concentrated to afford 79-1 (12.8 g, ~100% yield) as an oil, which was used for next step without further purification.

Step 2: tert-Butyl 3-((4-(1-(methoxyimino)propyl)thiazol-2-yl)(trimethylsilyloxy)methyl)-1H-indole-1-carboxylate (79-2)

NaOAc (722 mg, 8.8 mmol) and methoxylamine hydrochloride (355 mg, 4.2 mmol) were added to a solution of compound 79-1 (1.0 g, 2.2 mmol) in EtOH (5 mL) and $H_2O$ (15 mL) at room temperature. The mixture was heated to 70° C. and stirred for 2 h. After cooled to room temperature, the mixture was concentrated in vacuo. The residue was purified by silica gel column chromatography (hexane/EtOAc=5:1) to give compound 79-2 (340 mg, 32% yield).

Step 3: tert-Butyl 3-(hydroxy(4-(1-(methoxyimino)propyl)thiazol-2-yl)methyl)-1H-indole-1-carboxylate (79-3)

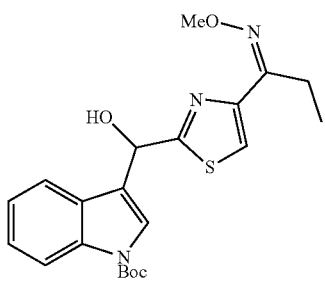

79-3

Compound 79-2 (340 mg, 0.7 mmol) was dissolved in THF (20 mL), TBAF (200 mg, 0.77 mmol) was added. The mixture was stirred for 2 h at room temperature, then quenched with water (50 mL), extracted with EtOAc (50 mL×3). The combined organic phases were washed with brine (100 mL×2), dried, concentrated to dryness. The residue was purified by silica gel chromatography (EtOAc/Hexan=1:3) and afforded compound 79-3 (210 mg, 72% yield).

Step 4: tert-Butyl 3-(4-(1-(methoxyimino)propyl)thiazole-2-carbonyl)-1H-indole-1-carboxylate (79-4)

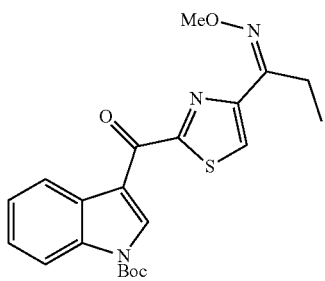

79-4

This compound was synthesized according to the protocol described in Example 75 from compound 79-3 (470 mg, 1.1 mmol) to give title compound 79-4 in the form of a yellow solid (268 mg, 57% yield).

Step 5: 1H-Indol-3-yl)(4-(1-(methoxyimino)propyl)thiazol-2-yl)methanone (PTC17341-21, ARI-054)

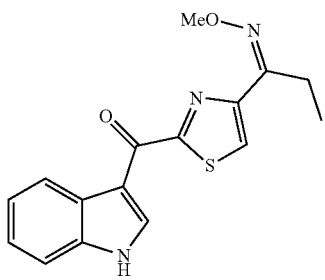

PTC17341-21

This compound was synthesized according to the protocol described in Example 71 from compound 79-4 (268 mg, 0.65 mmol) to give title compound PTC17341-21 (ARI-054) in the form of a yellow solid (95 mg, 47% yield). $^1$H-NMR (400 MHz, DMSO-d6): δ 12.32 (bs, 1H), 9.07 (s, 1H), 8.31~8.34 (m, 2H), 7.56~7.59 (m, 1H), 7.27~7.31 (m, 1H), 3.97 (s, 3H), 2.86~2.94 (q, J=7.6 Hz, 2H), 1.14~1.25 (m, 3H). LC-MS: m/z 314.3 [M+H]$^+$.

Example 128: Preparation of 1-(2-(6-fluoro-1H-indole-3-carbonyl)thiazol-4-yl)propan-1-one (ARI-143)

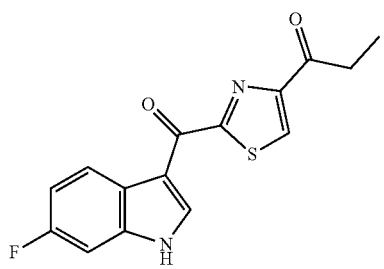 [SMILES: CCC(=O)c1csc(C(=O)c2c[nH]c3cc(F)ccc23)n1]

Starting with 6-fluoroindole and using the method described in Example 84—Step 6, the title compound was prepared.

Example 129: Preparation of 1-(2-(5,7-difluoro-1H-indole-3-carbonyl)thiazol-4-yl)propan-1-one (ARI-150)

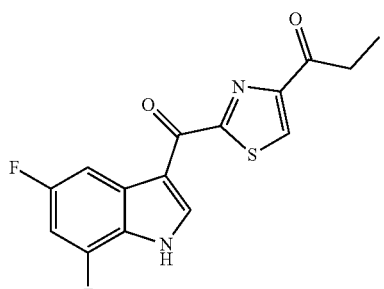

ARI-150

Figure 39:
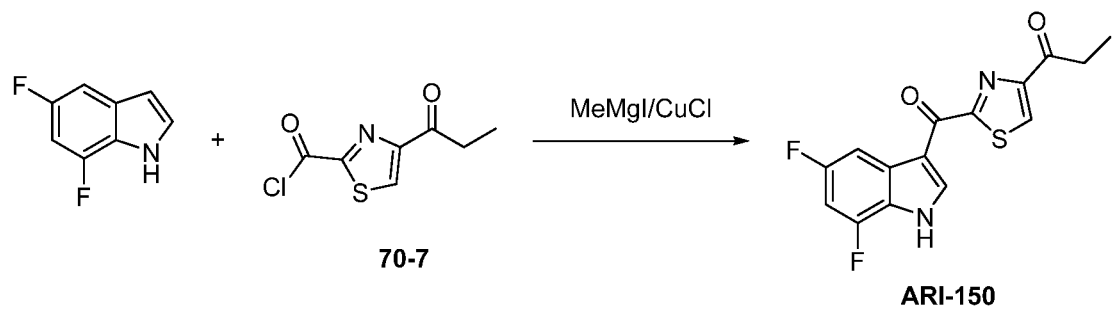
FIG. 39 shows a synthesis scheme for ARI-150 according to Example 129.

ARI-150 was synthesized according to the scheme of FIG. 39 and the protocol described in Example 84 from compound 70-7 (2.05 g, 10 mmol) and 5,7-difluoroindole to give title compound ARI-150 in the form of a yellow solid (1.51 g, 48% yield). $^1$H-NMR (400 MHz, DMSO-d6): δ 13.11 (bs, 1H), 9.19 (s, 1H), 8.88 (s, 1H), 7.83~7.87 (m, 1H), 7.24~7.31 (m, 1H), 3.23~3.28 (q, J=7.2 Hz, 2H), 1.13~1.18 (t, J=7.2 Hz, 3H). LC-MS: m/z 318.9 [M−H]$^-$

Example 130: Preparation of 2-(1-(tert-butoxycarbonyl)-1H-indole-3-carbonyl)thiazole-4-carboxylic acid (1-5)

Figure 40:
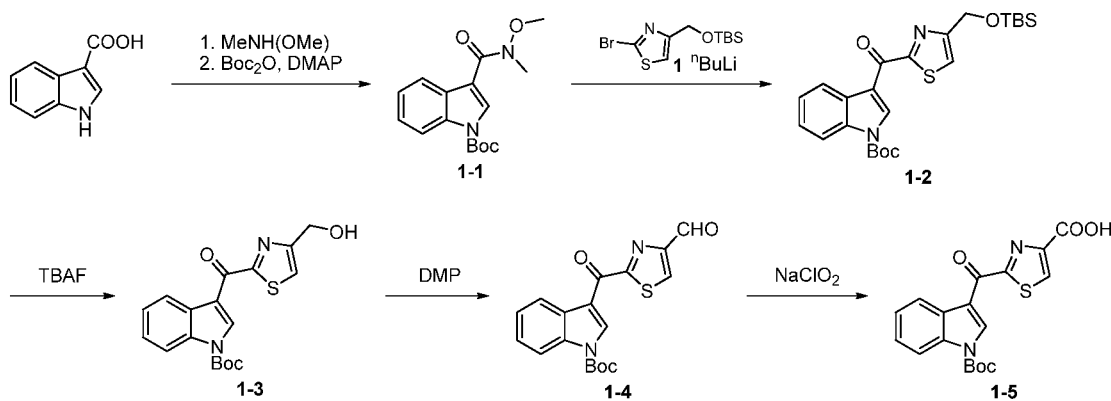
FIG. 40 shows a synthesis scheme for 2-(1-(tert-butoxycarbonyl)-1H-indole-3-carbonyl) thiazole-4-carboxylic acid according to Example 130.

This compound was synthesized according to the scheme of FIG. 40 and by the following method:

Step 1: tert-Butyl 3-(methoxy(methyl)carbamoyl)-1H-indole-1-carboxylate (1-1)

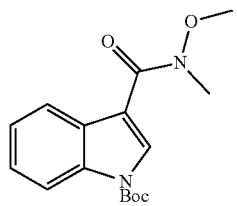

1-1

Oxalyl chloride (473.3 g, 3.73 mol) was added dropwise to a suspension of indol-3-carboxylic acid (400.0 g, 2.48 mol) in DCM (4 L) at 0° C. over 1 h. The mixture was allowed to warm to room temperature and stirred overnight. The mixture was concentrated to dryness to afford 1H-indole-3-carbonyl chloride (446.0 g).

The above 1H-indole-3-carbonyl chloride (446.0 g) was added portion-wise to a suspension of N,O-dimethylhydroxylamine hydrochloride (266.0 g, 2.73 mol) and TEA (551.1 g, 5.46 mol) in DCM (5 L) at room temperature over 1 h. The mixture was stirred overnight, then quenched with water (2 L). The organic phase was collected and washed with water (2 L×2), saturated aqueous NaHCO$_3$ (2 L×2), and brine (2 L×1), dried (Na$_2$SO$_4$), filtered and concentrated to dryness. The residue and DMAP (15.1 g, 0.124 mol) was dissolved in DMF (1 L) and DCM (4 L), cooled to 0° C. Boc$_2$O (540.64 g, 2.48) and DMAP (15.1 g, 0.124 mol) were added dropwise to over 1 h. The resulting mixture was allowed to warm to room temperature and stirred overnight. The mixture was quenched with water (2 L). The organic phase was separated and washed with water (2 L×2), saturated aqueous NaHCO$_3$ (2 L×2), and brine (2 L×1), dried (Na$_2$SO$_4$), filtered and concentrated to dryness. The residue was triturated with EtOAc/hexane (1:5, 1 L), filtered and dried to afford compound 1-1 (557.9 g, 75% yield) as off-white solid. $^1$H-NMR (400 MHz, DMSO-d6): δ 9.40 (s, 1H), 8.72 (s, 1H), 8.36~8.38 (m 1H), 8.15~8.18 (d, J=8.0 Hz, 1H), 7.40~7.50 (m, 2H), 3.80 (s, 3H), 3.40 (s, 3H), 1.69 (s, 9H).

Step 2: tert-Butyl 3-(4-((tert-butyldimethylsilyloxy)methyl)thiazole-2-carbonyl)-1H-indole-1-carboxylate (1-2)

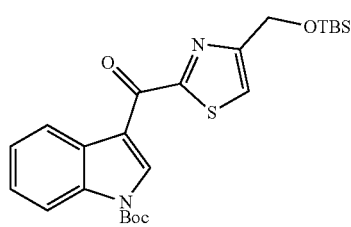

1-2

A solution of 2-bromo-4-((tert-butyldimethylsilyloxy)methyl)thiazole (135.0 g, 0.44 mol) in THF (1.5 L) was cooled to −78° C., and n-BuLi (1.6 M solution in hexane, 385 mL, 0.62 mol) was added dropwise at −78° C. over 1 h. The mixture was stirred for 0.5 h at this temperature, then a solution of compound 1-1 (120.0 g, 0.4 mol) in THF (500 mL) was added dropwise over 1 h. The mixture was stirred at −78° for 1 h then allowed to warm to 0° C. and quenched with aqueous 10% NH$_4$Cl (1 L). The organic phase was collected and washed with water (1 L×2), saturated aqueous NaHCO$_3$ (1 L×2), and brine (1 L×1), dried (Na$_2$SO$_4$), filtered and concentrated to dryness. The residue was triturated with EtOAc/hexane (1:5, 500 mL), filtered and dried to afford compound 1-2 (132.0 g, 70% yield) as off-white solid.

Step 3: tert-Butyl 3-(4-(hydroxymethyl)thiazole-2-carbonyl)-1H-indole-1-carboxylate (1-3)

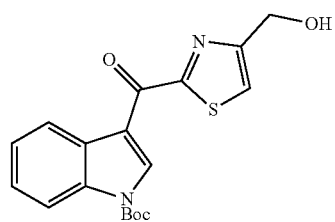

1-3

A solution of compound 1-2 (91.0 g, 0.19 mol) in THF (500 mL) and pyridine (50 mL) was cooled to 0° C., and HF-pyridine (30%, 50 mL) was added dropwise over 10 min. The mixture was stirred for 0.5 h at this temperature, then allowed to warm to room temperature and stirred overnight. The mixture was quenched with aqueous 10% NH$_4$Cl (1 L) and EtOAc (500 mL). The organic phase was collected and washed with water (500 mL×2), saturated aqueous NaHCO$_3$ (500 mL×2), and brine (500 mL×1), dried (Na$_2$SO$_4$), filtered and concentrated to dryness. The residue was triturated with EtOAc/hexane (1:5, 100 mL), filtered and dried to afford compound 1-3 (49.6 g, 73% yield) as off-white solid.

Step 4: tert-Butyl 3-(4-formylthiazole-2-carbonyl)-1H-indole-1-carboxylate (1-4)

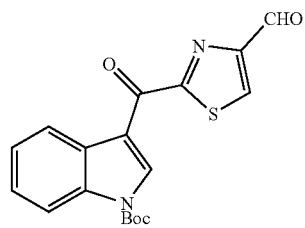

1-4

Dess-Martin periodinane (DMP, 26.1 g, 61 mmol) was added to a solution of compound 1-3 (20.0 g, 56 mmol) in DCM (350 mL) at 0° C. The mixture was stirred for 0.5 h at this temperature, then allowed to warm to room temperature and stirred overnight. The mixture was diluted with aqueous H$_2$O (500 mL) and DCM (500 mL), then filtered. The cake was washed with DCM (200 mL×3). The filtrate and washing were separated and the organic phase was collected, washed with aqueous 5% KHSO$_4$ (500 mL×3), saturated aqueous NaHCO$_3$ (500 mL×3), and brine (500 mL×1), dried (Na$_2$SO$_4$), filtered and concentrated to dryness. The residue was triturated with EtOAc/hexane (1:2, 50 mL), filtered and dried to afford compound 1-4 (20.2 g, 93% yield) as off-white solid. $^1$H-NMR (400 MHz, DMSO-d6): δ 10.06 (s, 1H), 9.52 (s, 1H), 9.12 (s, 1H), 8.35~8.40 (d, J=7.6 Hz, 1H), 8.14~8.17 (d, J=8.0 Hz, 1H), 7.40~7.50 (m, 2H), 1.71 (s, 9H). LC-MS: m/z: 357.4 [M+H]$^+$ Example 131: Preparation of (4-(5-amino-1,3,4-oxadiazol-2-yl)thiazol-2-yl)(5,6-difluoro-1H-indol-3-yl)methanone (ARI-154)

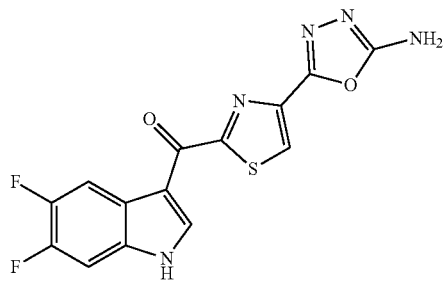 [SMILES: Nc1nnc(-c2csc(C(=O)c3c[nH]c4cc(F)c(F)cc34)n2)o1]

Figure 41:
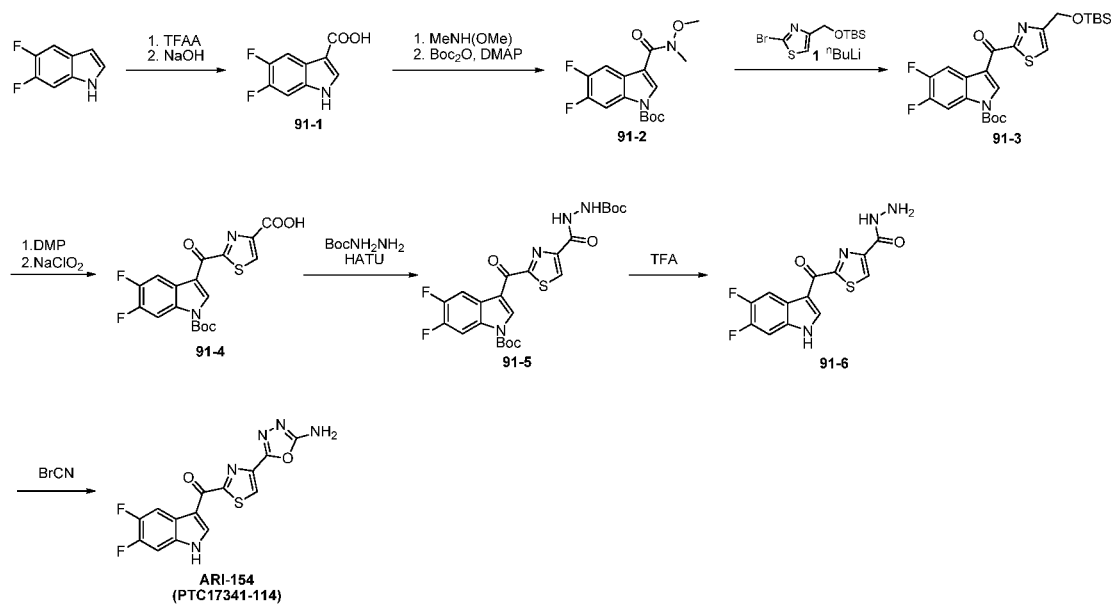
FIG. 41 shows a synthesis scheme for ARI-154 according to Example 131.

ARI-154 was synthesized according to the scheme of FIG. 41 and by the following method:

Step 1: 5,6-Difluoro-1H-indole-3-carboxylic acid (91-1)

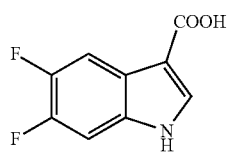

Trifluoroacetic anhydride (38 mL, 56.0 g, 0.27 mol) was added dropwise to a solution of 5,6-difluoro-1H-indole (0.22 mol) in DMF (300 mL) over 0.5 h at 0° C. The reaction mixture was allowed to warm to room temperature and stirred overnight. The mixture was quenched with water (1 L), many solid began to form, the mixture was stirred for 0.5 h, then filtered. The solid was collected, washed with water (200 mL×3), then added to aqueous sodium hydroxide (20%, 150 mL, 0.75 mol) and heated under reflux for 8 h. The reaction mixture was cooled and acidified with aqueous 3N HCl to pH of 3. Many solid began to form. The solid was collected by filter, washed with water (200 mL×3), dried to give title compound 91-1 (15.53 g, 59% yield).

Steps 2/3/4: 2-(1-(tert-butoxycarbonyl)-5,6-difluoro-1H-indole-3-carbonyl)thiazole-4-carboxylic acid (91-4)

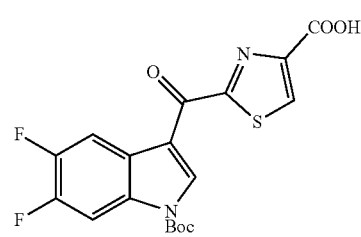

This compound was synthesized according to the protocol described in Example 130 from compound 91-1 (8.80 g, 44 mmol) to give title compound 91-4 in 36% yield.

Step 5: tert-Butyl 3-(4-(2-(tert-butoxycarbonyl)hydrazinecarbonyl)thiazole-2-carbonyl)-5,6-difluoro-1H-indole-1-carboxylate (91-5)

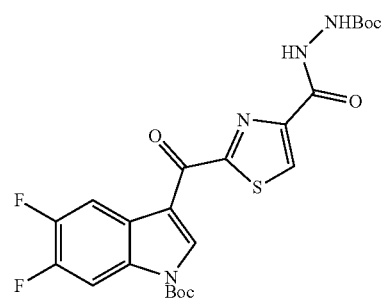

HATU (3.60 g, 95 mmol) and DIPEA (2.80 g, 22 mmol) were added to a suspension of compound 91-4 (3.00 g, 7.3 mmol) and Boc-hydrazine (1.50 g, 11 mmol) in DMF (20 mL) at 0° C. The mixture was allowed to warm to room temperature and stirred for 5 h. The mixture was diluted with H$_2$O (100 mL), extracted with EtOAc (100 mL×3). The combined organic phases were washed with brine (100 mL×2), dried, concentrated to dryness. The residue was purified by silica gel chromatography (EtOAc/Hexan=1:2 to 1:1) and afforded compound 91-5 (1.61 g, 42% yield).

Step 6: 2-(5,6-difluoro-1H-indole-3-carbonyl)thiazole-4-carbohydrazide (91-6)

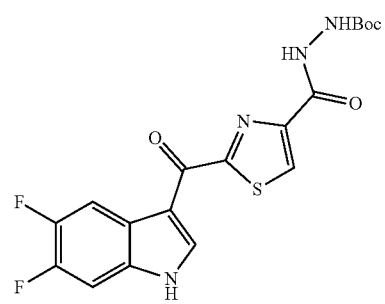

A solution of compound 91-6 (1.60 g, 3 mmol) in DCM (50 mL) and TFA (50 mL) was stirred at room temperature for 3 h. The mixture concentrated to dryness. The residue was suspended in EtOAc (20 mL), alkalified by saturated aqueous $NaHCO_3$ to pH of 7~8. The mixture was filtered to collect the solid. The solid was washed with water (10 mL×3) and EtOAc (10 mL×3), dried to afford 91-6 (0.92 g, 95% yield).

Step 7: (4-(5-amino-1,3,4-oxadiazol-2-yl)thiazol-2-yl)(5,6-difluoro-1H-indol-3-yl)methanone (ARI-154)

(PCT17341-114)

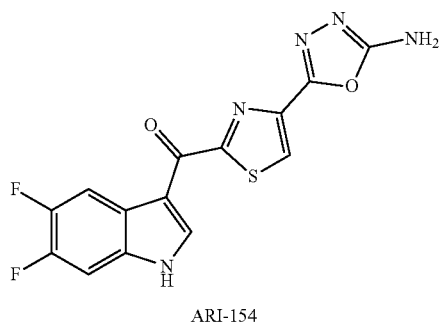

ARI-154

BrCN (0.50 g, 4.5 mmol) was added to a suspension of compound 91-6 (0.90 g, 2.8 mmol) in EtOH (250 mL) at room temperature. The mixture was heated to 65° C. and stirred for 20 h. After cooled to room temperature, the mixture was filtered to collect the solid. The solid was washed with EtOH (10 mL×3), dried to afford ARI-154 (520 mg, 52% yield) as yellow solid. 1H-NMR (400 MHz, DMSO-d6): δ12.55 (bs, 1H), 9.11 (s, 1H), 8.58 (s, 1H), 8.13~8.16 (m, 1H), 7.67~7.70 (m, 1H), 7.44 (s, 2H). LC-MS: m/z 346.0 [M–H]⁻.

Example 132: Preparation of methyl 2-(5-methoxy-1H-indole-3-carbonyl)thiazole-4-carboxylate (ARI-080)

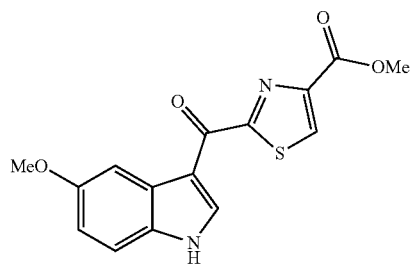 [SMILES: COC(=O)c1csc(C(=O)c2c[nH]c3ccc(OC)cc23)n1]

Starting with 2-(5-methoxy-1H-indole-3-carbonyl)thiazole-4-carboxylate and the method described in Example 65, the title compound was prepared.

Example 133: Preparation of (4-(5-amino-1,3,4-oxadiazol-2-yl)thiazol-2-yl)(5-fluoro-2-methyl-1H-indol-3-yl)methanone (ARI-135)

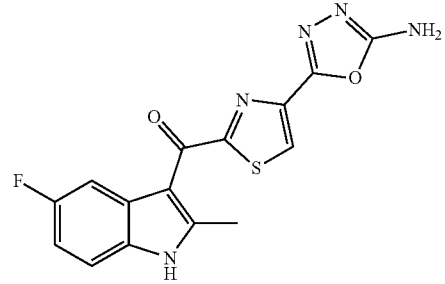 [SMILES: Cc1[nH]c2ccc(F)cc2c1C(=O)c1nc(-c2nnc(N)o2)cs1]

Starting with 5-fluoro-2-methyl-1H-indole and the method described in Example 131, the title compound was prepared.

Example 134: Preparation of (2-(1H-indole-3-carbonyl)thiazol-4-yl)(3-hydroxyazetidin-1-yl)methanone (ARI-045)

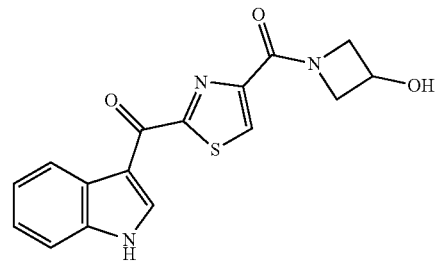 [SMILES: O=C(c1nc(C(=O)N2CC(O)C2)cs1)c1c[nH]c2ccccc12]

Using azetidine-3-ol instead of ethylamine and the method described in Example 24, the title compound was prepared.

Figure 42:
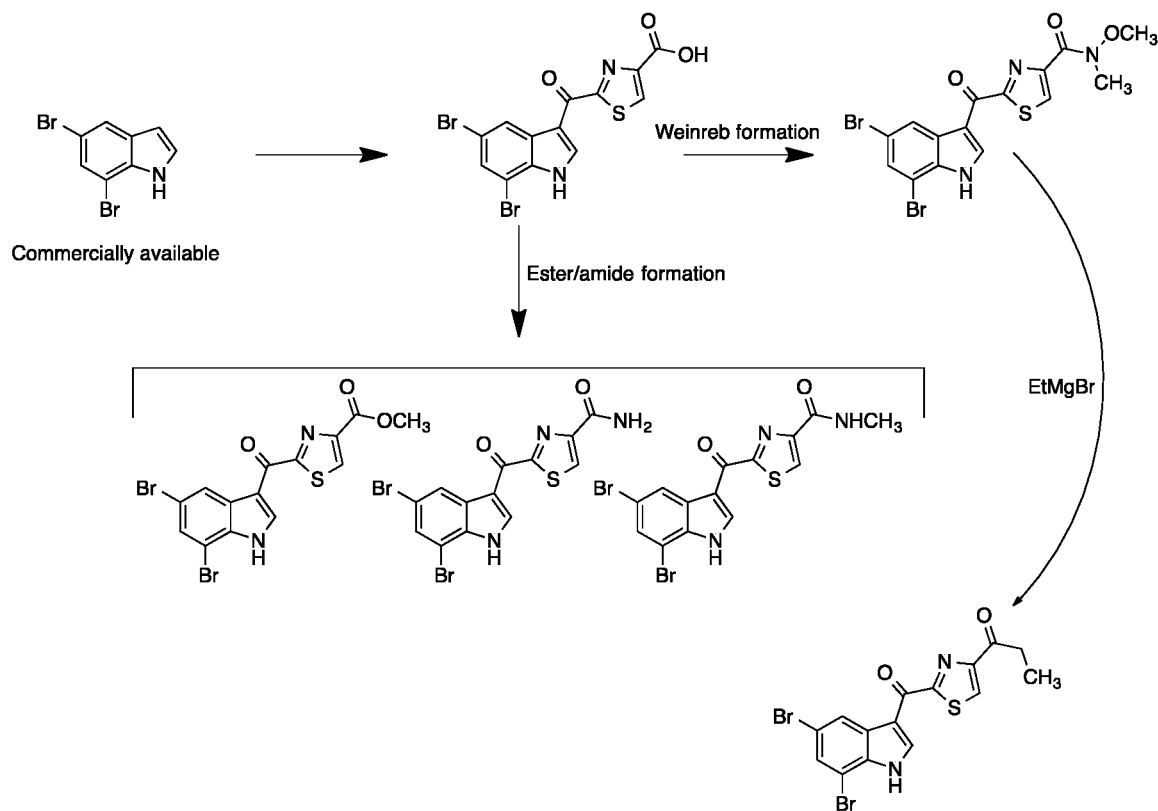
FIG. 42 shows a scheme of synthesizing dibromo compounds according to Example 135.

Example 135: Dibromo Indole Compounds 5,7-dibromo indole 3-carboxylic acid may be prepared according to Katner et al., "An Improved Synthesis of Indole-3-Carboxylic Acids," Organic Preparations and Procedures Vol. 2, Iss. 4, 1970, incorporated herein by reference in its entirety. FIG. 42 shows a scheme of synthesizing dibromo indole compounds.

Figure 43:
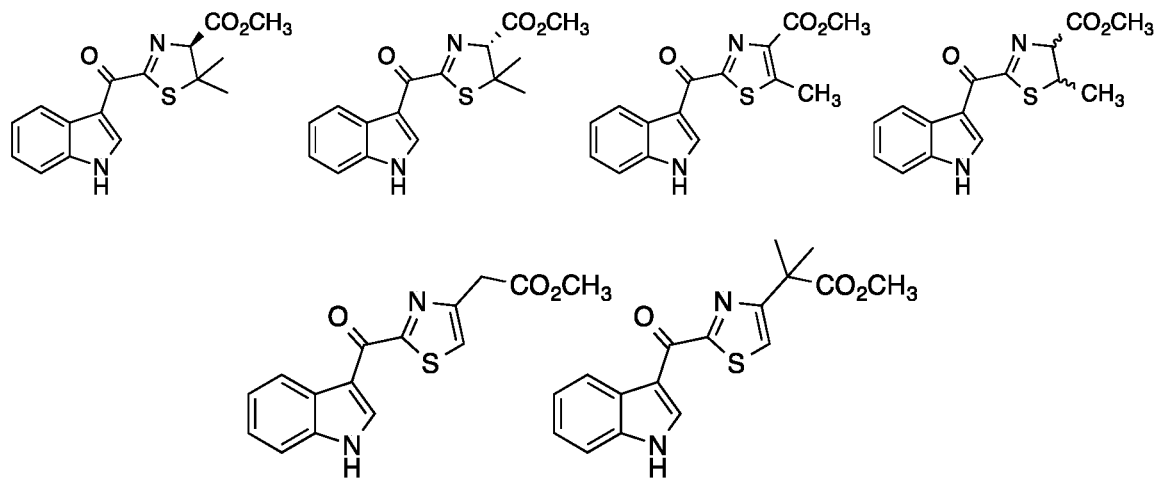
FIG. 43 shows exemplary compounds where thiazole and ester fragments are modified to potentially slow ester hydrolysis according to Example 136.

Example 136: Modification of the Thiazole and Ester Fragments to Potentially Slow Down Ester Hydrolysis FIG. 43 shows exemplary indole compounds where thiazole and ester fragments are modified to potentially slow ester hydrolysis. The compounds can be synthesized using cysteine derivatives, such as L and D penicillamine and 2-amino-3-sulfanyl butanoic acid, which are commercially available.

Example 137: Synthesis of ARI-1073 and ARI-024

Figure 44:
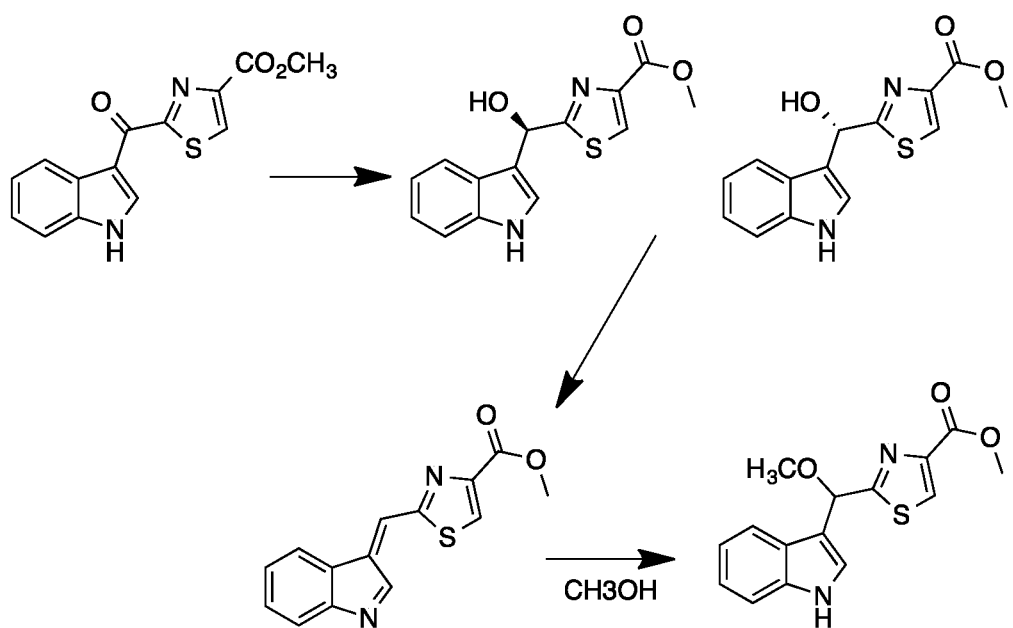
FIG. 44 describes a route of synthesis for ARI-1073 and ARI-024 according to Example 137.

FIG. 44 describes a route of synthesis for ARI-1073 and ARI-024.

Example 138: Synthesis of ARI-068, ARI-092, and ARI-094

Figure 45:
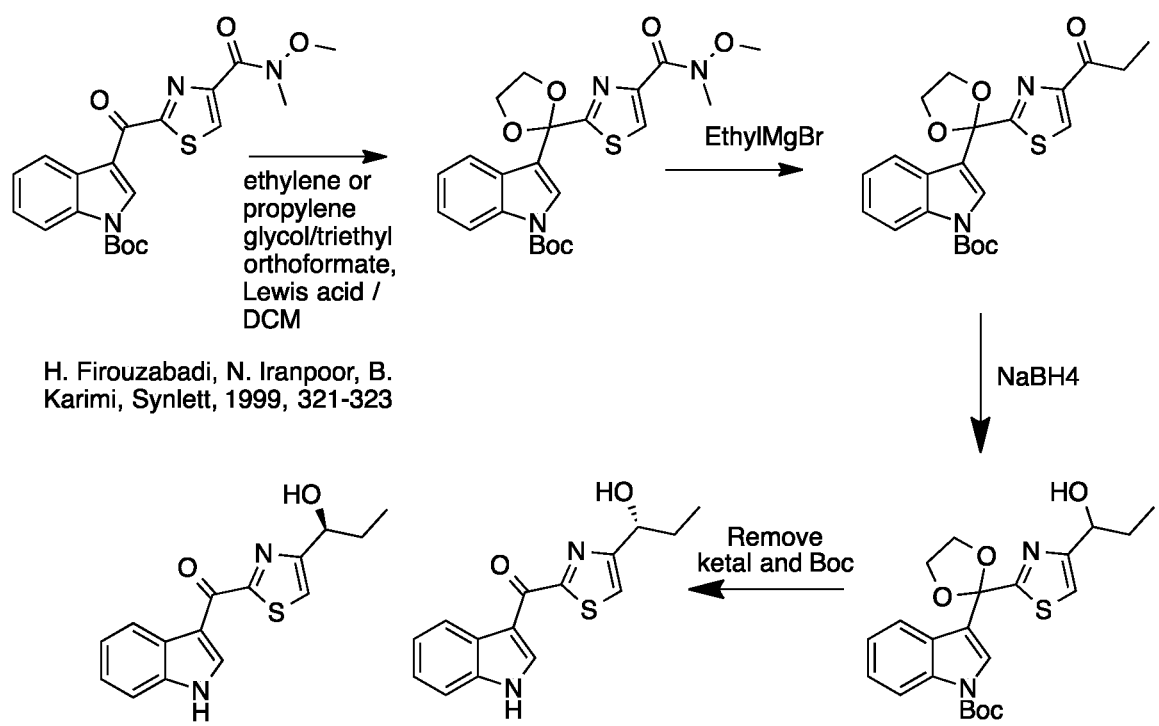
FIG. 45 illustrates a synthesis route for ARI-068, ARI-092, and ARI-094 according to Example 138.

FIG. 45 illustrates a synthesis route for ARI-068, ARI-092, and ARI-094.

Example 139: Synthesis of ARI-1029 and ARI-1030

Figure 46:
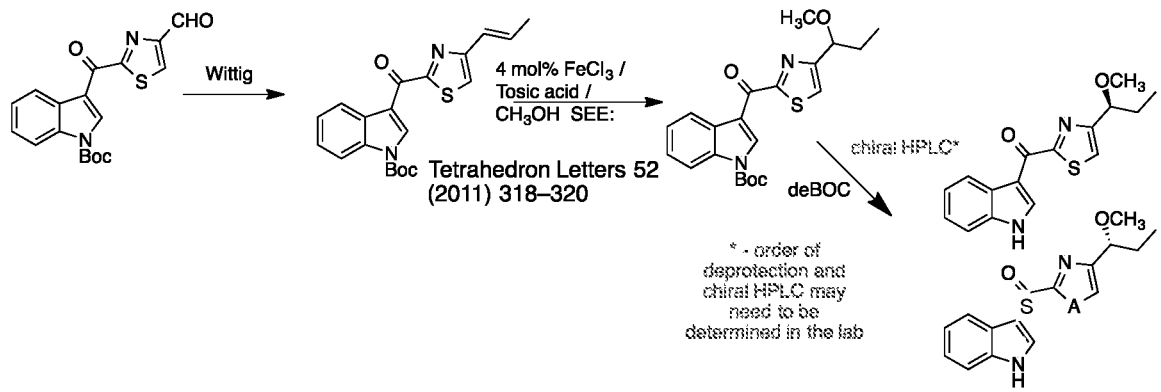
FIG. 46 illustrates a synthesis route for ARI-1029 and ARI-1030 according to Example 139.

FIG. 46 illustrates a synthesis route for ARI-1029 and ARI-1030.

Figure 47:
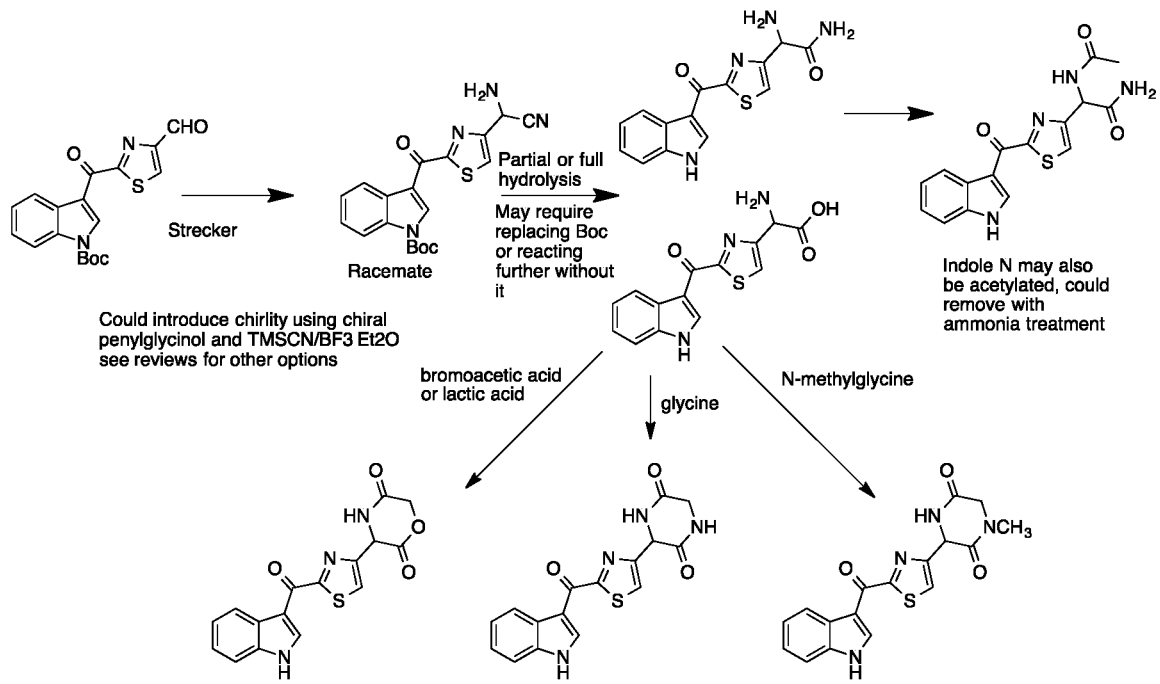
FIG. 47 illustrates a synthesis route for amino amides and cyclic versions of compounds according to Example 140.

Example 140: Synthesis of Amino Amides and Cyclic Versions of Indole Compounds FIG. 47 illustrates a synthesis route for amino amides and cyclic versions of indole compounds.

Example 141: Synthesis of Oxime Compounds with Hindered Ketones

Figure 48:
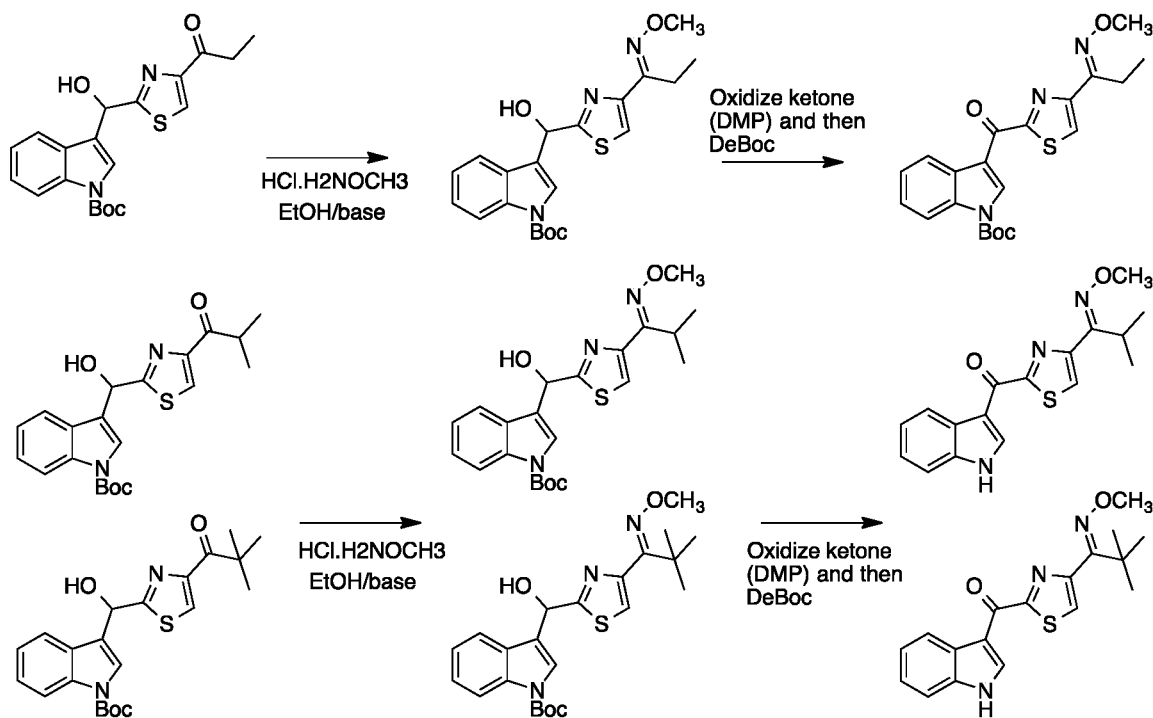
FIG. 48 illustrates a synthesis route for oxime compounds with hindered ketones according to Example 141.
Figure 59:
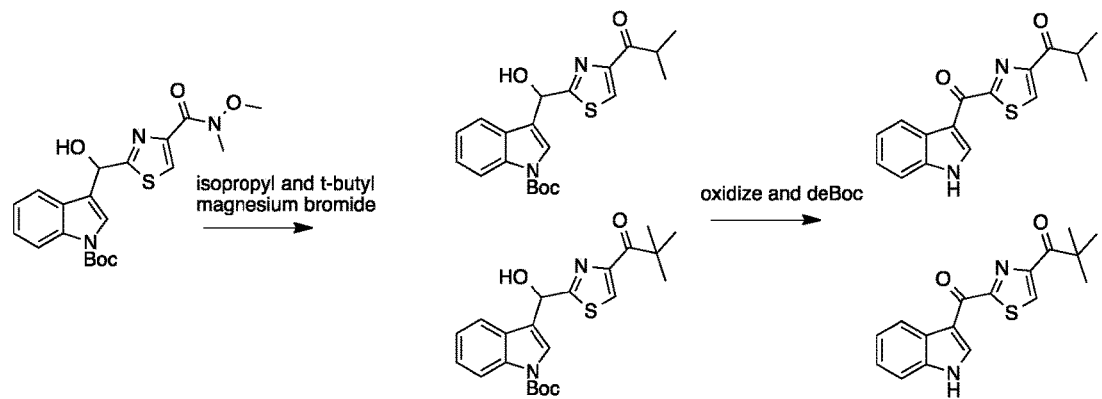
FIG. 59 shows a synthesis scheme for hindered ketones.
Figure 60A:
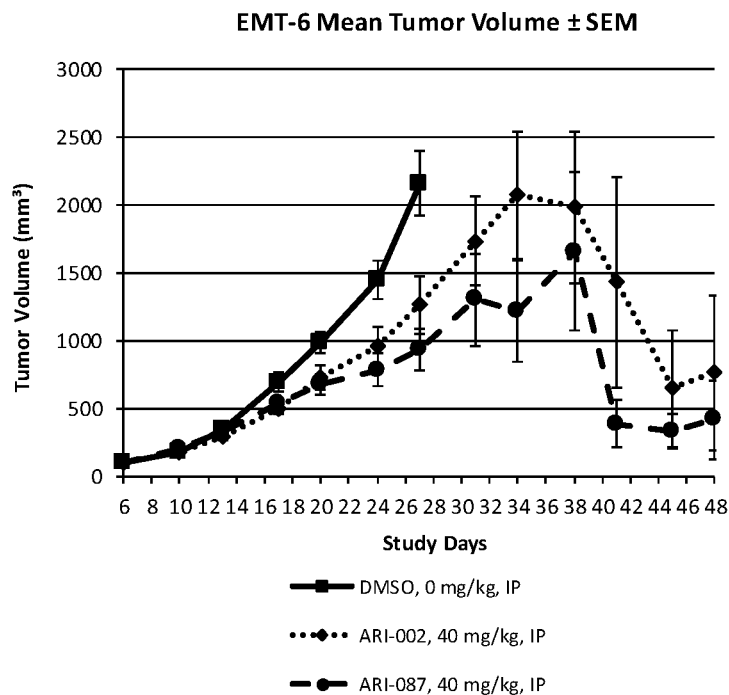
FIGS. 60A-D are graphs showing the tumor inhibitory activity of ARI-002 and ARI-087 in the indicated syngeneic mouse tumor models. A: EMT-6. B: Pan02. C: A20. D: LL/2. IP: intraperitoneal injection. Vehicle control: DMSO.
Figure 60B:
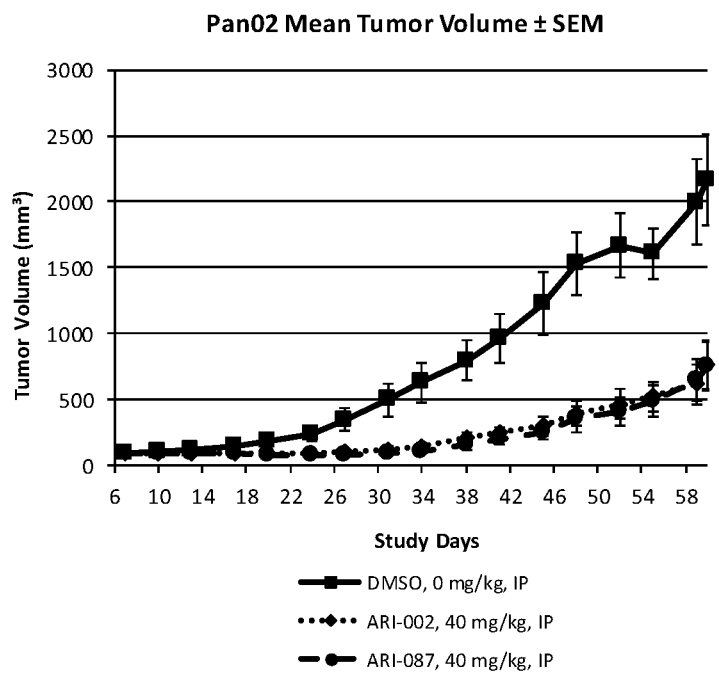
Figure 60C:
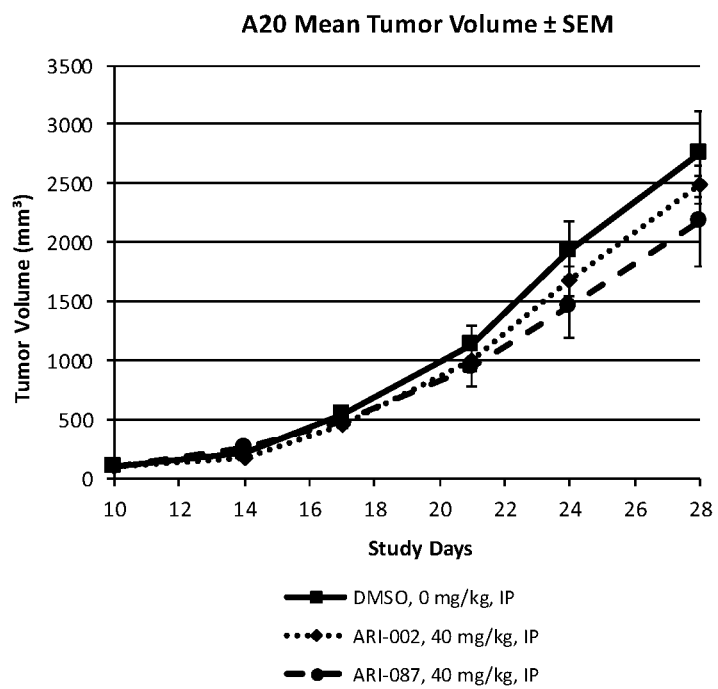
Figure 60D:
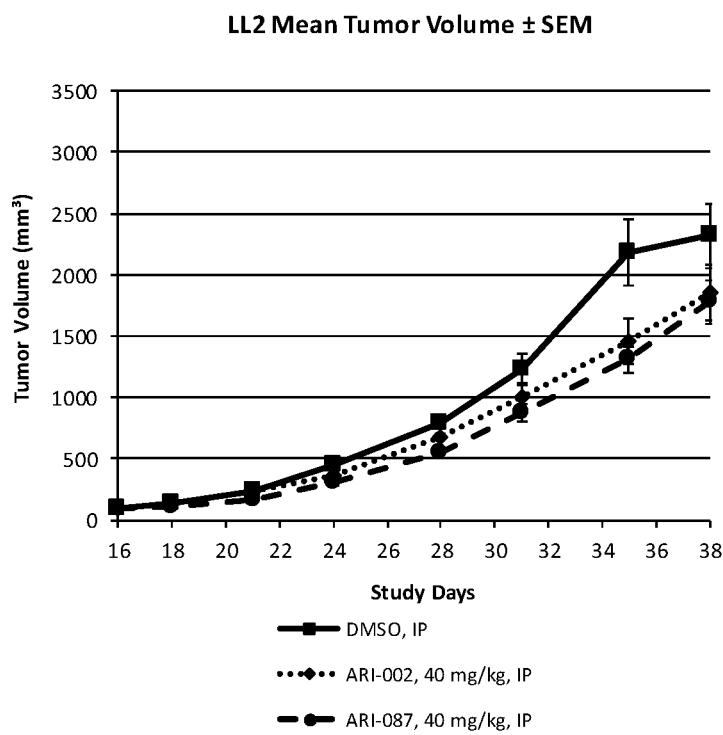

FIG. 48 illustrates a synthesis route for oxime compounds with hindered ketones. Additional routes to hindered ketones are shown in FIG. 59.

Example 142: Synthesis of Pyrazine Compounds

Figure 49:
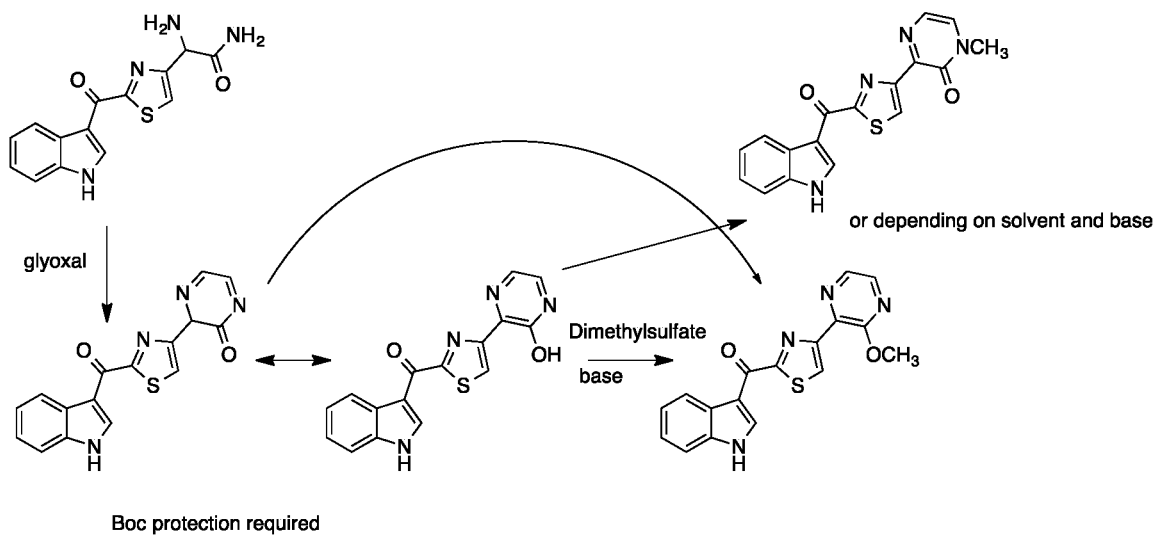
FIG. 49 illustrates a synthesis route for pyrazine compounds according to Example 142.

FIG. 49 illustrates a synthesis route for pyrazine compounds.

Example 143: Properties of Compounds with Thiazole and Indole Replacements

Figure 50:
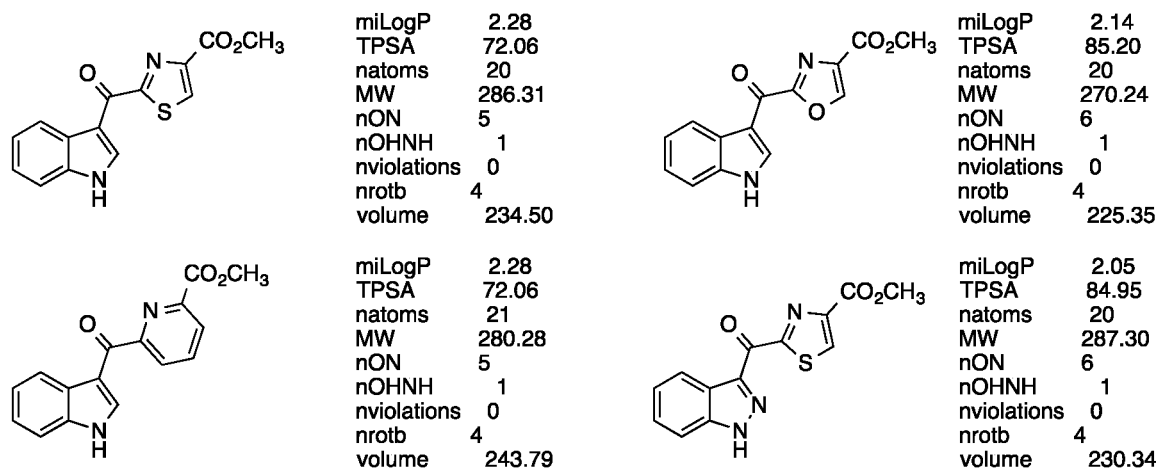
FIG. 50 compares the properties of compounds with thiazole and indole replacements according to Example 143.

FIG. 50 compares the properties of compounds with thiazole and indole replacements.

Example 144: Synthesis of ARI-020

Figure 51:
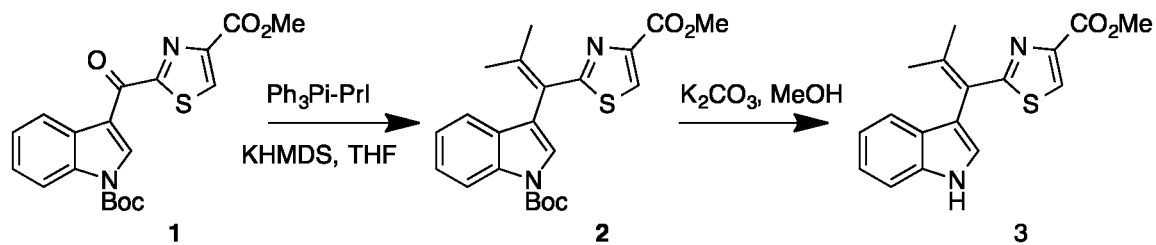
FIG. 51 shows a synthesis scheme for ARI-020 according to Example 144.

FIG. 51 illustrates a synthesis scheme of ARI-020 (corresponding to product 3 in the synthesis scheme). According to this scheme, the yield of product 2 from 300 mg starting material 1 was 224 mg (70%). 1H NMR and MS results were consistent. Additionally, the yield of product 3 from 224 mg of starting material 2 was 45 mg (27%). ARI-020 was isolated as a lyophilized white solid with an HPLC purity >99%. The structure was confirmed by 1H NMR and MS.

Example 145: Synthesis of ARI-018

Figure 52:
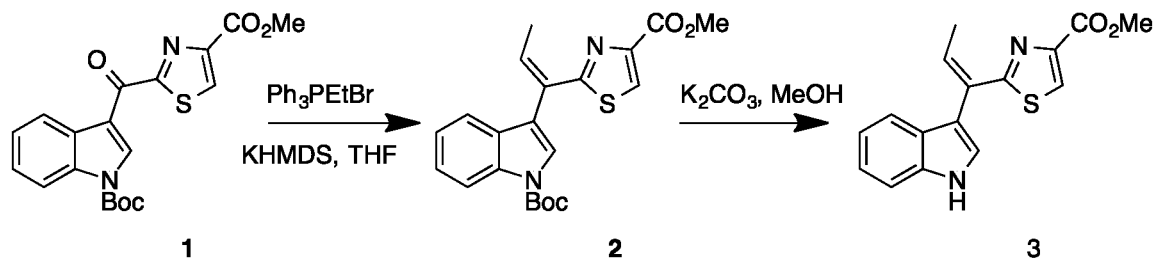
FIG. 52 shows a synthesis scheme for ARI-018 according to Example 145.

FIG. 52 illustrates a synthesis scheme of ARI-018 (corresponding to product 3 in the synthesis scheme). According to this scheme, the yield of product 2 (a mixture of E/Z isomers) from 300 mg starting material 1 was 230 mg (74%).

Example 146: Synthesis of ARI-019

Figure 53:
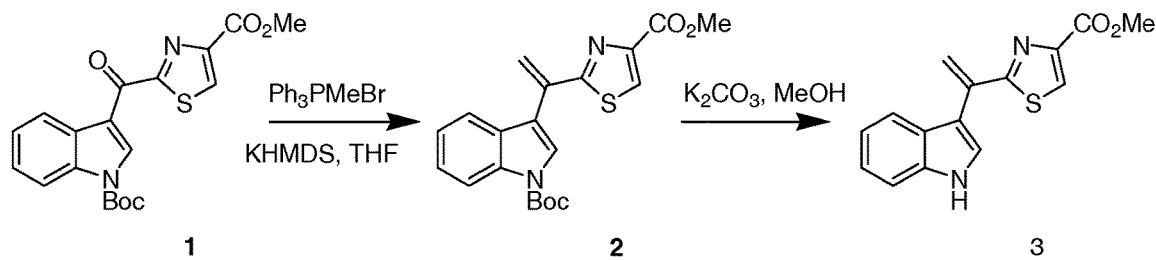
FIG. 53 shows a synthesis scheme for ARI-019 according to Example 146.

FIG. 53 illustrates a synthesis scheme of ARI-019 (corresponding to product 3 in the synthesis scheme). According to this scheme, the yield of product 2 from starting material 1 was 36%; and the yield of product 3 from starting material 2 was 22%. The synthesized ARI-019 was isolated in 90% HPLC purity after 2 columns.

Example 147: Synthesis of ARI-017

Figure 54:
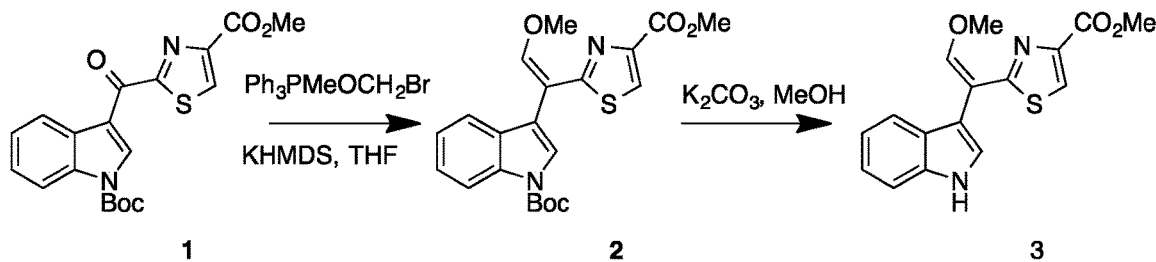
FIG. 54 shows a synthesis scheme for ARI-017 according to Example 147.

FIG. 54 illustrates a synthesis scheme of ARI-017 (corresponding to product 3 in the synthesis scheme). According to this scheme, the yield of product 2 (E/Z isomers after column) from 300 mg starting material 1 was 277 mg (86%).

Example 148: Synthesis of ARI-030

Figure 55:
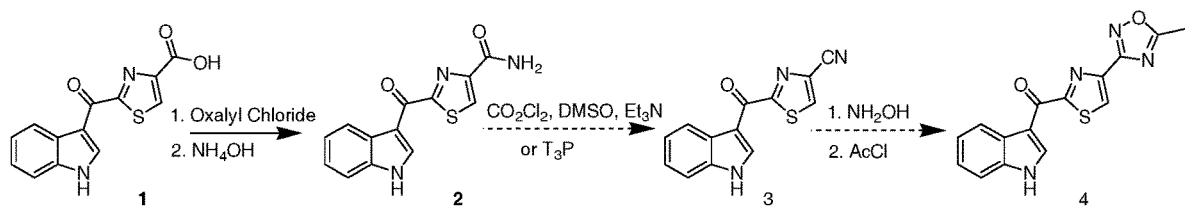
FIG. 55 shows a synthesis scheme for ARI-030 according to Example 148.

FIG. 55 illustrates a synthesis scheme for the preparation of ARI-030 (corresponding to product 4 in the synthesis scheme).

Example 149: Synthesis of an Aldehyde Intermediate

FIG. 56 shows a synthesis scheme of an aldehyde intermediate.

Example 150: Synthesis of ARI-021

FIG. 57 illustrates a synthesis scheme for the preparation of ARI-021 (corresponding to product 3 in the synthesis Scheme B). Scheme A shows Boc protection of the starting carboxylic acid, with a yield of 81% (product 1). Scheme B shows the subsequent Curtius reaction on product 1, with a yield of product 2 from starting material 1 (0.266 g) of 113 mg (48%). 1H NMR and MS results were consistent with the proposed structure.

Example 151: Synthesis of ARI-1057

Figure 58:
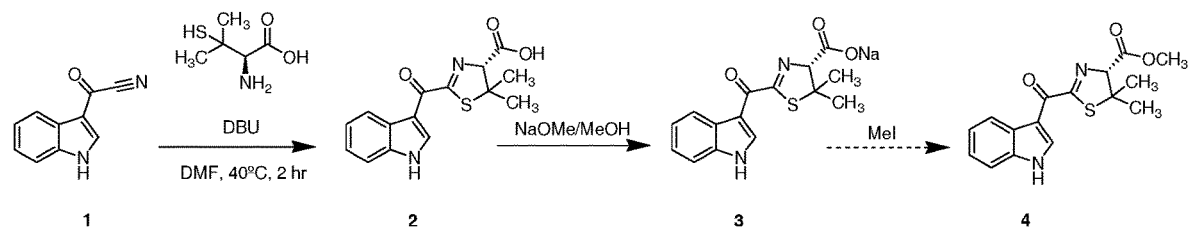
FIG. 58 shows a synthesis scheme for ARI-1057 according to Example 151.

FIG. 58 illustrates a synthesis scheme of ARI-1057 (corresponding to product 4 in the synthesis scheme).

Example 152: Stimulation of CYP1A1 in Human HepG2 Cells and Mouse Hepa1-6 Cells CYP1A1 induction is under the control of the AhR signaling pathway. This Example describes an in vitro assay (7-ethoxy-resorufin-O-deethylase (EROD) assay) that evaluated the AhR modulating activities of the indole compounds described herein. In this assay, the indole compounds were incubated with human HepG2 cells or mouse Hepa1-6 cells. The activity of CYP1A1 in the cells was measured by the conversion of substrate 7-ethoxyresorufin, with the readout being a fluorescence signal associated with the conversion product. The $EC_{50}$ values of the indole compounds as well as the maximum luminescence induced by them in the assay were determined.

Materials

Human HepG2 cells were obtained from Sigma Aldrich (Catalog 85011430-1VL). Mouse Hepa1-6 cells also were obtained from Sigma Aldrich (Catalog 92110305-1V).

Methods

Human HepG2 and Mouse Hepa1-6 cells were grown to 60-80% confluency in tissue culture flasks, lifted with non-enzymatic cell dissociation solution (cell stripper), seeded in a 384-well plate at 5,000 cells per well, treated with the test compounds, and incubated for 20 hours overnight at 37° C. The treatment medium was removed and a solution of substrate 7-ethoxyresorufin (ETX) was added to initiate the reaction. The plate was incubated at 37° C. for 30 minutes. The reaction was subsequently terminated by adding tempered methanol. Fluorescent emission was measured at 590 nm with excitation at 530 nm in a FLEXSTATION III instrument (Molecular Devices).

Results

Table 3 shows the EROD assay data of ARI-001 (ITE), ARI-002, and ARI-002 derivatives ARI-087, ARI-140, ARI-142, ARI-143, and ARI-149 using human HepG2 cells and mouse Hepa1-6 cells, respectively. The data for each cell line were obtained from the same plates.

TABLE 3

EROD Assay Data

| Compound ID | EC$_{50}$ (nM) in HepG2 | EC$_{50}$ (nM) in Hepa1-6 |
|---|---|---|
| ARI-001 | 28.9 | 64.0 |
| ARI-002 | 19.1 | 6.5 |
| ARI-087 | 34.2 | 5.8 |
| ARI-140 | 0.7 | 19.5 |
| ARI-142 | 64.8 | 12.8 |
| ARI-143 | 4.2 | 2.3 |
| ARI-149 | 19.2 | 0.6 |

The results from the above table show that in human HepG2 cells, ARI-087, ARI-140, ARI-143 and ARI-149 had EC$_{50}$ values that were similar to or lower than that of ARI-001 or ARI-002. ARI-142 was less active than ARI-002. Similar results were observed in the mouse Hepa1-6 cell assay, except that in that assay, ARI-140 was shown to be less active than ARI-002.

The human EROD assay shows that indole compounds comprising an oxadiazole moiety such as ARI-030, ARI-031, ARI-056, ARI-060, ARI-083, ARI-090, ARI-118, ARI-120, ARI-145, and ARI-148 were significantly more (about 4 to 900 times more) active than ARI-001, while ARI-146 was similar in activity to ARI-001. These more active oxadiazole derivatives of ITE could be categorized into three groups, based on their EC$_{50}$ values, in the order of increasing activity: (1) active: ARI-030 (5-methyl-1,2,4-oxadiazole), ARI-031 (3-methyl-1,2,4-oxadiazole), ARI-056 (1,3,4-oxadiazole) and ARI-060 (2-methyl-1,3,4 oxadiazole); (2) more active: ARI-083 (2-amino-1,3,4-oxadiazole), ARI-090 (2-amino-1,3,4-thiadiazole), ARI-145 (7-fluoroindolo-2-aminomethyl-1,3,4-oxadiazole), and ARI-148 (5-fluoroindolo-2-amino-1,3,4 oxadiazole); and (3) most active: ARI-118 (7-fluoroindolo-2-amino-1,3,4 oxadiazole ARI-118) and ARI-120 (5,6-dichloroindolo-2-amino-1,3,4 oxadiazole). ARI-002 was similarly active as the compounds in group (2). Of note, in this assay, ARI-118 was about 930 times more active than ARI-001 and about 13 times more active than ARI-002. Similar to the human EROD assay, the mouse EROD assay shows that ARI-118, ARI-120, and ARI-145 were the most active among the tested oxadiazole compounds.

The human and mouse EROD assays also show that ARI-004, ARI-049, ARI-055, ARI-065, ARI-066, and ARI-067 were less active—in many cases significantly less so—than ARI-002.

Example 153: Suppression of IL-21 Secretion by Activated Th17 Cells

IL-21 is a pro-inflammatory cytokine secreted by CD4$^+$ Th17 cells and is thought to serve as a T-cell growth factor playing overlapping roles with IL-2. This Example describes a study that measured the IC$_{50}$ values of the indole compounds disclosed herein for suppressing IL-21 secretion from human CD4$^+$ T cells that had been treated with stimulatory conditions that gave rise to TH17 cells (see, e.g., Dobritsa et al., J Biomol Screen. 18(1):75-84 (2013)).
Materials Human CD4$^+$ T cells were purchased from Lonza Walkersville Inc. (Walkersville, Md.). DMSO was obtained from Sigma (St. Louis, Mo.). Greiner cell culture plates, Gibco DMEM cell culture medium, media supplements, and antibiotics, as well as DYNABEADS Human T-Activator CD3/CD28 and R&D Systems TGF-β, IL-1β and IL-23 and Invitrogen IL-6 cytokines, were purchased through Fisher Scientific (Pittsburgh, Pa.). ALPHALISA assay plates and the Human Interleukin-21 ALPHALISA kit was obtained from Perkin Elmer (Boston, Mass.).
Methods
Cell Culture Conditions and Treatment Cell culture plates were pre-coated with test compounds in serial dilutions for generating a 10-point, 3-fold dose response curve with a top concentration of 1 µM or 100 nM. To do this, compounds were dissolved in DMSO and added to an ECHO qualified plate for transfer to the cell culture plate with the ECHO555. The indole compounds to be tested were dissolved in water and wells were backfilled with DMSO so that all treatments received 0.1% DMSO final volume. Positive control (0% inhibition) wells, in which compounds were replaced with 1.0% DMSO, were included on each plate. At least $15\times10^6$ frozen CD4$^+$ T cells per plate of compounds were thawed in a 37° C. water bath, and the cells were washed twice with 10 mL of the complete medium (DMEM supplemented with 10% fetal bovine serum (FBS), 100 U/mL penicillin, and 100 µg/mL streptomycin), followed by centrifugation (250×g, 10 min). Cells were re-suspended to the desired density, and cultured in 384-well treated sterile cell culture plates in a total volume of 50 µL per well. Each plate included wells with induced and un-induced cells.

Induced cells were activated in the complete medium with DYNABEADS Human T-Activator CD3/CD28 at a bead-to-cell ratio of 1:2.5 and stimulated with the following cytokines: transforming growth factor-β (TGF-β, 5 ng/mL), IL-6 (20 ng/mL), IL-23 (20 ng/mL), and IL-1β (10 ng/mL).

Un-induced cells were left in complete medium with no additional supplements. Plates were incubated at 37° C., 5% CO$_2$ for a total of 5 days. Upon completion of the 5 day incubation period, cells were spun down (1,000×g, 1 min) and supernatant was transferred to the ALPHALISA assay plate using the Mosquito HTS liquid handler (TTP Labtech Inc., Cambridge, Mass.).
IL-21 ALPHALISA Assay IL-21 levels in cell supernatants and cell-free control samples were measured using the ALPHALISA assay kit from Perkin Elmer, following the manufacturer's instructions. The assay was run at room temperature in 384-well ALPHAPLATES (cat. 6005350; Boston, Mass.). Briefly, immediately after transferring the cell supernatant to the assay plate, anti-IL-21 acceptor beads were added with the CERTUS FLEX liquid handler (LEAP Technologies, Morrisville, N.C.). The plate was sealed, spun down and incubated for 30 minutes. After incubation, the seal was removed, anti-IL-21 biotinylated antibody was added with the CERTUS FLEX, and the plate was sealed again, spun down and incubated for 60 minutes. Next, the seal was removed, streptavidin-coated donor beads were added with the CERTUS FLEX, and the plate was sealed, spun down and incubated for another 60 minutes. Finally, the seal was removed and the plate was read using the ENVISION reader (Perkin Elmer, Boston, Mass.) set with an excitation filter of 680 nm and an emission filter of 615 nm. Two independent IL-21 standard dilution curves were run per plate with analyte provided in the ALPHALISA kit.
Data Analysis For estimation of the assay performance, Z' values were calculated for each plate, comparing positive and negative controls. A Z' value ≥0.5 was chosen as the acceptance cutoff. The XLfit 5.2.0.0 software (IDBS, Guildford, UK) was used for curve fitting. $IC_{50}$ values were calculated using a four-parameter logistic fit model, model 205, and IL-21 standard curves were fitted using a linear polynomial model, model 100.

Results

Table 4 shows the $IC_{50}$ (nM) values of the various indole compounds herein for suppression IL-21 secretion.

TABLE 4

Suppression of IL-21 Secretion

| Analog Series | Compound ID | $IC_{50}$ (nM) |
| --- | --- | --- |
| Esters | ARI-001 | 38.2 |
|  | ARI-055 | 73.6 |
|  | ARI-066 | 48.6 |
| Ketones | ARI-002 | 31.8 |
|  | ARI-067 | 6.3 |
|  | ARI-087 | 25.4 |
|  | ARI-140 | 8.6 |
|  | ARI-142 | 208.8 |
|  | ARI-143 | 18.8 |
|  | ARI-149 | 30.3 |
| Oxa- or thia-diazoles | ARI-030 | 40.0 |
|  | ARI-031 | 42.6 |
|  | ARI-056 | 4.9 |
|  | ARI-060 | 110.0 |
|  | ARI-083 | 0.3 |
|  | ARI-090 | 8.4 |
|  | ARI-118 | 0.8 |
|  | ARI-120 | 0.3 |
|  | ARI-145 | 46.9 |
|  | ARI-146 | 13.4 |
|  | ARI-148 | 5.9 |
| Amides | ARI-004 | 231.1 |
|  | ARI-049 | 10.1 |
|  | ARI-065 | 14.0 |

The above table shows that in the ketone series, ARI-067, ARI-087, ARI-140, ARI-143 and ARI-149 all had $IC_{50}$ values similar to or lower than that of ARI-002. ARI-142 was the least active in suppressing IL-21 secretion. These data are consistent with the EROD data described above, except for ARI-140, which showed less activity in the mouse EROD assay, as noted previously. Overall, however, there was high concordance between both assays.

In the oxa- or thia-diazole series, ARI-30, ARI-031, and ARI-060 were among the least potent, as also shown in the EROD assays described above. ARI-083, ARI-118, and ARI-120 were the most potent. Notably, ARI-118 was about 32 times more potent than ARI-087 in this assay. ARI-118 and ARI-120 also were shown to be in the most active group in the EROD assays.

The above IL-21 secretion data also shows that while ARI-004 had weak activity, adding a 5-chloro or 5-fluoro group at its indole ring significantly improved its activity. However, the same modification did not improve ARI-001's activity (ester series) meaningfully.

Example 154: Determination of Metabolic Stability of Indole Compounds

The liver is an important organ in the body for drug metabolism. This Example describes hepatocyte intrinsic clearance assays using both human and mouse hepatocytes to evaluate the metabolic stability of the indole compounds disclosed herein. The parameters measured include $t_{1/2}$ (half-life), $CL_{int}$ (intrinsic clearance), and $E_H$ (hepatic extraction ratio).

Materials

Testosterone (Lot FE111011-01) was obtained from Cerilliant (Round Rock, Tex.). 7-hydroxycoumarin (Lot 11631ED) was obtained from Sigma Aldrich (St. Louis, Mo.). Cryopreserved human hepatocytes pooled from ten donor males (X008001), cryopreserved male IRC/CD-1 mouse hepatocytes (M005052), INVITROGRO HI Medium (incubation), and INVITROGRO HT Medium (thawing) were obtained from Bioreclamation IVT (Baltimore, Md.). All solvents were obtained from commercial sources and used without further purification.

Methods

Metabolic Stability Hepatocytes

Each test compound was prepared as a 1 mM stock solution in DMSO. A 2 µM solution of test compound and positive controls were prepared in INVITROGRO HI Medium (incubation). These solutions were pre-warmed in a sterile incubator set to maintain 37° C., 5% $CO_2$, and 98% humidity. Cryopreserved hepatocytes were prepared at a concentration of $2 \times 10^6$ living cells/mL in incubation media and pre-warmed in the incubator. The compound solutions and hepatocyte mixtures were then combined at a ratio of 1:1 (v:v). The final volume of the reaction mixture was 750 µL, containing 1 µM test compound (10 µM for 7-hydroxycoumarin) and $1 \times 10^6$ cells. The reaction mixture was placed in the incubator on a plate shaker. After 0, 15, 30, 60, 90, and 120 minutes of incubation, 100 µL of reaction mixtures were removed from the incubation plate and mixed with 150 µL of ice-cold acetonitrile in a designated well of a 96-well crash plate. The 96-well crash plate was placed on ice for 15 min, and samples were centrifuged (3,600 RPM, 10 min, 4° C.) to precipitate protein. The supernatants were diluted 1:1 (v:v) with water containing 0.15 µM verapamil and/or 1 µM tolbutamide (internal standards for positive and negative modes, respectively) in a 96-well shallow injection plate. This plate was sealed for LC-MS analysis. All measurements were done in duplicate.

LC-MS Analysis

Liquid Chromatography

Column: Waters Atlantis T3 Column, 100 Å, 3 µm, 2.1 mm×50 mm (Part #186003717). Mobile Phase A: Water with 0.1% formic acid. Mobile Phase B: Acetonitrile with 0.1% formic acid. Flow Rate: 0.7 mL/minute. Gradient Program:

| Time (min) | % A | % B |
| --- | --- | --- |
| 0.0 | 90 | 10 |
| 0.4 | 90 | 10 |
| 1.2 | 10 | 90 |
| 2.0 | 10 | 90 |
| 2.1 | 90 | 10 |
| 3.0 | 90 | 10 |

Total Run Time: 3 minutes. Autosampler: 10 µL injection volume. Autosampler Wash: A: 90% water, 10% acetonitrile; B: 90% acetonitrile, 10% water.

Mass Spectrometer

Instrument: AB SCIEX API4000. Interface: Turbo Ionspray. Mode: Q1 Multiple Ions. Method: 3.0 minute duration. Mass Spectrometer Source Settings:

| IS | TEM | CUR | GS1 | GS2 |
| --- | --- | --- | --- | --- |
| 5500 | 550 | 20 | 50 | 50 |

Data and Calculations

Determination of $t_{1/2}$, $CL_{int}$, $E_H$, and % R at 60 Minutes

The residual compound remaining (% R) was determined from LC-MS peak areas by comparison to the zero time point. Metabolic half-life ($t_{1/2}$) and intrinsic clearance ($CL_{int}$) values were calculated from the slope of the plot of In (% R) vs. time and the concentration of hepatocytes present in the incubation. Percent remaining at 60 minutes was calculated by plugging in the 60 minute value into the slope equation generated by the percent remaining time points.

Calculation of In Vivo Hepatic Clearance

In vivo hepatic clearance $CL_H$ was calculated using the well stirred liver model according to the following equation:

$$CL_H = \frac{Q_H \cdot f_u \cdot CL'_{int}}{Q_H + f_u \cdot CL'_{int}},$$

where $Q_H$ is the total liver blood flow, $f_u$ is unbound fraction of the drug, and $CL'_{int}$ is defined as follows:

$CL'_{int} = CL_{int} \times (10^6 \text{ cells/g of liver weight}) \times (\text{g liver weight/kg of body weight})$.

In the first approximation, used in this study, $f_u = 1$.

Hepatic extraction ratio $E_H$ was calculated using the following equation:

$$E_H = \frac{CL_H}{Q_H}$$

Corresponding physiological parameters used in calculations for all species are shown below in Table 5.

TABLE 5

Physiological Parameters of Mammalian Species Used for Calculation of $CL_H$

| Species | g liver wt/ kg body wt | $10^6$ cells/g liver wt | $Q_H$ (mL/min/ kg body wt) |
|---|---|---|---|
| Human | 26 | 99 | 21 |
| Mouse | 55 | 128 | 120 |

Results

Table 6 shows the $t_{1/2}$, $CL_{int}$, and $E_H$ of various indole compounds described herein as assayed on human and mouse hepatocytes.

TABLE 6

Metabolism of Indole Compounds

| Compound ID | Human Hepatocytes | | | Mouse Hepatocytes | | |
|---|---|---|---|---|---|---|
| | $t_{1/2}$ (min) | $CL_{int}$ (μL/min/ $10^6$ ells) | $E_H$ (%) | $t_{1/2}$ (min) | $CL_{int}$ (μL/min/ $10^6$ cells) | $E_H$ (%) |
| Ester Series | | | | | | |
| ARI-001 | 7.8 | 220.4 | 91 | 5.5 | 585.7 | 87 |
| ARI-055 | 67.3 | 10.3 | 56 | 135.1 | 5.1 | 23 |
| ARI-066 | 7.0 | 98.7 | 92 | 13.4 | 51.9 | 75 |
| Ketone Series | | | | | | |
| ARI-002 | 12.5 | 137.2 | 86 | 3.4 | 961.9 | 91 |
| ARI-067 | 300.2 | 2.3 | 22 | 212.3 | 3.3 | 16 |
| ARI-087 | 114.8 | 6.0 | 43 | 110.6 | 6.3 | 27 |
| ARI-140 | 200 | 3.5 | 30 | 450 | 1.5 | 8.3 |
| ARI-142 | 86 | 8.1 | 50 | 66 | 11 | 38 |
| ARI-143 | 154 | 4.5 | 36 | 306 | 2.3 | 12 |
| ARI-149 | 132 | 5.3 | 39 | 238 | 2.9 | 15 |
| Oxa- or Thiadiazole Series | | | | | | |
| ARI-030 | 378.6 | 1.8 | 18 | 17.1 | 40.5 | 70 |
| ARI-031 | 968.2 | 0.7 | 8 | 702.8 | 1.0 | 6 |
| ARI-056 | 39.2 | 17.7 | 68 | 26.8 | 25.8 | 60 |
| ARI-060 | 273.2 | 2.5 | 24 | 138.2 | 5.0 | 23 |
| ARI-083 | 646.9 | 1.1 | 12 | 968.3 | 0.7 | 4 |
| ARI-090 | 131.2 | 5.3 | 39 | 282.0 | 2.5 | 13 |
| ARI-118 | 927 | 0.7 | 8.4 | 842 | 0.8 | 4.6 |
| ARI-120 | 921 | 0.8 | 8.5 | 811 | 0.9 | 4.8 |
| ARI-145 | 170 | 4.1 | 33 | 136 | 5.1 | 23 |
| ARI-146 | 374 | 1.9 | 19 | 100 | 6.9 | 29 |
| ARI-148 | 282 | 2.5 | 23 | 190 | 3.6 | 18 |
| Amide Series | | | | | | |
| ARI-004 | 42.7 | 40.2 | 65 | 2.8 | 1,174.2 | 93 |
| ARI-049 | 232.9 | 3.0 | 27 | 95.2 | 7.3 | 30 |
| ARI-065 | 91.0 | 7.6 | 48 | 97.3 | 7.1 | 29 |

These results indicate that ARI-002, a ketone analog of ARI-001 (ITE), had high clearance in both human and mouse hepatoctyes, as indicated by the high extraction ratio ($E_H$). By contrast, derivatives of ARI-002 with fluorine or chlorine substitutions in the indole ring displayed much improved metabolic profiles. For example, in human hepatocytes, ARI-087 had 23 times lower clearance and two times lower $E_H$ as compared to ARI-002. In mouse hepatocytes, ARI-087 had 153 times lower clearance and three times lower $E_H$ as compared to ARI-002. Likewise, the clearance of ARI-143 was 30 times and 418 times lower than that of ARI-002 in human and mouse hepatocytes, respectively, and the $E_H$ of ARI-143 was two times and eight times lower than that of ARI-002 in human and mouse hepatocytes, respectively.

The oxa- or thia-diazole series of compounds similarly had markedly improved metabolic profiles than ARI-001 and ARI-002. For example, ARI-031, ARI-118, and ARI-120 had low clearance, as indicated by, e.g., their extraction ratios ($E_H$), in both human and mouse hepatocytes. Surprisingly, ARI-083, which has a 2-amino substitution at the 1,3,4-oxadiazole moiety, had lower clearance and hepatic extraction parameters than ARI-060, which has a 2-methyl substitution at the 1,3,4 oxadiazole moiety. ARI-118 and ARI-120 had even lower values than ARI-083, which is not substituted with halogen.

In the amide series, ARI-004's metabolic profile was improved by fluoro or chloro substitutions at the indole ring, as demonstrated by the lower clearance and $E_H$ value of ARI-049 and ARI-065 in both human and mouse hepatocytes. However, in the ester series, only the fluoro substitution (ARI-055) led to improvement in the metabolic profile of ARI-001.

It remains unclear whether halogen substitutions at the indole ring impact the activity and metabolic profiles of the indole compounds described herein. Preliminary studies analyzing metabolites of these compounds in hepatocytes by high-resolution mass spectrometry identified fewer primary metabolites of the indole ring of ARI-002, ARI-087 or ARI-143 than expected on the basis of what has typically been observed with indole metabolism. Moreover, in silico modeling of electron withdrawing and atomic charge on these molecules did not reveal anything that could explain the present in vitro results. These data suggest that the class of indole compounds disclosed herein is an entirely new class of molecules with unexpected and previously unknown properties.

Example 155: In Vivo Pharmacokinetic Studies in Rodents

This example describes pharmacokinetic (PK) studies of the various indole compounds described herein in rats, a rodent species widely used for pre-clinical toxicology evaluation. In the present studies, the test compounds were given to groups of Sprague-Dawley rats (N=3 in each group) intravenously (IV) at 2 mg/kg or orally (PO) at 10 mg/kg. IV doses were formulated in DMSO, while PO doses were formulated in a 50/50 mixture of PEG400 and Tween 80. Blood samples were collected at pre-dose and over a period of 24 hours post-dose. Plasma concentrations of the indole compounds were determined by HPLC. Table 7 below shows the results of the PK study on select indole compounds.

AUCinf. ARI-087 exhibited a PO AUCinf that was 81% of that of ARI-002 and absolute oral bioavailability that was 1.8 times higher than ARI-002. Surprisingly, ARI-143, which had IV PK profiles comparable to those of ARI-149, exhibited much better oral PK profiles than ARI-149: unlike ARI-149, ARI-143 had significantly higher PO AUCinf (2.6 times higher) and higher absolute oral bioavailability (1.8 times higher) than ARI-002.

Notably, although ketone compounds having 5-fluoro substitution (ARI-087) and 5-chloro substitution (ARI-067) at the indole ring had comparable metabolic profiles in vitro, the former substitution was shown to accord significantly lower plasma clearance and much better oral bioavailability than the latter substitution in the in vivo PK studies, where compound solubility and absorption in the animals were likely additional influential factors.

In the oxadiazole series, the PK studies in rats show that the indole compounds with an oxadiazole moiety, i.e., ARI-030, ARI-031, ARI-083, and ARI-118, had improved IV PK profiles compared to ARI-001, ARI-002, and ARI-004. A separate PK study performed in mice on ARI-030 and ARI-031 confirms the improvement accorded by the oxadiazole moiety over ARI-001 and ARI-002 (data not shown). Among the oxadiazole derivatives tested in rats, ARI-030,

TABLE 7

| | PK Studies | | | | | | |
|---|---|---|---|---|---|---|---|
| | IV (2 mg/kg) | | | | PO (10 mg/kg) | | |
| Compound ID | AUClast | AUCinf | Plasma Clearance | % of Hepatisc Blood Flow | AUClast | AUCinf | F % |
| ARI-001 | 173 | 174 | 12,147 | 289 | 1 | 4 | 0.4 |
| ARI-004 | 240 | 256 | 7,945 | 189 | 430 | 431 | 33.6 |
| | | | Ketone Series | | | | |
| ARI-002 | 1940 | 1940 | 1,090 | 26 | 1,060 | 1,060 | 10.9 |
| ARI-067 | 145 | 147 | 14,700 | 350 | 26 | 36 | 3.5 |
| ARI-087 | 838 | 873 | 3,510 | 84 | 858 | 859 | 19.7 |
| ARI-143 | 2,810 | 2,820 | 810 | 19 | 2,280 | 2,720 | 19.3 |
| ARI-149 | 4,390 | 4,390 | 542 | 13 | 1,480 | 1,490 | 6.8 |
| | | | Oxadiazole Series | | | | |
| ARI-030 | 3,920 | 4,120 | 1,180 | 28 | 180 | 183 | 0.9 |
| ARI-031 | 480 | 483 | 4,330 | 103 | 144 | 152 | 6.3 |
| ARI-083 | 1,360 | NA | 1,877 | 45 | 68 | NA | 1.0 |
| ARI-118 | 2,790 | 2,890 | 713 | 17 | 32 | 33 | 0.2 |

*AUClast: area under the plasma drug concentration versus time curve from time zero to time of last measurable concentration.
AUCinf: area under the plasma drug concentration versus time curve from time zero to infinity.
F: bioavailability (systemic availability of the administered dose; F % = 100 X (PO AUCinf X equivalent IV DOSE)/(IV AUCinf X equivalent PO Dose)).

In the ketone series, the PK data show that for IV administration, ARI-002 had lower plasma clearance, as well as higher AUCinf, compared to ARI-001. ARI-087 had 3.2 times higher plasma clearance than ARI-002, and an IV AUCinf that was 45% of that of ARI-002. ARI-143 exhibited plasma clearance that was 74% of ARI-002 and 1.5 times higher IV AUCinf than ARI-002. Among all the ketone compounds tested, ARI-149 had the lowest plasma clearance (50% of that of ARI-002) and the highest IV AUCinf (2.3 times higher than ARI-002).

For oral administration, ARI-149, while exhibiting a PO AUCinf that was about 1.4 times higher than that of ARI-002, exhibited an absolute oral bioavailability that was only 62% of ARI-002. These oral exposure data and absolute bioavailability values are consistent with ARI-149's high IV ARI-083, and ARI-118 displayed better IV PK profiles than ARI-031, with ARI-118 having the best profile.

Example 156: Anti-Tumor Activity of the Indole Compounds in Animal Models

This example describes in vivo studies that evaluated the anti-cancer efficacy of the disclosed indole compounds in syngeneic mouse tumor models. Mice implanted subcutaneously with four types of cancer cells were treated with test indole compounds or vehicle controls as described below.
Materials and Methods
Cell Culture A monolayer culture of tumor cells was maintained in vitro in DMEM or RPMI1640 medium supplemented with 10% fetal bovine serum at 37° C. in an atmosphere of 5% $CO_2$. Cells in exponential growth phase were harvested and quantitated by cell counter before tumor inoculation. The cell lines used are described in the table below.

| Cell Line | Cancer Type | Culture Medium |
|---|---|---|
| EMT-6 | breast cancer | DMEM + 10% FBS |
| Pan02 | pancreatic cancer | RPMI1640 + 10% FBS |
| LL/2 | lung cancer | DMEM + 10% FBS |
| A20 | B cell lymphoma | RPMI1640 + 10% FBS |

Subcutaneous Syngeneic Mouse Tumor Models

Four subcutaneous syngeneic mouse tumor models were generated by innoculating female BALB/C or C57BL/6 mice with cancer cells at their right lower or front flank as detailed in the table below:

| Cell line | Cell Number | Inoculation site | MouseStrain |
|---|---|---|---|
| EMT-6 | $5 \times 10^5$ | right lower flank | BALB/C |
| Pan02 | $3 \times 10^6$ | right front flank | C57BL/6 |
| LL/2 | $3 \times 10^5$ | right lower flank | C57BL/6 |
| A20 | $5 \times 10^5$ | right lower flank | BALB/C |

Each mouse was inoculated subcutaneously with tumor cells in 0.1 mL of PBS. Treatments were started when the mean tumor size reached approximately 80-120 mm³ (around 100 mm³). The administration of the indole compounds and the animal number in each study group are shown in the study design. The date of tumor cell inoculation was denoted as day 0.

Formulation of Indole Compounds

The indole compounds were dissolved in DMSO at the final concentration of 26.7 mg/ml and stored at room temperature.

Study Design

Randomization of animals was started when the mean tumor size reached approximately 90 mm³ to form the mouse study groups. The randomization was performed based on "Matched distribution" method using the multi-task method (StudyDirector™ software, version 3.1.399.19)/randomized block design. The mouse groups (ten in each group) were treated with vehicle (DMSO) or the indole compounds at a dose of 40 mg/kg by i.p. injection, QD for 28 days or longer.

Observation and Data Collection

After tumor cell inoculation, the mice were checked daily for morbidity and mortality. During routine monitoring, the mice were checked for tumor growth and any effects of the treatment on behavior such as mobility, food and water consumption, body weight gain/loss (body weights were measured twice per week after randomization), eye/hair matting, and any other abnormalities. Mortality and observed clinical signs were recorded for individual mice in detail.

Tumor volumes were measured twice per week in two dimensions using a caliper, and the volume was expressed in mm³ using the formula:

$$V=(L \times W \times W)/2,$$

where V is tumor volume, L is tumor length (the longest tumor dimension) and W is tumor width (the longest tumor dimension perpendicular to L). Dosing as well as tumor and body weight measurements was conducted in a Laminar Flow Cabinet. The body weights and tumor volumes were measured by using StudyDirector™ software (version 3.1.399.19).

Dosing Holiday

A dosing holiday was given to the mice after one measurement of body weight loss (BWL) >30%. The length of the dosing holiday was long enough for the body weight to recover to BWL <30%, at which time the treatment was resumed. The mice were not fed any additional nutrient supplement during the dosing holiday.

Experimental Termination

Tumor growth inhibition percentage (TGI %) is an indicator for antitumor activity of a drug compound, and expressed as:

$$TGI~(\%)=100 \times (1-T/C),$$

where T and C are the mean tumor volume (or weight) of the treated and control groups, respectively, on a given day. Statistical analysis of the difference in mean tumor volume (MTV) among the groups was conducted using the data collected on the day when the MTV of the vehicle group reached the humane endpoints, so that TGI could be derived for all or most mice enrolled in the study.

The body weight of all animals was monitored throughout the study and animals were euthanized if they lost over 20% of their body weight relative to the weight at the start of the study and could not recover within 72 hours.

All of the mice in the same group would be sacrificed when the MTV reached 2000 mm³, or an individual mouse would be sacrificed when the tumor volume reached 3000 mm³.

To deter cannibalization, any animal exhibiting an ulcerated or necrotic tumor would be separated immediately and singly housed and monitored daily before the animal was euthanized or until tumor regression was complete. Mouse with tumor ulceration of approximately 25% or greater on the surface of the tumor would be euthanized.

Statistical Analysis

For comparison between two groups, a Student's t-test was performed. All data were analyzed using SPSS 18.0 and/or GraphPad Prism 5.0. $P<0.05$ was considered statistically significant.

Results

In vivo studies were performed in the above-described syngeneic mouse tumor models to evaluate the anti-tumor activity of ARI-001, ARI-002, ARI-004; ARI-002 derivatives ARI-087, ARI-140, ARI-142, ARI-143, and ARI-149; and oxa- or thia-diazole derivatives ARI-090, ARI-118, ARI-120, ARI-145, ARI-146, and ARI-148.

In Studies 1 and 3, the anti-tumor activity of ARI-001 in parallel with ARI-002 at 160 mg/kg (mpk), and the anti-tumor activity of ARI-087 in parallel with ARI-002 at 40 mpk were assessed using the EMT-6, Pan02, A20, and LL/2 models. Because EMT-6 provides a fast-growing model that enables relatively quick differentiation of performance between compounds, this syngeneic mouse tumor model was chosen for the other studies. In Study 2, the anti-tumor activity of ARI-002 was compared with that of ARI-004 at 10, 40, and 80 mpk. In Study 4, the anti-tumor activity of ARI-087 was compared with that of ARI-140. In Study 5, the anti-tumor activity of ARI-087 was evaluated in parallel with ARI-143 and ARI-149 at 40 mpk. Table 8 summarizes the tumor growth inhibition (TGI) data collected on the indicated days post tumor inoculation. The vehicle arm was terminated on the indicated days (D), when the vehicle control mice reached the humane endpoints.

TABLE 8

TGI Data of in vivo Studies

| Compound ID | | EMT-6 | PanO2 | A20 | LL/2 |
|---|---|---|---|---|---|
| Study 1 | | | | | |
| ARI-001 | (160 mpk) | 53.0% D27 | 74.2% D28 | 54.5% D26 | 65.1% D28 |
| ARI-002 | (160 mpk) | 54.6% D27 | 77.9% D28 | 44.7% D26 | 69.0% D28 |
| Study 2 | | | | | |
| ARI-001 | (160 mpk) | 75.1% D27 | N/D* | N/D | N/D |
| ARI-002 | (10 mpk) | 14.9% D27 | | | |
| | (40 mpk) | 33.3% D27 | | | |
| | (80 mpk) | 54.6% D27 | | | |
| ARI-004 | (10 mpk) | −38.2% D27 | N/D | N/D | N/D |
| | (40 mpk) | 0.3% D27 | | | |
| | (80 mpk) | 15.8% D27 | | | |
| Study 3 | | | | | |
| ARI-002 | (40 mpk) | 41.4% D27 | 64.9% D60 | 9.7% D28 | 19.9% D38 |
| ARI-087 | (40 mpk) | 56.7% D27 | 64.9% D60 | 20.9% D28 | 23.3% D38 |
| ARI-030 | (40 mpk) | 21.9% D27 | 23.5% D60 | −0.8% D28 | 8.4% D28 |
| ARI-083 | (40 mpk) | 21.2% D27 | 2.7% D60 | 22% D28 | 24.0% D28 |
| Study 4 | | | | | |
| ARI-087 | (40 mpk) | 29.5% D28 | N/D | N/D | N/D |
| ARI-140 | (40 mpk) | 30.6% D28 | N/D | N/D | N/D |
| ARI-118 | (40 mpk) | 54.5% D28 | N/D | N/D | N/D |
| Study 5 | | | | | |
| ARI-087 | (40 mpk) | 42.2% D30 | N/D | N/D | N/D |
| ARI-143 | (40 mpk) | 65.9% D30 | N/D | N/D | N/D |
| ARI-149 | (40 mpk) | 42.7% D30 | N/D | N/D | N/D |
| ARI-120 | (40 mpk) | 27.2% D30 | N/D | N/D | N/D |
| ARI-145 | (40 mpk) | 10.5% D30 | N/D | N/D | N/D |
| ARI-146 | (40 mpk) | 23.2% D30 | N/D | N/D | N/D |
| ARI-148 | (40 mpk) | 4.8% D30 | N/D | N/D | N/D |
| Study 6 | | | | | |
| ARI-087 | (40 mpk) | 52.8% D26 | N/D | N/D | N/D |
| ARI-056 | (40 mpk) | 34.3% D26 | N/D | N/D | N/D |
| ARI-090 | (40 mpk) | 30.1% D26 | N/D | N/D | N/D |

*N/D: not determined.

The TGI data of Study 2 show that ARI-002 at 80 mpk had comparable efficacy as ARI-001 at 160 mpk. The TGI data of Study 3 show that in three of the tumor models (breast, lung, and lymphoma), ARI-087 exhibited better tumor inhibitory activity than parent compound ARI-002, while it exhibited similar tumor inhibitory activity compared to ARI-002 in the pancreatic cancer model. See the TGI Table above and FIGS. 60A-D. Due to its high potency, ARI-087 was selected as a positive control for subsequent in vivo anti-tumor studies.

Figure 61:
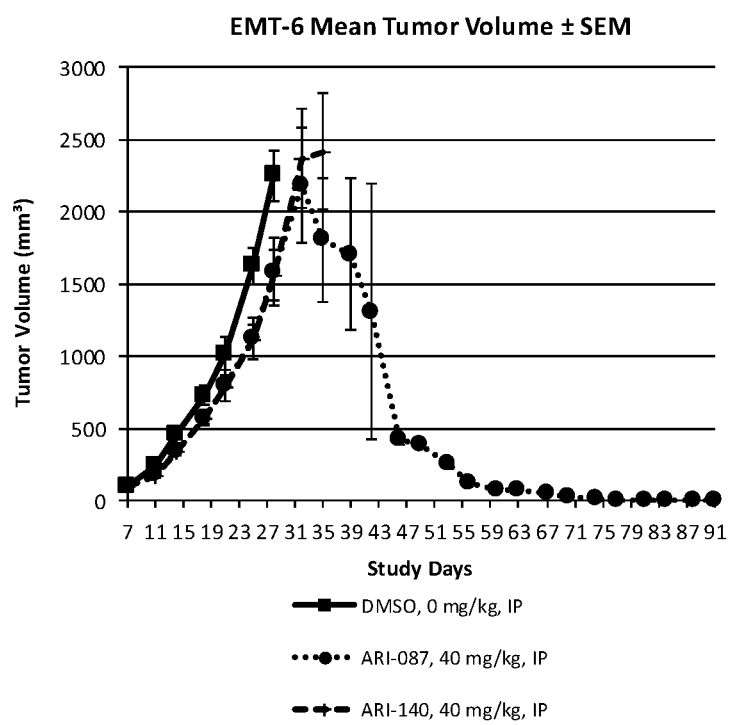
FIG. 61 is a graph comparing the tumor inhibitory activities of ARI-087 and ARI-140 in the EMT-6 syngeneic mouse tumor model.
Figure 62:
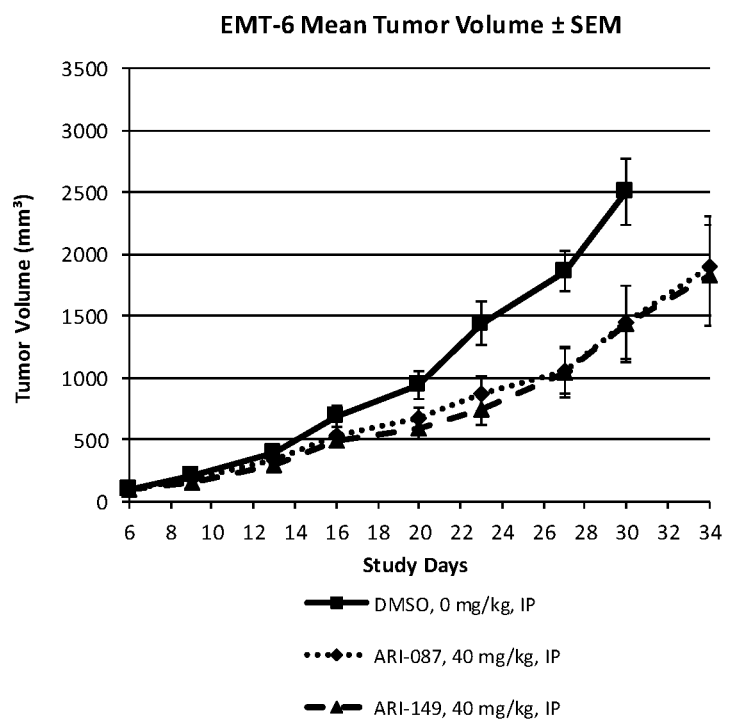
FIG. 62 is a graph comparing the tumor inhibitory activities of ARI-087 and ARI-149 in the EMT-6 syngeneic mouse tumor model.

Studies 4 and 5, together with unshown data, demonstrate that other ketone derivatives, ARI-140, ARI-142, and ARI-149 were similar to ARI-087 in anti-tumor potency. See the TGI Table above and FIGS. 61 and 62. The data also shows that in the EMT-6 model, ARI-087 delayed tumor growth and prolonged survival: at day 27 in the same study as ARI-002, the ARI-087 arm had 6 out of 10 animals with tumor volumes <1000 mm³, as compared to the ARI-002 arm, which had only 3 out of 10 animals with tumor volumes <1000 mm³.

Figure 63:
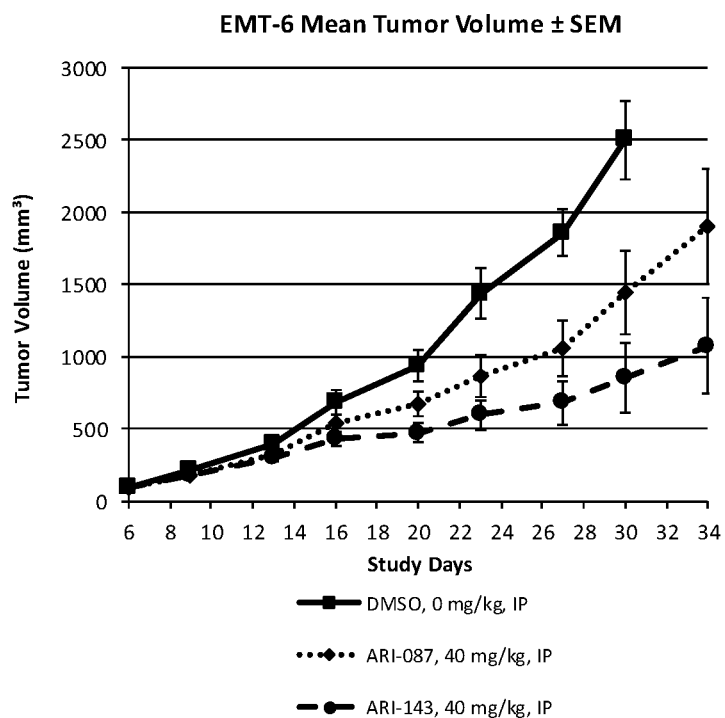
FIG. 63 is a graph comparing the tumor inhibitory activities of ARI-087 and ARI-143 in the EMT-6 syngeneic mouse tumor model.

Study 5 further shows that ARI-143 was the most potent ketone derivative in the EMT-6 tumor model. See the TGI Table above and FIG. 63. ARI-143 was shown to delay tumor growth and prolong survival; and it led to complete tumor regression (CR) in 2 out of 10 animals by day 51, both of which remained tumor-free, as compared to the ARI-087 arm, which which did not have any animal in CR. The superior anti-tumor efficacy of ARI-143 confirms the compound's properties exhibited in in vitro potency and metabolic assays, as well as suggested by the compound's in vivo PK data.

Further studies were performed to evaluate the anti-tumor activity of oxa- or thia-diazole derivatives ARI-030, ARI-056, ARI-083, ARI-090, ARI-118, ARI-120, ARI-145, ARI-146, and ARI-148 as compared to ARI-002 and ARI-087. The TGI data of Studies 3, 5, and 6 show that in the EMT-6 model, ARI-120, ARI-145, ARI-146, ARI-148, ARI-056, and ARI-090 showed less anti-tumor potency than ARI-087. See the TGI Table above.

Notably, the remaining oxadiazole derivative tested, ARI-118, exhibited superior anti-tumor activity than ARI-087. See the TGI Table above and FIG. 64. ARI-118 was shown to delay tumor growth and prolong survival; and it led to complete tumor regression (CR) in 1 out of 10 animals by day 46, as compared to the ARI-087 arm in the same study, which did not result in a CR until day 81.

Exemplary Embodiments

Non-limiting, exemplary embodiments of the present disclosure are provided below:

1. A compound of formula 2, or an enantiomer, diastereomer, or pharmaceutically acceptable salt thereof:

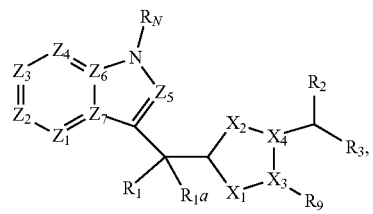

Structural Formula 2 wherein:

$X_1$ is N (nitrogen), O (oxygen), S (sulfur), or C (carbon); $X_2$ is N (nitrogen), O (oxygen) S (sulfur), or C (carbon); $X_3$ is N (nitrogen), O (oxygen), S (sulfur) or C (carbon); and $X_4$ is N (nitrogen) O (oxygen), S (sulfur), or C (carbon), such that at least one of $X_1$, $X_2$, $X_3$ and $X_4$ is N, each of $X_1$, $X_2$, $X_3$ and $X_4$ is optionally selected to form a heteroaromatic, wherein the bond between $X_1$ and the adjacent carbon, between $X_2$ and the adjacent carbon, between $X_1$ and $X_4$, between $X_2$ and $X_3$, and between $X_3$ and $X_4$ can be a single bond or a double bond and the valence of $X_1$, $X_2$, $X_3$ and $X_4$ is completed with H or $C_1$-$C_6$ alkyl (i.e., the ring can be aromatic, partially saturated, or saturated);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_2$ and $R_3$ are together selected from the group consisting of =O, =S, or =$NR_a$ ($R_a$ is H, $C_1$-$C_6$ alkyl, $C_1$-$C_6$ acyl, or —OR, R is H, $C_1$-$C_6$ alkyl, or $C_1$-$C_6$ acyl), or $R_2$ and $R_3$ are each independently selected from the group consisting of —$NR_aR_b$ ($R_a$ and $R_b$ are each independently H, $C_1$-$C_6$ alkyl, or $C_1$-$C_6$ acyl), hydrogen, deuterium, halo, amino, hydroxy, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_4$, $R_5$, $R_6$, $R_7$, $R_8$, and $R_9$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl; and $R_1$ and $R_{1a}$ are taken together to form =NR$_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, $R_2$ preferably can be =O, $R_3$ preferably can be —OR, wherein R is H or $C_1$-$C_6$ alkyl, or $R_1$ and $R_{1a}$ are taken together to form =CR$_b$R$_c$, wherein $R_b$ and $R_c$ are each independently H, $C_1$-$C_6$ alkyl, alkoxy (—O-alkyl), thioalkoxy (—S-alkyl), cyano (—CN), or amino, $R_2$ preferably can be =O, $R_3$ preferably can be —OR, wherein R is H or $C_1$-$C_6$ alkyl, or $R_1$ and $R_{1a}$ are taken together to form =O, =NOR$_a$, or =S, $R_2$ and $R_3$ preferably can be each independently —OR or —NR$_a$R$_b$, wherein R, $R_a$, and $R_b$ are each independently H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and optionally, adjacent R groups, together, can form a six- to twelve-membered ring.

2. A compound of formula 2a, or an enantiomer, diastereomer, or pharmaceutically acceptable salt thereof:

Structural Formula 2a

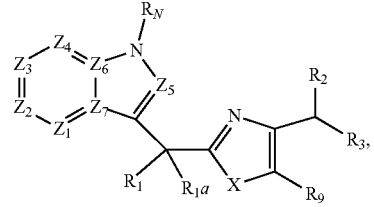

wherein:

X is either O (oxygen) or S (sulfur);

$Z_1$ is N or CR$_4$, $Z_2$ is N or CR$_5$, $Z_3$ is N or CR$_6$, $Z_4$ is N or CR$_7$, $Z_5$ is N or CR$_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_2$ and $R_3$ are together selected from the group consisting of =O, =S, or =NR$_a$ ($R_a$ is H, $C_1$-$C_6$ alkyl, $C_1$-$C_6$ acyl, or —OR, R is H, $C_1$-$C_6$ alkyl, or $C_1$-$C_6$ acyl), or $R_2$ and $R_3$ are each independently selected from the group consisting of —NR$_a$R$_b$ ($R_a$ and $R_b$ are each independently H, $C_1$-$C_6$ alkyl, or $C_1$-$C_6$ acyl), hydrogen, deuterium, halo, amino, hydroxy, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_4$, $R_5$, $R_6$, $R_7$, $R_8$, and $R_9$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl; and $R_1$ and $R_{1a}$ are taken together to form =NR$_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, $R_2$ preferably can be =O, $R_3$ preferably can be —OR, wherein R is H or $C_1$-$C_6$ alkyl, or $R_1$ and $R_{1a}$ are taken together to form =$CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, $R_2$ preferably can be =O, $R_3$ preferably can be —OR, wherein R is H or $C_1$-$C_6$ alkyl, or $R_1$ and $R_{1a}$ are taken together to form =O, =$NOR_a$, or =S, $R_2$ and $R_3$ preferably can be each independently —OR or —$NR_aR_b$, wherein R, $R_a$, and $R_b$ are each independently H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and optionally, adjacent R groups, together, can form a six- to twelve-membered ring.

3. A compound of formula 3, or an enantiomer, diastereomer, or pharmaceutically acceptable salt thereof:

Structural Formula 3

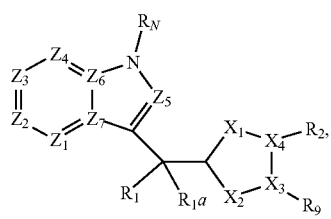

wherein:

$X_1$ is N (nitrogen), O (oxygen), S (sulfur), or C (carbon); $X_2$ is N (nitrogen), O (oxygen) S (sulfur), or C (carbon); $X_3$ is N (nitrogen), O (oxygen), S (sulfur) or C (carbon); and $X_4$ is N (nitrogen) O (oxygen), S (sulfur), or C (carbon), such that at least one of $X_1$, $X_2$, $X_3$ and $X_4$ is N, each of $X_1$, $X_2$, $X_3$ and $X_4$ is optionally selected to form a heteroaromatic, wherein the bond between $X_1$ and the adjacent carbon, between $X_2$ and the adjacent carbon, between $X_1$ and $X_4$, between $X_2$ and $X_3$, and between $X_3$ and $X_4$ can be a single bond or a double bond and the valence of $X_1$, $X_2$, $X_3$ and $X_4$ is completed with H or $C_1$-$C_6$ alkyl (i.e., the ring can be aromatic, partially saturated, or saturated);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form =$NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form =$CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form =O, =$NOR_a$, or =S, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and $R_2$ and $R_9$ are each independently selected from the group consisting of hydrogen, aryl, heteroaryl, cycloalkyl, heterocycloalkyl, alkyl, —$NR_{2a}C(O)OR_{2b}$, —$NR_{2a}C(O)R_{2b}$, —($C_0C_6$ alkyl)-$CONHSO_2R_{2a}$, —($C_0$-$C_6$ alkyl)-$CONHSO_2NR_{2a}R_{2b}$, —($C_0$-$C_6$ alkyl)-$SO_2NHCOR_{2a}$, —($C_0$-$C_6$ alkyl)-$SO_2NHR_{2a}$, —($C_0$-$C_6$ alkyl)-$CONR_{2a}OR_{2b}$,

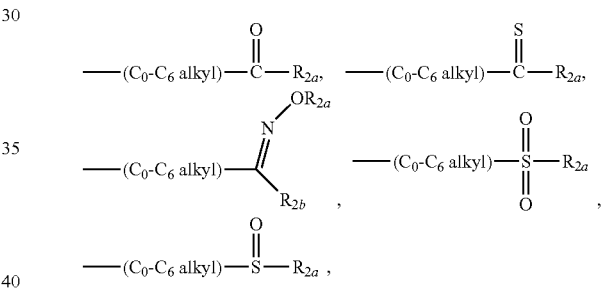

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, R$_{11}$ is directly connected to S), wherein R$_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

R$_N$ is H, CN, C$_1$-C$_6$ alkyl, —OH, —(CO)—OR, or —OR, wherein R is H, C$_1$-C$_6$ alkyl, or C$_1$-C$_6$ acyl; and optionally, adjacent R groups, together, can form a six- to twelve-membered ring.

4. A compound of formula 3c, or an enantiomer, diastereomer, or pharmaceutically acceptable salt thereof:

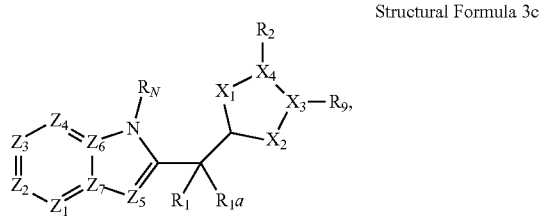

Structural Formula 3c wherein:

X$_1$ is N (nitrogen), O (oxygen), S (sulfur), or C (carbon); X$_2$ is N (nitrogen), O (oxygen) S (sulfur), or C (carbon); X$_3$ is N (nitrogen), O (oxygen), S (sulfur) or C (carbon); and X$_4$ is N (nitrogen) O (oxygen), S (sulfur), or C (carbon), such that at least one of X$_1$, X$_2$, X$_3$ and X$_4$ is N, each of X$_1$, X$_2$, X$_3$ and X$_4$ is optionally selected to form a heteroaromatic, wherein the bond between X$_1$ and the adjacent carbon, between X$_2$ and the adjacent carbon, between X$_1$ and X$_4$, between X$_2$ and X$_3$, and between X$_3$ and X$_4$ can be a single bond or a double bond and the valence of X$_1$, X$_2$, X$_3$ and X$_4$ is completed with H or C$_1$-C$_6$ alkyl (i.e., the ring can be aromatic, partially saturated, or saturated);

Z$_1$ is N or CR$_4$, Z$_2$ is N or CR$_5$, Z$_3$ is N or CR$_6$, Z$_4$ is N or CR$_7$, Z$_5$ is N or CR$_8$, Z$_6$ is N or C, Z$_7$ is N or C, wherein no more than two of Z$_1$, Z$_2$, Z$_3$, Z$_4$, Z$_5$, Z$_6$, and Z$_7$ are N;

R$_1$ and R$_{1a}$ are taken together to form =NR$_b$, wherein R$_b$ is H, C$_1$-C$_6$ alkyl, hydroxy, C$_1$-C$_6$ alkoxy (—O-alkyl), C$_1$-C$_6$ acyloxy, amino, or C$_1$-C$_6$ acyl, or R$_1$ and R$_{1a}$ are taken together to form =CR$_b$R$_c$, wherein R$_b$ and R$_c$ are each independently H, C$_1$-C$_6$ alkyl, alkoxy (—O-alkyl), thioalkoxy (—S-alkyl), cyano (—CN), or amino, or R$_1$ and R$_{1a}$ are taken together to form =O, =NOR$_a$, or =S, wherein R$_a$ is H, C$_1$-C$_6$ alkyl, or C$_1$-C$_6$ acyl, or R$_1$ and R$_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{12}$ (n=0 to 2, R$_{12}$ is directly connected to S), wherein R$_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and R$_2$ and R$_9$ are each independently selected from the group consisting of hydrogen, aryl, heteroaryl, cycloalkyl, heterocycloalkyl, alkyl, —NR$_{2a}$C(O)OR$_{2b}$, —NR$_{2a}$C(O)R$_{2b}$, —(C$_0$-C$_6$ alkyl)-CONHSO$_2$R$_{2a}$, —(C$_0$-C$_6$ alkyl)-CONHSO$_2$NR$_{2a}$R$_{2b}$, —(C$_0$-C$_6$ alkyl)-SO$_2$NHCOR$_{2a}$, —(C$_0$-C$_6$ alkyl)-SO$_2$NHR$_{2a}$, —(C$_0$-C$_6$ alkyl)-CONR$_{2a}$OR$_{2b}$,

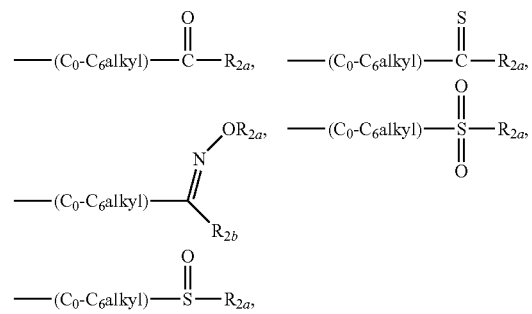

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, R$_{10}$ is directly connected to S), wherein R$_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein R$_{2a}$ and R$_{2b}$ are each independently H, C$_1$-C$_6$ alkyl, alkoxy (—O-alkyl), hydroxy, thioalkoxy (—S-alkyl), cyano (—CN), or amino;

R$_4$, R$_5$, R$_6$, R$_7$, and R$_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, R$_{11}$ is directly connected to S), wherein R$_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

R$_N$ is H, CN, C$_1$-C$_6$ alkyl, —OH, —(CO)—OR, or —OR, wherein R is H, C$_1$-C$_6$ alkyl, or C$_1$-C$_6$ acyl; and optionally, adjacent R groups, together, can form a six- to twelve-membered ring.

5. A compound of formula 3a, or an enantiomer, diastereomer, or pharmaceutically acceptable salt thereof:

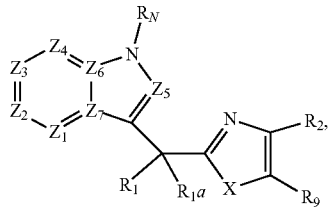

Structural Formula 3a wherein:

X is either O (oxygen) or S (sulfur);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form =$NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form =$CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form =O, =$NOR_a$, or =S, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n R_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and $R_2$ and $R_9$ are each independently selected from the group consisting of hydrogen, aryl, heteroaryl, cycloalkyl, heterocycloalkyl, alkyl, —$NR_{2a}C(O)OR_{2b}$, —$NR_{2a}C(O)R_{2b}$, —($C_0$-$C_6$ alkyl)-$CONHSO_2R_{2a}$, —($C_0$-$C_6$ alkyl)-$CONHSO_2NR_{2a}R_{2b}$, —($C_0$-$C_6$ alkyl)-$SO_2NHCOR_{2a}$, —($C_0$-$C_6$ alkyl)-$SO_2NHR_{2a}$, —($C_0$-$C_6$ alkyl)-$CONR_{2a}OR_{2b}$,

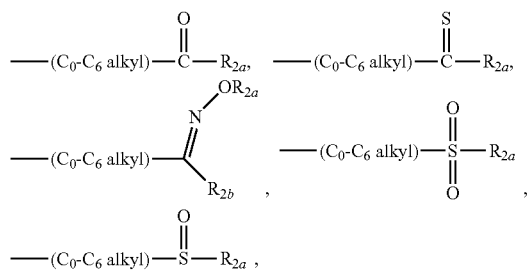

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n R_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n R_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl; and optionally, adjacent R groups, together, can form a six- to twelve-membered ring.

6. A compound of formula 3b, or an enantiomer, diastereomer, or pharmaceutically acceptable salt thereof:

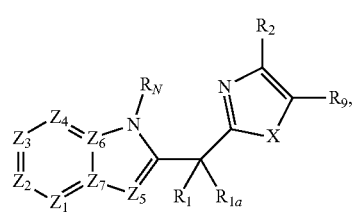

Structural Formula 3b wherein:

X is either O (oxygen) or S (sulfur);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form =$NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form =$CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form =O, =NOR$_a$, or =S, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and $R_2$ and $R_9$ are each independently selected from the group consisting of hydrogen, aryl, heteroaryl, cycloalkyl, heterocycloalkyl, alkyl, —NR$_{2a}$C(O)OR$_{2b}$, —NR$_{2a}$C(O)R$_{2b}$, —(C$_0$-C$_6$ alkyl)-CONHSO$_2$R$_{2a}$, —(C$_0$-C$_6$ alkyl)-CONHSO$_2$NR$_{2a}$R$_{2b}$, —(C$_0$-C$_6$ alkyl)-SO$_2$NHCOR$_{2a}$, —(C$_0$-C$_6$ alkyl)-SO$_2$NHR$_{2a}$, —(C$_0$-C$_6$ alkyl)-CONR$_{2a}$OR$_{2b}$,

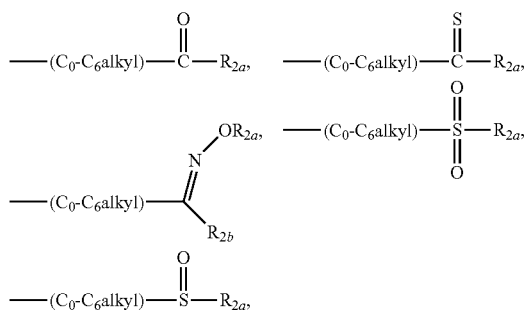

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl; and optionally, adjacent R groups, together, can form a six- to twelve-membered ring.

7. A compound of formula 4, or an enantiomer, diastereomer, or pharmaceutically acceptable salt thereof:

Structural Formula 4

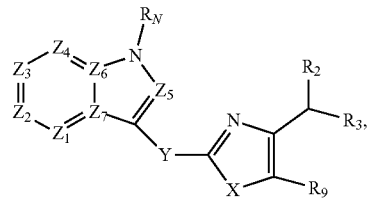

wherein:

X is O (oxygen) or S (sulfur);

Y is a bond, O (oxygen), S (sulfur), or

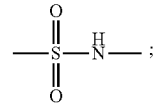

$Z_1$ is N or CR$_4$, $Z_2$ is N or CR$_5$, $Z_3$ is N or CR$_6$, $Z_4$ is N or CR$_7$, $Z_5$ is N or CR$_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_4$, $R_5$, $R_6$, $R_7$, $R_8$, and $R_9$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl;

$R_2$ and $R_3$ are together selected from the group consisting of =O, =S, or =NR$_a$ ($R_a$ is H, $C_1$-$C_6$ alkyl, $C_1$-$C_6$ acyl, or —OR, R is H, $C_1$-$C_6$ alkyl, or $C_1$-$C_6$ acyl), or $R_2$ and $R_3$ are each independently selected from the group consisting of —$NR_aR_b$ ($R_a$ and $R_b$ are each independently H, $C_1$-$C_6$ alkyl, or $C_1$-$C_6$ acyl), hydrogen, deuterium, halo, amino, hydroxy, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and optionally, adjacent R groups, together, can form a six- to twelve-membered ring.

8. A compound of formula 5, or an enantiomer, diastereomer, or pharmaceutically acceptable salt thereof:

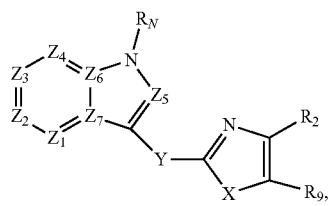

Structural Formula 5 wherein:

X is O (oxygen) or S (sulfur);

Y is a bond, O (oxygen), S (sulfur), or

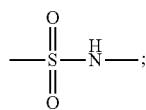

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_2$ and $R_9$ are each independently selected from the group consisting of hydrogen, aryl, heteroaryl, cycloalkyl, heterocycloalkyl, alkyl, —$NR_{2a}C(O)OR_{2b}$, —$NR_{2a}C(O)R_{2b}$, —($C_0$-$C_6$ alkyl)-$CONHSO_2R_{2a}$, —($C_0$-$C_6$ alkyl)-$CONHSO_2NR_{2a}R_{2b}$, —($C_0$-$C_6$ alkyl)-$SO_2NHCOR_{2a}$, —($C_0$-$C_6$ alkyl)-$SO_2NHR_{2a}$, —($C_0$-$C_6$ alkyl)-$CONR_{2a}OR_{2b}$,

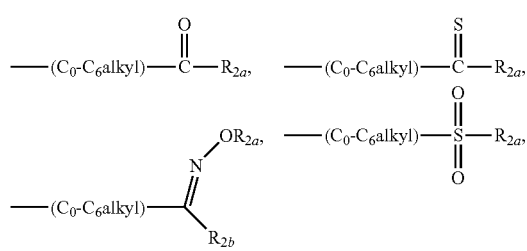

-continued

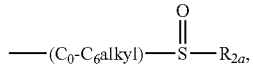

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl; and optionally, adjacent R groups, together, can form a six- to twelve-membered ring.

9. A compound of formula 6, or an enantiomer, diastereomer, or pharmaceutically acceptable salt thereof:

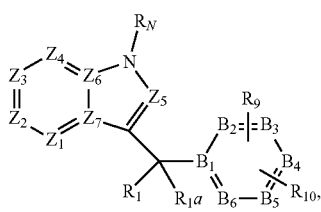

Structural Formula 6 wherein:

$R_1$ and $R_{1a}$ are taken together to form =$NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form =$CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or R₁ and R₁ₐ are taken together to form =O, =NORₐ, or =S, wherein Rₐ is H, $C_1$-$C_6$ alkyl, or $C_1$-$C_6$ acyl, or R₁ and R₁ₐ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R₁₄ (n=0 to 2, R₁₄ is directly connected to S), wherein R₁₄ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

Z₁ is N or CR₄, Z₂ is N or CR₅, Z₃ is N or CR₆, Z₄ is N or CR₇, Z₅ is N or CR₈, Z₆ is N or C, Z₇ is N or C, wherein no more than two of Z₁, Z₂, Z₃, Z₄, Z₅, Z₆, and Z₇ are N;

R₄, R₅, R₆, R₇, and R₈ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R₁₁ (n=0 to 2, R₁₁ is directly connected to S), wherein R₁₁ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

R_N is H, CN, $C_1$-$C_6$ alkyl, —OH, —(CO)—OR, or —OR, wherein R is H, $C_1$-$C_6$ alkyl, or $C_1$-$C_6$ acyl;

B₁, B₂, B₃, B₄, B₅, and B₆ are each independently C or N;

R₉ and R₁₀, the number of which, together, complete the valence of each of B₁, B₂, B₃, B₄, B₅, and B₆, are each independently selected from the group consisting of hydrogen, aryl, heteroaryl, cycloalkyl, heterocycloalkyl, alkyl, —NR₂ₐC(O)OR₂ᵦ, —NR₂ₐC(O)R₂ᵦ, —(C₀-C₆ alkyl)-CONHSO₂R₂ₐ, —(C₀-C₆ alkyl)-CONHSO₂NR₂ₐR₂ᵦ, —(C₀-C₆ alkyl)-SO₂NHCOR₂ₐ, —(C₀-C₆ alkyl)-SO₂NHR₂ₐ, —(C₀-C₆ alkyl)-CONR₂ₐOR₂ᵦ,

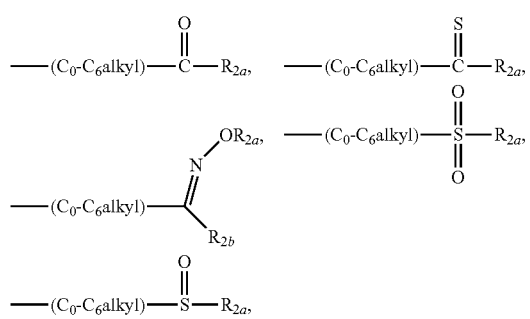

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R₁₂ (n=0 to 2, R₁₂ is directly connected to S), wherein R₁₂ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and

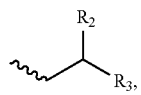

wherein R₂ₐ and R₂ᵦ are each independently H, $C_1$-$C_6$ alkyl, alkoxy (—O-alkyl), hydroxy, thioalkoxy (—S-alkyl), cyano (—CN), or amino;

wherein R₂ and R₃ are together selected from the group consisting of =O, =S, or =NRₐ (Rₐ is H, $C_1$-$C_6$ alkyl, $C_1$-$C_6$ acyl, or —OR, R is H, $C_1$-$C_6$ alkyl, or $C_1$-$C_6$ acyl), or R₂ and R₃ are each independently selected from the group consisting of —NRₐRᵦ (Rₐ and Rᵦ are each independently H, $C_1$-$C_6$ alkyl, or $C_1$-$C_6$ acyl), hydrogen, deuterium, halo, amino, hydroxy, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R₁₃ (n=0 to 2, R₁₃ is directly connected to S), wherein R₁₃ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and optionally, adjacent R groups, together, can form a six- to twelve-membered ring.

10. A compound of formula 7, or an enantiomer, diastereomer, or pharmaceutically acceptable salt thereof:

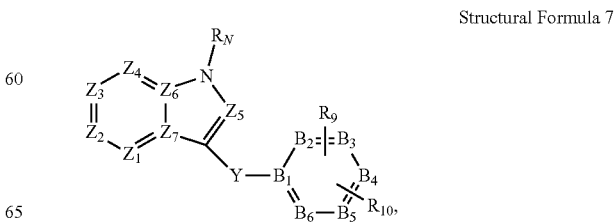

Structural Formula 7 wherein:

Y is a bond, O (oxygen), S (sulfur), or

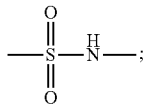

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $-S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, $C_1$-$C_6$ alkyl, —OH, —(CO)—OR, or —OR, wherein R is H, $C_1$-$C_6$ alkyl, or $C_1$-$C_6$ acyl;

$B_1$, $B_2$, $B_3$, $B_4$, $B_5$, and $B_6$ are each independently C or N;

$R_9$ and $R_{10}$, the number of which, together, complete the valence of each of $B_1$, $B_2$, $B_3$, $B_4$, $B_5$, and $B_6$, are each independently selected from the group consisting of hydrogen, aryl, heteroaryl, cycloalkyl, heterocycloalkyl, alkyl, $-NR_{2a}C(O)OR_{2b}$, $-NR_{2a}C(O)R_{2b}$, $-(C_0$-$C_6$ alkyl)-$CONHSO_2R_{2a}$, $-(C_0$-$C_6$ alkyl)-$CONHSO_2NR_{2a}R_{2b}$, $-(C_0$-$C_6$ alkyl)-$SO_2NHCOR_{2a}$, $-(C_0$-$C_6$ alkyl)-$SO_2NHR_{2a}$, $-(C_0$-$C_6$ alkyl)-$CONR_{2a}OR_{2b}$,

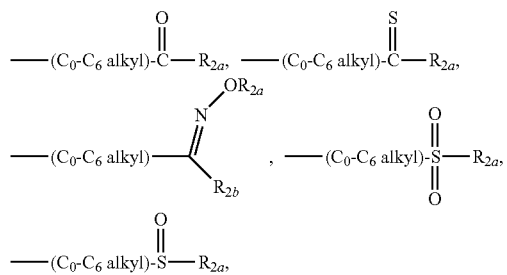

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $-S(O)_nR_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and

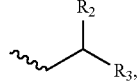

wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino;

wherein $R_2$ and $R_3$ are together selected from the group consisting of =O, =S, or =$NR_a$ ($R_a$ is H, $C_1$-$C_6$ alkyl, $C_1$-$C_6$ acyl, or —OR, R is H, $C_1$-$C_6$ alkyl, or $C_1$-$C_6$ acyl), or $R_2$ and $R_3$ are each independently selected from the group consisting of —$NR_aR_b$ ($R_a$ and $R_b$ are each independently H, $C_1$-$C_6$ alkyl, or $C_1$-$C_6$ acyl), hydrogen, deuterium, halo, amino, hydroxy, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $-S(O)_nR_{13}$ (n=0 to 2, $R_{13}$ is directly connected to S), wherein $R_{13}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and optionally, adjacent R groups, together, can form a six- to twelve-membered ring.

11. The compound of any one of embodiments 1-10, wherein each of $R_4$, $R_5$, $R_6$, and $R_7$ is hydrogen.
12. The compound of any one of embodiments 1-10, wherein at least one of $R_4$, $R_5$, $R_6$, and $R_7$ is F, Cl or Br and the others of $R_4$, $R_5$, $R_6$, and $R_7$ are hydrogen.
13. The compound of any one of embodiments 1-10, wherein at least two of $R_4$, $R_5$, $R_6$, and $R_7$, independently, are F, Cl or Br and the others of $R_4$, $R_5$, $R_6$, and $R_7$ are hydrogen.
14. The compound of embodiment 12 or 13, wherein the F, Cl or Br is at the indole ring carbon 5, 6, or 7.
15. The compound of any one of embodiments 1, 2, and 7, wherein $R_2$ is hydroxyl and $R_3$ is alkyl, aryl, nitro, or cyano.
16. The compound of any one of embodiments 1, 2, and 7, wherein $R_2$ is amino and $R_3$ is alkyl, aryl, nitro, or cyano.
17. The compound of embodiment 16, wherein the amino is unsubstituted.
18. The compound of any one of embodiments 1, 2, 7, and 15-17, wherein $R_8$ is hydrogen.
19. The compound of any one of embodiments 3-6 and 8, wherein $R_2$ is acyl, cyano, hydroxyl-substituted C1-C6 alkyl, amino-substituted C1-C6 alkyl, aryl, or heteroaryl.
20. The compound of embodiment 19, wherein the aryl is substituted aryl.
21. The compound of embodiment 20, wherein the aryl is substituted with halo, amino, hydroxyl, or C1-C6 alkyl.
22. The compound of embodiment 21, wherein the amino is unsubstituted amino.

23. The compound of embodiment 19, wherein the heteroaryl is substituted heteroaryl.

24. The compound of embodiment 23, wherein the heteroaryl is substituted with halo, amino, hydroxyl, or C1-C6 alkyl.

25. The compound of embodiment 24, wherein the amino is unsubstituted amino.

26. The compound of any one of embodiments 3-6, 8, and 19-25, wherein $R_8$ is hydrogen.

27. A compound represented by the following formula:

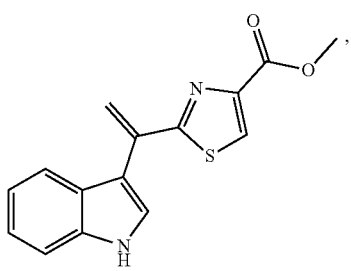

ARI-019 or an enantiomer, diastereomer, or pharmaceutically acceptable salt thereof.

28. A compound represented by the following formula:

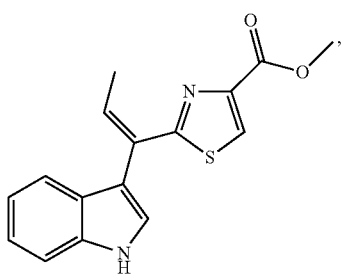

ARI-018 or an enantiomer, diastereomer, or pharmaceutically acceptable salt thereof.

29. A compound represented by the following formula:

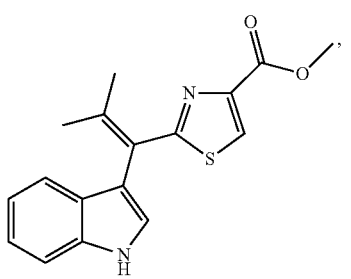

ARI-020 or an enantiomer, diastereomer, or pharmaceutically acceptable salt thereof.

30. A compound represented by the following formula:

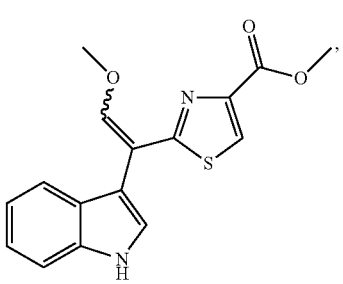

ARI-017 or an enantiomer, diastereomer, or pharmaceutically acceptable salt thereof.

31. A compound of formula 8, or an enantiomer, diastereomer, or pharmaceutically acceptable salt thereof,

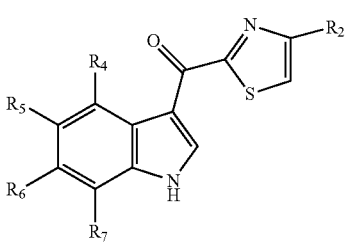

Structural Formula 8 wherein $R_2$ is selected from the group consisting of substituted alkyl, heteroaryl, and

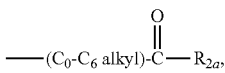

wherein $R_{2a}$ is H, C1-C6 alkyl, alkoxy (—O-alkyl), hydroxy, thioalkoxy (—S-alkyl), cyano (—CN), or amino; and $R_4$, $R_5$, $R_6$, and $R_7$, are each, independently, selected from the group consisting of hydrogen and halo.

32. The compound of embodiment 31, wherein $R_2$ is substituted alkyl.

33. The compound of embodiment 32, wherein the substituted alkyl is a C1-C6 alkyl substituted with one or more hydroxyl, amino, nitro, or cyano.

34. The compound of embodiment 31, wherein $R_2$ is heteroaryl.

35. The compound of embodiment 34, wherein the heteroaryl is oxadiazolyl or thiadiazolyl, optionally substituted with one or more hydroxyl, amino, nitro, cyano, C1-C6 alkyl, or C1-C6 alkyl amino.

36. The compound of embodiment 31, wherein $R_2$ is —C(O)—$R_{2a}$, and wherein $R_{2a}$ is C1-C6 alkyl.

37. The compound of any one of embodiments 31-36, wherein at least one of $R_4$, $R_5$, $R_6$, and $R_7$ is F, Cl or Br, and the others of $R_4$, $R_5$, $R_6$, and $R_7$ are hydrogen.

38. The compound of any one of embodiments 31-36, wherein at least two of $R_4$, $R_5$, $R_6$, and $R_7$ are F, Cl or Br, and the others of $R_4$, $R_5$, $R_6$, $R_7$ are hydrogen.

39. The compound of any one of embodiments 31-36, wherein $R_5$ is F, and $R_4$, $R_6$, and $R_7$ are hydrogen.

40. The compound of any one of embodiments 31-36, wherein $R_6$ is F, and $R_4$, $R_5$, and $R_7$ are hydrogen.

41. The compound of any one of embodiments 31-36, wherein R$_7$ is F, and R$_4$, R$_5$, and R$_6$ are hydrogen.
42. The compound of any one of embodiments 31-36, wherein R$_5$ is Cl, and R$_4$, R$_6$, and R$_7$ are hydrogen.
43. The compound of any one of embodiments 31-36, wherein R$_6$ is Cl and R$_4$, R$_5$, and R$_7$ are hydrogen.
44. The compound of any one of embodiments 31-36, wherein R$_7$ is Cl, and R$_4$, R$_5$, and R$_6$ are hydrogen.
45. The compound of any one of embodiments 31-36, wherein R$_5$ and R$_6$ are F, and R$_4$ and R$_7$ are hydrogen.
46. The compound of any one of embodiments 31-36, wherein R$_5$ and R$_7$ are F, and R$_4$ and R$_6$ are hydrogen.
47. The compound of any one of embodiments 31-36, wherein R$_6$ and R$_7$ are F, and R$_4$ and R$_5$ are hydrogen.
48. The compound of any one of embodiments 31-36, wherein R$_5$ and R$_6$ are Cl, and R$_4$ and R$_7$ are hydrogen.
49. The compound of any one of embodiments 31-36, wherein R$_5$ and R$_7$ are Cl, and R$_4$ and R$_6$ are hydrogen.
50. The compound of any one of embodiments 31-36, wherein R$_6$ and R$_7$ are Cl, and R$_4$ and R$_5$ are hydrogen.
51. The compound of any one of embodiments 31-36, wherein each of R$_4$, R$_5$, R$_6$ and R$_7$ is hydrogen.
52. The compound of embodiment 31, which is selected from any one of the compounds in the following table, or an enantiomer, diastereomer, or pharmaceutically acceptable salt thereof:

| ARI-# | Structural Formula |
|---|---|
| 031 | |
| 060 | |
| 083 | |
| 087 | |
| 090 | |
| 118 | |
| 120 | |
| 140 | |

| ARI-# | Structural Formula |
|---|---|
| 143 | 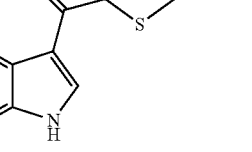 |
| 145 | 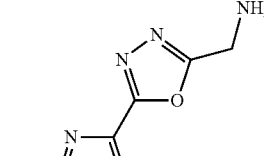 |
| 146 | 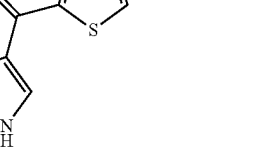 |
| 148 | 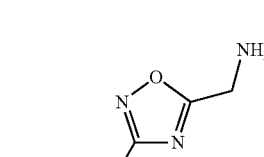 |
| 149 | 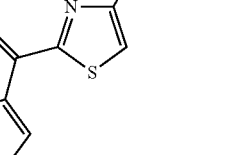 |

| ARI-# | Structural Formula |
|---|---|
| 150 |  |

53. A pharmaceutical composition comprising a compound of any one of embodiments 1-52 and a pharmaceutically acceptable carrier.

54. A method of stimulating the immune system in a patient in need thereof, comprising administering to the patient a therapeutically effective amount of a compound of any one of embodiments 1-52 or the pharmaceutical composition of embodiment 53.

55. The method of embodiment 54, wherein the compound decreases IL-21 level in the patient.

56. The method of embodiment 54 or 55, wherein the patient has cancer.

57. A method of treating cancer in a patient in need thereof, comprising administering to the patient a therapeutically effective amount of a compound of any one of embodiments 1-52 or the pharmaceutical composition of embodiment 53.

58. The method of embodiment 56 or 57, wherein the cancer is selected from the group consisting of lymphoma, leukemia, myeloma, prostate cancer, lung cancer, ovarian cancer, cervical cancer breast cancer, skin cancer, colorectal cancer, stomach cancer, pancreatic cancer, liver cancer, kidney cancer, bladder cancer, soft tissue cancer, glioma, and head and neck cancer.

59. The method of any one of embodiments 54-58, further comprising administering to the patient another cancer therapeutic agent.

60. A compound of any one of embodiments 1-52, or a pharmaceutical composition of embodiment 53 for use in stimulating the immune system or treating cancer in a method of any one of embodiments 54-59.

61. Use of a compound of any one of embodiments 1-52 for the manufacture of a medicament for stimulating the immune system or treating cancer in a method of any one of embodiments 54-59.

Unless otherwise defined herein, scientific and technical terms used in connection with the present invention shall have the meanings that are commonly understood by those of ordinary skill in the art. Exemplary methods and materials are described below, although methods and materials similar or equivalent to those described herein can also be used in the practice or testing of the present invention. In case of conflict, the present specification, including definitions, will control. Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein. Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers. All publications and other references mentioned herein are incorporated by reference in their entirety. Although a number of documents are cited herein, this citation does not constitute an admission that any of these documents forms part of the common general knowledge in the art.

Other embodiments of the present disclosure are within the scope of the following claims.

The invention claimed is:

1. An enantiomerically pure compound of Structural Formula 8, or a diastereomer or pharmaceutically acceptable salt thereof,

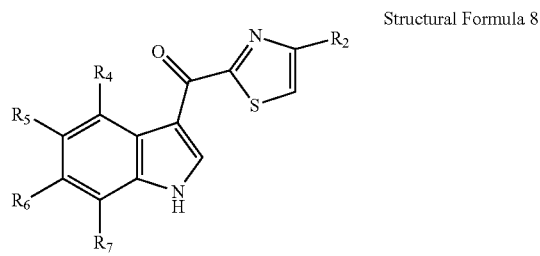

Structural Formula 8 wherein $R_2$ is a C1-C6 alkyl substituted with one or more hydroxyl, alkoxy, nitro, or cyano; and $R_4$, $R_5$, $R_6$, and $R_7$, are each, independently, selected from the group consisting of hydrogen and halo.

2. The compound of claim 1, wherein at least one of $R_4$, $R_5$, $R_6$, and $R_7$ is F, Cl, or Br, and the others of $R_4$, $R_5$, $R_6$, and $R_7$ are hydrogen.

3. The compound of claim 1, wherein $R_5$ is F or Cl, and $R_4$, $R_6$, and $R_7$ are hydrogen.

4. The compound of claim 1, wherein $R_6$ is F or Cl, and $R_4$, $R_5$, and $R_7$ are hydrogen.

5. The compound of claim 1, wherein $R_7$ is F or Cl, and $R_4$, $R_5$, and $R_6$ are hydrogen.

6. The compound of claim 1, wherein $R_5$ and $R_6$ are independently F or Cl, and $R_4$ and $R_7$ are hydrogen.

7. The compound of claim 1, wherein $R_5$ and $R_7$ are F or Cl, and $R_4$ and $R_6$ are hydrogen.

8. The compound of claim 1, wherein $R_6$ and $R_7$ are F or Cl, and $R_4$ and $R_5$ are hydrogen.

9. The compound of claim 1, wherein each of $R_4$, $R_5$, $R_6$ and $R_7$ is hydrogen.

10. The compound of claim 1, which is selected from any one of the compounds in the following table, or an enantiomer, diastereomer, or pharmaceutically acceptable salt thereof:

| ARI-# | Structural Formula |
|---|---|
| 092 | ![structure] |
| 094 | ![structure] |
| 1029 | ![structure] |
| 1030 | ![structure] |

11. The compound of claim 1, wherein the C1-C6 alkyl is substituted with one or more hydroxyl.

12. The compound of claim 1, wherein the C1-C6 alkyl is substituted with one or more alkoxy.

13. The compound of claim 1, wherein the C1-C6 alkyl is substituted with one or more nitro.

14. The compound of claim 1, wherein the C1-C6 alkyl is substituted with one or more cyano.

15. A pharmaceutical composition comprising a compound of claim 1 and a pharmaceutically acceptable carrier.

* * * * *